(12) United States Patent
Parsons et al.

(10) Patent No.: US 12,391,689 B2
(45) Date of Patent: *Aug. 19, 2025

(54) SYNTHESIS OF KEY INTERMEDIATE OF KRAS G12C INHIBITOR COMPOUND

(71) Applicant: Amgen Inc., Thousand Oaks, CA (US)

(72) Inventors: Andrew Thomas Parsons, Cambridge, MA (US); Brian McNeil Cochran, San Diego, CA (US); William Powazinik, IV, Thousand Oaks, CA (US); Marc Anthony Caporini, Belmont, MA (US)

(73) Assignee: AMGEN INC., Thousand Oaks, CA (US)

( * ) Notice: Subject to any disclaimer, the term of this patent is extended or adjusted under 35 U.S.C. 154(b) by 593 days.

This patent is subject to a terminal disclaimer.

(21) Appl. No.: 17/689,741

(22) Filed: Mar. 8, 2022

(65) Prior Publication Data

US 2022/0220112 A1    Jul. 14, 2022

Related U.S. Application Data

(63) Continuation of application No. 16/685,841, filed on Nov. 15, 2019, now Pat. No. 11,299,491.

(60) Provisional application No. 62/768,802, filed on Nov. 16, 2018.

(51) Int. Cl.
| | | |
|---|---|---|
| *C07D 471/04* | (2006.01) | |
| *A61K 31/235* | (2006.01) | |
| *A61K 31/341* | (2006.01) | |
| *A61K 31/4985* | (2006.01) | |
| *C07C 69/76* | (2006.01) | |
| *C07C 309/24* | (2006.01) | |
| *C07D 307/06* | (2006.01) | |

(52) U.S. Cl.
CPC ............ *C07D 471/04* (2013.01); *C07C 69/76* (2013.01); *C07C 309/24* (2013.01)

(58) Field of Classification Search
CPC .............. A61K 31/341; A61K 31/4985; A61K 31/235; C07D 471/04; C07D 307/06; C07C 69/76
See application file for complete search history.

(56) References Cited

U.S. PATENT DOCUMENTS

| | | | |
|---|---|---|---|
| 4,232,027 | A | 11/1980 | Turk et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,151,413 | A | 9/1992 | Caufield et al. |
| 5,256,790 | A | 10/1993 | Nelson |

(Continued)

FOREIGN PATENT DOCUMENTS

| | | |
|---|---|---|
| CN | 101239913 | 8/2008 |
| DE | 19629652 A1 | 1/1998 |

(Continued)

OTHER PUBLICATIONS

"A Phase 1, Study Evaluating the Safety, Tolerability, PK, and Efficacy of AMG 510 in Subjects With Solid Tumors With a S Mutation." NCT03600883, comparison of version submitted Oct. 29, 2018 and Oct. 9, 2019 (update posted Oct. 10, 2019), for full history of change see https://clinicaltrials.gov/ct2/history/NCT03600883 (last accessed Nov. 11, 2020), pp. 1-22.

(Continued)

*Primary Examiner* — James H Alstrum-Acevedo
*Assistant Examiner* — Chris E Simmons
(74) *Attorney, Agent, or Firm* — Mark Metzke

(57) ABSTRACT

The present invention relates to an improved, efficient, scalable process to prepare intermediate compounds, such as compound 5M, having the structure

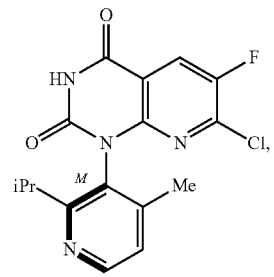

useful for the synthesis of compounds that target KRAS G12C mutations, such as

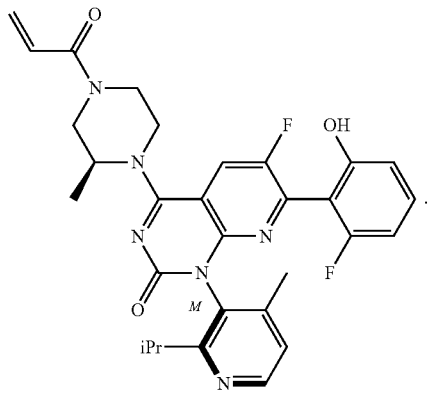

13 Claims, 51 Drawing Sheets

(56) References Cited

U.S. PATENT DOCUMENTS

| | | | |
|---|---|---|---|
| 5,258,389 A | 11/1993 | Goulet et al. | |
| 5,521,184 A | 5/1996 | Zimmerman | |
| 5,650,415 A | 7/1997 | Tang et al. | |
| 5,656,643 A | 8/1997 | Spada et al. | |
| 5,712,291 A | 1/1998 | D'Amato | |
| 5,728,813 A | 3/1998 | Lyman et al. | |
| 5,747,498 A | 5/1998 | Schnur et al. | |
| 5,770,599 A | 6/1998 | Gibson | |
| 5,789,427 A | 8/1998 | Chen et al. | |
| 5,792,783 A | 8/1998 | Tang et al. | |
| 5,861,510 A | 1/1999 | Piscopio et al. | |
| 5,863,949 A | 1/1999 | Robinson et al. | |
| 5,892,112 A | 4/1999 | Levy et al. | |
| 5,969,110 A | 10/1999 | Beckmann et al. | |
| 5,981,245 A | 11/1999 | Fox et al. | |
| 5,990,141 A | 11/1999 | Hirth et al. | |
| 6,057,124 A | 5/2000 | Bartley et al. | |
| 6,111,090 A | 8/2000 | Gorman et al. | |
| 6,232,447 B1 | 5/2001 | Cerretti | |
| 6,235,764 B1 | 5/2001 | Larson et al. | |
| 6,258,812 B1 | 7/2001 | Bold et al. | |
| 6,413,932 B1 | 7/2002 | Cerretti et al. | |
| 6,515,004 B1 | 2/2003 | Misra et al. | |
| 6,596,852 B2 | 7/2003 | Cerretti et al. | |
| 6,630,500 B2 | 10/2003 | Gingrich et al. | |
| 6,656,963 B2 | 12/2003 | Firestone et al. | |
| 6,713,485 B2 | 3/2004 | Carter et al. | |
| 6,727,225 B2 | 4/2004 | Wiley | |
| 7,025,962 B1 | 4/2006 | Gorman et al. | |
| 7,358,384 B2 | 4/2008 | Morii et al. | |
| 7,361,760 B2 | 4/2008 | Sircar et al. | |
| 7,618,632 B2 | 11/2009 | Collins et al. | |
| 7,812,135 B2 | 10/2010 | Smith et al. | |
| 7,838,700 B2 | 11/2010 | Martin et al. | |
| 8,388,967 B2 | 3/2013 | Smith et al. | |
| 8,586,023 B2 | 11/2013 | Shiku et al. | |
| 8,591,886 B2 | 11/2013 | Ponath et al. | |
| 10,519,146 B2 | 12/2019 | Lanman et al. | |
| 10,532,042 B2 | 1/2020 | Lanman et al. | |
| 10,640,504 B2 | 5/2020 | Lanman et al. | |
| 10,988,485 B2 | 4/2021 | Minatti et al. | |
| 11,045,484 B2 | 6/2021 | Wurz et al. | |
| 11,053,226 B2 | 7/2021 | Shin et al. | |
| 11,090,304 B2 | 8/2021 | Allen et al. | |
| 11,096,939 B2 | 8/2021 | Booker et al. | |
| 11,299,491 B2 * | 4/2022 | Parsons | C07C 69/76 |
| 11,905,281 B2 | 2/2024 | Lanman et al. | |
| 2002/0042368 A1 | 4/2002 | Fanslow, III et al. | |
| 2003/0105091 A1 | 6/2003 | Riedl et al. | |
| 2003/0162712 A1 | 8/2003 | Cerretti et al. | |
| 2009/0012085 A1 | 1/2009 | Baum et al. | |
| 2014/0288045 A1 | 9/2014 | Ren et al. | |
| 2015/0239900 A1 | 8/2015 | Li et al. | |
| 2016/0159738 A1 | 6/2016 | Ren et al. | |
| 2016/0166571 A1 | 6/2016 | Janes et al. | |
| 2016/0297774 A1 | 10/2016 | Li et al. | |
| 2018/0015087 A1 | 1/2018 | Liu et al. | |
| 2018/0072723 A1 | 3/2018 | Blake et al. | |
| 2018/0334454 A1 | 11/2018 | Lanman et al. | |
| 2019/0077801 A1 | 3/2019 | Lanman et al. | |
| 2019/0336514 A1 | 11/2019 | Wurz et al. | |
| 2019/0343838 A1 | 11/2019 | Allen et al. | |
| 2019/0345169 A1 | 11/2019 | Minatti et al. | |
| 2019/0374542 A1 | 12/2019 | Allen et al. | |
| 2019/0375749 A1 | 12/2019 | Chen et al. | |
| 2020/0030324 A1 | 1/2020 | Booker et al. | |
| 2020/0055845 A1 | 2/2020 | Lanman et al. | |
| 2020/0069657 A1 | 3/2020 | Lanman et al. | |
| 2020/0165231 A1 | 5/2020 | Shin et al. | |
| 2020/0207766 A1 | 7/2020 | Lanman et al. | |
| 2020/0222407 A1 | 7/2020 | Lipford et al. | |
| 2020/0360374 A1 | 11/2020 | Henary et al. | |
| 2020/0369662 A1 | 11/2020 | Chaves et al. | |
| 2021/0009577 A1 | 1/2021 | Lanman et al. | |

FOREIGN PATENT DOCUMENTS

| | | |
|---|---|---|
| EP | 0090505 A2 | 10/1983 |
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1999 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 1446372 B1 | 4/2009 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1998034918 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |

(56) References Cited

FOREIGN PATENT DOCUMENTS

| | | |
|---|---|---|
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2003042132 A1 | 5/2003 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2005005434 A1 | 1/2005 |
| WO | 2005007190 A1 | 1/2005 |
| WO | 2005011700 A2 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2011028683 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021097207 A1 | 5/2021 |
| WO | 2021097212 A1 | 5/2021 |
| WO | 2021126816 A1 | 6/2021 |
| WO | 2022076623 A1 | 4/2022 |
| WO | 2022109242 A1 | 5/2022 |
| WO | 2023172858 A1 | 9/2023 |

OTHER PUBLICATIONS

"Acute Leukemia," *The Merck Manual* (Online Edition), pp. 1-6 (2013).

"KRASG12C Inhibitor," Mirati Therapeutics, retrieved on Nov. 27, 2018, from https://www.mirati.com/mrtx849/, 5 pages.

Ahmadian, et al., "Guanosine triphosphatase stimulation of oncogenic Ras mutants," *PNAS*, 96: 7065-7070, 1999.

Airoldi, et al., "Glucose-Derived Ras Pathway Inhibitors: Evidence of Ras-Ligand Binding and Ras-GEF (Cdc25) Interaction Inhibition," *ChemBioChem*, 8: 1376-1379 (2007).

ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," *Biochem. J.*, 385 (2): 399-408 (2005).

Bhatia, et al., "A Review on Bioisosterism: A Rational Approach for Drug Design and Molecular Modification," *Pharmacologyonline*, 1:272-299 (2011).

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).

Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).

Canon, et al., "The clinical KRAS(G12C) inhibitor AMG 510 drives anti-tumour immunity," *Nature*, 575(7781): 217-223 (2019).

Cee, et al., "Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.

Cohen, "The development and therapeutic potential of protein kinase inhibitors," *Current Opinion in Chemical Biology*, 3:459-465 (1999).

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).

Dermer, et al., "Another Anniversary for the War on Cancer," *Bio/Technology*, 12: 320 (1994).

Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).

Erkkilä, et al., "Mild Organocatalytic α-Methylenation of Aldehydes," *J. Org. Chem.*, 71 (6), 2538-2541 (2006).

Extended European Search Report for European Patent Application No. 19208193.2, dated Jun. 3, 2020, pp. 1-8.

Fakih, et al., "Phase 1 study evaluating the safety, tolerability, pharmacokinetics (PK), and efficacy of AMG 510, a novel small

(56) References Cited

OTHER PUBLICATIONS molecule KRASG12C inhibitor, in advanced solid tumors," *Journal of Clinical Oncology*, 37(15 suppl) (May 20, 2019) 3003, published online May 26, 2019.

Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.

Final Office Action for U.S. Appl. No. 15/984,855, mailed Mar. 28, 2019, 7 pages.

Final Office Action for U.S. Appl. No. 16/661,907, mailed Mar. 27, 2020, 29 pages.

Freshney, et al., Culture of Animal Cells, *A Manual of Basic Technique*, Alan R. Liss, Inc, New York, p. 4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," *Expert. Opin. Investig. Drugs*, 13: 787-797 (2004).

Goldberg, et al., "Role of PD-1 and its ligand, B7-H1, in early fate decisions of CD8 T cells," *Blood*, 110(1): 186-192 (2007).

Goldstein, et al., "Biological efficacy of a chimeric antibody to the epidermal growth factor receptor in a human tumor xenograft model," *Clin. Cancer Res.*, 1: 1311-1318 (1995).

Golub, et al., "Molecular Classification of Cancer: Class Discovery and Class Prediction by Gene Expression Monitoring," *Science*, 286: 531-537(1999).

Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.

Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

Govindan, et al., "Phase 1 Study of AMG 510, a Novel KRAS G12C Inhibitor, in Advanced Solid Tumors with KRAS p.G12C Mutation," Poster, ESMO Congress, Barcelona, Spain, Sep. 27, 2019-Oct. 1, 2019.

Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.

Gura, "Cancer Models: Systems for Identifying New Drugs Are Often Faulty," *Science*, 278(5340):1041-1042 (1997).

Halford, "Amgen unveils its Kras covalent inhibitor AMG 510," *Chemical & Engineering News* 97(14):4 (2019).

Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).

Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).

Hichri, et al., "A Convenient Synthesis of 1,3,2-Benzodiazaphophorine-2-Oxide," *Phosphorus, Sulfur, and Silicon*, 190: 29-35 (2015).

Hichri, et al., CAPLUS Abstract, 162:245378 (2015).

Hocker, et al., "Andrographolide derivatives inhibit guanine nucleotide exchange and abrogate oncogenic Ras function," *PNAS*, 110(25): 10201-10206 (2013).

Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).

International Search Report for PCT/US2017/067801, mailed Jul. 25, 2018, 6 pages.

International Search Report for PCT/US2018/033714, mailed Jul. 17, 2018, 3 pages.

International Search Report for PCT/US2018/050044, mailed Oct. 30, 2018, 7 pages.

International Search Report for PCT/US2019/030593, mailed Aug. 6, 2019, 4 pages.

International Search Report for PCT/US2019/030606, mailed Jul. 23, 2019, 5 pages.

International Search Report for PCT/US2019/031535, mailed Jul. 25, 2019, 7 pages.

International Search Report for PCT/US2019/034974, mailed Aug. 9, 2019, 5 pages.

International Search Report for PCT/US2019/036397, mailed Aug. 26, 2019, 5 pages.

International Search Report for PCT/US2019/036626, mailed Jun. 2, 2020, 5 pages.

International Search Report for PCT/US2019/061815, mailed Mar. 5, 2020, 6 pages.

International Search Report for PCT/US2019/062051, mailed Mar. 2, 2020, 3 pages.

International Search Report for PCT/US2020/032686, mailed Aug. 14, 2020, 4 pages.

International Search Report for PCT/US2020/033831, mailed Jul. 9, 2020, 6 pages.

International Search Report for PCT/US2020/033832, mailed Jul. 8, 2020, 4 pages.

Janes, et al., "Targeting KRAS Mutant Cancers with a Covalent G12C-Specific Inhibitor," *Cell*, 172: 578-589 (2018).

Jarvis, "Notorious KRAS: Taking down cancer researchers' biggest foe," *Chemical & Engineering News*, 97(37), 9 pages (2019).

Jin, et al., "Inhibition of AKT survival pathway by a small molecule inhibitor in human endometrial cancer cells," *Br. J. Cancer*, 91: 1808-1812 (2004).

Johnson et al., "Relationships between drug activity in NCI preclinical in vitro and in vivo models and early clinical trials," *British Journal of Cancer*, 84(10): 1424-1431 (2001).

Lanman, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.

Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4455 (2019).

Lanman, et al., "Discovery of a Covalent Inhibitor of KRAS$^{G12C}$ (AMG 510) for the Treatment of Solid Tumors," *J. Med. Chem.*, 63: 52-65 (2020).

Li, et al., "Targeting Protein-Protein Interaction with Covalent Small-Molecule Inhibitors," *Current Topics in Medicinal Chemistry*, 19(21): 1872-1876 (2019).

Lim, et al., "Therapeutic Targeting of Oncogenic K-Ras by a Covalent Catalytic Site Inhibitor," *Angew. Chem. Int. Ed*, 53: 199-204 (2014).

Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.

Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).

Lopez, et al., "Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.

Lu, et al., "KRAS G12C Drug Development: Discrimination between Switch II Pocket Configurations Using Hydrogen/Deuterium-Exchange Mass Spectrometry," *Structure*, 25: 1-7 (2017).

Maurer, et al., "Small-molecule ligands bind to a distinct pocket in Rad and inhibit SOS-mediated nucleotide exchange activity," *PNAS*, 109(14): 5299-5304 (2012).

(56) References Cited

OTHER PUBLICATIONS

McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
Morrissey et al., "Immunotherapy and Novel Combinations in Oncology: Current Landscape, Challenges, and Opportunities," *Clin. Transl. Sci.*, 9(2):89-104 (2016).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Non-Final Office Action (Corrected) for U.S. Appl. No. 16/125,359, mailed Apr. 8, 2019, 13 pages.
Non-Final Office Action for U.S. Appl. No. 15/849,905, mailed Mar. 20, 2019, 18 pages.
Non-Final Office Action for U.S. Appl. No. 15/984,855, mailed Sep. 27, 2018, 25 pages.
Non-Final Office Action for U.S. Appl. No. 16/125,359, mailed Apr. 5, 2019, 13 pages.
Non-Final Office Action for U.S. Appl. No. 16/402,538, mailed Oct. 30, 2019, 12 pages.
Non-Final Office Action for U.S. Appl. No. 16/402,589, mailed Mar. 6, 2020, 17 pages.
Non-Final Office Action for U.S. Appl. No. 16/407,889, mailed Jul. 1, 2020, 6 pages.
Non-Final Office Action for U.S. Appl. No. 16/428,163, mailed Sep. 15, 2020, 6 pages.
Non-Final Office Action for U.S. Appl. No. 16/436,647, mailed Aug. 7, 2020, 19 pages.
Non-Final Office Action for U.S. Appl. No. 16/438,349, mailed Dec. 13, 2019, 15 pages.
Non-Final Office Action for U.S. Appl. No. 16/661,907, mailed Nov. 18, 2019, 20 pages.
Notice of Allowance mailed Jul. 24, 2020 for U.S. Appl. No. 16/402,538, 8 pages.
Notice of Allowance mailed Sep. 16, 2020 for U.S. Appl. No. 16/402,589, 5 pages.
Notice of Allowance mailed Sep. 9, 2020 for U.S. Appl. No. 16/438,349, 9 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Pearce, et al., "Failure modes in anticancer drug discovery and development," *Cancer Drug Design and Discovery*, Edited by Stephen Neidle, Chapter 18, pp. 424-435 (2008).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).

Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).
Rex, et al., "Abstract 3090: In vivo characterization of AMG 510—a potent and selective $KRAS^{G12C}$ covalent small molecule inhibitor in preclinical $KRAS^{G12C}$ cancer models," Poster, American Association for Cancer Research (AACR) Annual Meeting, Atlanta, GA, USA, Mar. 29-Apr. 3, 2019.
Rex, et al., "Abstract 3090: In vivo characterization of AMG 510—a potent and selective $KRAS^{G12C}$ covalent small molecule inhibitor in preclinical $KRAS^{G12C}$ cancer models," Proceedings of the American Association for Cancer Research Annual Meeting 2019; Mar. 29-Apr. 3, 2019; Atlanta, GA, USA, AACR, *Cancer Res.* 79(13 Suppl): Abstract nr 3090 (2019).
Saiki, et al., "Abstract 4484: Discovery and in vitro characterization of AMG 510—a potent and selective covalent small-molecule inhibitor of $KRAS^{G12C}$," Presentation, American Association for Cancer Research (AACR) Annual Meeting, Atlanta, GA, USA, Mar. 29-Apr. 3, 2019.
Saiki, et al., "Abstract 4484: Discovery and in vitro characterization of AMG 510—a potent and selective covalent small-molecule inhibitor of $KRAS^{G12C}$," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4484 (2019).
Sarkar, et al., "Indole-3-Carbinol and Prostate Cancer[1,2]," *J. Nutr.*, 134(12 Suppl): 3493S-3498S (2004).
Shima, et al., "In silico discovery of small-molecule Ras inhibitors that display antitumor activity by blocking the Ras-effector interaction," *PNAS*, 110(20): 8182-8187 (2013).
Simone, "Part XIV Oncology: Introduction," *Cecil Textbook of Medicine*, 20th Edition, 1:1004-1010 (1996).
Singh, et al., "Improving Prospects for Targeting RAS," *J. Clinc. Oncl*, 33(31): 3650-3660 (2015).
Statsyuk, "Let K-Ras activate its own inhibitor," *Nature Structural & Molecular Biology*, 25:435-439 (2018).
Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*,, 5(1): 125-133 (1997).
Teramoto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2018/050044, mailed Oct. 30, 2018, 7 pages.
Written Opinion for PCT/US2019/030593, mailed Aug. 6, 2019, 5 pages.
Written Opinion for PCT/US2019/030606, mailed Jul. 23, 2019, 6 pages.

(56) References Cited

OTHER PUBLICATIONS

Written Opinion for PCT/US2019/031535, mailed Jul. 25, 2019, 7 pages.
Written Opinion for PCT/US2019/034974, mailed Aug. 9, 2019, 5 pages.
Written Opinion for PCT/US2019/036397, mailed Aug. 26, 2019, 5 pages.
Written Opinion for PCT/US2019/036626, mailed Jun. 2, 2020, 12 pages.
Written Opinion for PCT/US2019/061815, mailed Mar. 5, 2020, 4 pages.
Written Opinion for PCT/US2019/062051, mailed Mar. 2, 2020, 5 pages.
Written Opinion for PCT/US2020/032686, mailed Aug. 14, 2020, 6 pages.
Written Opinion for PCT/US2020/033831, mailed Jul. 9, 2020, 7 pages.
Written Opinion for PCT/US2020/033832, mailed Jul. 8, 2020, 6 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS-PDEδ interaction impairs oncogenic KRAS signaling," *Nature*, 1-5 (2017).
International Search Report for PCT/US2019/62064, mailed Oct. 29, 2020, 9 pages.
Written Opinion for PCT/US2019/62064, mailed Oct. 29, 2020, 13 pages.
Hong, et al., "KRAS$^{G12C}$ Inhibition with Sotorasib in Advanced Solid Tumors," *N. Engl. Med.*, 383:1207-1217 (2020).
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Canon, et al., "The clinical KRAS(G12C) inhibitor AMG 510 drives anti-tumour immunity," *Nature*, 575(7781): 217-223 (2019) (Supplementary Material, pp. 1-55).
Database Registry [Online], Chemical Abstracts Service, Columbus, Ohio, US; Jul. 31, 2017 (Jul. 31, 2017), XP002801805, retrieved from STN Database accession No. 2105944-09-8.
Final Office Action for U.S. Appl. No. 16/436,647, mailed Mar. 24, 2021, 7 pages.
Meanwell, "Synopsis of Some Recent Tactical Application of Bioisosteres in Drug Design," *J. Med. Chem.* 54:2529-2591 (2011).
Non-Final Office Action for U.S. Appl. No. 16/675,121, mailed Feb. 2, 2021, 10 pages.
Non-Final Office Action for U.S. Appl. No. 16/817,109, mailed Mar. 3, 2021, 12 pages.
Notice of Allowance mailed Jan. 14, 2021 for U.S. Appl. No. 16/402,589, 5 pages.
Notice of Allowance, mailed Dec. 21, 2020, for U.S. Appl. No. 16/407,889, 5 pages.
Notice of Allowance, mailed Feb. 18, 2021, for U.S. Appl. No. 16/687,546, 9 pages.
Notice of Allowance, mailed Jan. 26, 2021, for U.S. Appl. No. 16/438,349, 9 pages.
Notice of Allowance, mailed Jan. 27, 2021, for U.S. Appl. No. 16/428,163, 9 pages.
Notice of Allowance, mailed Mar. 30, 2021, for U.S. Appl. No. 16/402,538, 8 pages.
Shibata et al., "A Convenient Synthesis of 3-Cyano-2-methylpyridines under Ultrasonic Irradiation," *Bull. Chem. Soc. Jpn.*, 61:2199-2200 (1988).
Stanetty et al., "Synthesis of Aza Analogs of the Herbicide Sindone B," *Monatshefte Fuer Chemie*, 130:441-450 (1999).
Third Party Observation filed for PCT/US2020/033831, submitted Jan. 15, 2021, 2 pages.
4-methyl-2-(1-methylethyl)-3-Pyridinamine, STN Registry, CAS RN 1698293-93-4, STN entry date May 5, 2015 (May 5, 2015).
Amgen Press Release, "Amgen Announces New Clinical Data Evaluating Novel Investigational KRAS(G12C) Inhibitor in Larger Patient Group at WCLC 2019," dated Sep. 8, 2019 (last accessed Apr. 13, 2021).
Govindan et al., "OA01.06 Safety, Efficacy, and Pharmacokinetics of AMG 510, a Novel KRAS$^{G12C}$ Inhibitor, in Patients with Non-Small Cell Lung Cancer," *J. Thorac. Oncol.*, 14(11, Supplement 1):S1125-1126 (Nov. 2019).
International Search Report for PCT/US2020/060415, mailed Feb. 3, 2021, 5 pages.
International Search Report for PCT/US2020/065050, mailed Mar. 29, 2021, 7 pages.
Notice of Allowance mailed Jun. 30, 2021 for U.S. Appl. No. 16/438,349, pp. 1-9.
Notice of Allowance, mailed Apr. 19, 2021, for U.S. Appl. No. 16/428,163, 9 pages.
Written Opinion for PCT/US2020/060415, mailed Feb. 3, 2021, 9 pages.
Written Opinion for PCT/US2020/065050, mailed Mar. 29, 2021, 8 pages.
Noriyuki, "API Form Screening and Selection at the Drug Discovery Stage", Pharm Stage, vol. 6, No. 10, Jan. 15, 2007, pp. 20-25 (incl. English translation).
Hirayama, "Handbook for Making Crystal of Organic Compound,— Principles and Know-how-", Maruzen Co., Ltd., Jul. 25, 2008, pp. 57-84 (incl. English translation).
Kojima, "Aiming to Improve the Efficiency of Crystallization Selection in Drug Development", Pharmaceutics, Sep. 1, 2008, vol. 68, No. 5, pp. 344-349 (incl. English translation).
Notice of Allowance, mailed Oct. 20, 2021, for U.S. Appl. No. 16/438,349, 9 pages.
Notice of Allowance, mailed Sep. 22, 2021, for U.S. Appl. No. 16/878,824, 8 pages.
Notice of Allowance, mailed Sep. 9, 2021, for U.S. Appl. No. 16/675,121, 7 pages.
PubChem CID 108190520, 2-isopropyl-4-methylpyridin-3-amine, available at https://pubchem.ncbi.nlm.nih.gov/compound/108190520 (last accessed Aug. 30, 2021).
Beaver, et al., Axial Chirality in the Sotorasib Drug Substance, Part 2: Leveraging a high-Temperature Thermal Racemization to Recyle the Classical Resolution Waste System, *Org. Process res. Dev.* 26: 2636-2645 (2022).
Clarke, et al., "Dissecting mechanisms of resistance to targeted drug combination therapy in human colorectal cancer" in Oncogene 38:5076-90 (2019).
Cox, et al.,. "Drugging the undruggable RAS: mission possible?" in *Nat Rev Drug Discov* 13:828-51 M(2014).
Dai et al., "Synthesis of Substituted Pyridines via Formal (3+3) Cycloaddition of Enamines with Unsaturated Aldehydes and Ketones," J. Org. Chem., 87:8437-44 (2022).
Del Re, et al., "Implications of KRAS mutations in acquired resistance to treatment in NSCLC" in *Oncotarget* 9:6630-43 (2018).
Fiala, et al.,. "G12V and G12A Kras mutations are associated with poor outcome in patients with metastatic colorectal cancer treated with bevacizumab" in *Tumour Biol* 37:6823-30 (2016).
International Search Report and Written Opinion, European Patent Office, PCT/US2021/053859, dated Jan. 20, 2022.

(56) References Cited

OTHER PUBLICATIONS

Kargbo RB. "Inhibitors of G12C mutant Ras proteins for the treatment of cancers" in *ACS Med Chem Lett* 10:10-1 (2018).

Lanman, et al., Addressing Atropisomerism in the Development of Sotorasib, a Covalent Inhibitor of KRAS G12C: Structural, Analytical and Synthetic Considerations, *ACS Publications* 55: 289-2903 (2022).

Lievre, et al.,. "KRAS mutation status is predictive of response to cetuximab therapy in colorectal cancer" in *Cancer Res* 66:3992-5 (2006).

Lito, et al., "Allele-specific inhibitors inactivate mutant KRAS G12C by a trapping mechanism" in *Science* 351:604-8 (2016).

Massarelli, et al., "KRAS mutation is an important predictor of resistance to therapy with epidermal growth factor receptor tyrosine kinase inhibitors in non-small-cell lung cancer" in *Clin Cancer Res* 13:2890-6 (2007).

McCormick F. "K-Ras protein as a drug target" in *J Mol Med (Berl)* 2016;94:253-8; Jones RP, Sutton PA, Evans JP, et al. "Specific mutations in KRAS codon 12 are associated with worse overall survival in patients with advanced and recurrent colorectal cancer" in *Br J Cancer* 116:923-9 (2017).

Murray et al., "Kinetic and Mechanistic Investigations to Enable a Key Suzuki Coupling for Sotorasib Manufacture_What a Difference a Base Makes," Org. Proc. Res. Dev., 27(1):198-205 (2023).

Nadal E, et al., "KRAS-G12C mutation is associated with poor outcome in surgically resected lung adenocarcinoma" in *J Thorac Oncol* 9:1513-22 (2014).

Neumann, et al.,. "Frequency and type of KRAS mutations in routine diagnostic analysis of metastatic colorectal cancer" in *Pathol Res Pract* 205:858-62 (2009).

Non-Final Office Action for U.S. Appl. No. 17/031,607, mailed Mar. 31, 2023, 7 pages.

Notice of Allowance, mailed Aug. 13, 2019, for U.S. Appl. No. 15/984,855, 5 pages.

Notice of Allowance, mailed Oct. 3, 2023, for U.S. Appl. No. 17/031,607, 7 pages.

Ostrem, et al., "Direct small molecule inhibitors of KRAS: from structural insights to mechanism-based design" in *Nat Rev Drug Discov* 15:771-85 (2016).

Parsons, et al., Axial Chirality in the Sotorasib Drug Substance, Part 1: Development of a Classical Resolution to Prepare an Atropisomerically Pure Sotorasib Intermediate, *Org. Process res. Dev.* 26: 2629-2635 (2022).

Restriction Requirement, mailed Apr. 14, 2022, for U.S. Appl. No. 17/031,607, 5 pages.

Restriction Requirement, mailed May 7, 2025, for U.S. Appl. No. 18/987,568, 5 pages.

Restriction Requirement, mailed Feb. 24, 2025 for U.S. Appl. No. 18/987,607, 7 pages.

Simanshu, et al., "RAS proteins and their regulators in human disease" in *Cell* 170:17-33 (2017).

Suzawa, et al., "Activation of KRAS mediates resistance to targeted therapy in MET exon 14-mutant non-small cell lung cancer" in *Clin Cancer Res* 2019;25:1248-60 (2019).

Synoradski, et al., Tartaric Acid and Its o-Acyl derivatives. Part 2. Applications of Tartaric Acid and of O-Acyl Tartaric Acids and anhydrides. Resolution of Racemates, Organic Prep. Proc. Int. 40(2): 163-200 (2008).

Xing, et al., An Improved Efficient Process for the Production of highly Pure Dexmethylphenidate Hydrochloride, *J. Heterocylic Chem.*, 54:1298-1303 (2017).

Zhang, et al., Development of a Commercial manufacturing Process for Sotorasib a First-in-Class KRAS G12C Inhibitor, *Org. Process Res. Dev.* 26:3115-3125 (2002).

\* cited by examiner

CA = (1S)-(-)-Camphanic acid
CA Type A = (1S)-(-)-Camphanic acid cocrystal Type A
CA Type B = (1S)-(-)-Camphanic acid cocrystal Type B
Dr Type C = Dione racemate Type C
Dr Type D = Dione racemate Type D A = (+)-2, 3-Dibenzoyl-D-tartaric acid
B = (+)-2, 3-Dibenzoyl-D-tartaric acid cocrystal
C = Dione racemate Type D A = D-(+)-Malic acid
B = D-(+)-Malic acid cocrystal
C = FB Type C A = M-cocrystal Type A ref.

A = P-cocrystal Type A ref.

A = M-cocrystal Type A ref.
B = P-cocrystal Type A ref.

A = Dione racemate Type A ref.  
B = 20 °C (Type D)  
C = 30 °C (Type D)  
D = 40 °C (Type C)  
E = M-Dione Type A ref.  
F = P-Dione Type B ref.

A = Dione racemate Type A ref.  
B = 50 °C (Type C)  
C = 60 °C (Type C)  
D = 65 °C (Type C)  
E = M-Dione Type A ref.  
F = P-Dione Type B ref.

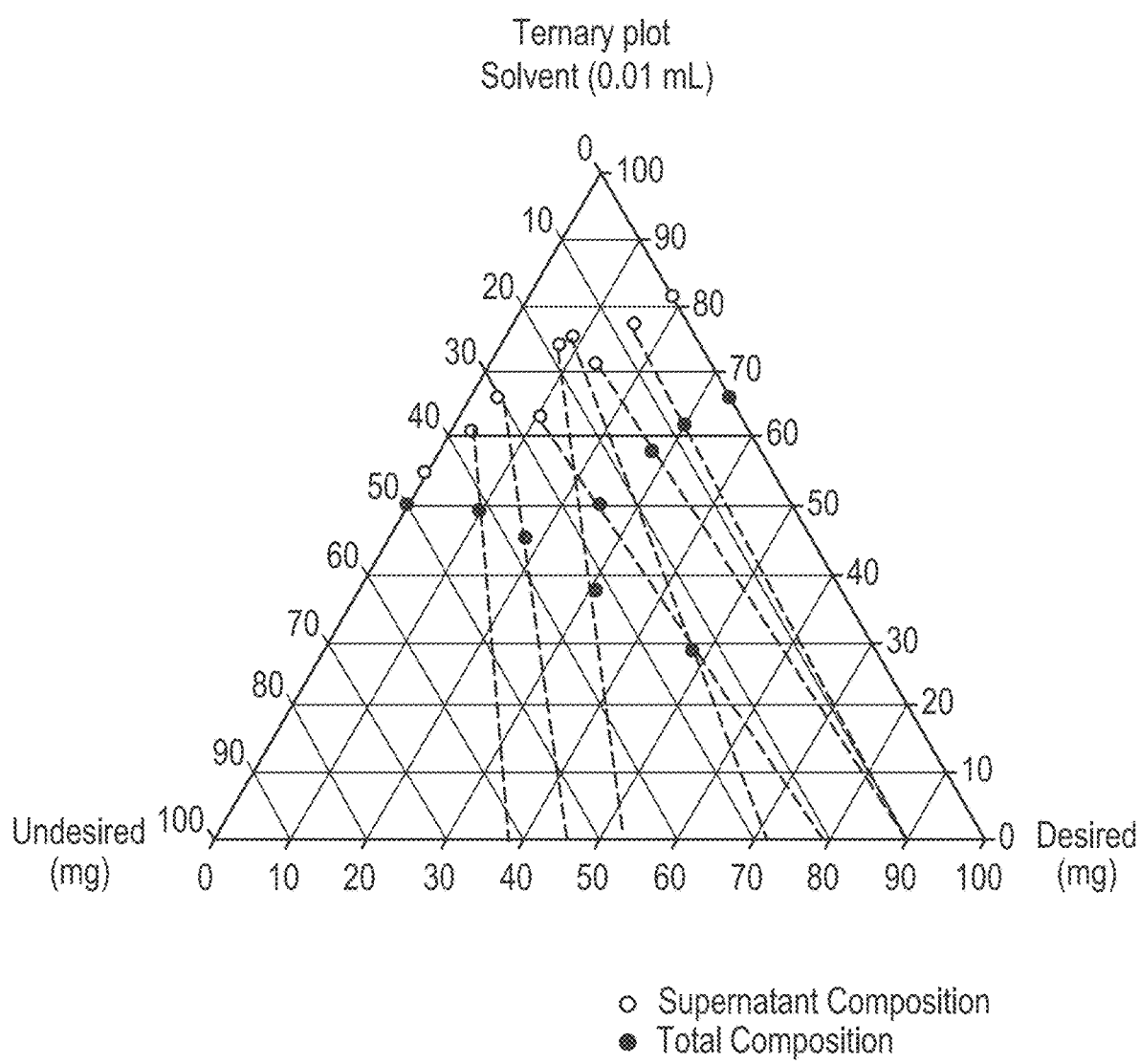

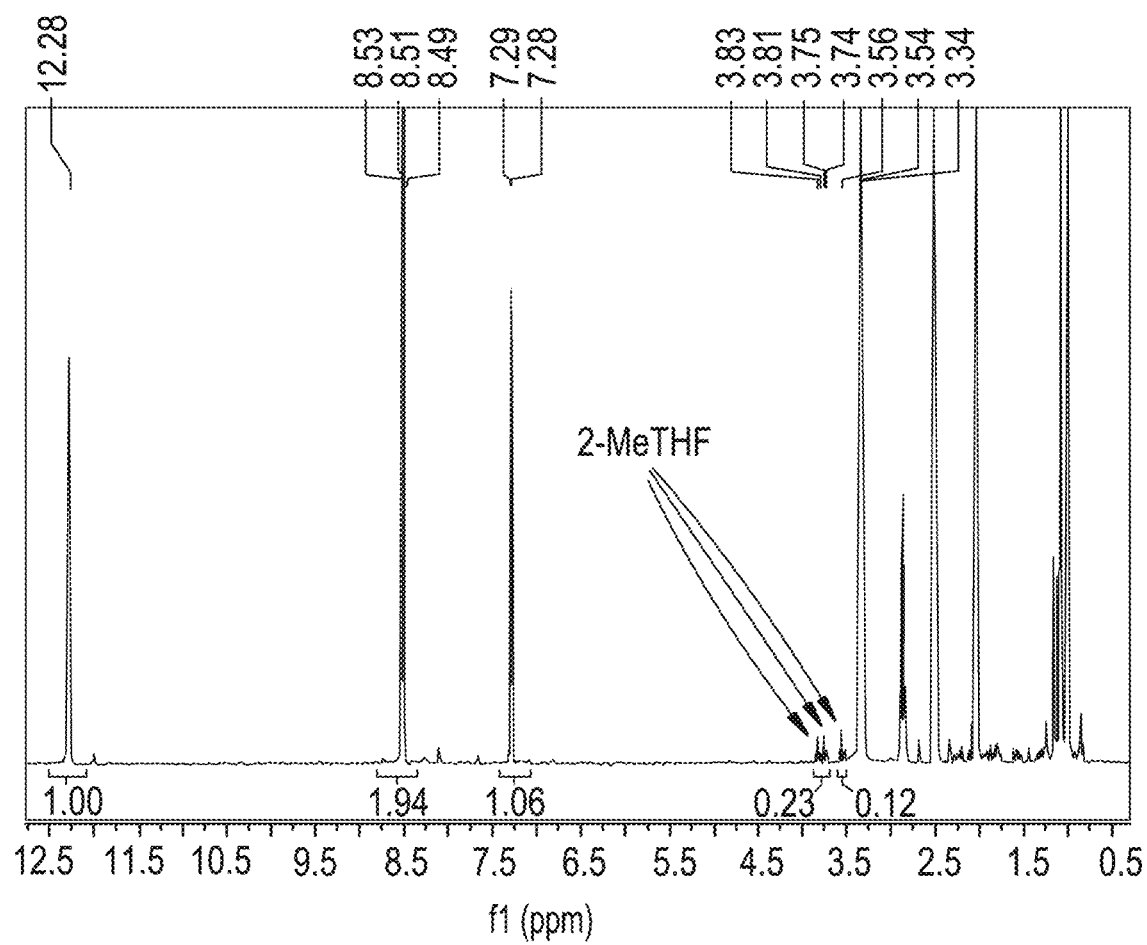

A = Dione racemate Type A
B = Dione racemate Type B
C = Dione racemate Type C
D = Dione racemate Type D
E = Dione racemate Type E A = Dione racemate Type C
B = 20 °C
C = 30 °C
D = 40 °C
E = 50 °C
F = 60 °C
G = 65 °C A = DBTA
B = M-Dione cocrystal
C = P-Dione
D = P-Dione cocrystal

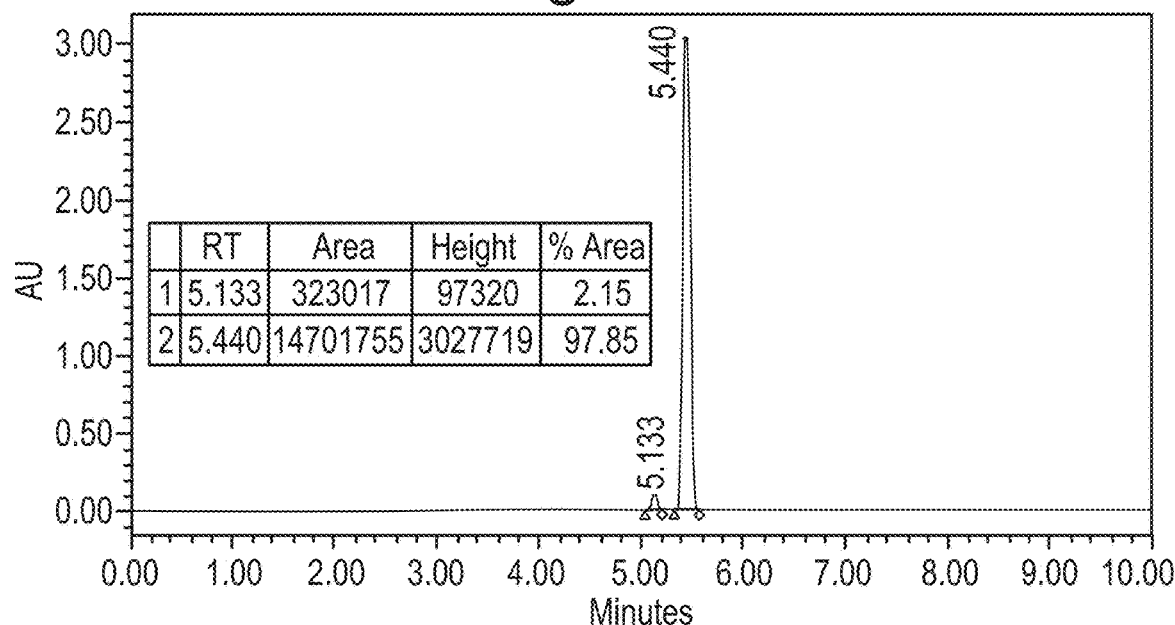
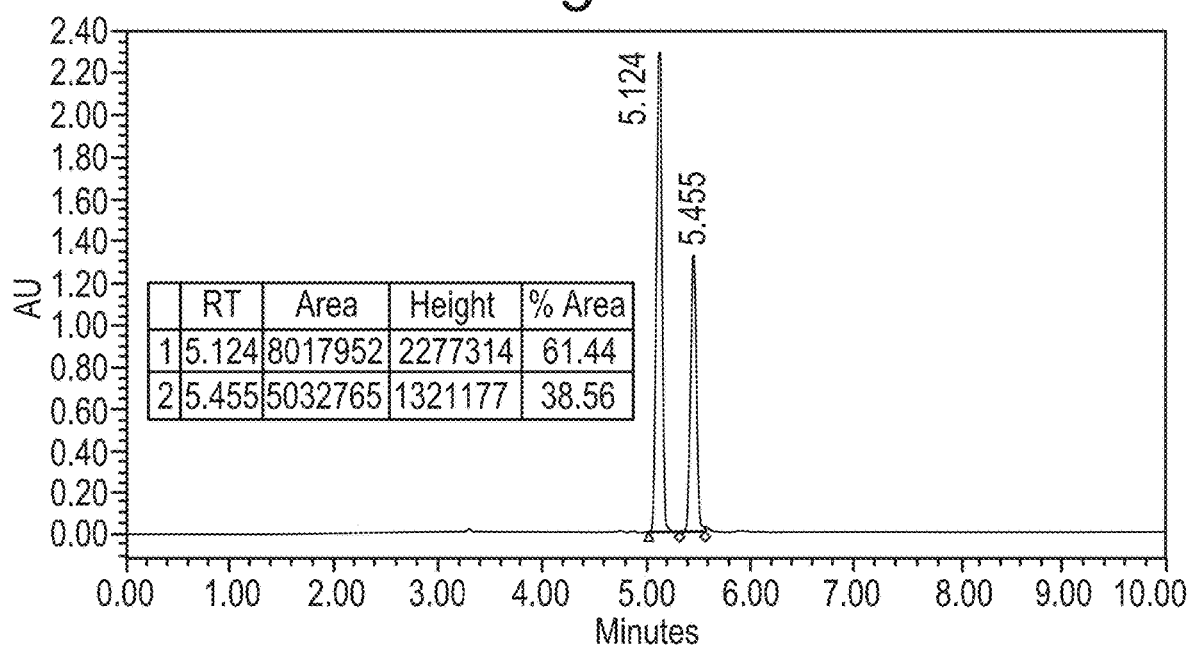

SYNTHESIS OF KEY INTERMEDIATE OF KRAS G12C INHIBITOR COMPOUND

CROSS-REFERENCE TO RELATED APPLICATIONS

The present application is a continuation of U.S. patent application Ser. No. 16/685,841, filed on Nov. 15, 2019, which claims the benefit of U.S. Provisional Application No. 62/768,802, filed Nov. 16, 2018, each of which is incorporated herein by reference in its entirety for all purposes.

FIELD OF THE INVENTION

The present invention relates to an improved, efficient, scalable process to prepare intermediate compounds, such as compound 5M, having the structure

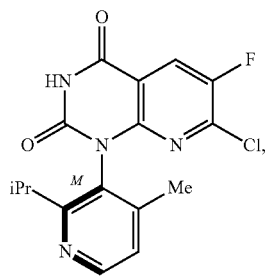

useful for the synthesis of compounds that inhibit KRAS G12C mutations.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

BRIEF DESCRIPTION OF THE FIGURES

FIG. 1 shows the crystal arrangement of composition 4a.
FIG. 2-1 shows XRPD overlay of Dione racemate Type A-E.
FIG. 2-2 shows XRPD overlay of (1S)-(−)-camphanic acid cocrystal.
FIG. 2-3 shows XRPD overlay of (+)-2,3-dibenzoyl-D-tartaric acid cocrystal.
FIG. 2-4 shows XRPD overlay of D-(+)-malic acid cocrystal.
FIG. 2-5 shows XRPD overlay of M-Dione cocrystal at different temperatures.
FIG. 2-6 shows XRPD overlay of P-Dione cocrystal at different temperatures.
FIG. 2-7 shows XRPD overlay of M-Dione cocrystal and P-Dione cocrystal mixture at different temperatures.
FIG. 2-8 shows XRPD Overlay of Dione racemate at different temperatures (I/II).
FIG. 2-9 shows XRPD overlay of Dione racemate at different temperatures (II/II).
FIG. 2-10 shows Ternary Phase Diagram of M/P-Dione cocrystals.
FIG. 2-11 shows Ternary phase diagram of M/P-Dione.
FIG. 3-1 shows XRPD of Dione racemate Type A.
FIG. 3-2 shows TGA/DSC overlay of Dione racemate Type A.
FIG. 3-3 shows $^1$H NMR spectrum of Dione racemate Type A.
FIG. 3-4 shows PLM image of Dione racemate Type A.
FIG. 3-5 shows XRPD of Dione racemate Type B.
FIG. 3-6 shows TGA/DSC overlay of Dione racemate Type B.
FIG. 3-7 shows $^1$H NMR spectrum of Dione racemate Type B.
FIG. 3-8 shows XRPD of Dione racemate Type C.
FIG. 3-9 shows TGA/DSC overlay of Dione racemate Type C.
FIG. 3-10 shows $^1$H NMR spectrum of Dione racemate Type C.
FIG. 3-11 shows XRPD of Dione racemate Type D.
FIG. 3-12 shows TGA/DSC overlay of Dione racemate Type D.
FIG. 3-13 shows $^1$H NMR spectrum of Dione racemate Type D.
FIG. 3-14 shows XRPD of Dione racemate Type E.
FIG. 3-15 shows TGA/DSC overlay of Dione racemate Type E.
FIG. 3-16 shows $^1$H NMR spectrum of Dione racemate Type E.
FIG. 3-17 shows XRPD of M-Dione cocrystal Type A.
FIG. 3-18 shows TGA/DSC overlay of M-Dione cocrystal Type A.
FIG. 3-19 shows $^1$H NMR spectrum of M-Dione cocrystal Type A.
FIG. 3-20 shows XRPD of P-Dione cocrystal Type A.
FIG. 3-21 shows TGA/DSC overlay of P-Dione cocrystal Type A.
FIG. 3-22 shows $^1$H NMR spectrum of P-Dione cocrystal Type A.
FIG. 3-23 shows XRPD overlay of Dione racemate forms.
FIG. 3-24 shows XRPD of competitive slurry samples.
FIG. 3-25 shows XRPD overlay of prepared P-Dione cocrystal.
FIG. 3-26 shows $^1$H NMR spectrum overlay of M/P-Dione cocrystals.
FIG. 3-27 shows XRPD overlay of prepared P-Dione cocrystal.
FIG. 4-1 shows Inter-conversion diagram of M-Dione DBTA Cocrystal crystal forms.
FIG. 5-1 shows XRPD overlay of M-dione DBTA cocrystal crystal forms (Type A E).
FIG. 5-2 shows XRPD overlay of M-dione DBTA cocrystal crystal forms (Type F K).
FIG. 5-3 shows XRPD overlay of M-dione DBTA cocrystal crystal forms (Type L Q).
FIG. 5-4 shows XRPD pattern of Type A.
FIG. 5-5 shows TGA/DSC curves of Type A.
FIG. 5-6 shows $^1$H NMR of Type A.
FIG. 5-7 shows XRPD overlay of Type B.

FIG. 5-8 shows TGA/DSC curves of Type B.
FIG. 5-9 shows $^1$H NMR of Type B.
FIG. 5-10 shows XRPD pattern of Type C.
FIG. 5-11 shows TGA/DSC curves of Type C.
FIG. 5-12 shows $^1$H NMR of Type C.
FIG. 5-13 shows XRPD pattern of Type D.
FIG. 5-14 shows TGA/DSC curves of Type D.
FIG. 5-15 shows $^1$H NMR of Type D.
FIG. 5-16 shows XRPD pattern of Type E.
FIG. 5-17 shows TGA/DSC curves of Type E.
FIG. 5-18 shows $^1$H NMR of Type E.
FIG. 5-19 shows XRPD pattern of Type F.
FIG. 5-20 shows TGA/DSC curves of Type F.
FIG. 5-21 shows $^1$H NMR of Type F.
FIG. 5-22 shows XRPD pattern of Type G.
FIG. 5-23 shows TGA/DSC curves of Type G.
FIG. 5-24 shows $^1$H NMR of Type G.
FIG. 5-25 shows XRPD pattern of Type H.
FIG. 5-26 shows TGA/DSC curves of Type H.
FIG. 5-27 shows $^1$H NMR of Type H.
FIG. 5-28 shows XRPD pattern of Type I.
FIG. 5-29 shows TGA/DSC curves of Type I.
FIG. 5-30 shows $^1$H NMR of Type I.
FIG. 5-31 shows XRPD pattern of Type J.
FIG. 5-32 shows TGA/DSC curves of Type J.
FIG. 5-33 shows $^1$H NMR of Type J.
FIG. 5-34 shows XRPD pattern of Type K.
FIG. 5-35 shows TGA/DSC curves of Type K.
FIG. 5-36 shows $^1$H NMR of Type K.
FIG. 5-37 shows XRPD pattern of Type L.
FIG. 5-38 shows TGA/DSC curves of Type L.
FIG. 5-39 shows $^1$H NMR of Type L.
FIG. 5-40 shows XRPD pattern of Type M.
FIG. 5-41 shows TGA/DSC curves of Type M.
FIG. 5-42 shows $^1$H NMR of Type M.
FIG. 5-43 shows XRPD pattern of Type N.
FIG. 5-44 shows TGA/DSC curves of Type N.
FIG. 5-45 shows $^1$H NMR of Type N.
FIG. 5-46 shows XRPD pattern of Type O.
FIG. 5-47 shows TGA/DSC curves of Type O.
FIG. 5-48 shows $^1$H NMR of Type O.
FIG. 5-49 shows XRPD pattern of Type P.
FIG. 5-50 shows TGA/DSC curves of Type P.
FIG. 5-51 shows $^1$H NMR of Type P.
FIG. 5-52 shows XRPD pattern of Type Q.
FIG. 5-53 shows TGA/DSC curves of Type Q.
FIG. 5-54 shows $^1$H NMR of Type Q.
FIG. 6-1 shows HPLC of M-5 from resolution with 1,3-diphenyl-3-oxopropanesulfonic acid.
FIG. 6-2 shows HPLC of 5 (P-atropisomer excess) from resolution with 1,3-diphenyl-3-oxopropanesulfonic acid.

SUMMARY

Figure 1:
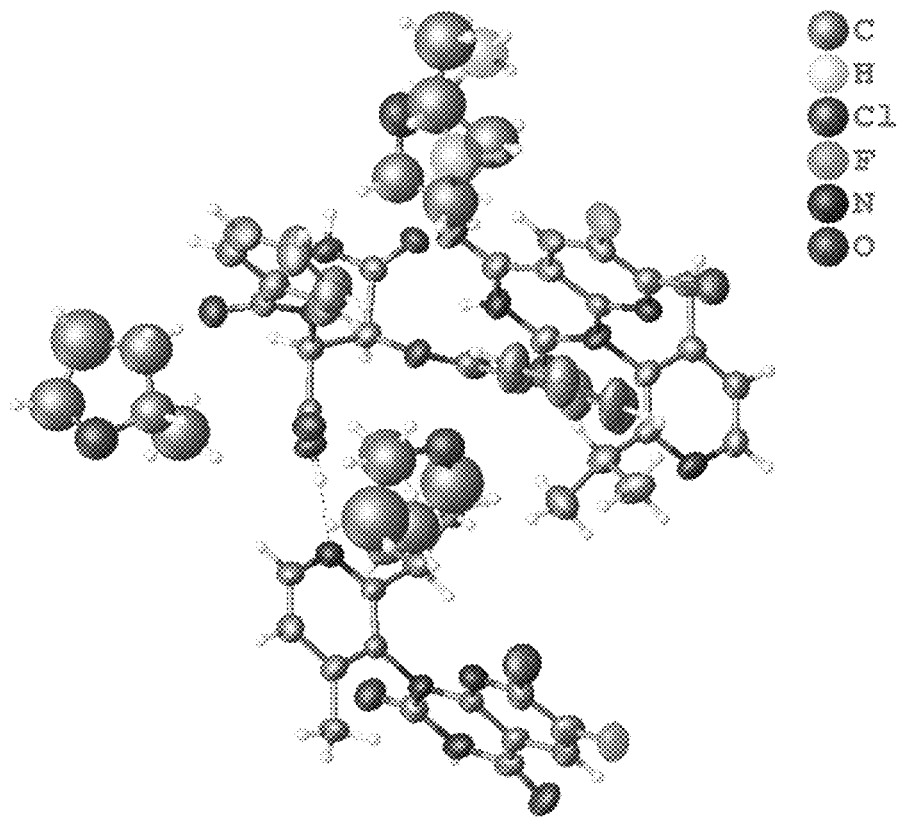

The present invention relates to improved preparation of a compound having the following chemical structure:

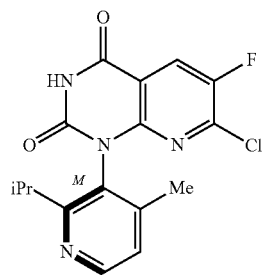

and key intermediates thereof, i.e., compositions and compounds comprising the following chemical structures:

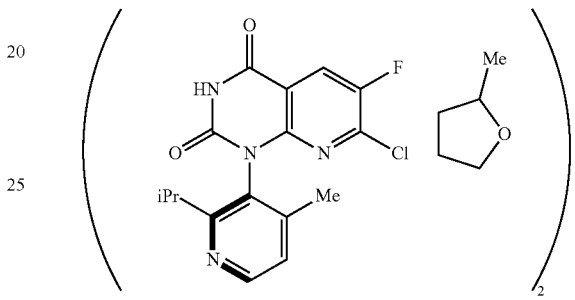

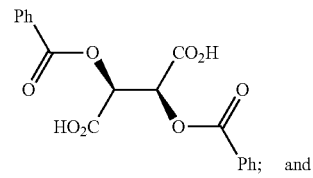

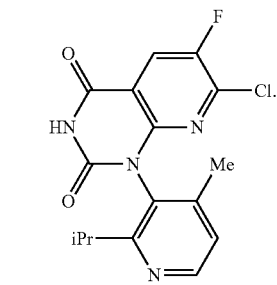

The present invention additional relates to a method of preparing Compound 5M having the following chemical structure

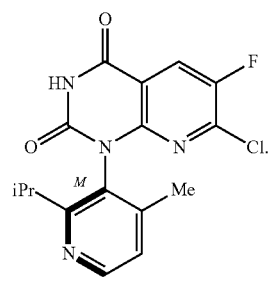

The present invention additional relates to a composition comprising a structure

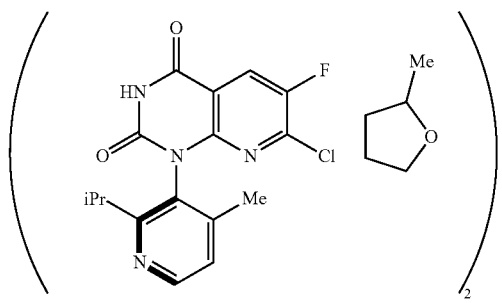

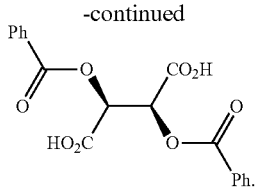

DETAILED DESCRIPTION

Definitions

Abbreviations: The following abbreviations may be used herein:

| | |
|---|---|
| ACN | Acetonitrile |
| AcOH | acetic acid |
| aq or aq. | Aqueous |
| BOC or Boc | tert-butyloxy carbonyl |
| BuOH | n-butanol |
| BuOAc | Butanol acetate |
| cpme | cyclopentyl methyl ether |
| $CHCl_3$ | Trichloromethane |
| DCE | 1,2-dichloroethane |
| DABCO | 1,4-diazabicyclo[2.2.2]octane |
| DCM | Dichloromethane |
| DMA | N,N-Dimethylacetamide |
| DMAP | 4-dimethylaminopyridine |
| DME | 1,2-dimethoxy ethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | Equivalent |
| ESI or ES | electrospray ionization |
| Et | Ethyl |
| $Et_2O$ | diethyl ether |
| EtOAc | ethyl acetate |
| EtOH | ethanol |
| g | Grams |
| h | Hour |
| $H_2O$ | water |
| HPLC | high pressure liquid chromatography |
| iPr | Isopropyl |
| IPA | Isopropyl alcohol |
| IPAc | Isopropyl acetate |
| $iPr_2NEt$ or DIPEA | N-ethyl diisopropylamine (Hünig's base) |
| KHMDS | potassium hexamethyldisilazide |
| KOAc | potassium acetate |
| LDA | Lithium diisopropylamide |
| Lawesson's reagent | 2,4-bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide |
| LC MS, LCMS, LC-MS or LC/MS | liquid chromatography mass spectroscopy |
| LG | Leaving group (e.g., halogen, mesylate, triflate) |
| LHMDS or LiHMDS | lithium hexamethyldisilazide |
| m/z | mass divided by charge |
| Me | Methyl |
| MeCN | Acetonitrile |
| MeOH | Methanol |
| Met | Metal species for cross-coupling (e.g., MgX, ZnX, $SnR_3$, $SiR_3$, $B(OR)_2$) |
| 2-MeTHF | 2-Methyltetrahydrofuran |
| mg | Milligrams |
| min | Minutes |
| MIBK | 4-Methyl-2-pentanone |
| mL | Milliliters |
| MS | mass spectra |
| MTBE | Methyl tert-butyl ether |
| n-BuLi | n-butyl Lithium |

| | |
|---|---|
| NaHMDS | sodium hexamethyldisilazide |
| NBS | N-bromosuccinimide |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$•DCM | [1,1'-Bis(diphenylphosphino)ferrocene]dichloropalladium(II), complex with dichloromethane |
| Pd(PPh$_3$)$_4$ | Tetrakis(triphenylphosphine)palladium(0) |
| Ph | Phenyl |
| PR or PG or Prot. group | protecting group |
| rbf | round-bottom flask |
| RP-HPLC | reverse phase high pressure liquid chromatography |
| RT or rt | room temperature |
| sat. or satd. | saturated |
| SFC | supercritical fluid chromatography |
| SPhos Pd G3 or SPhos G3 | (2-Dicyclohexylphosphino-2',6'-dimethoxybiphenyl)[2-(2'-amino-1, 1'-biphenyl)]palladium(II) methanesulfonate |
| TBAF | tetra-n-butylammonium fluoride |
| TBTU | N,N,N',N'-Tetramethyl-O-(benzotriazol-1-yl)uronium tetrafluoroborate |
| t-BuOH | tert-butanol |
| TEA or Et$_3$N | Trimethylamine |
| TFA | trifluoroacetic acid |
| THF | Tetrahydrofuran |
| UV | Ultraviolet |
| XRPD | X-Ray Powder Diffraction |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-C$_8$ hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term C$_{m-n}$ means the alkyl group has "m" to "n" carbon atoms. The term "alkylene" refers to an alkyl group having a substituent. An alkyl (e.g., methyl), or alkylene (e.g., —CH$_2$—), group can be substituted with one or more, and typically one to three, of independently selected, for example, halo, trifluoromethyl, trifluoromethoxy, hydroxy, alkoxy, nitro, cyano, alkylamino, C$_{1-8}$alkyl, C$_{2-8}$alkenyl, C$_{2-8}$alkynyl, —NC, amino, —CO$_2$H, —CO$_2$C$_1$-C$_8$alkyl, —OCOC$_1$-C$_8$alkyl, C$_3$-C$_{10}$ cycloalkyl, C$_3$-C$_{10}$ heterocycloalkyl, C$_5$-C$_{10}$aryl, and C$_5$-C$_{10}$ heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —NR$_2$ group, wherein each R is, e.g., H or a substituent. In some embodiments, the amino group is further substituted to form an ammonium ion, e.g., NR$_3^+$. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxylate, amine, and amide. An "amide" or "amido" group interchangeably refers to a group similar to an amine or amino group but further including a C(O), e.g., —C(O)NR$_2$.

As used herein, the term "aryl" refers to a C$_{6-14}$ monocyclic or polycyclic aromatic group, preferably a C$_{6-10}$ monocyclic or bicyclic aromatic group, or C$_{10-14}$ polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to C$_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, C$_{1-8}$alkyl, C$_{2-8}$alkenyl, C$_{2-8}$alkynyl, —CF$_3$, —OCF$_3$, —NO$_2$, —CN, —NC, —OH, alkoxy, amino, —CO$_2$H, —CO$_2$C$_1$-C$_8$alkyl, —OCOC$_1$-C$_8$alkyl, C$_3$-C$_{10}$ cycloalkyl, C$_3$-C$_{10}$ heterocycloalkyl, C$_5$-C$_{10}$ aryl, and C$_5$-C$_{10}$ heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, $C_{1-8}$alkyl, $C_{2-8}$alkenyl, $C_{2-8}$alkynyl, —$OCF_3$, —$NO_2$, —CN, —NC, —OH, alkoxy, amino, —$CO_2H$, —$CO_2C_1$-$C_8$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to $C_{10-14}$ bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, $C_{1-8}$alkyl, $C_{2-8}$alkenyl, $C_{2-8}$alkynyl, —$OCF_3$, —$NO_2$, —CN, —NC, —OH, alkoxy, amino, —$CO_2H$, —$CO_2C_1$-$C_8$alkyl, —$OCOC_1$-$C_8$alkyl, $C_3$-$C_{10}$ cycloalkyl, $C_3$-$C_{10}$ heterocycloalkyl, $C_5$-$C_{10}$ aryl, and $C_5$-$C_{10}$ heteroaryl.

As used herein, the term Boc refers to the structure

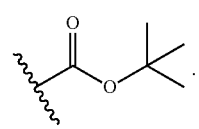 [SMILES: *C(=O)OC(C)(C)C]

EMBODIMENTS

Embodiment 1

In one embodiment of the invention, the present invention comprises a composition, the composition comprising a compound of Formula 4:

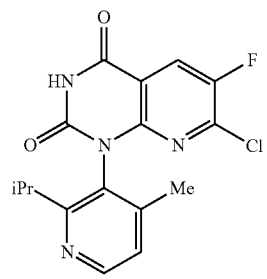

4 and a compound of Formula B:

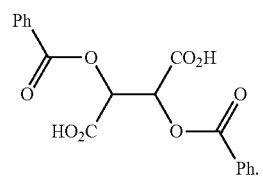

B

Embodiment 2

In another embodiment of the present invention, the present invention comprises the composition of embodiment 1, wherein the compound of Formula 4 is a compound of Formula 5M:

5M

Embodiment 3

In another embodiment of the present invention, the present invention comprises the composition of embodiment 1, wherein the compound of Formula 4 is a compound of Formula 5P:

5P

Embodiment 4

In another embodiment of the present invention, the present invention comprises the composition of any one of embodiments 1-3, wherein the compound of Formula B is a compound of formula B1:

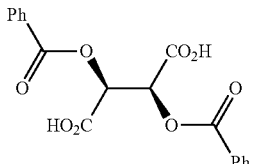

Embodiment 5

In another embodiment of the present invention, the present invention comprises the composition of any one of embodiments 1-3, wherein the compound of Formula B is a compound of formula B2:

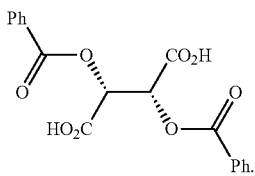

Embodiment 6

In another embodiment of the present invention, the present invention comprises the composition of any one of embodiments 1-5, wherein the composition comprises a 2 to 1 ratio of the compound of Formula 4 to the compound of Formula B.

Embodiment 7

In another embodiment of the present invention, the present invention comprises the composition of any one of embodiments 1-6, wherein the composition further comprises 2-methyltetrahydrofuran having the formula:

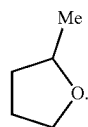

Embodiment 8

In another embodiment of the present invention, the present invention comprises the composition of any one of embodiments 1-7, wherein the ratio of the 2-methyltetrahydrofuran to the compound of formula B is 2 to 1.

Embodiment 9

In another embodiment of the present invention, the present invention comprises the composition of embodiment 1, wherein the composition has the formula:

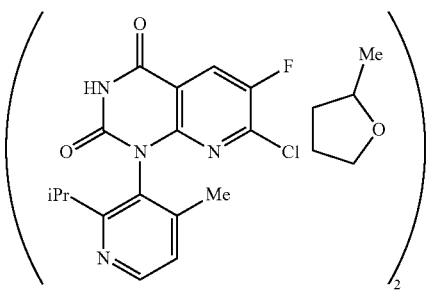

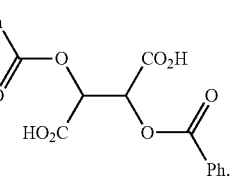

Embodiment 10

In another embodiment of the present invention, the present invention comprises the composition of embodiment 9, wherein the composition has the formula:

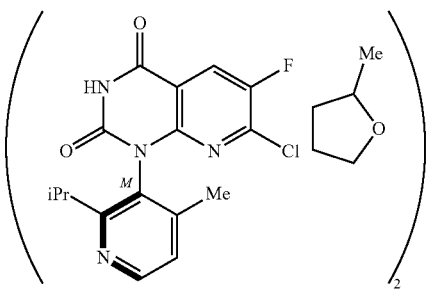

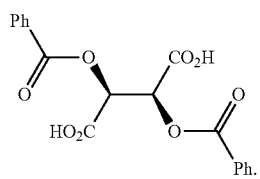

Embodiment 11

In another embodiment of the present invention, the present invention comprises the composition of embodiment 9, wherein the composition has the formula:

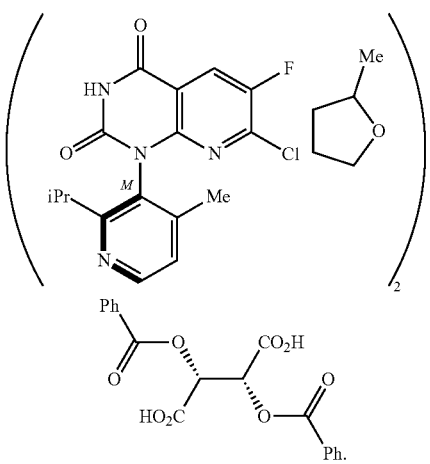

Embodiment 12

In another embodiment of the present invention, the present invention comprises the composition of embodiment 9, wherein the composition has the formula:

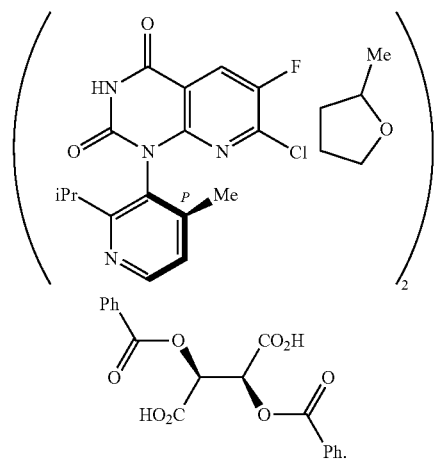

Embodiment 13

In another embodiment of the present invention, the present invention comprises the composition of embodiment 9, wherein the composition has the formula:

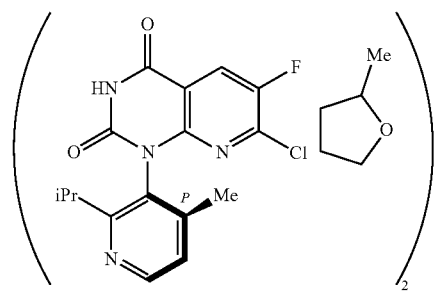

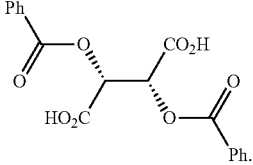

Embodiment 14

In another embodiment of the present invention, the present invention comprises the composition of any one of embodiments 1-13, wherein the composition is in a crystalline state.

Embodiment 15

In another embodiment of the present invention, the present invention comprises a method of making a composition of formula 4a, the method comprising reacting a compound 4, having the following chemical structure:

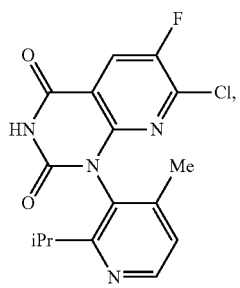

with a compound B1, having the formula:

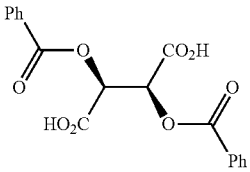

in the presence of 2-methyltetrahydrofuran to form the composition of formula 4a, having the structure:

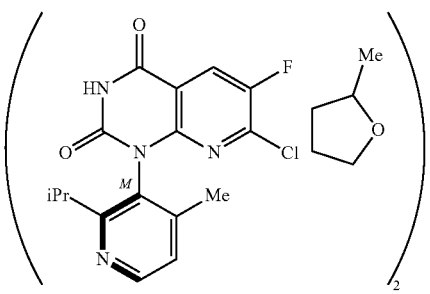

-continued

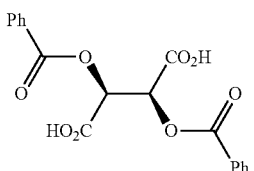

Embodiment 16

In another embodiment of the present invention, the present invention comprises a method of obtaining a compound of formula 5M, having the following chemical structure:

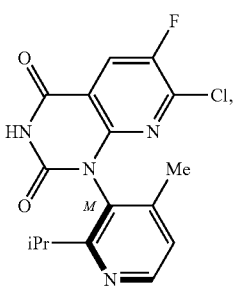

5M the method comprising:

a) reacting a compound 4, having the following chemical structure:

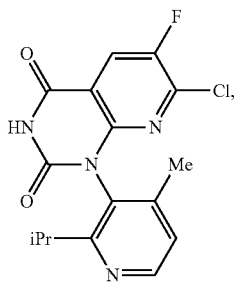

4 with a compound B1, having the formula:

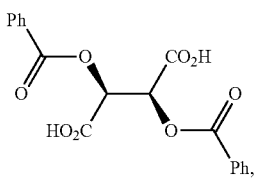 [SMILES: O=C(O[C@H](C(=O)O)[C@H](OC(=O)c1ccccc1)C(=O)O)c1ccccc1]

in the presence of 2-methyltetrahydrofuran to form a composition of formula 4a, having the structure:

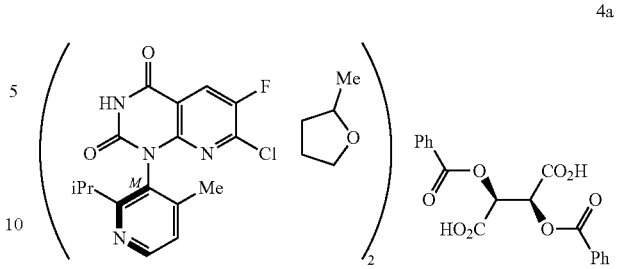

4a as crystals;
b) isolating composition 4a, and
c) treating the isolated composition 4a with a base to produce the compound of formula 5M.

Embodiment 17

In another embodiment of the present invention, the present invention comprises the method according to Embodiment 16, wherein the base is $Na_2HPO_4$.

Embodiment 18

In another embodiment of the present invention, the present invention comprises the method according to Embodiment 16, wherein the base is $NaHCO_3$.

Embodiment 19

In another embodiment of the present invention, the present invention comprises the composition, the composition comprising a compound of Formula 4:

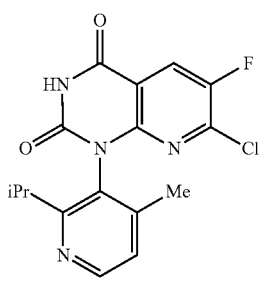

4 and a compound of Formula 11:

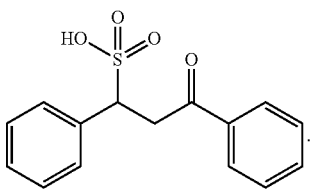

11

Embodiment 20

In another embodiment of the present invention, the present invention comprises the composition of embodiment 19, wherein the compound of Formula 4 is a compound of Formula 5M:

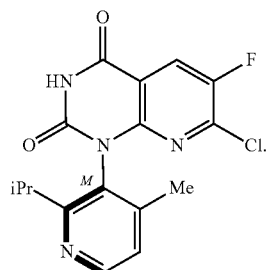

Embodiment 21

In another embodiment of the present invention, the present invention comprises the composition of embodiment 19, wherein the compound of Formula 4 is a compound of Formula 5P:

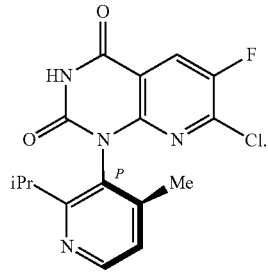

Embodiment 22

In another embodiment of the present invention, the present invention comprises the composition of any one of embodiments 19-21, wherein the compound of Formula 11 is a compound of formula 11a:

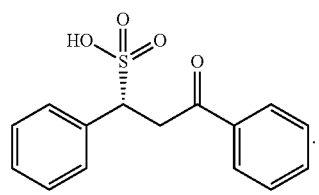

Embodiment 23

In another embodiment of the present invention, the present invention comprises the composition of any one of embodiments 19-21, wherein the compound of Formula 11 is a compound of formula 11b:

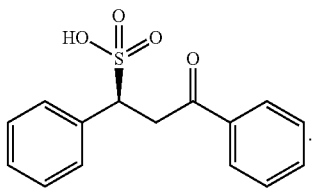

Embodiment 24

In another embodiment of the present invention, the present invention comprises the composition of embodiment 19, wherein the composition has the formula:

Embodiment 25

In another embodiment of the present invention, the present invention comprises the composition of embodiment 19, wherein the composition has the formula:

Embodiment 26

In another embodiment of the present invention, the present invention comprises the composition of embodiment 19, wherein the composition has the formula:

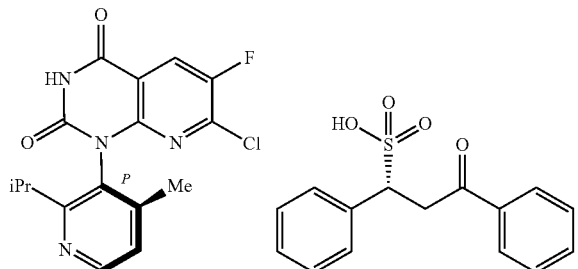

Embodiment 27

In another embodiment of the present invention, the present invention comprises the composition of embodiment 19, wherein the composition has the formula:

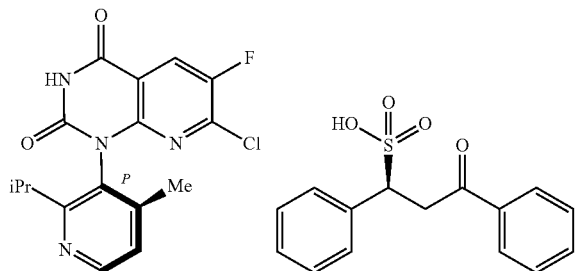

Embodiment 28

In another embodiment of the present invention, the present invention comprises the composition of any one of embodiments 19-27, wherein the composition comprises a 1 to 1 ratio of the compound of Formula 4 to the compound of Formula 11.

Embodiment 29

In another embodiment of the present invention, the present invention comprises the method of embodiment 16, wherein the compound of formula 5M is used as an intermediate to generate a compound having the Formula 9:

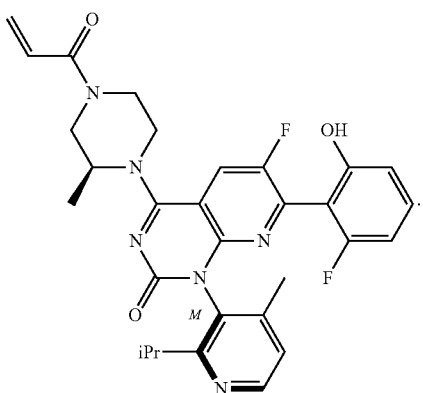

Embodiment 30

The method of embodiment 29, wherein the method further comprises mixing the compound of Formula 9 with at least one pharmaceutically acceptable excipient to form a pharmaceutical composition.

Compounds of the Disclosure

Provided herein are KRAS inhibitors having structures discussed in more detail below.

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$F, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, groups such as, but not limited to, the following groups

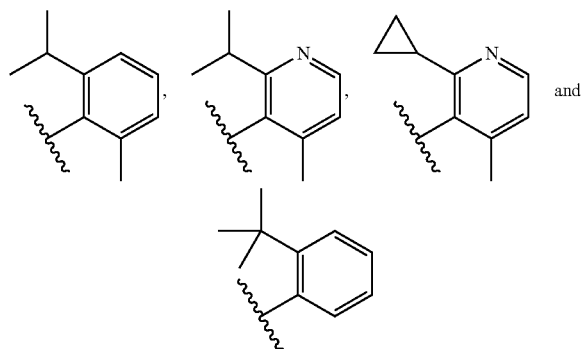

may exhibit restricted rotation.

The term "monohydrate" means a salt of Compound 9 having about one associated water molecule. Those skilled in the art appreciate that the exact number of the associated water molecules may vary slightly at any time with variable temperature, pressure, and other environmental influence. All slight variations of the number of the associated water molecules are contemplated to be within the scope of the present invention.

The term "dihydrate" means a salt of Compound 9 having about two associated water molecules. Those skilled in the art appreciate that the exact number of the associated water molecules may vary slightly at any time with variable temperature, pressure, and other environmental influence. All slight variations of the number of the associated water molecules are contemplated to be within the scope of the present invention.

The term "co-crystal" means a crystalline material comprising two or more compounds at ambient temperature (20° C. to 25° C., preferably 20° C.), of which at least two are held together by weak interaction, wherein at least one of the compounds is a co-crystal former and the other is Compound 5. Weak interaction is being defined as an interaction which is neither ionic nor covalent and includes for example: hydrogen bonds, van der Waals forces, and π-π interactions.

The term "amorphous form" or "amorphous" means a material that lacks long range order and as such does not show distinct X-ray diffraction peaks, i.e. a Bragg diffraction peak. The XRPD pattern of an amorphous material is characterized by one or more amorphous halos.

The term "amorphous halo" is an approximately bell-shaped maximum in the X-ray powder pattern of an amorphous substance.

The term "substantially pure" refers to a solid form of Compound 9 having purity greater than about 95%, specifically greater than about 99.5%, more specifically greater than about 99.8% and still more specifically greater than about 99.9%.

The term "patient" means animals, such as dogs, cats, cows, horses, sheep and humans. Particular patients are mammals. The term patient includes males and females.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

Pharmaceutical Compositions, Dosing, and Routes of Administration

Also provided herein are pharmaceutical compositions that include a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pennsylvania, 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the interne.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), Venclexta™ (venetoclax) and Adriamycin™, (docorubicin) as well as a host of chemotherapeutic agents. Non-limiting examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, chlorocyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931 788, WO 90/05719, WO 99/52910, WO 99/52889, WO 99/29667, WO1999007675, European Patent Publication EP1786785, European Patent Publication No. EP1181017, United States Publication No. US20090012085, United States Publication U.S. Pat. Nos. 5,863,949, 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, andMMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RH retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN, now Pfizer, Inc.), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, now CASI Pharmaceuticals, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC: antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, now CASI Pharmaceuticals, USA); troponin I, (Harvard University, USA); SU 6668, (SUGEN, now Pfizer, Inc., USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, now CASI Pharmaceuticals, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 176; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TGO2 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163 L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fluchloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12):1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

The KRAS$^{G12C}$ inhibitors of the present invention can be used in combination with MEK inhibitors. Particular MEK inhibitors that can be used in the combinations of the present invention include PD-325901, trametinib, pimasertib, MEK162 [also known as binimetinib], TAK-733, GDC-0973 and AZD8330. A particular MEK inhibitor that can be used along with KRAS$^{G12C}$ inhibitor in the combinations of the present invention is trametinib (tradename: Mekinist®, commercially available from Novartis Pharmaceuticals Corp.). Another particular MEK inhibitor is N-(((2R)-2,3-dihydroxypropyl)oxy)-3,4-difluoro-2-((2-fluoro-4-iodophenyl)amino)benzamide, also known as AMG 1009089, 1009089 or PD-325901.

Another particular MEK inhibitor that can be used in the combinations of the present invention includes cobimetinib. MEK inhibitors include, but are not limited to, CI-1040, AZD6244, PD318088, PD98059, PD334581, RDEA119, ARRY-142886, and ARRY-438162.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydroimidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Aktl) (Barnett et al. (2005) Biochem. 1, 385 (Pt. 2), 399-408); Akt-1-1,2 (inhibits AK1 and 2) (Barnett et al. (2005) Biochem. J. 385 (Pt. 2), 399-408); API-59CJ-Ome (e.g., Jin et al. (2004) Br J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl)rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MC$_1$-1 inhibitors include, but are not limited to, AMG-176, MIK665, and 563845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

KRAS$^{G12C}$ inhibitors can also be used in combination with SHP2 inhibitors in the present invention. SHP2 inhibitors that can be used in the present combinations include, but are not limited to, SHP099, and RMC-4550 or RMC-4630, from Revolutions Medicines in Redwood City, CA.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rittman® (rituximab), Lucentis® (ranibizumab), and Eylea® (aflibercept).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Anti-PD-1 inhibitors, including but not limited to antibodies include, but are not limited to, pembrolizumab (Keytruda®) and nivolumab (Opdive). Exemplary anti-PD-1 antibodies and methods for their use are described by Goldberg et al., Blood 110(1):186-192 (2007), Thompson et al., Clin. Cancer Res. 13(6):1757-1761 (2007), and Korman et al., International Application No. PCT/JP2006/309606 (publication no. WO 2006/121168 A1), each of which are expressly incorporated by reference herein. include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090box.c, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

All patents and other publications recited herein are hereby incorporated by reference.

The processes presented below illustrate specific embodiments of the present invention. These processes are meant to be representative and are not intended to limit the scope of the claims in any manner.

Representative Examples of the Invention

The following intermediate compounds of 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one are representative examples of the invention and are not intended to be construed as limiting the scope of the present invention.

A synthesis of Compound 9 and the relevant intermediates is described in U.S. Ser. No. 15/984,855, filed May 21, 2018, which claims priority to and the benefit claims the benefit of U.S. Provisional Application No. 62/509,629, filed on May 22, 2017, which are incorporated herein by reference in their entireties for all purposes. 6-Fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one was prepared using the following process, in which the isomers of the final product were isolated via chiral chromatography.

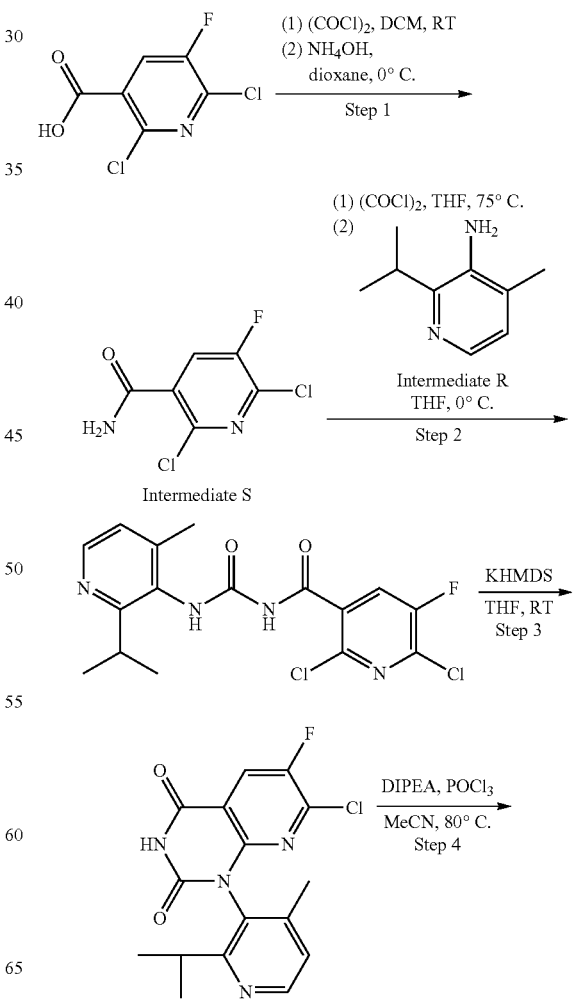

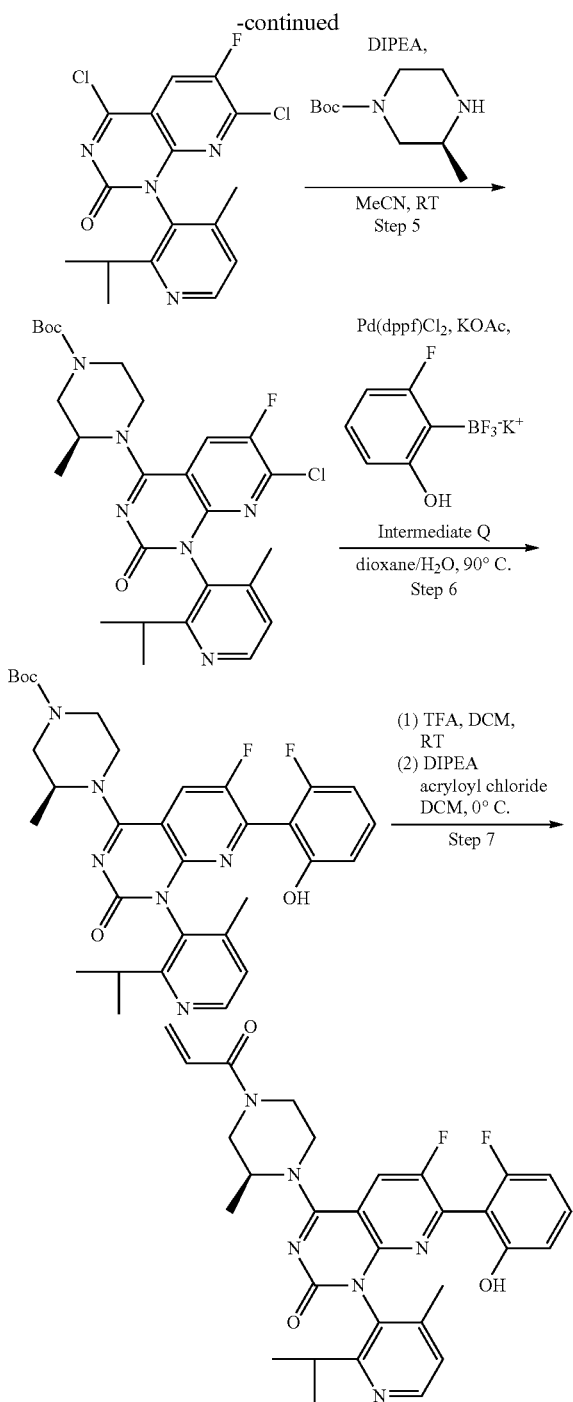

Step 1: 2,6-Dichloro-5-fluoronicotinamide (Intermediate S). To a mixture of 2,6-dichloro-5-fluoro-nicotinic acid (4.0 g, 19.1 mmol, AstaTech Inc., Bristol, PA) in dichloromethane (48 mL) was added oxalyl chloride (2M solution in DCM, 11.9 mL, 23.8 mmol), followed by a catalytic amount of DMF (0.05 mL). The reaction was stirred at room temperature overnight and then was concentrated. The residue was dissolved in 1,4-dioxane (48 mL) and cooled to 0° C. Ammonium hydroxide solution (28.0-30% NH3 basis, 3.6 mL, 28.6 mmol) was added slowly via syringe. The resulting mixture was stirred at 0° C. for 30 min and then was concentrated. The residue was diluted with a 1:1 mixture of EtOAc/Heptane and agitated for 5 min, then was filtered. The filtered solids were discarded, and the remaining mother liquor was partially concentrated to half volume and filtered. The filtered solids were washed with heptane and dried in a reduced-pressure oven (45° C.) overnight to provide 2,6-dichloro-5-fluoronicotinamide. $^1$H NMR (400 MHz, DMSO-$d_6$) δ ppm 8.23 (d, J=7.9 Hz, 1H) 8.09 (br s, 1H) 7.93 (br s, 1H). m/z (ESI, +ve ion): 210.9 (M+H)$^+$.

Step 2: 2,6-Dichloro-5-fluoro-N-((2-isopropyl-4-methylpyridin-3-yl)carbamoyl)nicotinamide. To an ice-cooled slurry of 2,6-dichloro-5-fluoronicotinamide (Intermediate S, 5.0 g, 23.9 mmol) in THF (20 mL) was added oxalyl chloride (2 M solution in DCM, 14.4 mL, 28.8 mmol) slowly via syringe. The resulting mixture was heated at 75° C. for 1 h, then heating was stopped, and the reaction was concentrated to half volume. After cooling to 0° C., THF (20 mL) was added, followed by a solution of 2-isopropyl-4-methylpyridin-3-amine (Intermediate R, 3.59 g, 23.92 mmol) in THF (10 mL), dropwise via cannula. The resulting mixture was stirred at 0° C. for 1 h and then was quenched with a 1:1 mixture of brine and saturated aqueous ammonium chloride. The mixture was extracted with EtOAc (3×) and the combined organic layers were dried over anhydrous sodium sulfate and concentrated to provide 2,6-dichloro-5-fluoro-N-((2-isopropyl-4-methylpyridin-3-yl)carbamoyl) nicotinamide. This material was used without further purification in the following step. m/z (ESI, +ve ion): 385.1 (M+H)$^+$.

Step 3: 7-Chloro-6-fluoro-1-(2-isopropyl-4-methylpyridin-3-yl)pyrido[2,3-d]pyrimidine-2,4(1H,3H)-dione. To an ice-cooled solution of 2,6-dichloro-5-fluoro-N-((2-isopropyl-4-methylpyridin-3-yl)carbamoyl)nicotinamide (9.2 g, 24.0 mmol) in THF (40 mL) was added KHMDS (1 M solution in THF, 50.2 mL, 50.2 mmol) slowly via syringe. The ice bath was removed and the resulting mixture was stirred for 40 min at room temperature. The reaction was quenched with saturated aqueous ammonium chloride and extracted with EtOAc (3×). The combined organic layers were dried over anhydrous sodium sulfate and concentrated. The residue was purified by silica gel chromatography (eluent: 0-50% 3:1 EtOAc-EtOH/heptane) to provide 7-chloro-6-fluoro-1-(2-isopropyl-4-methylpyridin-3-yl) pyrido[2,3-d]pyrimidine-2,4(1H,3H)-dione. $^1$H NMR (400 MHz, DMSO-$d_6$) δ ppm 12.27 (br s, 1H), 8.48-8.55 (m, 2H), 7.29 (d, J=4.8 Hz, 1H), 2.87 (quin, J=6.6 Hz, 1H), 1.99-2.06 (m, 3H), 1.09 (d, J=6.6 Hz, 3H), 1.01 (d, J=6.6 Hz, 3H). $^{19}$F NMR (376 MHz, DMSO-$d_6$) δ: -126.90 (s, 1F). m/z (ESI, +ve ion): 349.1 (M+H)$^+$.

Step 4: 4,7-Dichloro-6-fluoro-1-(2-isopropyl-4-methylpyridin-3-yl)pyrido[2,3-d]pyrimidin-2(1H)-one. To a solution of 7-chloro-6-fluoro-1-(2-isopropyl-4-methylpyridin-3-yl)pyrido[2,3-d]pyrimidine-2,4(1H,3H)-dione (4.7 g, 13.5 mmol) and DIPEA (3.5 mL, 20.2 mmol) in acetonitrile (20 mL) was added phosphorus oxychloride (1.63 mL, 17.5 mmol), dropwise via syringe. The resulting mixture was heated at 80° C. for 1 h, and then was cooled to room temperature and concentrated to provide 4,7-dichloro-6-fluoro-1-(2-isopropyl-4-methylpyridin-3-yl)pyrido[2,3-d] pyrimidin-2(1H)-one. This material was used without further purification in the following step. m/z (ESI, +ve ion): 367.1 (M+H)$^+$.

Step 5: (S)-tert-Butyl 4-(7-chloro-6-fluoro-1-(2-isopropyl-4-methylpyridin-3-yl)-2-oxo-1,2-dihydropyrido[2,3-d] pyrimidin-4-yl)-3-methylpiperazine-1-carboxylate. To an ice-cooled solution of 4,7-dichloro-6-fluoro-1-(2-isopropyl-4-methylpyridin-3-yl)pyrido[2,3-d]pyrimidin-2(1H)-one (13.5 mmol) in acetonitrile (20 mL) was added DIPEA (7.1 mL, 40.3 mmol), followed by (S)-4-N-Boc-2-methyl piperazine (3.23 g, 16.1 mmol, Combi-Blocks, Inc., San Diego, CA, USA). The resulting mixture was warmed to room temperature and stirred for 1 h, then was diluted with cold saturated aqueous sodium bicarbonate solution (200 mL) and EtOAc (300 mL). The mixture was stirred for an additional 5 min, the layers were separated, and the aqueous layer was extracted with more EtOAc (1×). The combined organic layers were dried over anhydrous sodium sulfate and concentrated. The residue was purified by silica gel chromatography (eluent: 0-50% EtOAc/heptane) to provide (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate. m/z (ESI, +ve ion): 531.2 (M+H)$^+$.

Step 6: (3S)-tert-Butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. A mixture of (S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (4.3 g, 8.1 mmol), potassium trifluoro(2-fluoro-6-hydroxyphenyl)borate (Intermediate Q, 2.9 g, 10.5 mmol), potassium acetate (3.2 g, 32.4 mmol) and [1,1'-bis(diphenylphosphino)ferrocene]dichloropalladium(II), complex with dichloromethane (661 mg, 0.81 mmol) in 1,4-dioxane (80 mL) was degassed with nitrogen for 1 min. De-oxygenated water (14 mL) was added, and the resulting mixture was heated at 90° C. for 1 h. The reaction was allowed to cool to room temperature, quenched with half-saturated aqueous sodium bicarbonate, and extracted with EtOAc (2×) and DCM (1×). The combined organic layers were dried over anhydrous sodium sulfate and concentrated. The residue was purified by silica gel chromatography (eluent: 0-60% 3:1 EtOAc-EtOH/heptane) to provide (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate. $^1$H NMR (400 MHz, DMSO-d$_6$) δ ppm 10.19 (br s, 1H), 8.38 (d, J=5.0 Hz, 1H), 8.26 (dd, J=12.5, 9.2 Hz, 1H), 7.23-7.28 (m, 1H), 7.18 (d, J=5.0 Hz, 1H), 6.72 (d, J=8.0 Hz, 1H), 6.68 (t, J=8.9 Hz, 1H), 4.77-4.98 (m, 1H), 4.24 (br t, J=14.2 Hz, 1H), 3.93-4.08 (m, 1H), 3.84 (br d, J=12.9 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=10.8, 6.8 Hz, 3H), 1.26-1.32 (m, 1H), 1.07 (dd, J=6.6, 1.7 Hz, 3H), 0.93 (dd, J=6.6, 2.1 Hz, 3H). $^{19}$F NMR (376 MHz, DMSO-d$_6$) δ: −115.65 (s, 1F), −128.62 (s, 1F). m/z (ESI, +ve ion): 607.3 (M+H)$^+$.

Step 7: 6-Fluoro-7-(2-fluoro-6-hydroxyphenyl)-1-(4-methyl-2-(2-propanyl)-3-pyridinyl)-4-(2S)-2-methyl-4-(2-propenoyl)-1-piperazinyl)pyrido[2,3-d]pyrimidin-2(1H)-one. Trifluoroacetic acid (25 mL, 324 mmol) was added to a solution of (3S)-tert-butyl 4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (6.3 g, 10.4 mmol) in DCM (30 mL). The resulting mixture was stirred at room temperature for 1 h and then was concentrated. The residue was dissolved in DCM (30 mL), cooled to 0° C., and sequentially treated with DIPEA (7.3 mL, 41.7 mmol) and a solution of acryloyl chloride (0.849 mL, 10.4 mmol) in DCM (3 mL; added dropwise via syringe). The reaction was stirred at 0° C. for 10 min, then was quenched with half-saturated aqueous sodium bicarbonate and extracted with DCM (2×). The combined organic layers were dried over anhydrous sodium sulfate and concentrated. The residue was purified by silica gel chromatography (eluent: 0-100% 3:1 EtOAc-EtOH/heptane) to provide 6-fluoro-7-(2-fluoro-6-hydroxyphenyl)-1-(4-methyl-2-(2-propanyl)-3-pyridinyl)-4-(2S)-2-methyl-4-(2-propenoyl)-1-piperazinyl)pyrido[2,3-d]pyrimidin-2(1H)-one. $^1$H NMR (400 MHz, DMSO-d$_6$) δ ppm 10.20 (s, 1H), 8.39 (d, J=4.8 Hz, 1H), 8.24-8.34 (m, 1H), 7.23-7.32 (m, 1H), 7.19 (d, J=5.0 Hz, 1H), 6.87 (td, J=16.3, 11.0 Hz, 1H), 6.74 (d, J=8.6 Hz, 1H), 6.69 (t, J=8.6 Hz, 1H), 6.21 (br d, J=16.2 Hz, 1H), 5.74-5.80 (m, 1H), 4.91 (br s, 1H), 4.23-4.45 (m, 2H), 3.97-4.21 (m, 1H), 3.44-3.79 (m, 2H), 3.11-3.31 (m, 1H), 2.67-2.77 (m, 1H), 1.91 (s, 3H), 1.35 (d, J=6.8 Hz, 3H), 1.08 (d, J=6.6 Hz, 3H), 0.94 (d, J=6.8 Hz, 3H). $^{19}$F NMR (376 MHz, DMSO-d$_6$) δ ppm −115.64 (s, 1F), −128.63 (s, 1F). m/z (ESI, +ve ion): 561.2 (M+H)$^+$.

The present invention comprises the following steps wherein the resolution of the rac-Dione in Steps 4 and 5 promotes the successful separation of the atropisomers:

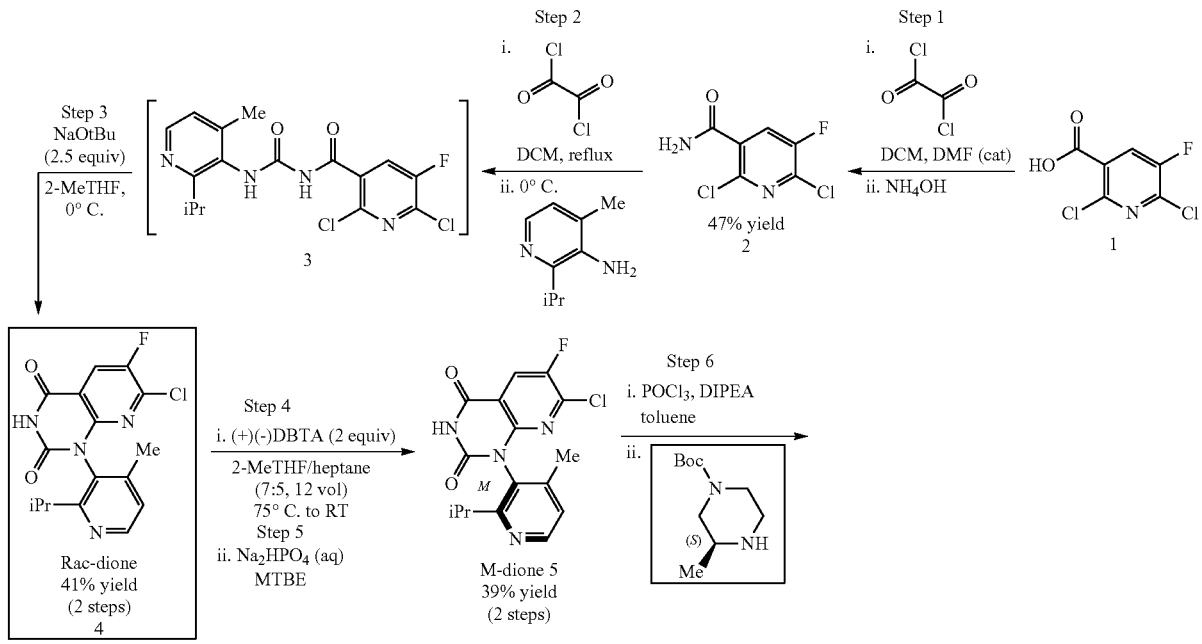

-continued
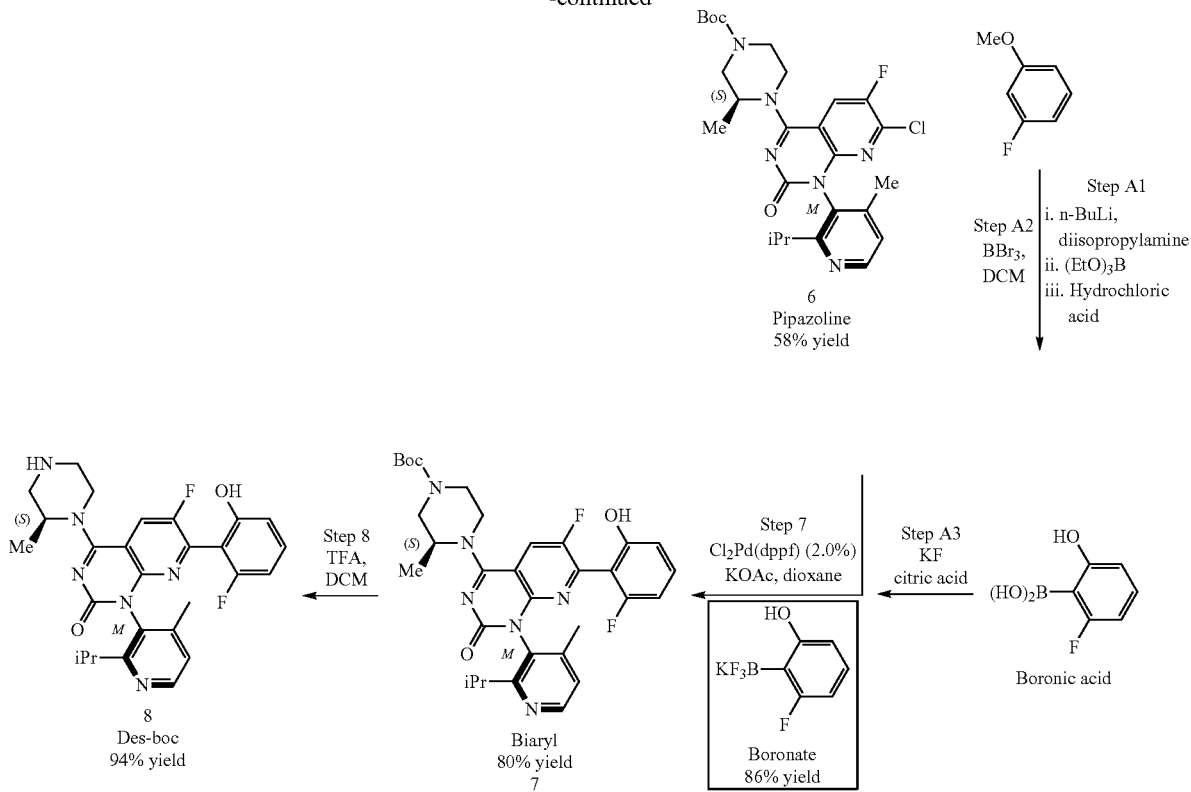
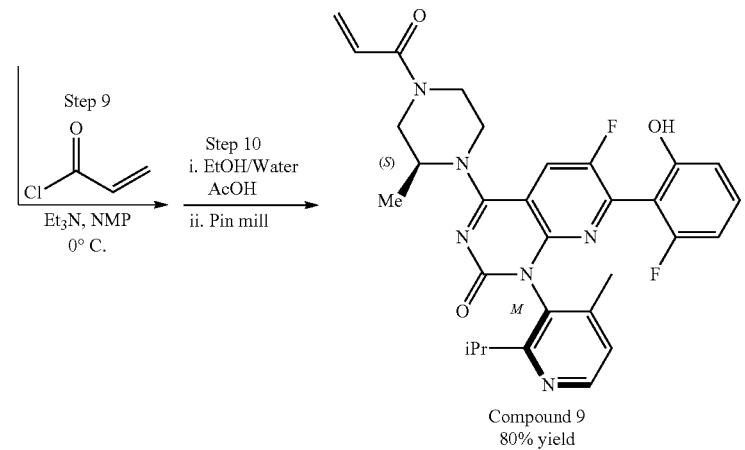
Process Description
Step 1
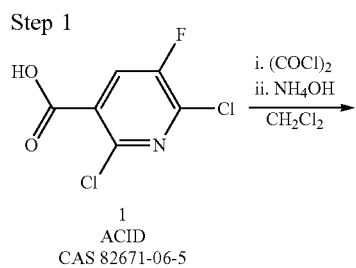
-continued
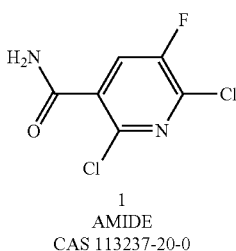

| Material | CAS # | MW (g/mol) | Equivalents/ Volumes | Moles | Theoretical |
|---|---|---|---|---|---|
| 2,6-dichloro-5-fluoro-3-pyridinecarboxylic acid | 82671-06-5 | 209.99 | 1.0 equiv. | 119.1 | 25 kg |
| DCM | 74-09-2 | 84.93 | 16.51 equiv. | 2354.9 | 200 kg |
| DMF | 68-12-2 | 73.09 | 0.068 equiv. | 8.1 | 592 g (627 mL) |
| Oxalyl Chloride | 79-37-8 | 126.93 | 1.25 equiv. | 148.9 | 18.9 kg |
| Ammonium Hydroxide | 1336-21-6 | 35.05 | 5 equiv. | 595.5 | 40.2 L |
| Water | 7732-18-5 | 18.02 | N/A | N/A | 261 L |

To a solution of 2,6-dichloro-5-fluoro-3-pyridinecarboxylic acid (Compound 1) (25 kg; 119.1 mol) in dichloromethane (167 kg) and DMF (592 g) was added Oxalyl chloride (18.9 kg; 148.9 mol) while maintaining an internal temp between 15-20° C. Additional dichloromethane (33 kg) was added as a rinse and the reaction mixture stirred for 2 h. The reaction mixture is cooled then quenched with ammonium hydroxide (40.2 L; 595.5 mol) while maintaining internal temperature 0±10° C. The resulting slurry was stirred for 90 min then the product collected by filtration. The filtered solids were washed with DI water (3×87 L) and dried to provide 2,6-dichloro-5-fluoronicotinamide (Compound 2).

Step 2

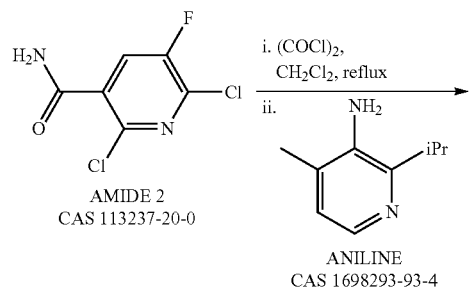

AMIDE 2
CAS 113237-20-0 i. (COCl)$_2$, CH$_2$Cl$_2$, reflux
ii. NH$_2$

ANILINE
CAS 1698293-93-4

In reactor A, a solution of 2,6-dichloro-5-fluoronicotinamide (Compound 2) (16.27 kg; 77.8 mol) in dichloromethane (359.5 kg) was added oxalyl chloride (11.9 kg; 93.8 mol) while maintaining temp <25° C. for 75 min. The resulting solution was then headed to 40° C.±3° C. and aged for 3 h. Using vacuum, the solution was distilled to remove dichloromethane until the solution was below the agitator. Dichloromethane (300 kg) was then added and the mixture cooled to 0±5° C. To a clean, dry reactor (reactor B) was added, 2-isopropyl-4-methylpyridin-3-amine (ANILINE) (12.9 kg; 85.9 mol) followed by dichloromethane (102.6 kg). The ANILINE solution was azeodried via vacuum distillation while maintaining a internal temperature between 20-25°), replacing with additional dichloromethane until the solution was dry by KF analysis (limit <0.05%). The solution volume was adjusted to approx. 23 L volume with dichloromethane. The dried ANILINE solution was then added to reactor A while maintaining an internal temperature of 0±5° C. throughout the addition. The mixture was then heated to 23° C. and aged for 1 h. the solution was polish filtered into a clean reactor to afford 2,6-dichloro-5-fluoro-N-((2-isopropyl-4-methylpyridin-3-yl)carbamoyl)nicotinamide (Compound 3) as a solution in DCM and used directly in the next step.

Step 3

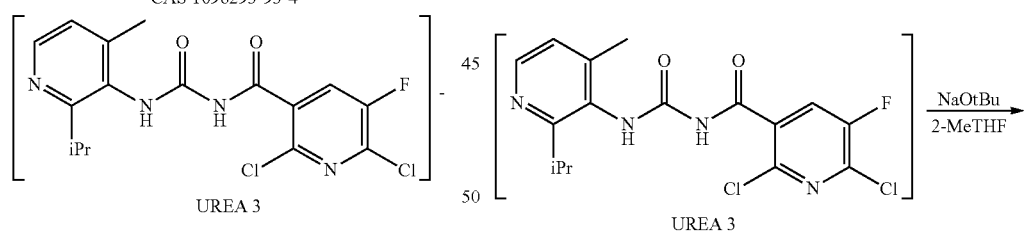

UREA 3

NaOtBu / 2-MeTHF

UREA 3

| Material | CAS# | MW (g/mol) | Equivalents Volumes | Moles | Theoretical |
|---|---|---|---|---|---|
| Amide (2,6-dichloro-5-fluoronicotinamide) | 113237-20-0 | 209.99 | 1.0 equiv. | 77.8 | 16.27 kg |
| Oxalyl Chloride | 79-37-8 | 126.93 | 1.2 equiv. | 93.8 | 11.9 kg (7.9 L) 730.7 kg |
| Dichloromethane | 75-09-2 | 84.93 | N/A | N/A | (551.5 L) |
| Aniline DCM Solution 2-isopropyl-4-methylpyridin-3-amine | 1698293-93-4 | 150.22 | 1.1 equiv. | 85.9 | 12.9 kg (Aniline contained wt) |

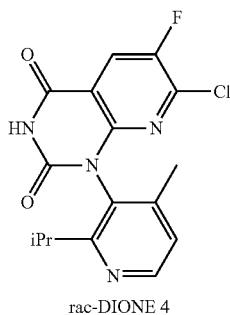

rac-DIONE 4

| Material | CAS # | MW (g/mol) | Equivalents/ Volumes | Moles | Theoretical |
|---|---|---|---|---|---|
| Urea, solution in DCM 2,6-dichloro-5-fluoro-N-{[4-methyl-2-(propan-2-yl)pyridin-3-yl]carbamoyl}pyridine-3-carboxamide | N/A | 385.22 | 1.0 equiv. | 38.9 | 208.3 kg (15 kg contained weight) |
| 2-methyltetrahydrofuran | 96-47-9 | 86.13 | N/A | N/A | 308 kg (358 L) |
| Sodium tert-butoxide | 865-48-5 | 96.11 | 2.0 equiv | 97.8 | 9.4 kg |
| Ammonium Chloride | 12125-02-9 | 53.49 | N/A | 430 | 23.0 kg |
| Hydrochloric Acid | 7467-01-0 | 36.46 | N/A | 41 | 1.6 kg |
| Magnesium Sulfate | 7487-88-9 | 120.37 | N/A | 195 | 23.5 kg |
| Sodium Chloride | 7647-14-5 | 58.44 | N/A | 282 | 16.5 kg |
| Heptane | 142-82-5 | 100.21 | N/A | N/A | 94 L |
| 10% citric acid | | | | | 75 kg |

A dichloromethane solution of 2,6-dichloro-5-fluoro-N-{[4-methyl-2-(propan-2-yl)pyridin-3-yl]carbamoyl} pyridine-3-carboxamide (UREA(Compound 3)) (15 kg contained; 38.9 mol) was solvent exchanged into 2-MeTHF using vacuum distillation while maintaining internal temperature of 20-25° C. The reactor volume was adjusted to 40 L and then additional 2-MeTHF was charged (105.4 kg). Sodium t-butoxide was added (9.4 kg; 97.8 mol) while maintaining 5-10° C. The contents where warmed to 23° C. and stirred for 3 h. The contents where then cooled to 0-5C and ammonium chloride added (23.0 kg; 430 mol) as a solution in 60 L of DI water. The mixture was warmed to 20 C and DI water added (15 L) and further aged for 30 min. Agitation was stopped and the layers separated. The aqueous layer was removed and to the organic layer was added DI water(81.7 L). A mixture of conc HCl (1.5 kg) and water (9 L) was prepared then added to the reactor slowly until pH measured between 4-5. The layers were separated, and the aqueous layer back extracted using 2-MeTHF (42.2 kg). The two organic layers combined and washed with a 10% citric acid solution (75 kg) followed by a mixture of water (81.7 L) and saturated NaCl (19.8 kg). The organic layer was then washed with saturated sodium bicarbonate (75 kg) repeateding if necessary to achieve a target pH of ≥7.0 of the aqueous. The organic layer was washed again with brine (54.7 kg) and then dried over magnesium sulfate (5 kg). The mixture was filtered to remove magnesium sulfate rinsing the filtered bed with 2-MeTHF (49.2 kg). The combined filtrate and washes where distilled using vacuum to 40 L volume. The concentrated solution was heated to 55° C. and heptane (10-12 kg) slowly added until cloud point. The solution was cooled to 23° C. over 2 h then heptane (27.3 kg) was added over 2 h. The product slurry was aged for 3 h at 20-25° C. then filtered and washed with a mixture of 2-MeTHF (2.8 kg) and heptane (9 kg). The product was dried using nitrogen and vacuum to afford solid 7-chloro-6-fluoro-1-(2-isopropyl-4-methylpyridin-3-yl)pyrido[2,3-d]pyrimidine-2,4(1H,3H)-dione (rac-DIONE (Compound 4)).

Step 4

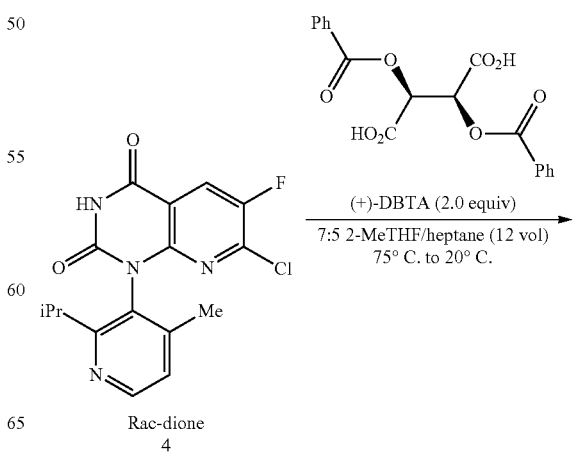

Rac-dione 4

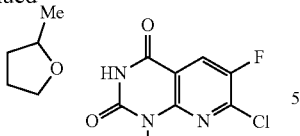
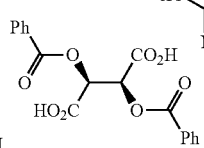
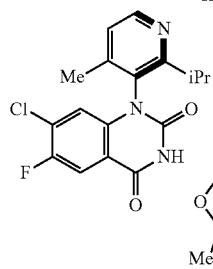

M-Dione/DBTA/2-MeTHF cocrystal
4a

| Material | CAS # | MW (g/mol) | Equivalents/ Volumes | Moles | Theoretical |
|---|---|---|---|---|---|
| Rac-dione | N/A | 348.76 | 1.0 | | |
| (+)-2,3-dibenzoyl-D-tartaric acid | 17026-42-5 | 358.30 | 2.0 | | |
| 2-methyltetrahydrofuran | 96-47-9 | 86.13 | 7.0 | | |
| heptane | 142-82-5 | 100.21 | 2.0 | | |
| heptane | 142-82-5 | 100.21 | 3.0 | | |
| 2-methyltetrahydrofuran | 96-47-9 | 86.13 | 4.0 | | |
| heptane | 142-82-5 | 100.21 | 2.0 | | |

To a vessel, an agitated suspension of Compound 4, (1.0 eq.) in 2-methylterahydrofuran (7.0 L/kg) was added (+)-2,3-dibenzoyl-D-tartaric acid (2.0 eq.) under an atmosphere of nitrogen. 2-MeTHF is chiral, but it is used as a racemic mixture. The different enantiomers of 2-MeTHF are incorporated randomly into the co-crystal. The resulting suspension was warmed to 75° C. and aged at 75° C. until full dissolution was observed (≤30 mins.). The resulting solution was polish filtered at 75° C. into a secondary vessel. To the polish filtered solution was charged n-Heptane (2.0 L/kg) at a rate that maintained the internal temperature above 65° C. The solution was then cooled to 60° C., seeded with crystals (0.01 kg/kg) and allowed to age for 30 minutes. The resulting suspension was cooled to 20° C. over 4 hours and then sampled for chiral purity analysis by HPLC. To the suspension, n-Heptane (3.0 L/kg) was charged and then aged for 4 hours at 20° C. under an atmosphere of nitrogen. The suspension was filtered, and the isolated solids were washed two times with (2:1) n-Heptane:2-methyltetrahydrofuran (3.0 L/kg). The material was dried with nitrogen and vacuum to afford M-Dione:DBTA: Me-THF complex (Compound 4a).

Step 5

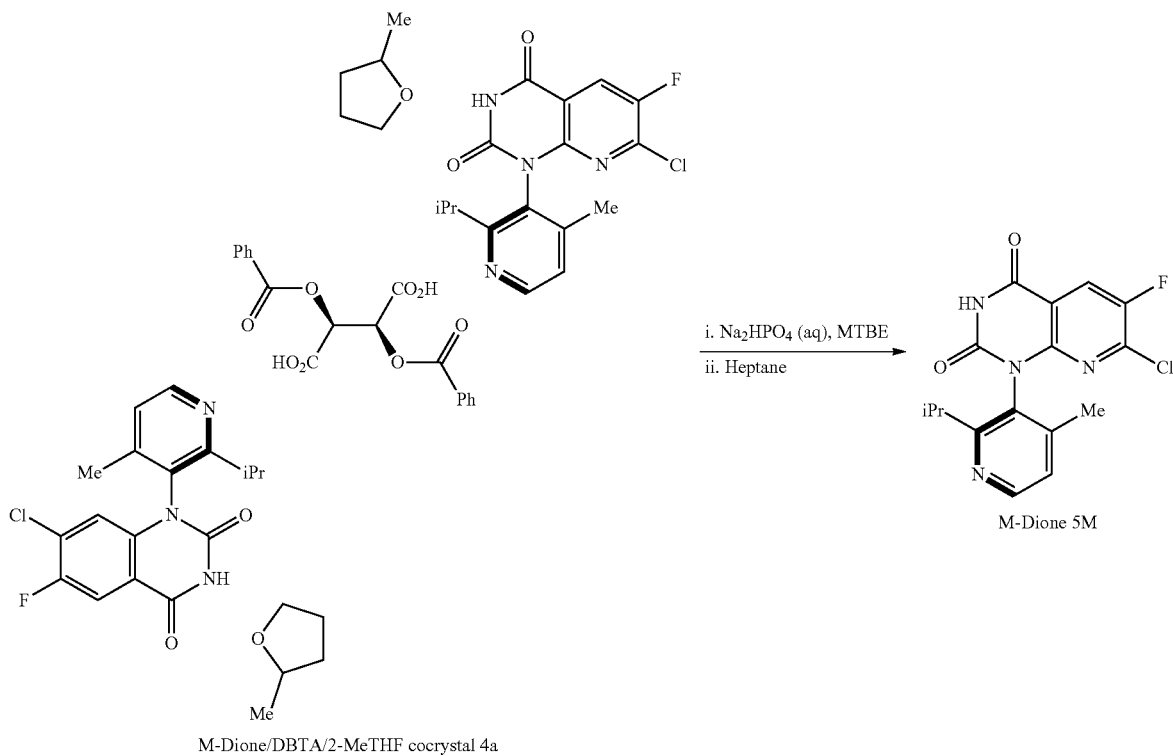

M-Dione/DBTA/2-MeTHF cocrystal 4a

| Material | CAS # | MW (g/mol) | Equivalents/ Volumes | Moles | Theoretical |
|---|---|---|---|---|---|
| M-Dione/DBTA/Me-THF cocrystal | N/A | 1228.08 | 1.0 | 74.2 | 46.9 kg (25.9 kg corrected for M-dione) |
| Methyl tert-butyl ether | 1634-04-4 | 88.15 | 45.0 | 17593 | 2100 L |
| Disodium hydrogen phosphate | 7558-79-4 | 141.96 | 2.0 | 148.4 | 21.1 kg |
| USP purified water | | | | | As needed |
| Magnesium sulfate | 7487-88-9 | 120.37 | N/A | N/A | 25 kg |
| Heptane | 142-82-5 | 100.20 | 60.0 | 19322 | 2835 L |

To vessel A, a suspension of disodium hydrogen phosphate (21.1 kg, 2.0 equiv) in DI water (296.8 L, 6.3 L/kg) was agitated until dissolution was observed (≥30 min.). To vessel B, a suspension of the M-Dione:DBTA: Me-THF complex (Composition 4a)[46.9 kg (25.9 kg corrected for M-dione, 1.0 equiv.)] in methyl tert-butyl ether (517.8 L, 11.0 L/kg) was agitated for 15 to 30 minutes. The resulting solution from vessel A was added to vessel B, and then the mixture was agitated for more than 3 hours. The agitation was stopped, and the biphasic mixture was left to separate for more than 30 minutes. The lower aqueous phase was removed and then back extracted with methyl tert-butyl ether (77.7 L, 1.7 L/kg). The organic phases were combined in vessel B and dried with magnesium sulfate (24.8 kg, 0.529 kg/kg). The resulting suspension from vessel B was agitated for more than three hours and then filtered into vessel C. To vessel B, a methyl tert-butyl ether (46.9 L, 1.0 L/kg) rinse was charged and then filtered into vessel C. The contents of vessel C were cooled to 10° C. and then distilled under vacuum while slowly being warmed to 35° C. Distillation was continued until 320-350 kg (6.8-7.5 kg/kg) of methyl tert-butyl ether was collected. After cooling the contents of vessel C to 20° C., n-Heptane (278.7 L, 5.9 L/kg) was charged over one hour and then distilled under vacuum while slowly being warmed to 35° C. Distillation was continued until a 190-200 kg (4.1-4.3 kg/kg) mixture of methyl tert-butyl ether and n-Heptane was collected. After cooling the contents of vessel C to 20° C., n-Heptane (278.7 L, 5.9 L/kg) was charged a second time over one hour and then distilled under vacuum while slowly being warmed to 35° C. Distillation was continued until a 190-200 kg (4.1-4.3 kg/kg) mixture of methyl tert-butyl ether and n-Heptane was collected. After cooling the contents of vessel C to 20° C., n-Heptane (195.9 L, 4.2 L/kg) was charged a third time over one hour and then sampled for solvent composition by GC analysis. The vessel C suspension continued to agitate for more than one hour. The suspension was filtered, and then washed with a n-Heptane (68.6 L, 1.5 L/kg) rinse from vessel C. The isolated solids were dried at 50° C., and a sample was submitted for stock suitability. Afforded 7-chloro-6-fluoro-(1M)-1-[4-methyl-2-(propan-2-yl)pyridin-3-yl]pyrido[2,3-d]pyrimidine-2,4(1H,3H)-dione (M-DIONE) Compound 5M.

The first-generation process highlighted above has been successfully scaled on 200+ kg of rac-dione starting material (Compound 5). In this process, seeding the crystallization with the thermodynamically-stable rac-dione crystal form (which exhibits low solubility) would cause a batch failure. Based on our subsequent studies, we found that increasing the DBTA equivalents and lowering the seed temperature by adjusting heptane charge schedule improves robustness of the process. The improved process is resistant to the presence of the thermodynamically-stable rac-dione crystal form and promotes successful separation of atropisomers. Subsequent batches will incorporate the improved process for large scale manufacture.

Step 6

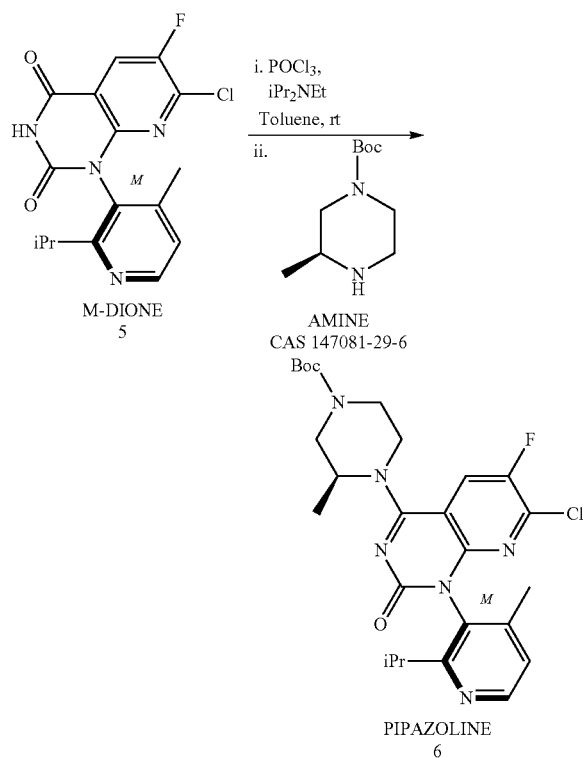

7-chloro-6-fluoro-(1M)-1-[4-methyl-2-(propan-2-yl)pyridin-3-yl]pyrido[2,3-d]pyrimidine-2,4(1H,3H)-dione (M-DIONE) (3.7 kg; 9.8 mol) was combined in reactor (A) with 10.5 kg of toluene and distilled down to an oil to remove water while maintaining a set point of 45° C. Toluene (21 kg) was added to the residue and the mixture stirred for 30 min at 40-45° C. The contents where cooled to 22° C. then phosphoryl chloride (1.8 kg; 11.7 mol) added. The mixture was cooled to 0-5° C. before adding N,N-Diisopropylethylamine (2.5 kg; 19.34 mol) while maintaining a temperature <5° C. The solution was aged for 3 h at 22° C. In a separate reactor (B), (s)-1-boc-3-methylpiperazine (2.21 kg; 10.8 mol) and N,N-diisopropylethylamine (1.26 kg; 9.75 mol)) where combined in toluene (6 kg) and then charged to reactor (A) while maintaining <25° C. The reaction mixture was aged for 15 min at 22 C then quenched with sodium bicarbonate (973 g) in water (12.9 L) while maintaining a temperature <25 C. The mixture was stirred for 30 min then DCM (36.8 kg) added while continuing to stir for 1 h. The layers were allowed to separate, and the lower organic layer drained to reactor (C). The aqueous layer in reactor (A) was back extracted using DCM (18.4 kg) and the combined organic layers washed with brine solution (6.0 kg NaCl; 16.5 kg DI water). The organic layer was distilled under atmospheric pressure maintaining an internal temperature between 45-55 C. DCM is replaced during the distillation to azeotropically dry the solution. Following the distillation, the solution volume was adjusted to 19 L using DCM. The solution was cooled to 30 C and polish filtered. The filtrate was combined with ethyl acetate (8.5 kg) and then distilled at atmospheric pressure until 11-13 kg is collected in the receiver. The solution was seeded with 30 g of authentic product and aged for 1 h at 25-30° C. then further distilled under atmospheric pressure at 45-55 C internal temperature until 8.2 kg of distillate had been collected. The slurry was cooled to 22° C. and aged overnight then further cooled to 0-5° C. The product was collected by filtration and washed twice using ethyl acetate (4.2 kg each). The cake was dried with nitrogen and vacuum to afford tert-butyl (3S)-4-{7-chloro-6-fluoro-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 6, PIPAZOLINE).

| Material | CAS # | MW (g/mol) | Equivalents/ Volumes | Moles | Theoretical |
|---|---|---|---|---|---|
| M-DIONE | N/A | 348.76 | 1 equiv. | 9.8 | 3.7 kg |
| Toluene | 108-88-3 | 92.14 | N/A | 375 | 34.6 kg (40 L) |
| Phosphoryl chloride | 10025-87-3 | 153.33 | 1.2 equiv. | 11.7 | 1.8 kg (1.1 L) |
| N,N-Diisopropylethylamine | 7087-68-5 | 129.24 | 3.0 equiv. | 29.4 | 3.8 kg (5.1 L) |
| (s)-1-Boc-3-methylpiperazine | 147081-29-6 | 200.28 | 1.1 equiv. | 10.8 | 2.214 kg |
| Sodium bicarbonate | 144-55-8 | 84.01 | N/A | N/A | 973 g |
| Dichloromethane | 75-09-2 | 84.93 | N/A | 871 | 74 kg (55.6 L) |
| Sodium Chloride | 7647-14-5 | 58.44 | N/A | 103 | 6.0 kg |
| Ethyl acetate | 141-78-6 | 88.11 | N/A | 288 | 25.4 kg (28.2 L) |

Step 7

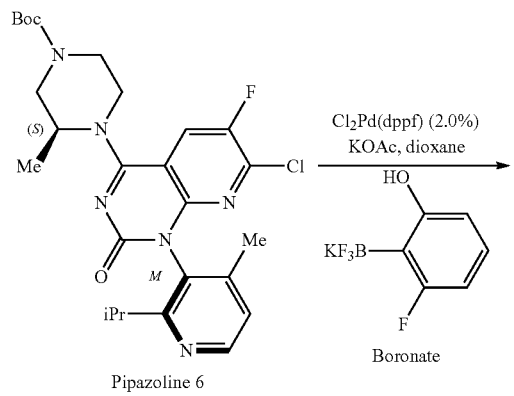

Pipazoline 6

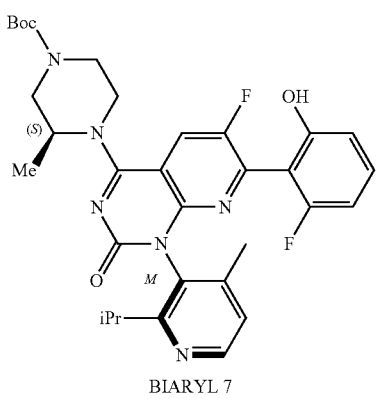

BIARYL 7

To a reactor was added degassed dioxane (74.2 kg), tert-butyl (3S)-4-{7-chloro-6-fluoro-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 6, Pipazoline) (24.0 kg, 45.2 mol), potassium acetate (22.2 kg, 45.2 mol), and (dppf)PdCl$_2$ (0.74 kg, 1.01 mol). The reactor was inerted with nitrogen gas. The solution was sparged with nitrogen gas until the oxygen content was <500 mg/L. The reaction was heated to 87.5° C. A solution of potassium trifluoro(2-fluoro-6-hydroxyphenyl)borate (12.6 kg, 54.3 mol) in degassed dioxane (49.4 kg) and degassed water (14.4 kg) with oxygen content <500 mg/L was transferred to the reaction, maintaining an internal temperature of 82.5° C.±7.5° C. The reaction was adjusted to 87.5° C.±1.5° C. and stirred for 75 min±15 min. A 1.0 M EDTA solution (47.3 kg) followed by water (40.1 kg) was charged to the reactor while maintaining an internal temperature of 85° C.±5° C. The reaction was cooled to 20° C.±3° C. over >2 h and then stirred for >16 h. The reaction was filtered and the crude solids were rinsed with water (3×120 kg). The solids were rinsed with a mixture of heptane (28.8 kg) and 2-propanol (33.1 kg) and then dried at <50° C. for >10 h. A clean reactor was loaded with crude solids and dichloromethane (240 kg). The contents were stirred at 20° C.±5° C. for >30 min. To the reactor was added Si-Thiol (144 kg) and dichloromethane (14.9 kg). The reaction was stirred at 20° C.±5° C. for 18 h. The reaction was filtered and rinsed with dichloromethane (84 kg). The solution was distilled and solvent swapped to 2-propanol. The reaction was heated to 60° C.±3° C. and heptane (108 kg) was charged while maintaining a reaction temperature of 60° C.±3° C. The reaction was stirred for 45 min and then cooled and stirred at 20° C.±5° C. for 2.5 h. The reaction was filtered and rinsed with 50% v/v heptane/2-propanol (61.9 kg). The isolated solids were dried at <50° C. for >12 h to afford tert-butyl (3S)-4-{6-fluoro-7-(2-fluoro-6-hydroxyphenyl)-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 7, BIARYL).

| Material | CAS # | MW (g/mol) | Equivalents/ Volumes | Moles | Theoretical |
|---|---|---|---|---|---|
| [1,1'-Bis(diphenylphosphino)ferrocene]dichloropalladium(II) | 72287-26-4 | 731.714 | 0.020 | 1.01 | 0.74 kg |
| Dichloromethane | 75-09-2 | 84.93 | | N/A | 400 kg |
| 1,4-Dioxane | 123-91-1 | 88.1052 | 5.0 | N/A | 168 kg |
| Ethylenediaminetetraacetic acid disodium salt dihydrate | 6381-92-6 | 336.207 | 1.0 | 45.2 | 15.2 kg |
| Heptane | 142-82-5 | 100.21 | | | 200 kg |
| Nitrogen | | | | | As needed |
| Pipazoline | N/A | 531.0 | 1.0 | 45.2 | 24.0 kg |
| Potassium acetate | 127-08-2 | 98.1417 | 5.0 | 225.99 | 22.2 kg |
| Potassium trifluoro(2-fluoro-6-hydroxyphenyl)borate | N/A | 233.03 | 1.20 | 54.24 | 12.6 kg |
| 2-Propanol | 67-63-0 | 66.10 | | N/A | 850 kg |
| Si-Thiol | N/A | N/A | | N/A | 13.2 kg |
| Sodium hydroxide | 1310-73-2 | 40.00 | | | 6.5 kg |
| USP purified water | | | | | As needed |

Step 8

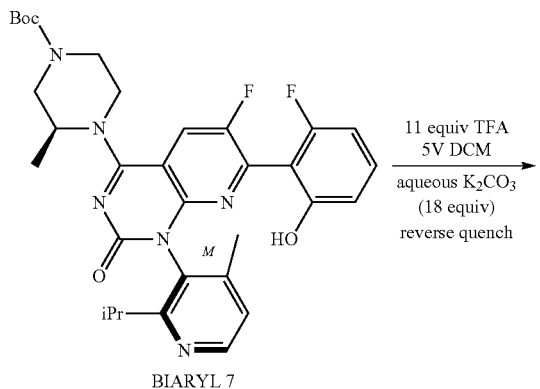

BIARYL 7

11 equiv TFA
5V DCM
aqueous K₂CO₃
(18 equiv)
reverse quench
→

Des-BOC 8

To a reactor was added tert-butyl (3S)-4-{6-fluoro-7-(2-fluoro-6-hydroxyphenyl)-(1M)-1-[4-methyl-2-(propan-2-yl)pyridin-3-yl]-2-oxo-1,2-dihydropyrido[2,3-d]pyrimidin-4-yl}-3-methylpiperazine-1-carboxylate (Compound 7, BIARYL) (2.75 kg, 5.27 mol), DCM (13.7 L), and TFA (5.67 kg, 49.7 mol). The reaction was stirred for 8-16 h at 20±5° C. To a second reactor was added potassium carbonate (11.24 kg), water (54.8 L), and methanol (13.7 L) to form a homogenous solution. The reaction mixture was added to the potassium carbonate solution over 2 h. The mixture was stirred at 20±5° C. for an additional 12 h. The resulting slurry was filtered and rinsed with water (2×27.5 L). The wet cake was dried for 24 h to give 6-fluoro-7-(2-fluoro-6-hydroxyphenyl)-4-[(2S)-2-methylpiperazin-1-yl]-(1M)-1-[4-methyl-2-(propan-2-yl)pyridin-3-yl]pyrido[2,3-d]pyrimidin-2(1H)-one (Compound 8, DESBOC).

Step 9

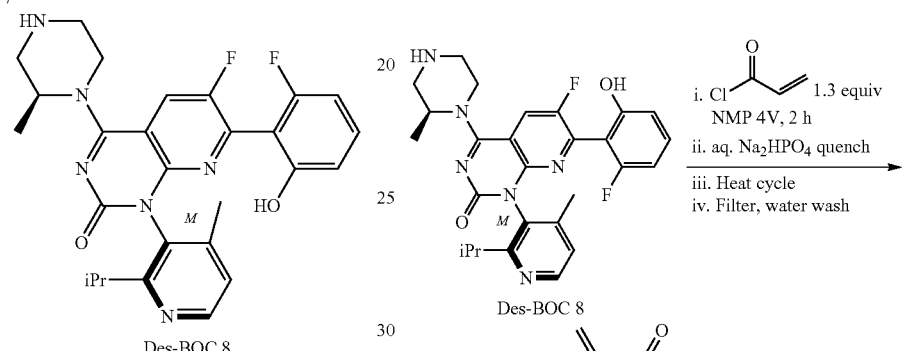

i. Cl—(acryloyl) 1.3 equiv
NMP 4V, 2 h
ii. aq. Na₂HPO₄ quench
iii. Heat cycle
iv. Filter, water wash Des-BOC 8 → Crude 9

General Note: All equivalents and volumes are reported in reference to BIARYL 7

| Material | CAS # | MW (g/mol) | Equivalents/ Volumes | Moles | Theoretical |
|---|---|---|---|---|---|
| BIARYL 7 | NA | 606.67 | 1.0 equiv. | 5.27 | 2.75 kg |
| TFA | 76-05-1 | 114.02 | 11 equiv. | 49.7 | 5.67 kg |
| DCM | 74-09-2 | 84.93 | 5 vol | NA | 13.71 L |
| Methanol | 67-56-1 | 32.04 | 5 vol | NA | 13.71 L |
| Water | 7732-18-5 | 18.02 | 20 vol | NA | 54.8 L |
| Potassium Carbonate | 584-08-7 | 138.20 | 18 equiv. | 94.91 | 11.24 kg |
| DCM | 74-09-2 | 84.93 | 1 vol | NA | 2.75 L |
| Water | 7732-18-5 | 18.02 | 10 vol | NA | 27.5 L |
| Water | 7732-18-5 | 18.02 | 10 vol | NA | 27.5 L |

General Note: All equivalents and volumes are reported in reference to Des-BOC

| Material | CAS # | MW (g/mol) | Equivalents/ Volumes | mmol | mass | volume |
|---|---|---|---|---|---|---|
| Des-BOS | NA | 506.56 | 1.0 equiv. | 308.4 | 156.25 g | — |
| Acryloyl chloride[1] | 814-68-6 | 90.51 | 1.3 equiv. | 401.0 | 36.29 g | — |
| NMP N-methyl pyrrolidinone[2] | 872-50-4 | 99.13 | 4 vol | NA | — | 625 mL |
| Water | 7732-18-5 | 18.02 | 20 vol | NA | 3125 g | 3125 mL |
| Na₂HPO₄[3] | 7558-79-4 | 141.96 | 4 equiv. | 1233.6 | 175.12 g | — |
| Water | 7732-18-5 | 18.02 | 20 vol | NA | 3125 g | 3,125 mL |

[1]acryloyl chloride was added over 7 mins on this scale. Avoid over cooling reaction. Colder reaction temperatures led to slower reaction time leading to higher levels of m/z 1066 impurity as the starting material reacts with the product. Ideal temp range is 22-25 C.
[2]NMP content of dried cake typically 1-2 wt %.
[3]Disodium phosphate in table is as anhydrous basis. Hydrate may be used, adjust mass accordingly to obtain desired mmol.

6-fluoro-7-(2-fluoro-6-hydroxyphenyl)-4-[(2S)-2-methylpiperazin-1-yl]-(1M)-1-[4-methyl-2-(propan-2-yl)pyridin-3-yl]pyrido[2,3-d]pyrimidin-2(1H)-one (Compound 8, DESBOC) (156.25 g) was combined with N-methyl pyrrolidinone (625 mL) and stirred at ambient temperature. To the resulting solution was added acryloyl chloride (36.29 g; 401.0 mmol) while maintaining <30° C. internal temperature. The contents where stirred for 2 h at 25 C. In a separate reactor a solution of disodium phosphate (175.1 g; 1234 mmol) in DI water (3.1 L) was prepared. The crude product solution was then transferred to the reactor containing the disodium phosphate solution over >2 h at 25° C. The slurry was heated to 45° C. midway through the addition and after complete addition, aged for 2 h at the same temperature. The mixture was cooled to 25 C and aged for 4 h before collecting the solids by vacuum filtration. The solids where washed twice with water (1.5 L each) and the product dried under nitrogen and vacuum to afford the product 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (crude Compound 9).[4]

[4] Results for this lead lot: 154.06 g isolated mass, 93% wt, 82.9% corrected yield, 18,000 ppm NMP Step 10

6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (crude Compound 9) (142.33 g; 253.9 mmol) was combined with ethanol (996 mL) and water (270 mL). Acetic acid (21.8 ml; 380.8 mmol) was added and the mixture heated to 75° C. to form a solution which was polish filtered into a clean reactor. The solution was cool to 45° C. and then water (1067 mL) was added while maintaining an internal temperature >40° C. The solution was seeded with authentic Compound 9 and the resulting mixture aged for 30 min. Water (1138 mL) was then added over 2 h. The mixture was cooled to 25° C. and aged for 8 h after which the solid was collected by vacuum filtration and washed using a mixture of ethanol (355.8 mL) and water (711.6 mL). The solid was dried using vacuum and nitrogen to obtain 6-fluoro-7-(2-fluoro-6-hydroxyphenyl)-(1M)-1-[4-methyl-2-(propan-2-yl)pyridin-3-yl]-4-[(2S)-2-methyl-4-(prop-2-enoyl)piperazin-1-yl]pyrido[2,3-d]pyrimidin-2(1H)-one (Compound 9).

Step A1 Reaction Scheme and Charge Table

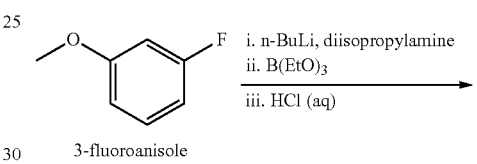

3-fluoroanisole i. n-BuLi, diisopropylamine
ii. B(EtO)$_3$
iii. HCl (aq)

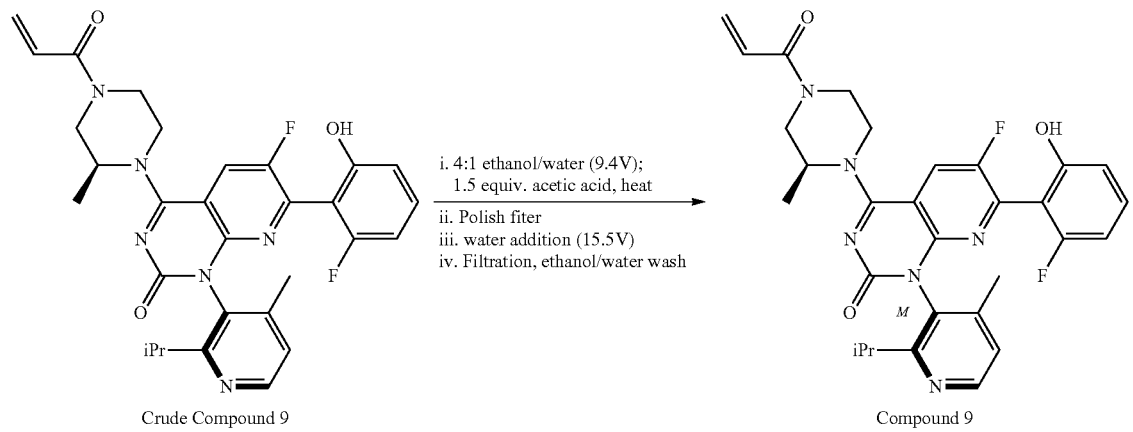

Crude Compound 9    Compound 9 i. 4:1 ethanol/water (9.4V); 1.5 equiv. acetic acid, heat
ii. Polish fiter
iii. water addition (15.5V)
iv. Filtration, ethanol/water wash General Note: All equivalents and volumes are reported in reference to crude drug substance

| Material | CAS # | MW (g/mol) | Equivalents/Volumes | mmol | mass | volume |
|---|---|---|---|---|---|---|
| Crude Compound 9 | NA | 560.60 | 1.0 equiv. | 253.9 | 142.33 g | — |
| Ethanol (200 proof) | 64-17-5 | — | 7.5 V | — | — | 1067 mL |
| USP Water | — | 18.02 | 1.9 V | — | — | 270 mL |
| Acetic acid | 64-19-7 | 60.05 | 1.5 equiv. | 380.8 | 22.87 g | 21.82 mL |
| WFI Water | — | 18.02 | 15.5 vol | — | — | 2200 mL |
| Ethanol (for wash) | 64-17-5 | — | 2.5 V | — | — | 356 mL |
| WFI Water (for wash) | — | — | 5.0 V | — | — | 712 mL |
| Compound 9 seed[5] | — | 560.60 | 0 | — | 0.3-0.7 g | — |

[5] Seed performs best when reduced in particle size via milling or with other type of mechanical grinding if mill is not available (mortar/pestle). Actual seed utilized will be based on seed availability. 0.25%-0.5% is seed is target amount.

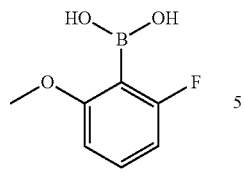

(2-fluoro-6-methoxyphenyl)
boronic acid

| Material | CAS # | MW (g/mol) | Equivalents/ Volumes | mol | Mass (g) | Volume (L) |
|---|---|---|---|---|---|---|
| 3-Fluoroanisole | 456-49-5 | 126.13 | 1.0 | 1.19 | 150 | 0.136 |
| n-butyllithium (2.5 M in hexane) | 109-72-8 | 64.06 | 1.5 | 1.78 | N/A | 0.712 |
| diisopropylamine | 108-18-9 | 101.19 | 1.4 | 1.66 | 168 | 0.233 |
| Triethylborate | 150-46-9 | 145.99 | 2.0 | 2.38 | 347.5 | 0.405 |
| Tetrahydrofuran | 109-99-9 | 72.11 | 12 vol | N/A | N/A | 1.8 |
| Hydrochloric acid (2N) | 7647-01-0 | 36.46 | 10 vol | N/A | N/A | 1.5 |
| Methyl tert-butyl ether | 1634-04-4 | 88.15 | 12 Vol | N/A | N/A | 1.8 |
| Heptane | 142-82-5 | 100.20 | 10.5 Vol | N/A | N/A | 1.575 |

Reactor A was charged with THF (6 vol) and Diisopropylamine (1.4 equiv). The resulting solution was cooled to −70° C. and n-BuLi (2.5 M in hexane, 1.5 equiv) was slowly added. After addition is complete, a solution of 3-fluoroanisole (1.0 equiv) in THF (6 vol) was added slowly and kept at −70° C. for 5 min. B(EtO)$_3$ (2.0 equiv) was added slowly and kept at −70° C. for 10 min. The reaction mixture was quenched with 2N HCl. The quenched reaction mixture was extracted with MTBE (3×4 vol). The combined organic phases were concentrated to 1.5-3 total volumes. Heptane (7-9 vol) was added drop-wise and the mixture was cooled to 0-10° C. and stirred for 3 h. The mixture was filtrated and rinsed with heptane (1.5 vol). The solid was dried under nitrogen at <30° C. to afford (2-fluoro-6-methoxyphenyl) boronic acid.

Step A2 Reaction Scheme and Charge Table

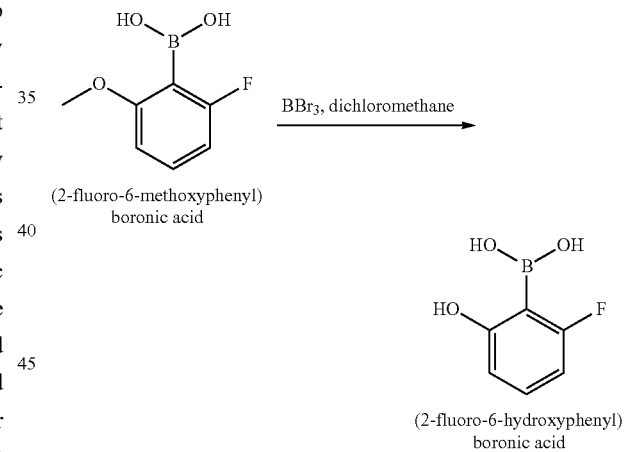

| Material | CAS # | MW (g/mol) | Equivalents/ Volumes | mol | Mass (g) | Volume (L) |
|---|---|---|---|---|---|---|
| (2-fluoro-6-methoxyphenyl) boronic acid. | 78495-63-3 | 169.95 | 1.0 | 0.118 | 20 | N/A |
| Boron tribromide | 10294-33-4 | 250.52 | 1.5 | 0.177 | 44.2 | 0.017 |
| Dichloromethane | 75-09-2 | 84.93 | 4 vol | N/A | N/A | 0.080 |
| Water | 7732-18-5 | 18.02 | 13 vol | N/A | N/A | 0.26 |
| Methyl tert-butyl ether | 1634-04-4 | 88.15 | 13 Vol | N/A | N/A | 0.26 |
| Heptane | 142-82-5 | 100.20 | 10 Vol | N/A | N/A | 0.20 |

Reactor A was charged with dichloromethane (4 vol) and 2-fluoro-6-methoxy-4-methylphenylboronic acid (1 equiv). The reaction mixture was cooled to −30° C. and 1.5 BBr3 (1.5 equiv) was added dropwise. When the addition completed, the mixture was warmed to 25° C. and stirred 2 h. The reaction mixture was quenched into ice cold (0-5° C.) water (10 vol). MTBE (10 vol) was added and the mixture warmed to 25° C. and stirred for 1-2 h or until all solids dissolved. The aqueous phase was separated and extracted with MTBE (3 vol). The combined organic extracts were washed with water (3 vol) and then concentrated to 1 total volumes. Heptane (10 vol) was added to the mixture and stirred for 2 h. The resulting product was isolated by filtration and dried at <30° C. to afford (2-fluoro-6-hydroxyphenyl)boronic acid.

Step A3 Reaction Scheme and Charge Table

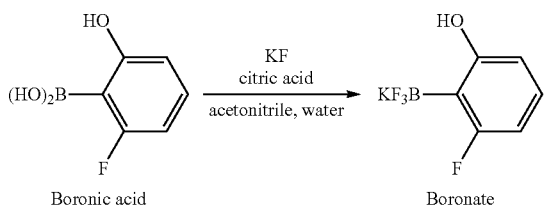

Boronic acid → Boronate

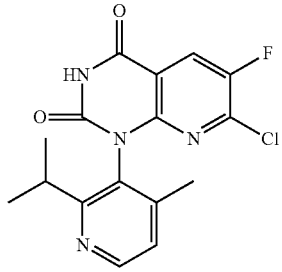

Compound 4

| Material | CAS # | MW (g/mol) | Equivalents/ Volumes | mol | Mass (kg) | Volume (L) |
|---|---|---|---|---|---|---|
| (2-fluoro-6-hydroxyphenyl) boronic acid | 1256345-60-4 | 155.92 | 1.0 | 89.79 | 14.00 | N/A |
| Citric acid monohydrate | 5949-29-1 | 210.14 | 1.64 | 147.26 | 30.94 | N/A |
| Acetonitrile | 75-05-8 | 41.05 | 21 Vol | N/A | 220.1 | 294 |
| Potassium fluoride | 7789-23-3 | 58.10 | 4.00 | 359.16 | 20.87 | N/A |
| USP Water | 7732-18-5 | 18.02 | 2.0 Vol | N/A | 28.00 | 28.00 |
| Celite | N/A | N/A | N/A | N/A | 7.00 | N/A |
| 2-Propanol | 67-63-0 | 60.10 | 25 Vol | N/A | 275 | 350 |

Step A3

Potassium Fluoride (21.0 kg; 20.87 mol) was combined with water (28 L) in a reactor (reactor A) and the contents stirred for 30 min. In a separate reactor (reactor B), (2-fluoro-6-hydroxyphenyl)boronic acid (14.00 kg, 89.79 mol) was charged followed by acetonitrile (206.1 kg) and citric acid (30.94 kg; 147.26 mol) at 25 C. The contents of reactor A was added to reactor B at 25C and stirred at that temperature for 10 h. The reaction mixture was filtered through a bed of celite (7.0 kg) and rinsed with acetonitrile (42 kg). The filtrate was combined with isopropanol (56 kg) and then distilled under vacuum at a temperature <35° C. replacing the distilled volume to the reactor with isopropanol and repeated as needed to complete the solvent swap from acetonitrile to isopropanol. The slurry was cooled to 15C and aged for 1 h before filtered and washing with 28 kg of isopropanol. The cake was dried using vacuum and nitrogen and packaged to afford Compound A3.

Resolution of the M-Dione Compound 5

Chromatographic Resolution of M-Dione Intermediate

Numerous chiral chromatographic techniques and methods were used to isolate the M-dione from Compound 4. The techniques and stationary phases are well known in the art and are outlined in Table 1.

TABLE 1

| Technique | Stationary Phase | Mobile Phase | Yield^ |
|---|---|---|---|
| SFC | Chiralpak ® AD | 40% methanol/60% CO2 * | ~95% |
| HPLC | Chiralpak ® AD | 90/10/0.1 ethanol/ methanol/ triethylamine | ~94% |
| HPLC | Chiralpak ® IG | 60/40/0.1 ethanol/ methanol/ Triethylamine | ~92% |

TABLE 1-continued

| Technique | Stationary Phase | Mobile Phase | Yield^ |
|---|---|---|---|
| Simulated Moving Bed (SMB) | Chiralpak ® IC | Acetonitrile | ~96% |

^Yield is defined as % of available M-Dione that was recovered at the required purity of >98% ee.
* This separation was performed multiple times. For each lot of material, the mobile phase may have been slightly modified to accommodate for variations in the lots. Additional mobile phases used for purification included:
1) 25/75 methanol/CO₂,
2) 30/70 methanol/CO₂, and
3) 50/50 methanol/CO₂.
The SFC, HPLC, and SMB techniques are well known in the art and the Chiralpak ® stationary phases are commercially available from commercial sources, such as Fisher Scientific and Daicel Corporation.

However, it is desired to develop a more efficient process to isolate the M-Dione (Compound 5).

Classical Resolution

The present invention is directed to the development of a viable classical resolution process for M/P-Dione racemate (Compound 4).

A total of 100 cocrystal screening experiments were performed and three potential cocrystals of Dione were identified. Based on the highest area ratio of M/P-Dione in the residual solid and lowest area ratio in the supernatant, (+)-2,3-dibenzoyl-D-tartaric acid (DBTA) was selected as the chiral reagent for resolution.

According to the results from 100 cocrystal screening experiments and 20 more solvent screening, 2-MeTHF/n-heptane was found to provide a better resolution result than other solvent systems. Based on the solubility results of M-Dione cocrystal and P-Dione cocrystal in different ratios of 2-MeTHF and n-heptane, 2-MeTHF/n-heptane (1.4:1, v/v) was selected as the optimal solvent composition for resolution.

In order to find out any possible form conversion to Dione racemate or M/P-Dione during crystallization process of chiral resolution, the solubility of M-Dione cocrystal, P-Dione cocrystal, M+P-Dione cocrystal mixture (1:1, w/w), Dione racemate and DBTA were determined at different temperatures in 2-MeTHF/n-heptane (1.4:1, v/v). No form change was observed for M-Dione cocrystal and P-Dione cocrystal at different temperatures for 7 days. However, Dione racemate Type C was obtained after stirring of a mixture of M+P-Dione cocrystal mixture (1:1, w/w) at different temperatures for 7 days. Dione racemate Type D (20 and 30° C.) or Dione racemate Type C (40, 50, 60 and 65° C.) were observed after stirring of Dione racemate at corresponding temperatures for 7 days. A solubility of ~100 mg/mL was observed under all the temperatures for DBTA.

To further optimize the resolution process, the ternary phase diagram of M/P-Dione cocrystal was drawn based on the equilibrium solubility results and no eutectic point was obtained likely because racemate Type C could crystallize out when both M-Dione cocrystal and P-Dione cocrystal were present. Another ternary phase diagram of M/P-Dione was drawn based on the equilibrium solubility results and no eutectic point was obtained likely because Dione racemate Type C or Type D could crystallize out when both M-Dione and P-Dione were present.

In summary, a chiral reagent (DBTA) and a solvent system ((2-MeTHF/n-heptane (1.4:1, v/v)) were identified for resolution of Dione racemate. Small scale crystallization process using the resolving reagent and solvent system could achieve a yield of 39% and ee purity of 99% for M-Dione. In addition, polymorphism of Dione racemate was observed and investigated during screening experiments.

2 Screening Experiment 2.1 Cocrystal Screening

Figures 1, 2:
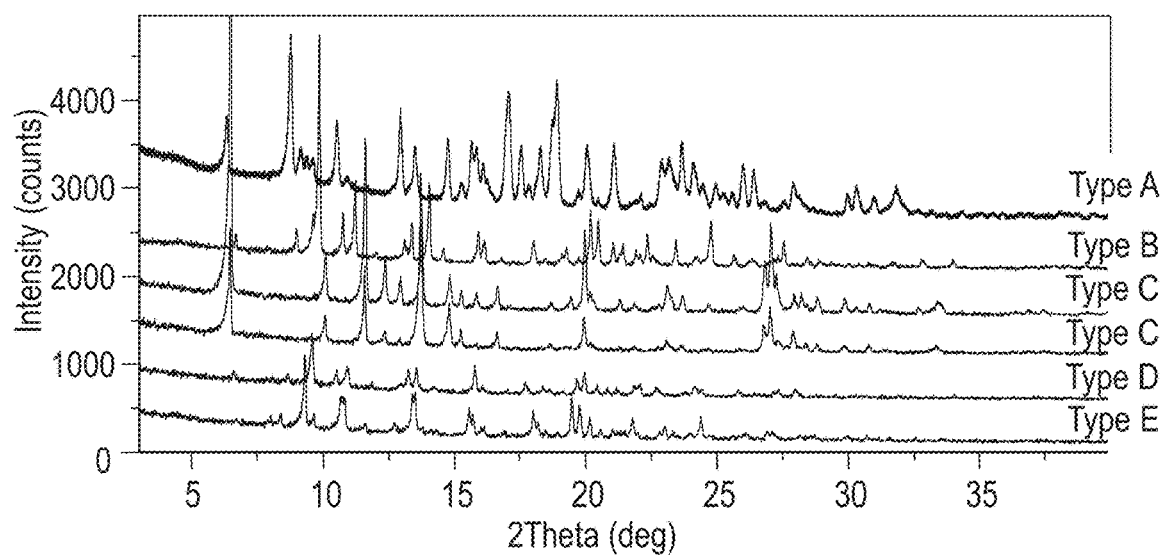
Figure 2:
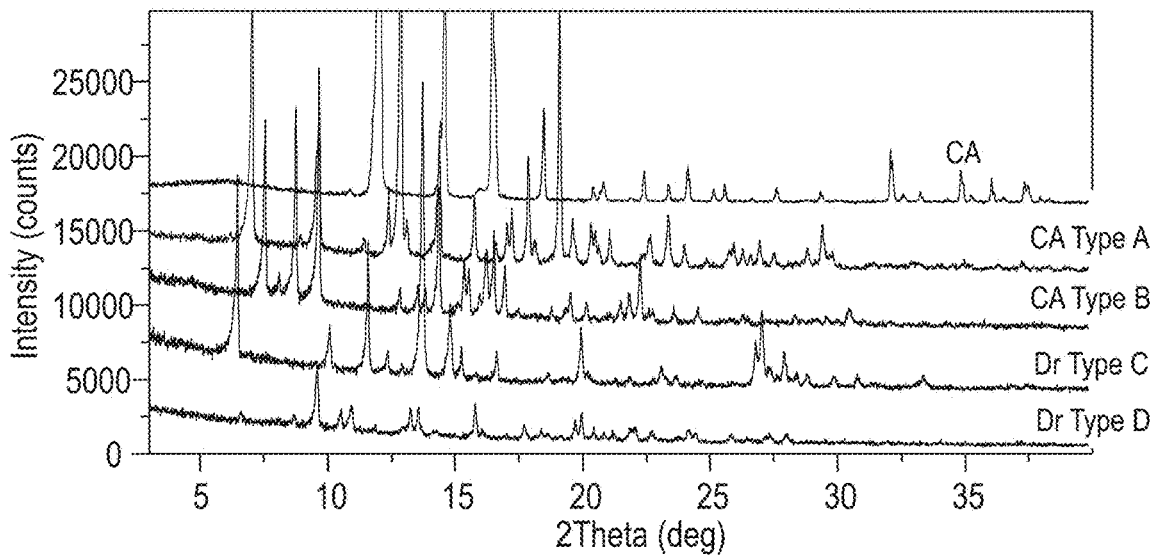
Figures 2, 3:
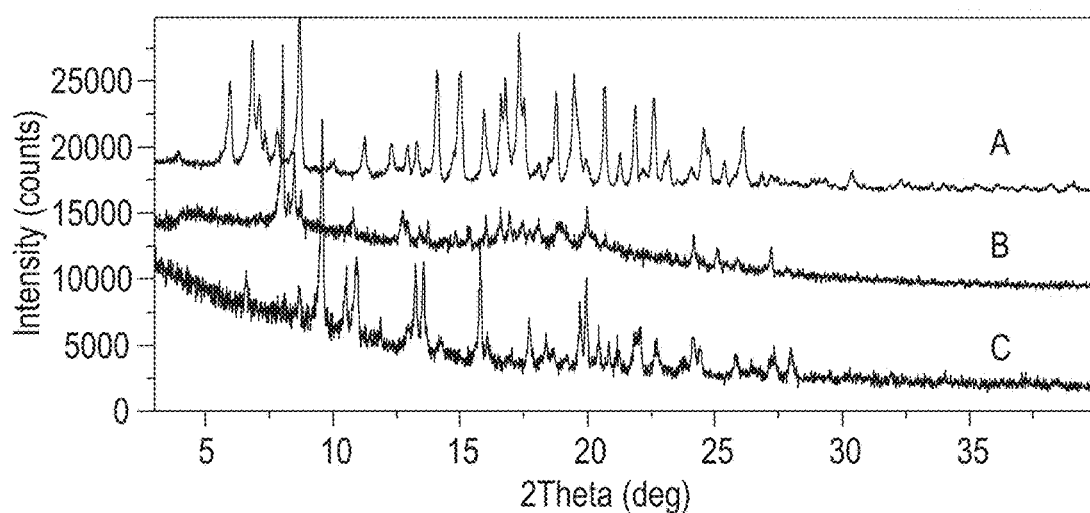
Figures 2, 3, 4:
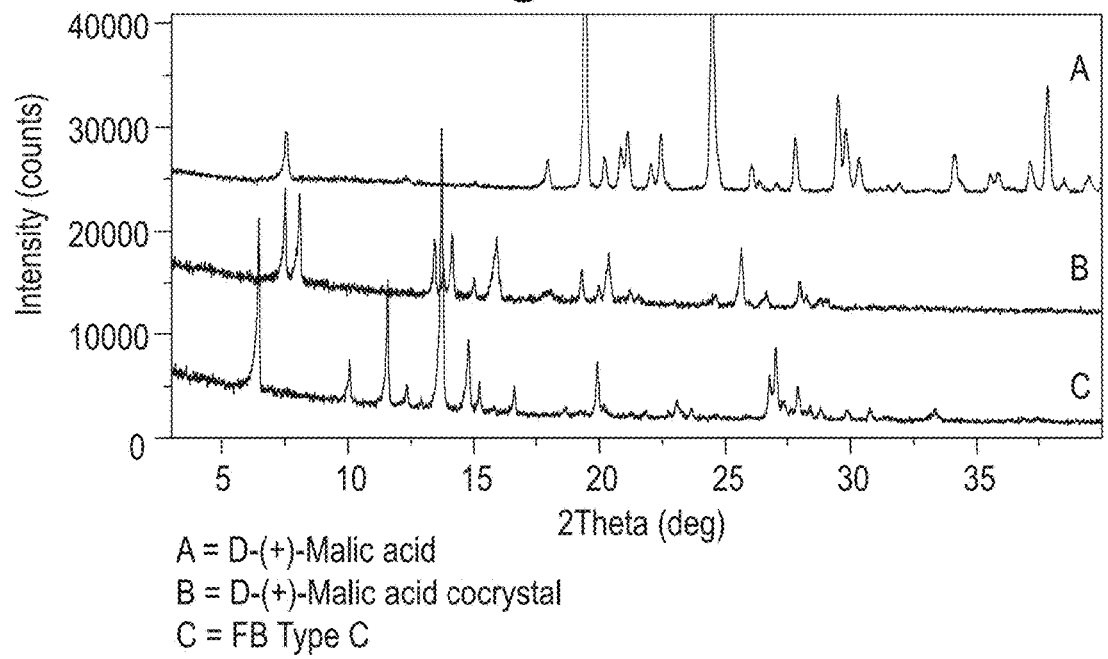

A total of 100 cocrystal screening experiments were performed using 20 acids and 5 solvent systems (Results summarized in Table 2-1). In general, Dione racemate and acid in the molar ratio at 1:1 was mixed and stirred at RT for 3 days before isolation for XRPD. Based on the XRPD results, three potential acids that could form cocrystals of Dione racemate were identified, including (1S)-(−)-camphanic acid (FIG. 2-2), (+)-2,3-dibenzoyl-D-tartaric acid (FIG. 2-3) and D-(+)-malic acid (FIG. 2-4). Four new freebase crystal forms were also obtained based on XRPD results, which were assigned as Dione racemate Type B~E.

As showed in Table 2-2, the supernatant and residual solid of the three potential cocrystals were further tested by HPLC. The ratio of M-Dione/P-Dione was measured and summarized in Table 2-2. As a result, DBTA cocrystal showed an area ratio of M-Dione/P-Dione at 0.11 in the supernatant and 4.4 in the residual solid, which suggested that M-Dione and P-Dione showed a good resolution after forming cocrystal with DBTA. Thus, DBTA was selected as the chiral reagent for further resolution optimization.

TABLE 2-1

Summary of cocrystal screening experiments

| Solvent<br>Acid | Acetone | H₂O/ACN<br>(1:1, v/v) | EtOAc | 2-MeTHF/<br>n-heptane<br>(1:1, v/v) | MTBE/<br>n-heptane<br>(1:1, v/v) |
|---|---|---|---|---|---|
| blank | Type B⁺ | Type C⁺ | Type C⁺ | Type D⁺ | Type E⁺ |
| L-Aspartic acid | Type B | Type C | Type C + acid | Type D | Type E |
| (R)-1,4-Benzodioxane-2-carboxylic acid | Type B | Type C | Type C | Type D | Type E + acid |
| (1S)-(−)-Camphanic acid | Type B | Type C | Cocrystal Type A* | Cocrystal Type B* | Cocrystal Type A* |
| (−)-Camphoric acid | Type B | Type C + acid | Type C + acid | Type D | Type E + acid |
| (+)-2,3-Dibenzoyl-D-tartaric acid | Type B | Type C | Amorphous | Cocrystal Type A# | Cocrystal Type A# |
| D-Glutamic acid | Type B | Type C | Type C + acid | Type D | Type E |
| D-(+)-Malic acid | Type B | Type C | Cocrystal Type A$ | Type D | Type E |
| (R)-(−)-Mandelic acid | Type B | Type C | Type C | Type D | Type E + acid |
| (−)-Menthyloxyacetic acid | Type B | Type C | Type C | Type D | Type E |
| (S)-(+)-α-Methoxyphenylacetic acid | Type B | Type C | Type C | Type D | Type E |
| (R)-(+)-α-Methoxy-α-trifluoromethylphenylacetic acid | Type B | Type C | Type C | Type D | Type E |
| (R)-(−)-5-Oxo-2-tetrahydrofurancarboxylic acid | Type B | Type C | Type C | Type D | Type E |
| (R)-(+)-N-(1-Phenylethyl)succinamic acid | Type B | Type C | Type C | Type D | Type E + acid |
| (S)-(+)-2-Phenylpropionic acid | Type B | Type C | Type C | Type D | Type E |
| L-Pyroglutamic acid | Type B | Type C | Type C | Type D | Type E + acid |
| D-(−)-Quinic acid | Type B + acid | Type C | Type C + acid | Type D + acid | Type E + acid |
| L-(+)-Tartaric acid | Type B | Type C | Type C | Type D | Type E |
| L-Ascorbic acid | Type B+acid | Type C | Type C+30acid | Type D | Type E |

TABLE 2-1-continued

Summary of cocrystal screening experiments

| Solvent<br>Acid | Acetone | H₂O/ACN<br>(1:1, v/v) | EtOAc | 2-MeTHF/<br>n-heptane<br>(1:1, v/v) | MTBE/<br>n-heptane<br>(1:1, v/v) |
|---|---|---|---|---|---|
| N,N-Bis[(R)-(−)-1-phenylethyl]phthalamic acid | Type B | Type C | Type C | Type D | Type E + acid |
| (S)-phenylsuccinic acid | Type B | Type C | Type C + acid | Type D | Type E + acid |

†Denotes crystal form of free rac-dione (no co-crystal formed),
*(1S)-(−)-Camphanic acid cocrystal,
(+)-2,3-Dibenzoyl-D-tartaric acid cocrystal,
$D-(+)-Malic acid cocrystal

TABLE 2-2

HPLC data summary of three cocrystals

| | Peak area | | | | | |
|---|---|---|---|---|---|---|
| | Supernatant | | | Solid | | |
| Sample | P-Dione (area) | M-Dione (area) | M/P | P-Dione (area) | M-Dione (area) | M/P |
| (1S)-(−)-Camphanic acid cocrystal Type A (810465-06-C3) | 9021.4 | 8274.2 | 0.9 | 6418.6 | 6360.4 | 1.0 |
| (1S)-(−)-Camphanic acid cocrystal Type B (810465-06-D3) | 4673.2 | 4303.4 | 0.9 | 4768.3 | 4736.9 | 1.0 |
| DBTA cocrystal Type A (810465-06-D5) | 17673.1 | 1858.6 | 0.11 | 1180.2 | 5249.8 | 4.4 |
| D-(+)-Malic acid cocrystal Type A (810465-06-C7) | 11382.6 | 10696.5 | 0.9 | 6443.3 | 6366.7 | 1.0 |

2.2 Solvent Screening

To select a suitable solvent to further resolute M-Dione and P-Dione, the area ratio from HPLC of M/P-Dione was collected in 20 more solvent/solvent mixtures. As listed in Table 2-3, 2-MeTHF showed the best resolution with the M-Dione/P-Dione area ratio of 0.7 in the supernatant and 4.1 in the residual solid. However, 2-MeTHF/n-heptane (1:1, v/v) showed a better resolution result during cocrystal screening (Table 2-2), thus 2-MeTHF/n-heptane was selected for further optimization. The area ratio from HPLC of M/P-Dione was collected in different ratios of 2-MeTHF/n-heptane with different acid/base ratios. Results in Table 2-4 showed that higher ratio of acid/FB (2:1 or 1.5:1) in 2-MeTHF/n-heptane (8:1 or 4:1, v/v) is desirable to improve the ratio of M/P-Dione in isolated solids.

The solubility of M-cocrystal and P-cocrystal in different ratios of 2-MeTHF/n-heptane was also performed at 5 and 25° C., which were summarized in Table 2-5. M-cocrystal was provided by client and P-cocrystal was prepared via reverse anti-solvent and anti-solvent (the experimental details refer to Section 4.3). The solubility result in Table 2-5 showed that the volume ratio of 2-MeTHF/n-heptane at 1.5:1 could afford the best resolution at RT. More resolution experiments were performed by client, from which a volume ratio of 1.4:1 showed the best resolution result. Thus, the volume ratio of 2-MeTHF/n-heptane at 1.4:1 was selected as the solvent system for resolution.

TABLE 2-3

Solvent screening of Dione racemate DBTA cocrystal
(M-Dione/P-Dione area ratio)

| Solvent | Supernatant | Solid | Solvent | Supernatant | Solid |
|---|---|---|---|---|---|
| 2-MeTHF | 0.7 | 4.1 | DMSO/n-heptane (1:1, v/v) | NA | NA |
| MTBE | 0.04 | 3.5 | DMF/n-heptane (1:1, v/v) | 0.9 | 1.0 |
| MeOH | 0.9 | 1.0 | Toluene/n-heptane (1:1, v/v) | 0.8 | 1.0 |
| IPA | 1.0 | 1.0 | Acetic acid | NA | NA |
| EtOH/n-heptane (1:1, v/v) | 0.9 | 1.0 | Formic acid | NA | NA |
| MIBK | 0.9 | 1.0 | DCM | NA | NA |
| MEK | 1.0 | 1.0 | Cumene | 0.9 | 1.0 |
| IPAc | 0.9 | 1.0 | 1-Butanol | 0.9 | 1.0 |
| THF | NA | NA | n-Propanol | 0.9 | 1.0 |
| NMP | NA | NA | 1,3-Dimethyl-2-imidazolidinone | 0.9 | 1.0 |

NA: A clear solution was obtained and no solid was isolated.

TABLE 2-4

Results of acid/base ratio and 2-MeTHF/n-heptane ratio screening with Dione racemate DBTA cocrystal (M-Dione/P-Dione area ratio)

| 2-MeTHF/n-heptane (v/v) | Acid/base ratio | | | | | | | | | | | |
|---|---|---|---|---|---|---|---|---|---|---|---|---|
| | 2:1 | | | 1.5:1 | | | 1:1.5 | | | 1:2 | | |
| | Form | L | S | Form | L | S | Form | L | S | Form | L | S |
| 8:1 | CA | 0.4 | 13.4 | CA | 0.4 | 8.9 | CA | 0.5 | 7.0 | CA | 0.6 | 2.6 |
| 4:1 | CA | 0.3 | 8.7 | CA | 0.3 | 6.2 | CA | 0.4 | 6.2 | CA | 0.4 | 5.7 |
| 2:1 | CA | 0.2 | 6.0 | CA | 0.2 | 5.6 | CA | 0.2 | 4.7 | CA | 0.2 | 5.2 |
| 1:2 | CA | 0.3 | 1.2 | CA | 0.1 | 1.3 | CA | 0.1 | 1.4 | CA | 0.1 | 1.7 |
| 1:4 | DA | 1.4 | 1.0 | CA | 0.4 | 1.0 | CA + DA | 0.1 | 1.0 | CA | 0.1 | 1.0 |
| 1:8 | CA + DA | 0.9 | 1.0 | DA | 0.5 | 1.0 | DA | 0.3 | 1.0 | DA | 0.3 | 1.0 |

L: Supernatant,
S: Solid,
CA: Cocrystal Type A,
DA: Dione racemate Type A

TABLE 2-5

2-MeTHF/n-heptane ratio screening of M/P-Dione cocrystals

| Temperature (° C.) | 2-MeTHF/n-heptane (v/v) | M-Dione cocrystal | | P-Dione cocrystal | |
|---|---|---|---|---|---|
| | | Solubility (mg/mL) | XRPD | Solubility (mg/mL) | XRPD |
| 5 | 1:1 | 11.3 | Type A* | 38.5 | Type A# |
| | 1.5:1 | 17.3 | Type A* | 60.8 | Type A# |
| | 2:1 | 22.2 | Type A* | 66.9 | Type A# |
| | 3:1 | 28.6 | Type A* | 86.6 | Type A# |
| | 4:1 | 30.8 | Type A* | 82.9 | Type A# |
| | 6:1 | 47.1 | Type A* | 92.1 | NA |
| | 8:1 | 55.1 | Type A* | 90.6 | NA |
| 25 | 1:1 | 13.4 | Type A* | 52.9 | Type A# |
| | 1.5:1 | 20.3 | Type A* | 80.8 | Type A# |
| | 2:1 | 28.1 | Type A* | 81.7 | Type A# |
| | 3:1 | 39.0 | Type A* | 87.0 | NA |
| | 4:1 | 43.0 | Type A* | 86.5 | NA |
| | 6:1 | 53.2 | Type A* | 81.9 | NA |
| | 8:1 | 65.0 | Type A* | 89.2 | NA |

*M-cocrystal Type A
P-cocrystal Type A

2.3 Solubility of Dione DBTA Cocrystal, Dione Racemate and DBTA

The 7-day equilibrium solubility of M-Dione cocrystal, P-Dione cocrystal, M+P-Dione cocrystal mixture (1:1, w/w) and Dione racemate were set up at different temperatures (20, 30, 40, 50, 60, 65, 75 and 80° C.) in 2-MeTHF/n-heptane (1.4:1, v/v). Color change was observed at 75 and 80° C. after 5 days suggestive of degradation, so the solubility was not collected. No form change was observed upon stirring of M-cocrystal and P-cocrystal at different temperatures for 7 days (FIG. 2-5 and FIG. 2-6). Dione racemate Type C was obtained after stirring of a mixture of M-Dione cocrystal and P-Dione cocrystal mixture (1:1, w/w) at different temperatures for 7 days (FIG. 2-7). Dione racemate Type D (20 and 30° C.) and Dione racemate Type C (40, 50, 60 and 65° C.) were observed after stirring of Dione racemate at different temperature for 7 days (FIG. 2-8 and FIG. 2-9).

The 5-day equilibrium solubility of DBTA was set up at different temperatures (20, 30, 40, 50, 60 and 65° C.) in 2-MeTHF/n-heptane (1.4:1, v/v). A solubility of ~100 mg/mL was observed under all the temperatures. No significant difference was observed with varying temperatures (Table 2-7).

TABLE 2-6

Solubility of Dione DBTA cocrystal, mixture of M/P-Dione cocrystal, Dione racemate in 2-MeTHF/n-heptane (1.4:1, v/v)

| Sample ID | Material | Temperature (° C.) | Solubility (mg/mL) M-Dione | Solubility (mg/mL) P-Dione | Crystal Form |
|---|---|---|---|---|---|
| 1-01-A1 | M-Dione cocrystal | 20 | 13.1 | — | M-cocrystal Type A |
| 1-01-A2 | | 30 | 15.8 | — | M-cocrystal Type A |
| 1-01-A3 | | 40 | 18.4 | — | M-cocrystal Type A |
| 1-01-A4 | | 50 | 17.2 | — | M-cocrystal Type A |
| 1-01-A5 | | 60 | 34.6 | — | M-cocrystal Type A |
| 1-01-A6 | | 65 | 35.4 | — | M-cocrystal Type A |
| 1-01-B1 | P-Dione, cocrystal | 20 | — | 39.4 | P-cocrystal Type A |
| 1-01-B2 | | 30 | — | 56.5 | P-cocrystal Type A |
| 1-01-B3 | | 40 | — | 55.8 | P-cocrystal Type A |
| 1-01-B4 | | 50 | — | 79.9 | P-cocrystal Type A |
| 1-01-B5 | | 60 | — | 113.9 | P-cocrystal Type A |
| 1-01-B6 | | 65 | — | 110.0 | P-cocrystal Type A |
| 1-01-C1 | M + P- Dione cocrystal mixture | 20 | 7.3 | 10.4 | Dione racemate Type C |
| 1-01-C2 | | 30 | 9.2 | 16.0 | Dione racemate Type C |
| 1-01-C3 | | 40 | 9.8 | 12.2 | Dione racemate Type C |
| 1-01-C4 | | 50 | 12.1 | 21.9 | Dione racemate Type C |
| 1-01-C5 | | 60 | 18.7 | 26.7 | Dione racemate Type C |
| 1-01-C6 | | 65 | 13.4* | 18.0* | Dione racemate Type C |
| 1-01-D1 | Dione racemate | 20 | 18.0 | 15.2 | Dione racemate Type C |
| 1-01-D2 | | 30 | 20.1 | 17.1 | Dione racemate Type C |
| 1-01-D3 | | 40 | 11.5 | 9.9 | Dione racemate Type C |
| 1-01-D4 | | 50 | 14.2 | 11.8 | Dione racemate Type C |
| 1-01-D5 | | 60 | 13.7 | 11.7 | Dione racemate Type C |
| 1-01-D6 | | 65 | 15.3 | 13.1 | Dione racemate Type C |

TABLE 2-7

Solubility of DBTA in 2-MeTHF/n-heptane (1.4:1, v/v)

| Sample ID | Temperature (° C.) | Solubility (mg/mL) |
|---|---|---|
| 1-15-A1 | 20 | 99.1 |
| 1-15-A2 | 30 | 100.3 |

TABLE 2-7-continued

Solubility of DBTA in 2-MeTHF/n-heptane (1.4:1, v/v)

| Sample ID | Temperature (° C.) | Solubility (mg/mL) |
|---|---|---|
| 1-15-A3 | 40 | 98.9 |
| 1-15-A4 | 50 | 88.0 |
| 1-15-A5 | 60 | 105.0 |
| 1-15-A6 | 65 | 96.1 |

2.4 Ternary Phase Diagram 2.4.1 M/P-Dione Cocrystals

M-Dione cocrystal and P-Dione cocrystal were weighed as corresponding mass listed in the Table 2-8 and were stirred in 2-MeTHF/n-heptane (1.4:1, v/v) at RT for 72 hours. The ternary phase diagram of M/P-Dione cocrystal was drawn based on 72-hour equilibrium solubility data and no eutectic point was obtained (FIG. 2-10).

TABLE 2-8

Solubility data summary for M/P-Dione cocrystals

| # | Weight of M-cocrystal (mg) | Weight of P-cocrystal (mg) | de (%) | Supernatant [M] mg/mL | [P] mg/mL | de (%) | [M]/[P] | Solid M mg | P mg | de (%) |
|---|---|---|---|---|---|---|---|---|---|---|
| 1 | 50.7 | 0 | 100.0 | 22.9 | 0.0 | 100.0 | NA | 27.8 | 0.0 | 100.0 |
| 2 | 0 | 99.7 | −100.0 | 0.0 | 81.2 | −100.0 | NA | 0.0 | 18.5 | −100.0 |
| 3 | 21.1 | 83.4 | −59.6 | 5.1 | 59.4 | −84.2 | 11.680 | 16.0 | 24.0 | −20.0 |
| 4 | 41 | 83.5 | −34.1 | 5.9 | 45.0 | −76.9 | 7.658 | 35.1 | 38.5 | −4.6 |
| 5 | 84 | 85 | −0.6 | 11.5 | 23.7 | −34.9 | 2.070 | 72.5 | 61.3 | 8.4 |
| 6 | 167.7 | 83.1 | 33.7 | 12.2 | 20.8 | −26.2 | 1.711 | 155.5 | 62.3 | 42.8 |
| 7 | 49.7 | 50.4 | −0.7 | 17.5 | 40.8 | −40.0 | 2.331 | 32.2 | 9.6 | 54.1 |
| 8 | 49.7 | 25 | 33.1 | 19.9 | 21.8 | −4.6 | 1.095 | 29.8 | 3.2 | 80.7 |
| 9 | 49.2 | 12.2 | 60.3 | 21.3 | 9.6 | 37.9 | 0.451 | 27.9 | 2.6 | 82.9 |

2.4.2 M/P-Dione

M-Dione and P-Dione were weighed as corresponding mass listed in the Table 2-9 and were stirring in 2-MeTHF/n-heptane (1.4:1, v/v) at RT for 5 days. The ternary phase diagram was drawn based on 5-day equilibrium solubility data in 1.0 mL of 2-MeTHF/n-heptane (1.4:1, v/v) at RT. M-Dione Type A, P-Dione Type A, Dione racemate Type C and Type D were observed in the residual solid of solubility samples. No eutectic points were obtained in the phase diagram (FIG. 2-11).

TABLE 2-9

Data summary of Ternary Phase Diagram for M/P-Dione

| # | Weight of M-Dione (mg) | Weight of P-Dione (mg) | de (%) | Supernatant [M] mg/mL | [P] mg/mL | de (%) | [M]/[P] | Solid M mg | P mg | de (%) | XRPD |
|---|---|---|---|---|---|---|---|---|---|---|---|
| 1 | 99.3 | 0 | 100.0 | 80.1 | 0 | 100.0 | NA | 19.2 | 0.0 | 100.0 | A |
| 2 | 0 | 100.6 | −100.0 | 0 | 77.1 | −100.0 | NA | 0.0 | 23.5 | −100.0 | A |
| 3 | 20.2 | 119.3 | −71.0 | 7.7 | 50.3 | −73.6 | 0.2 | 12.5 | 69.0 | −69.2 | A + RD |
| 4 | 89.8 | 90.3 | −0.3 | 16.2 | 17.5 | −3.9 | 0.9 | 73.6 | 72.8 | 0.6 | RD |
| 5 | 121.1 | 40.7 | 49.7 | 53.0 | 1.6 | 94.2 | 33.4 | 68.1 | 39.1 | 27.0 | A + RC |
| 6 | 90.2 | 19.5 | 64.4 | 52.6 | 1.4 | 94.8 | 37.6 | 37.6 | 18.1 | 35.0 | A + RC |
| 7 | 41.6 | 39.9 | 2.1 | 9.8 | 9.0 | 4.4 | 1.1 | 31.8 | 30.9 | 1.4 | RC |
| 8 | 39.2 | 120.3 | −50.8 | 7.6 | 48.1 | −72.8 | 0.2 | 31.6 | 72.2 | −39.1 | A + RD |
| 9 | 119.1 | 20.5 | 70.6 | 54.1 | 1.6 | 94.4 | 34.5 | 65.0 | 18.9 | 54.9 | A + RC |

RC: Dione racemate Type C;

RD: Dione racemate Type D;

A: M or P-Dione Type A (the XRPD patterns of M-Dione Type A and P-Dione Type A were same and were not distinguished).

3 Solid State Characterization of Crystal Forms

A total of five Dione racemate crystal forms and two cocrystal forms were obtained. All these forms were characterized by XRPD, TGA, DSC, PLM and $^1$H NMR and summarized in Table 2-10. The solid state characterization data suggested Dione racemate Type A and Type D were identified as 2-MeTHF solvates, Type B as an acetone solvate, Type C as an anhydrate, and Type E as a MTBE solvate.

Both M-Dione cocrystal Type A and P-Dione cocrystal Type A were found to be as 2-MeTHF solvates. All the characterization data are demonstrated in FIG. 3-1 to FIG. 3-22.

TABLE 2-10

Summary of crystal forms

| Sample ID | Crystal form | Endotherm (peak, ° C.) | TGA (wt %) | $^1$H NMR (wt %) |
|---|---|---|---|---|
| 5-05-A | Dione racemate Type A | 110.2, 248.6, 213.4* | 2.5 (150° C.) | 2.4 (2-MeTHF) |
| 1-10-A1 | Dione racemate Type B | 113.4, 126.0, 250.9 | 9.8 (150° C.) | 6.2 (acetone) |
| 1-01-D5 | Dione racemate Type C | 251.9 | 3.0 (150° C.) | ND[&] |
| 1-01-D1 | Dione racemate Type D | 120.5, 253.3 | 15.4 (150° C.) | 12.0 (2-MeTHF) |
| 1-10-A4 | Dione racemate Type E | 151.6, 158.6, 248.7 | 14.7 (160° C.) | 7.5 (MTBE) |
| 5-17-A | M-Dione cocrystal Type A | 109.6, 119.2 | 6.6 (125° C.) | 10.6 (2-MeTHF) |
| 5-16-A | P-Dione cocrystal Type A | 88.3, 112.3, 132.8 | 9.2 (140° C.) | 10.6 (2-MeTHF) |

*exothermic peak;
[&]not detected.

3.1.1 Competitive Slurry of Dione Racemate Forms

Dione racemate Type B~E were successfully re-produced via slurry of Dione racemate Type A in acetone, H$_2$O/ACN (1:1, v/v), 2-MeTHF/n-heptane (1.4:1, v/v) and MTBE/n-heptane (1:1, v/v) at RT, respectively.

Around 5 mg of each Dione racemate forms (Type A~E) were weighed into an HPLC vial, 0.3 mL of saturated Dione racemate solution in 2-MeHTF/n-heptane (1.4:1, v/v) was added into the vial and the mixture was then stirred at 20, 30, 40, 50, 60 and 65° C. for 5 days.

All the freebase forms converted to Dione racemate Type C via competitive slurry in 2-MeHTF/n-heptane (1.4:1, v/v) at target temperatures, suggesting Dione racemate Type C is the most thermodynamically stable form in 2-MeHTF/n-heptane (1.4:1, v/v) from 20 to 65° C.

TABLE 2-11

Competitive slurry results

| Starting Form | Experiment ID | Solvent | Temperature (° C.) | Solid Form |
|---|---|---|---|---|
| Dione racemate Type A~E | 1-16-B1 | 2-MeTHF/ n-heptane (1.4:1, v/v) | 20 | Dione racemate Type C |
| | 1-16-B2 | | 30 | Dione racemate Type C |
| | 1-16-B3 | | 40 | Dione racemate Type C |
| | 1-16-B4 | | 50 | Dione racemate Type C |
| | 1-16-B5 | | 60 | Dione racemate Type C |
| | 1-16-B6 | | 65 | Dione racemate Type C |

3.2 Preparation of P-Dione Cocrystal
3.2.1 Small Scale 2 g P-dione and 1 g DBTA were dissolved in 18 mL 2-MeTHF at 65° C. to get an almost clear solution. 18 mL heptane was added to this solution in 1 h. The solution was cooled to 20° C. over 4 h and aged overnight. The solution was evaporated using air blow at RT for about 1 h and a yellowish oily-like paste was obtained. Another 54 mL heptane was added to the mixture with stirring for 2 h. The suspension was filtered. The solid sample was assigned as 810465-16-A.

3.2.2 Large Scale 10 g P-dione and 5 g DBTA were dissolved in 100 mL 2-MeTHF at 65° C. The solution was filtered by 0.45 μm PTFE filter and a clear solution was obtained. The clear solution was added dropwise to a suspension of 400 mL heptane containing ~1 g seeds (810465-16-A) produced from the first run. The suspension was kept stirring at RT for 5 h before isolation. About 10 g of the P-Dione cocrystal (810465-20-A) was produced with a yield of ~66%.

4 Instruments and Methods
4.1 XRPD

For XRPD analysis, PANalytical X-ray powder diffract meters were used in reflection mode. The XRPD parameters used are listed in Table 4-1.

TABLE 4-1

Parameters for XRPD test

| Parameters | PANalytical | PANalytical | PANalytical |
|---|---|---|---|
| Model | Empyrean | X' Pert$^3$ | X' Pert$^3$ |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 | Cu, kα Kα1 (Å): 1.540598, Kα2 (Å): 1.544426 Kα2/Kα1 intensity ratio: 0.50 |
| X-Ray tube setting | 45 kV, 40 mA | 45 kV, 40 mA | 45 kV, 40 mA |
| Divergence slit | Automatic | ⅛° | Fixed ⅛° |
| Scan mode | Continuous | Continuous | Continuous |
| Scan range (°2TH) | 3°-40° | 3°-40° | 3°-40° |
| Scan step time (s) | 17.8 | 46.7 | 18.9 |
| Step size (°2TH) | 0.0167 | 0.0263 | 0.0131 |
| Test Time | 5 min 30 s | 5 min 04 s | 4 min 15 s |

4.2 TGA and DSC

TGA data were collected using a TA discovery 550, Q500 and Q5000 TGA from TA Instruments. DSC was performed using Q500, Q5000 and Discovery 2500 DSC from TA Instruments. Detailed parameters used are listed in Table 4-2 4-2.

TABLE 4-2

Parameters for TGA and DSC tests

| Parameters | TGA | DSC |
|---|---|---|
| Method | Ramp | Ramp |
| Sample pan | Aluminum, open | Aluminum, crimped |
| Temperature | RT-350° C. | 25° C.-300 ° C. |
| Heating rate | 10° C./min | 10° C./min |
| Purge gas | $N_2$ | $N_2$ |

4.3 HPLC

Agilent 1100/1260 HPLC was utilized to test solubility, with detailed methods listed in Table 4-3.

TABLE 4-3

HPLC method for solubility test

| | |
|---|---|
| HPLC | Agilent 1100 with DAD detector |
| Column | CHIRALPAK IC-3, 4.6 × 100 mm, 3 um |
| Mobile phase | A: n-Heptane |
| | B: MeOH/EtOH (1:1, v/v) |
| Isocratic elution | A:B = 75:25, 60:40 |
| Run time | 10.0 min |
| Post time | 0.0 min |
| Flow rate | 1.0 mL/min |
| Injection volume | 5 μL |
| Detector wavelength | UV at 215 nm |
| Column temperature | 40° C. |
| Sampler temperature | RT |
| Diluent | EtOH |

TABLE 4-4

HPLC method for solubility test (DBTA)

| | |
|---|---|
| HPLC | Agilent 1260 with DAD detector |
| Column | Agilent ZORBAX 300SB-C3, 150 × 4.6 mm, 3.5 μm |
| Mobile phase | A: 0.05% TFA in $H_2O$ |
| | B: 0.05% TFA in ACN |
| Isoctatic elution | A:B = 65:35 |
| Run time | 5.0 min |
| Post time | 0.0 min |
| Flow rate | 0.6 mL/min |
| Injection volume | 5 μL |
| Detector wavelength | UV at 215 nm |
| Column temperature | 40° C. |
| Sampler temperature | RT |
| Diluent | EtOH |

4.4 $^1$H NMR $^1$H NMR spectrum was collected on Bruker 400M NMR Spectrometer using DMSO-d6 as solvent.

4.5 PLM

Polarized light microscopic picture was captured on Nikon DS-Fi2 upright microscope at room temperature.

Additional Screening of Compound 5 with 1,3-diphenyl-3-oxopropanesulfonic Acid 11b.

Due to the low basicity of the pyridine moiety in compound 5 and the limited 'hits' in terms of the formation of crystalline salts using the standard screening set, it was chosen to screen racemic compound 4 with 1,3-diphenyl-3-oxopropanesulfonic acid 11b on a 0.06 mmol scale.

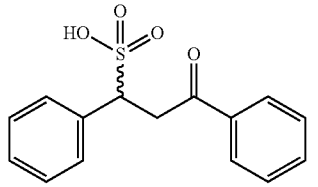

11-RAC

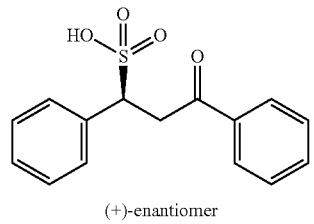

(+)-enantiomer

11a

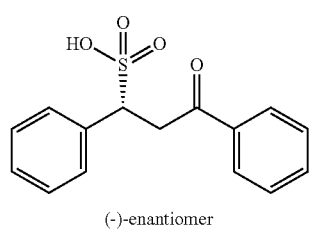

(-)-enantiomer

11b

Gram scale resolution of racemic compound 5: A 250 mL round-bottom flask was charged with 2.0 g racemic compound 4 (5.7 mmol, 1.0 eq.) in 200 mL EtOH:AcOH (90:10 v:v). After the material had dissolved, 832 mg of sulfonic acid 11b (2.9 mmol, 0.5 eq.) was added to the solution. The clear solution was left to stir for 15 hours at a stirring speed of 800 rpm. A white precipitate had formed which was isolated from the mother liquor. The isolated salt was suspended in $CH_2Cl_2$ which was treated with a concentrated aqueous $NaHCO_3$ solution using a separatory funnel. The organic layer was isolated and the basic aqueous layer was extracted with $CH_2Cl_2$ (2×). The organic layers were combined and dried over $Na_2SO_3$. Evaporation of the solvent yielded 415 mg of (M)-5 (96% ee) (see FIG. 6-1).

Figures 2, 3, 4, 5:
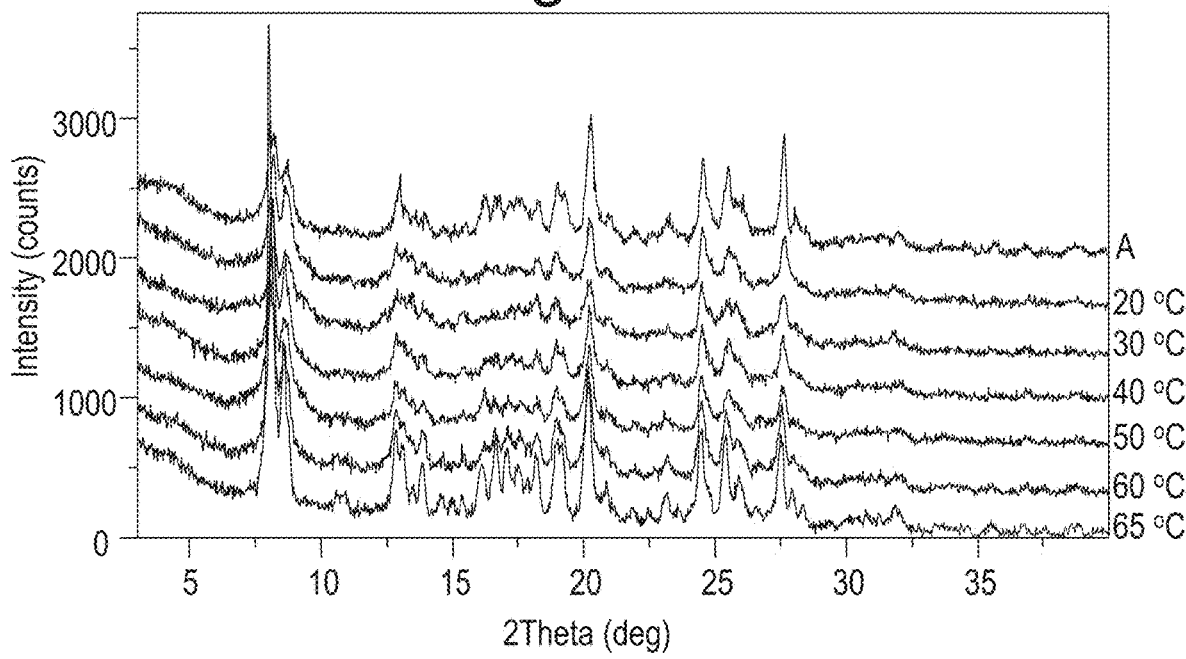
Figures 2, 3, 4, 5, 6:
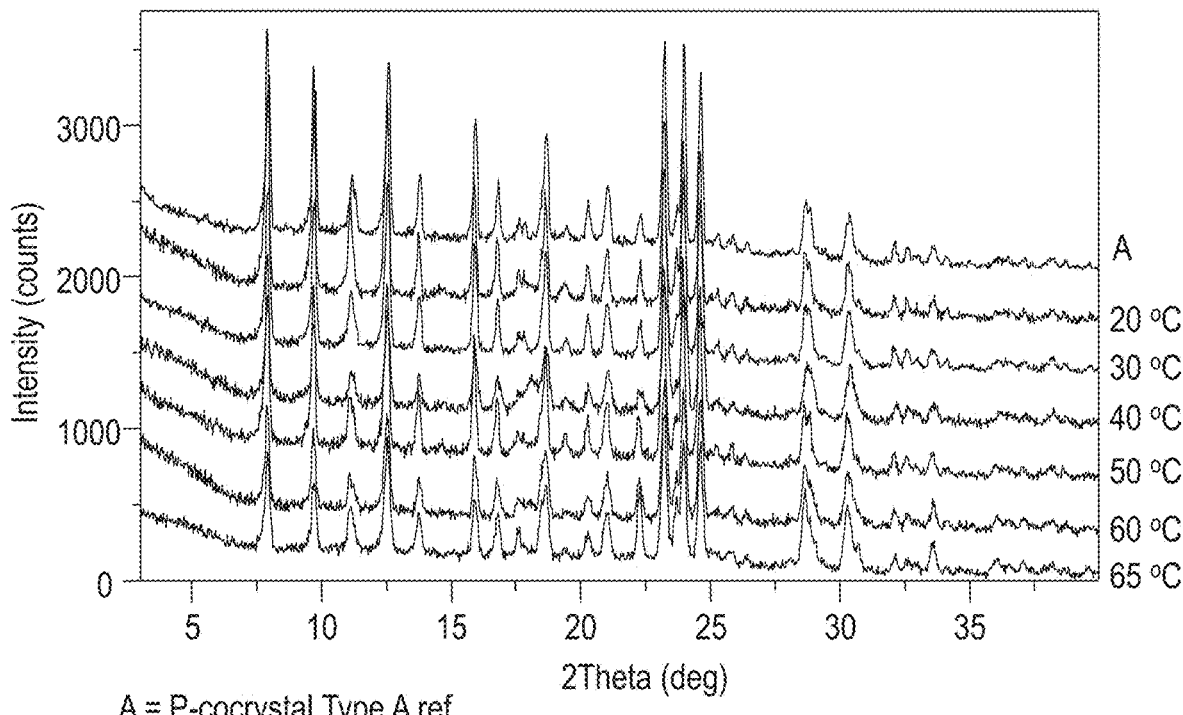
Figures 2, 3, 4, 5, 6, 7:
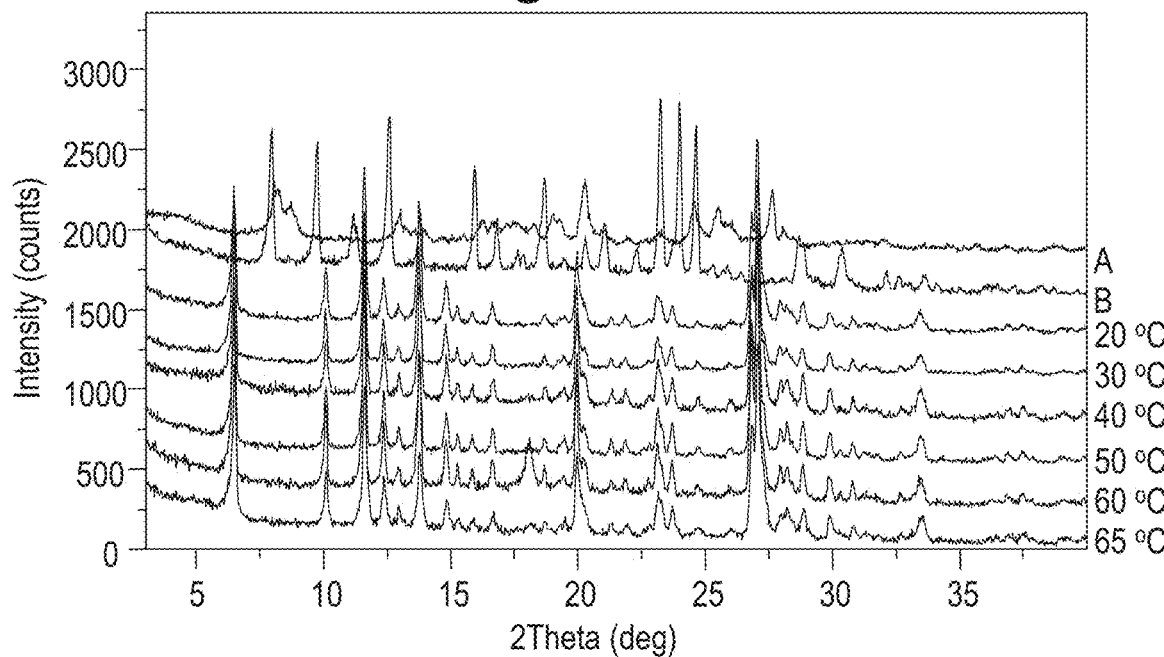
Figures 2, 3, 4, 5, 6, 7, 8:
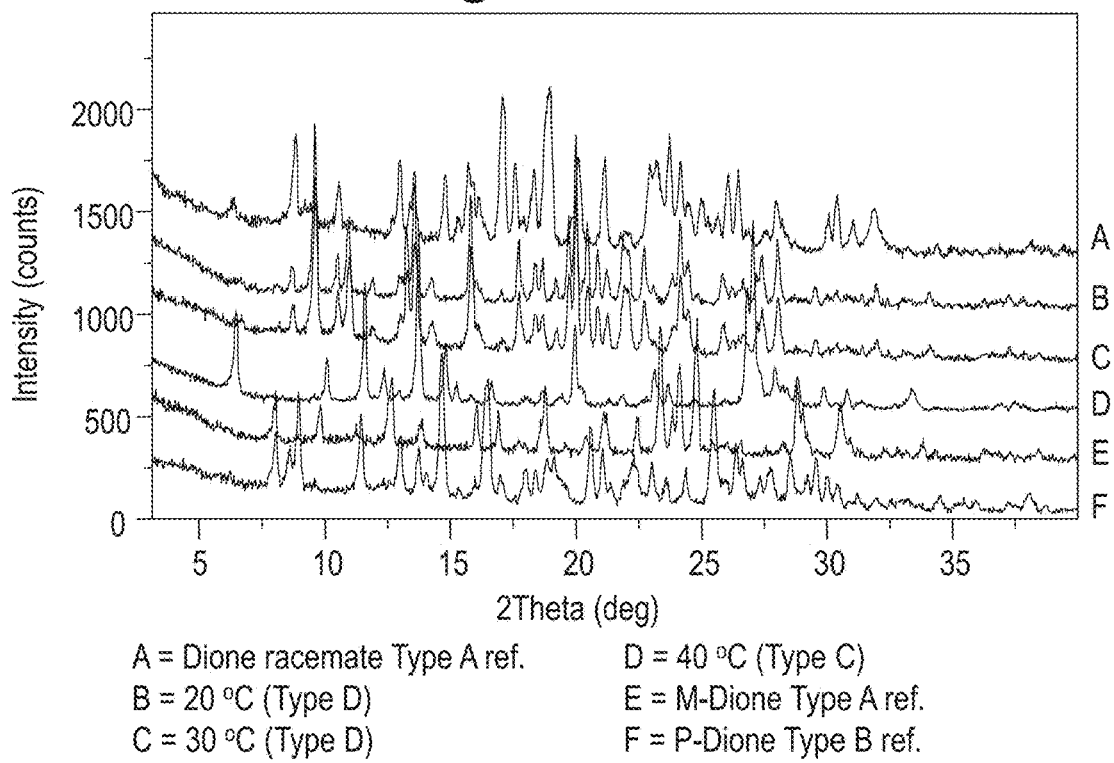
Figures 2, 3, 4, 5, 6, 7, 8, 9:
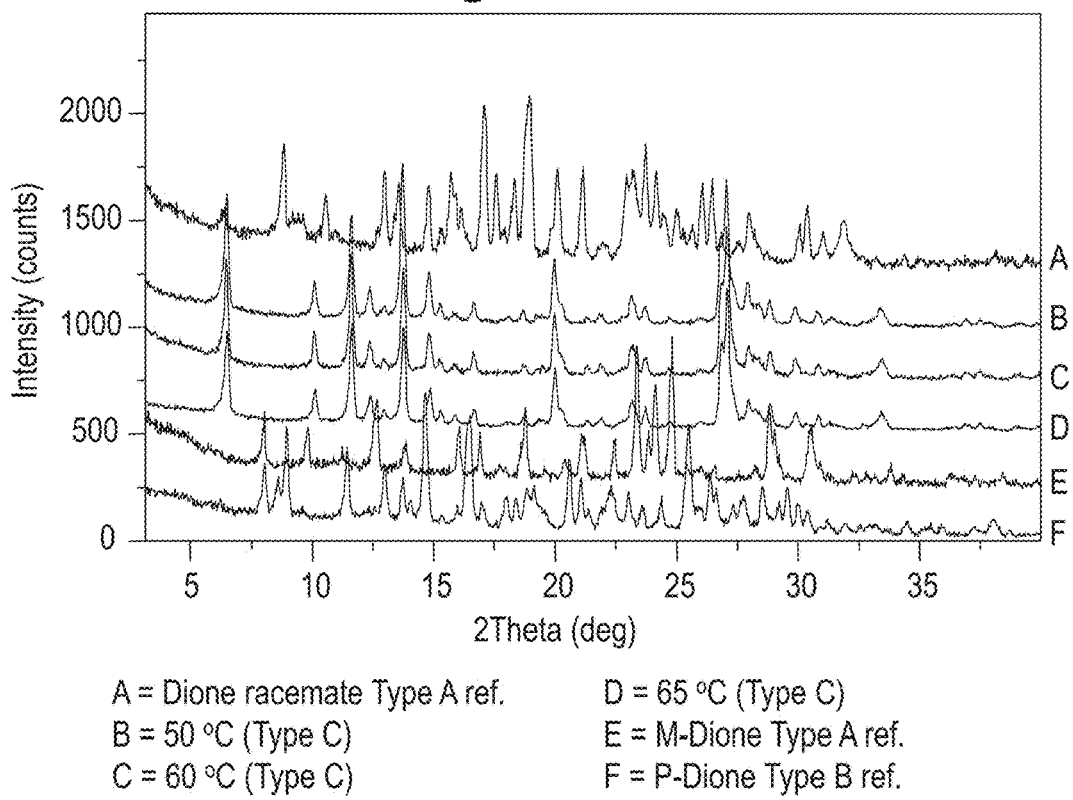
Figures 2, 3, 4, 5, 6, 7, 8, 9, 10, 11:
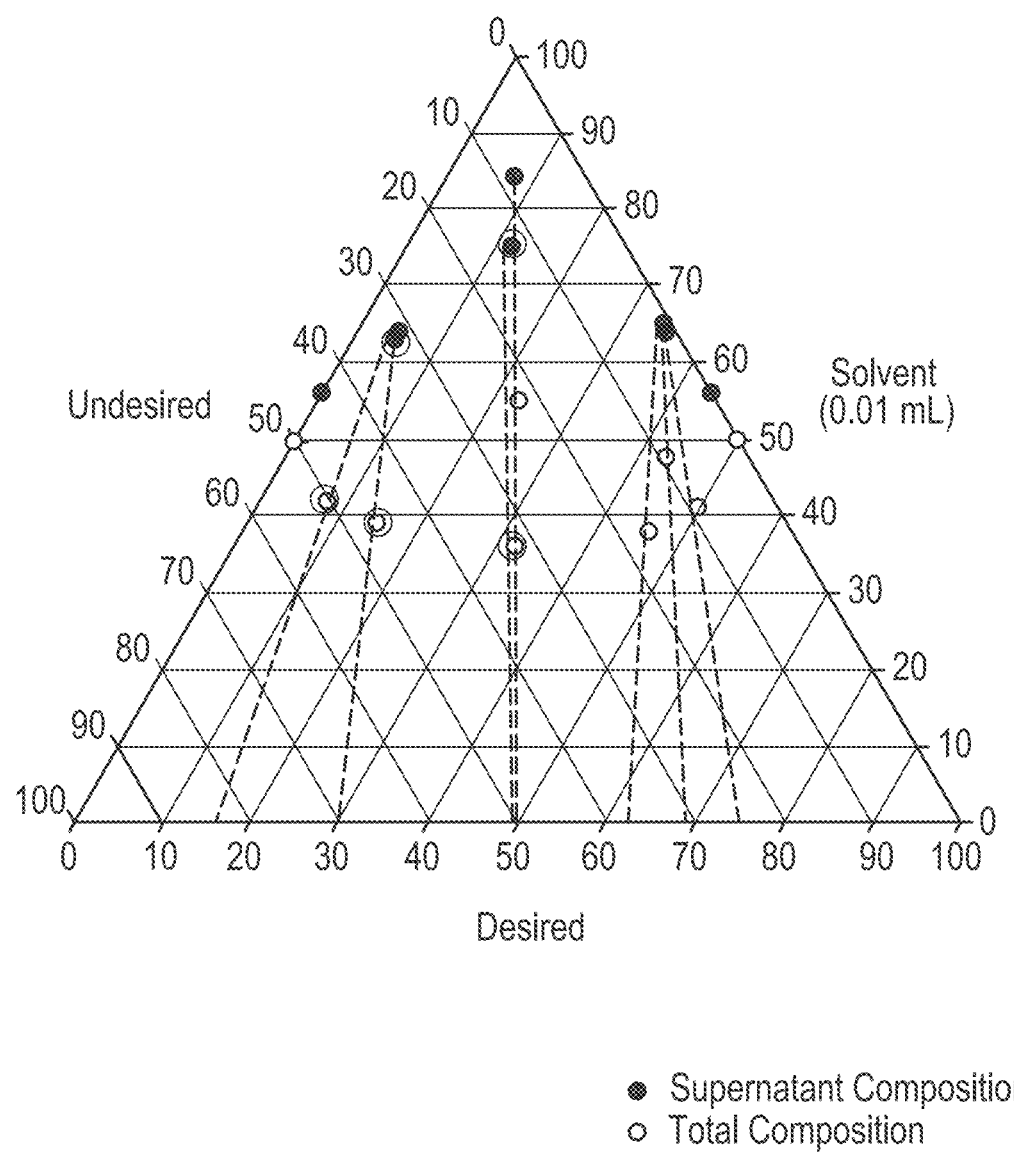
Figures 1, 3:
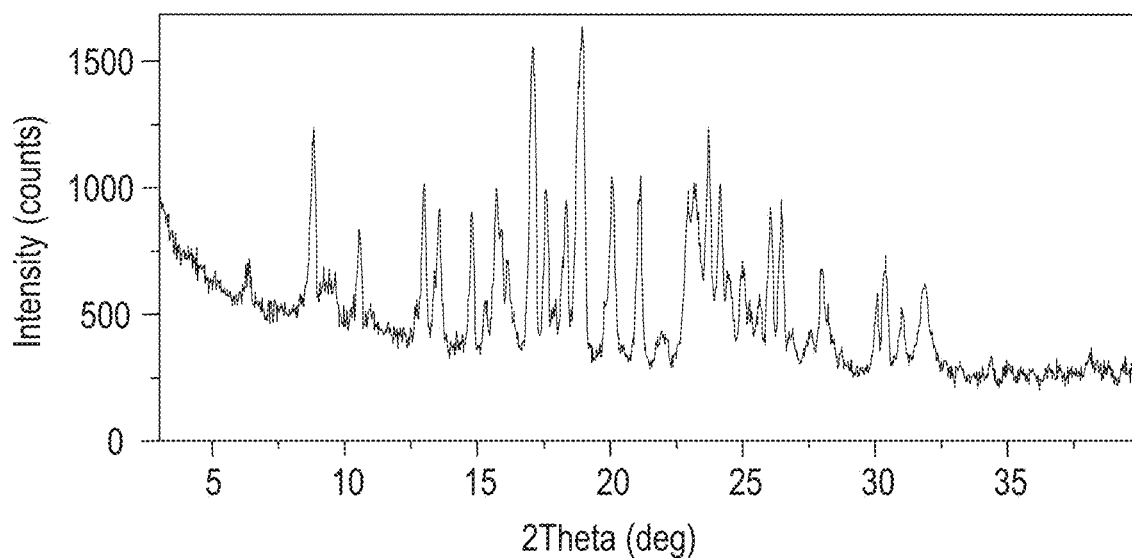
Figures 2, 3:
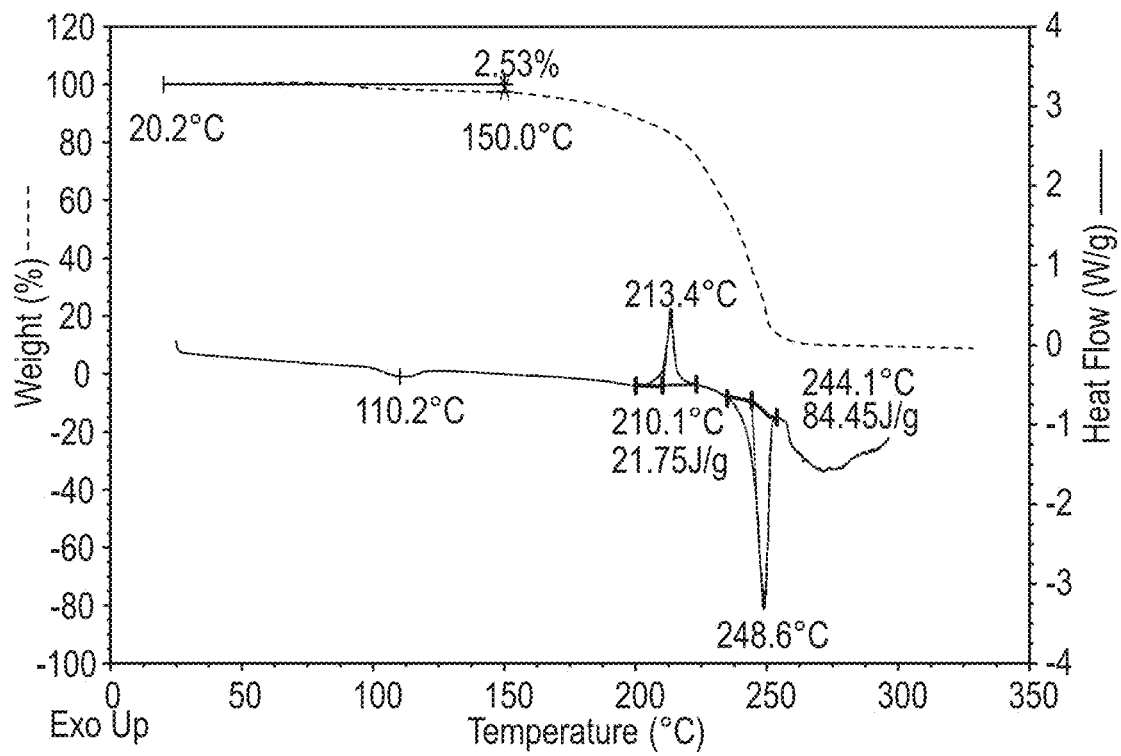
Figures 3, 4:
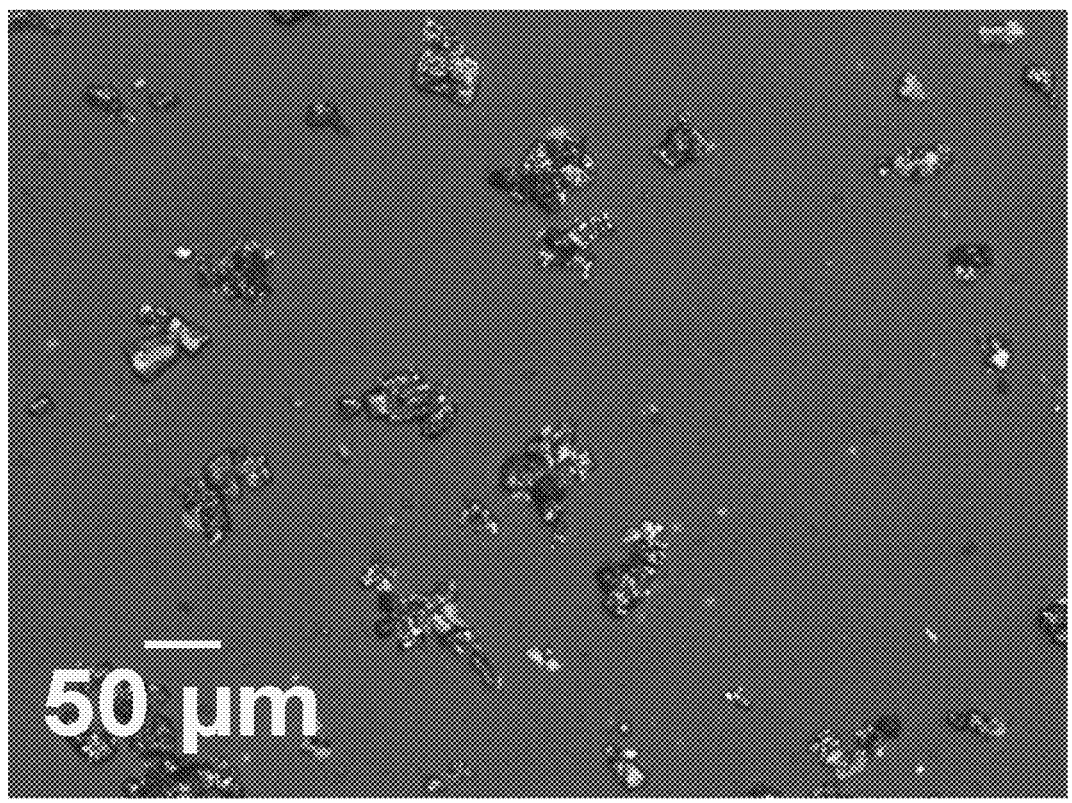
Figures 3, 4, 5:
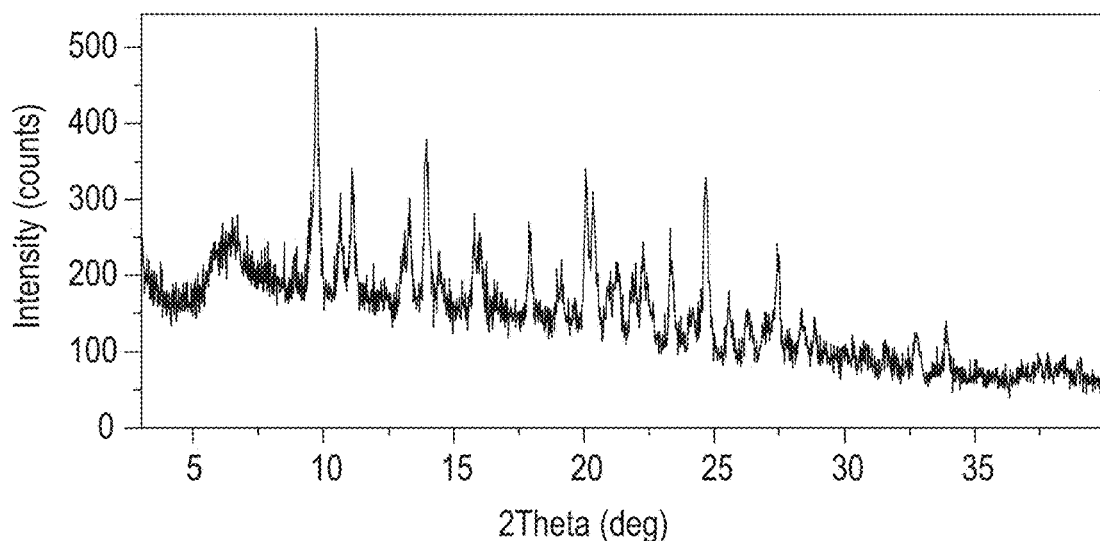
Figures 3, 4, 5, 6:
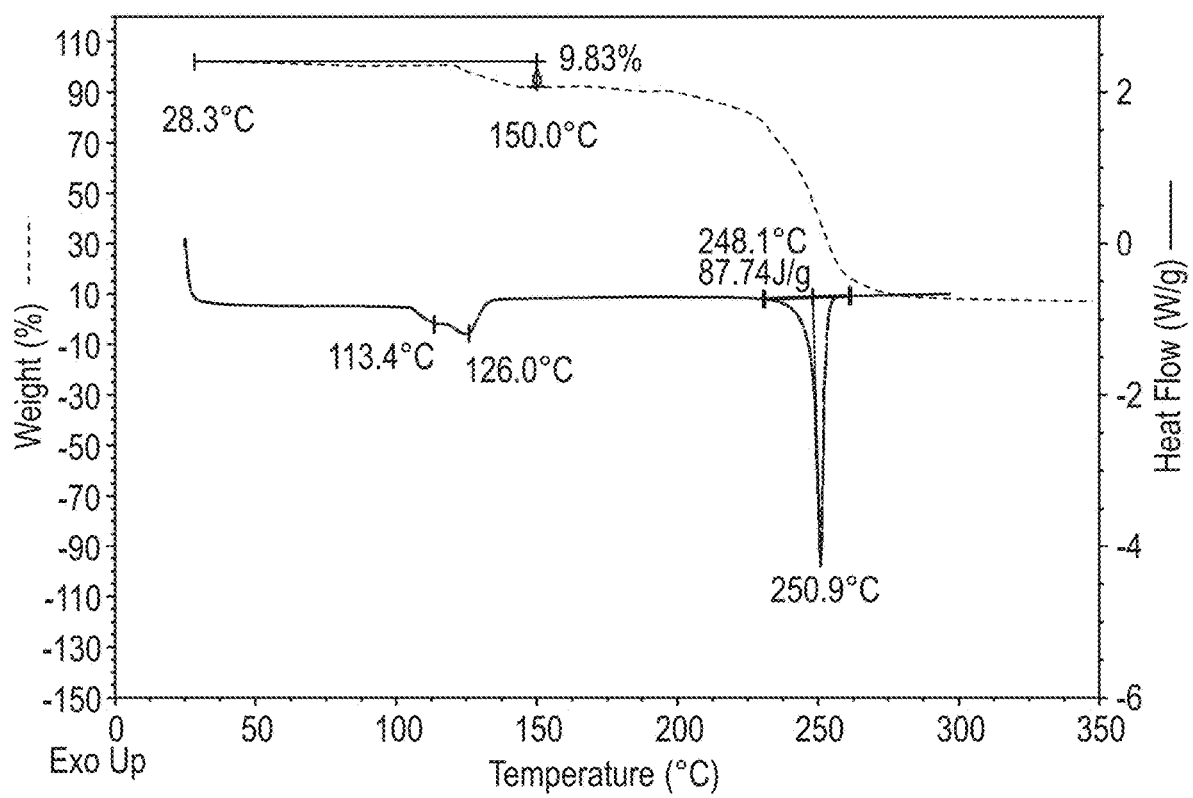
Figures 3, 4, 5, 6, 7:
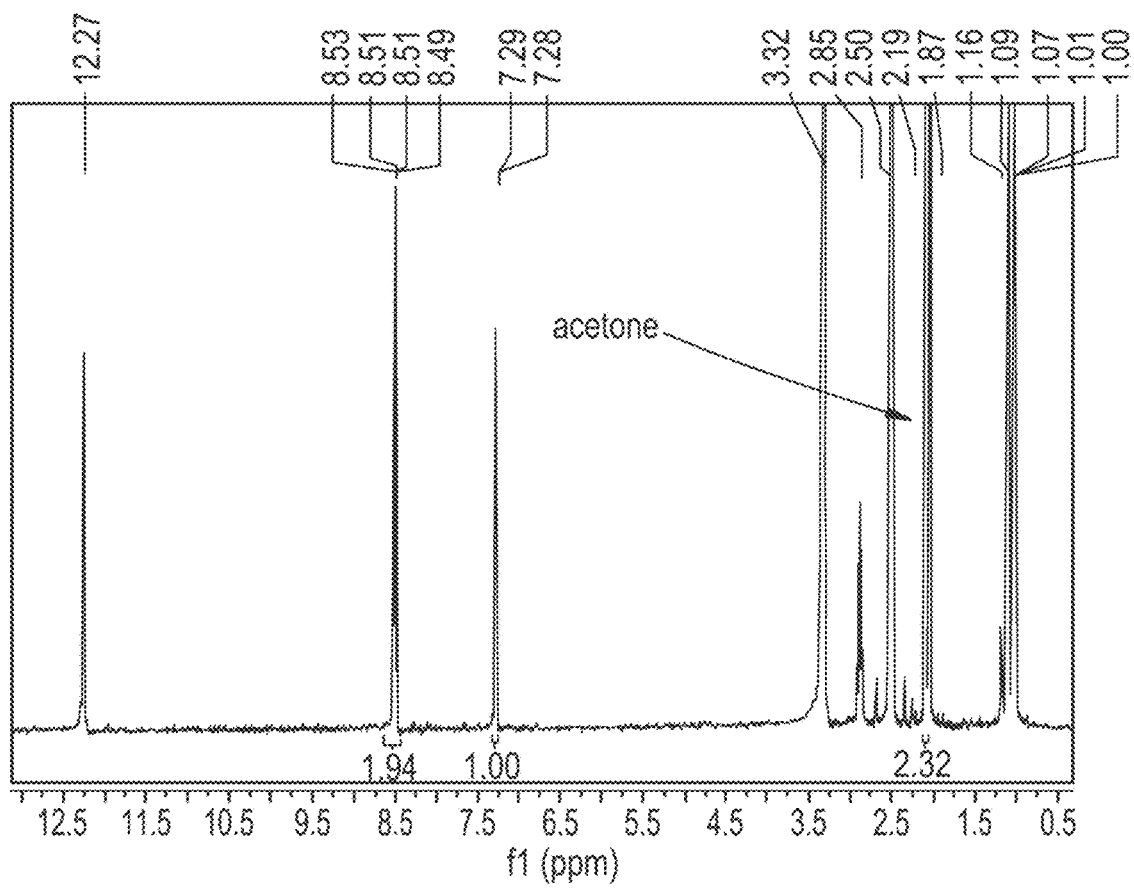
Figures 3, 4, 5, 6, 7, 8:
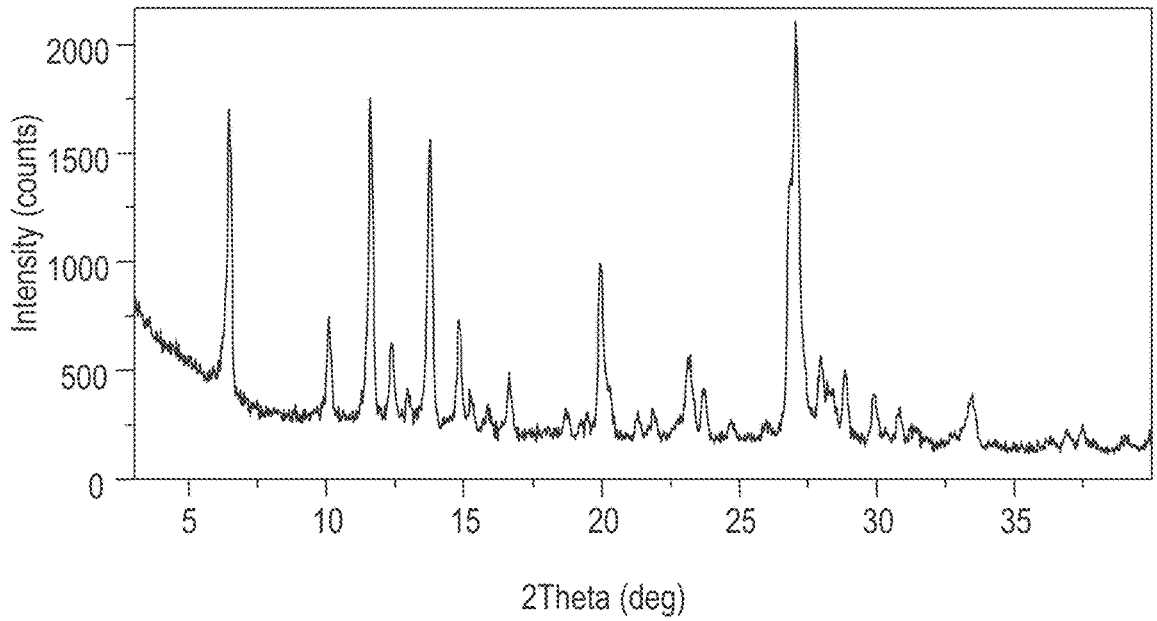
Figures 3, 4, 5, 6, 7, 8, 9:
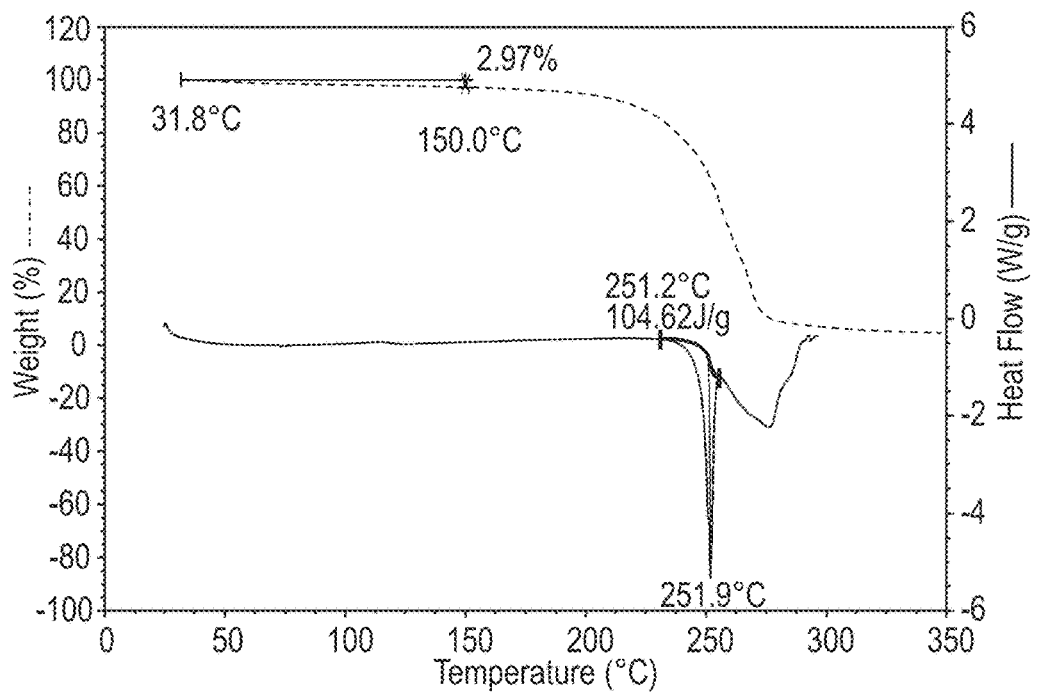
Figures 3, 4, 5, 6, 7, 8, 9, 10:
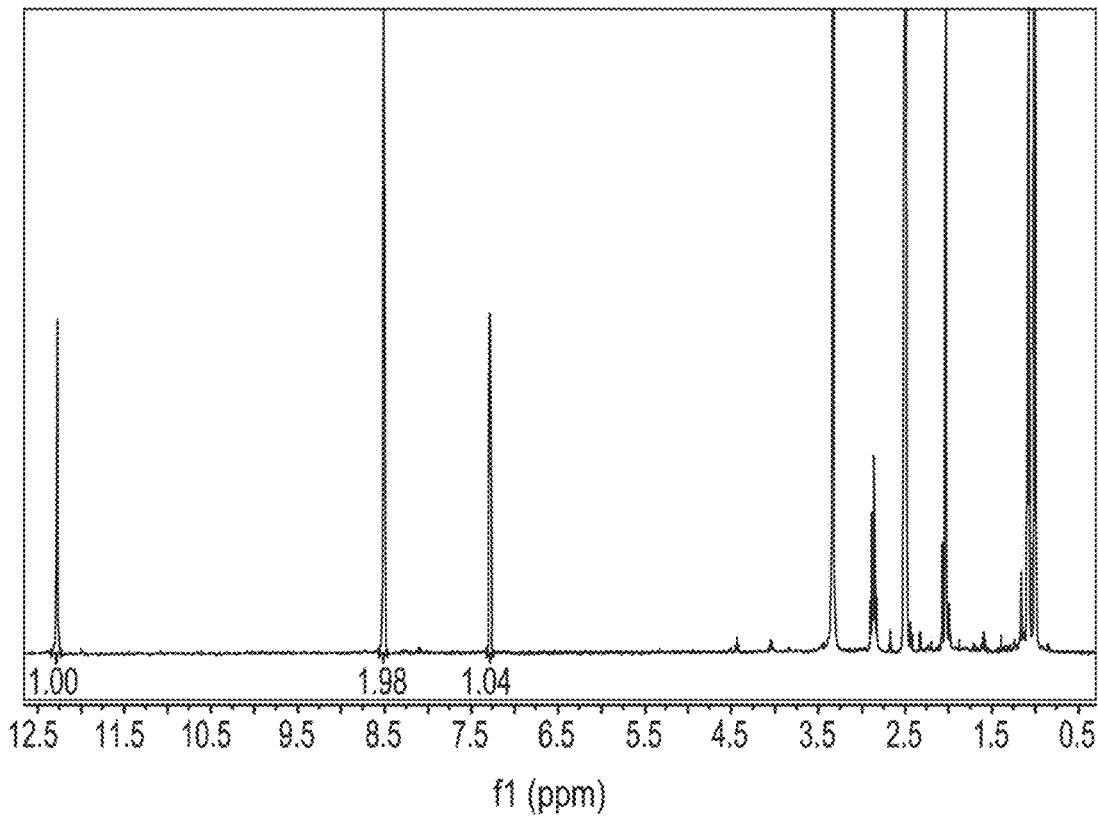
Figures 3, 4, 5, 6, 7, 8, 9, 10, 11:
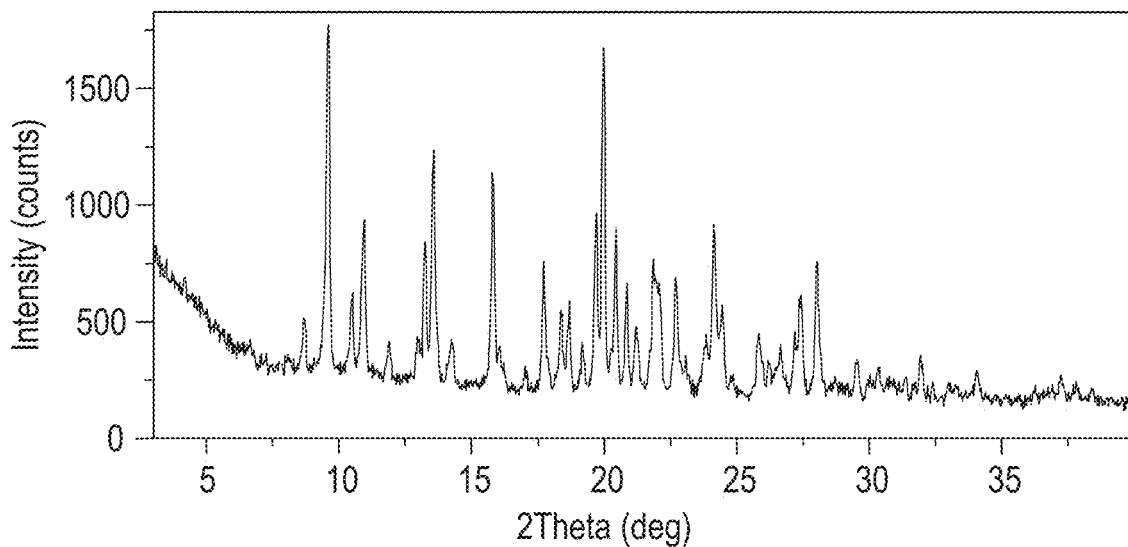
Figures 3, 4, 5, 6, 7, 8, 9, 10, 11, 12:
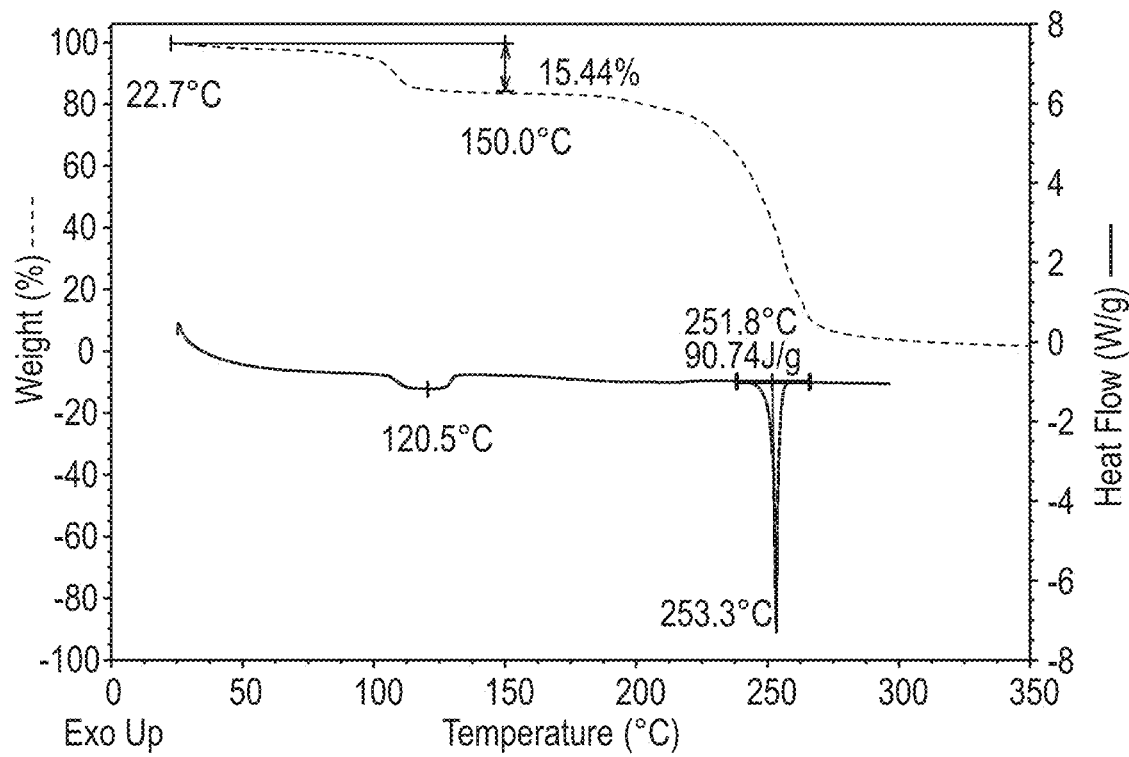
Figures 3, 4, 5, 6, 7, 8, 9, 10, 11, 12, 13:
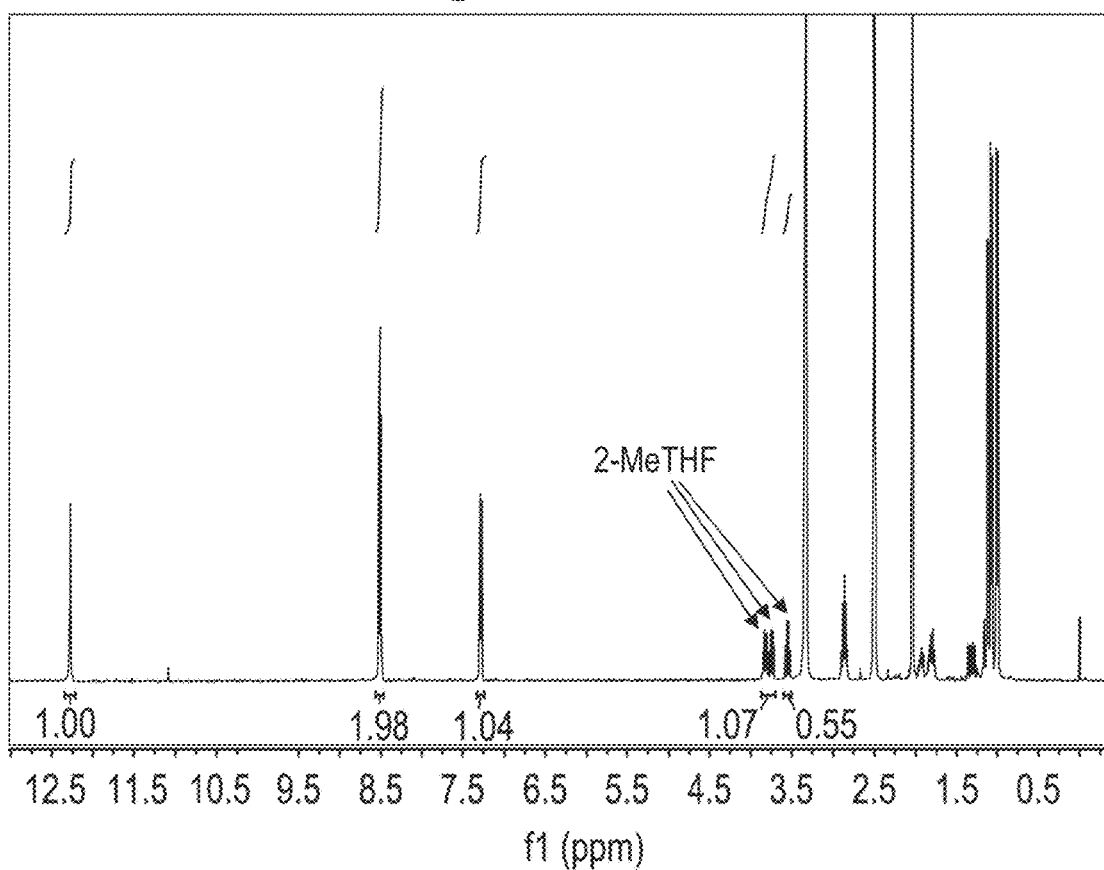
Figures 3, 4, 5, 6, 7, 8, 9, 10, 11, 12, 13, 14:
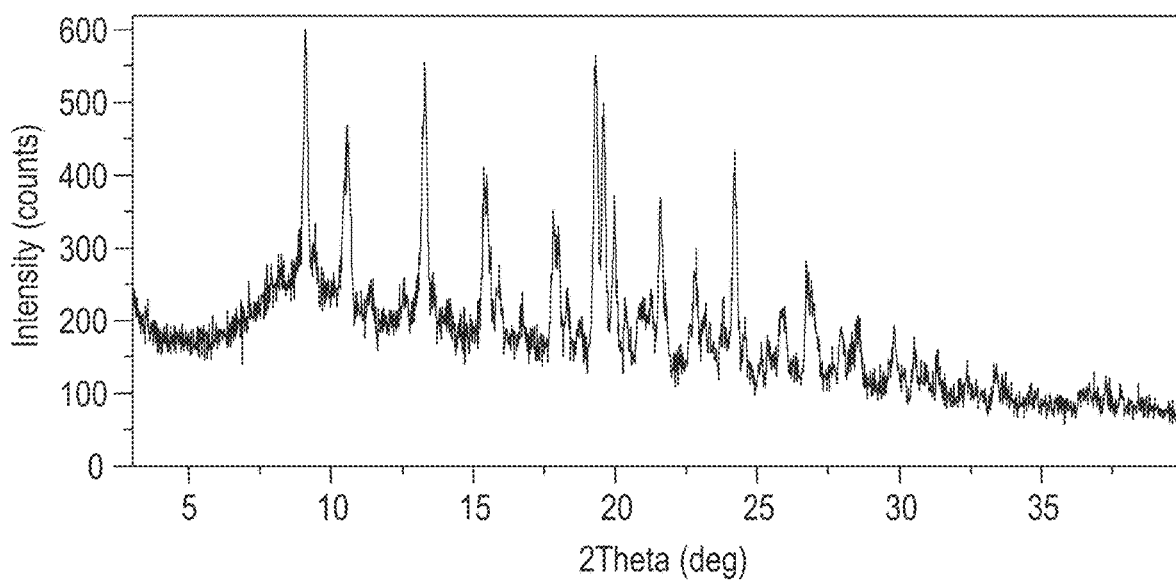
Figures 3, 4, 5, 6, 7, 8, 9, 10, 11, 12, 13, 14, 15:
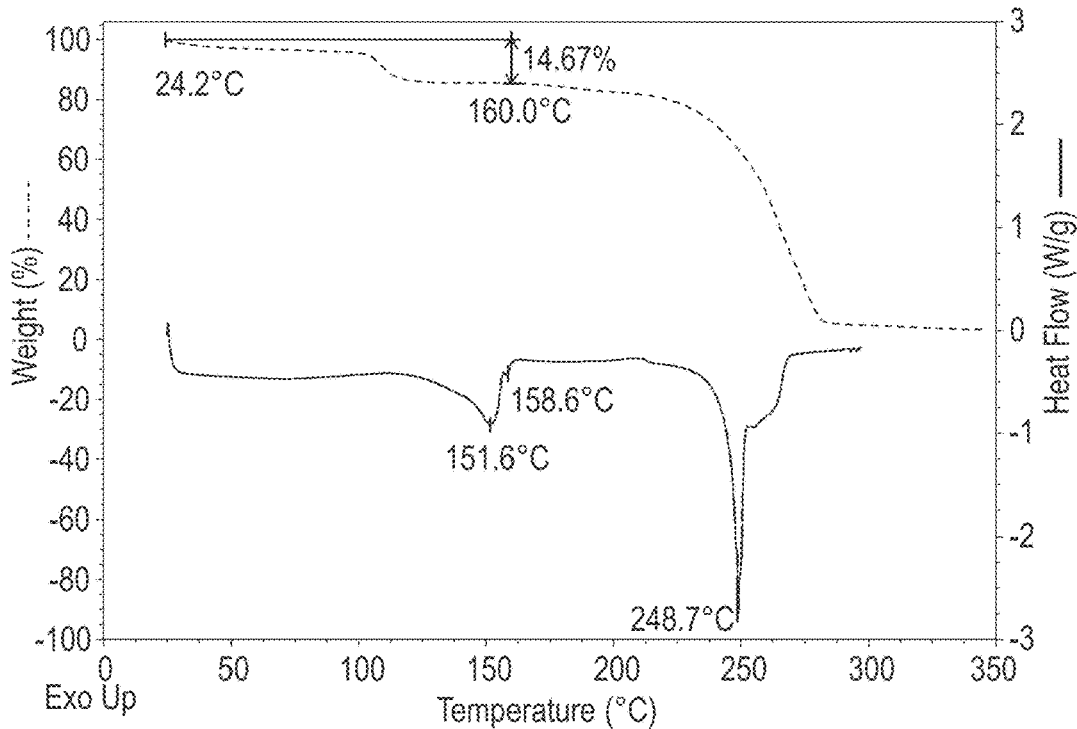
Figures 3, 4, 5, 6, 7, 8, 9, 10, 11, 12, 13, 14, 15, 16:
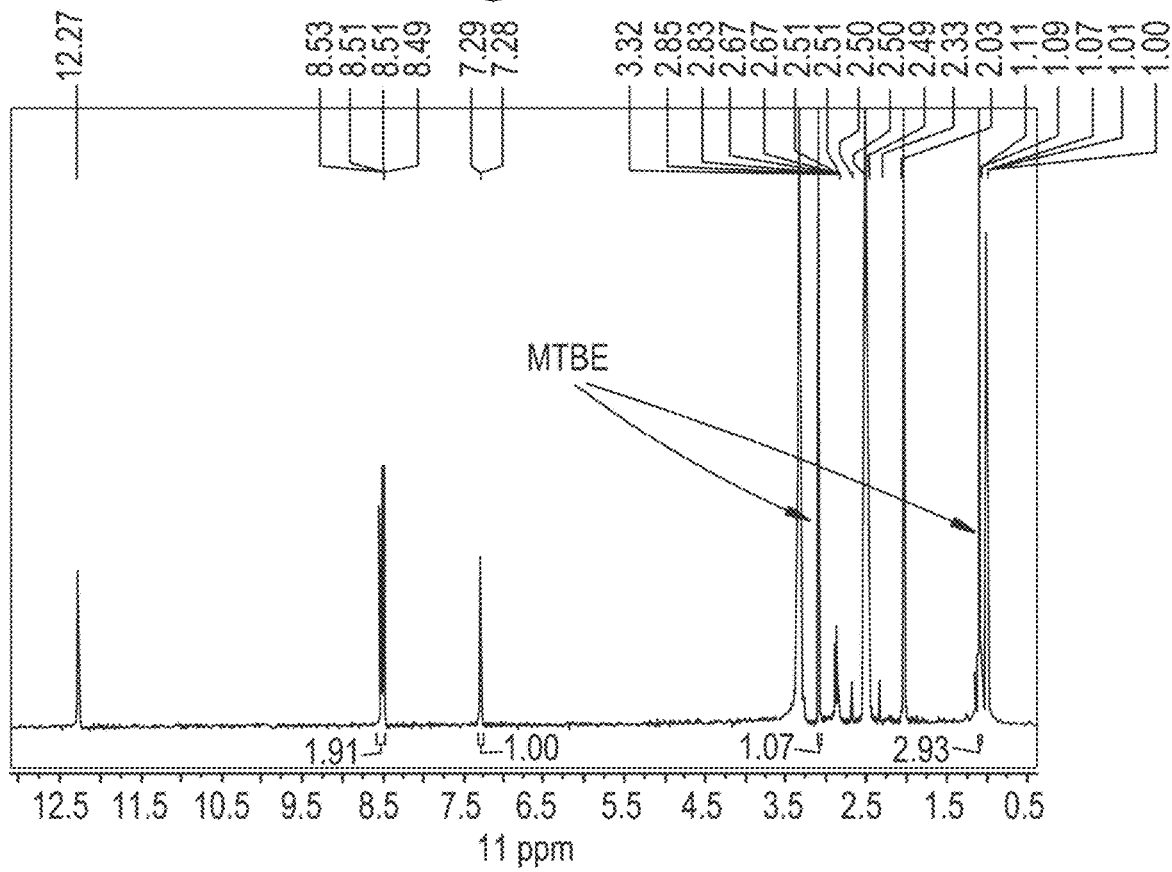
Figures 3, 4, 5, 6, 7, 8, 9, 10, 11, 12, 13, 14, 15, 16, 17:
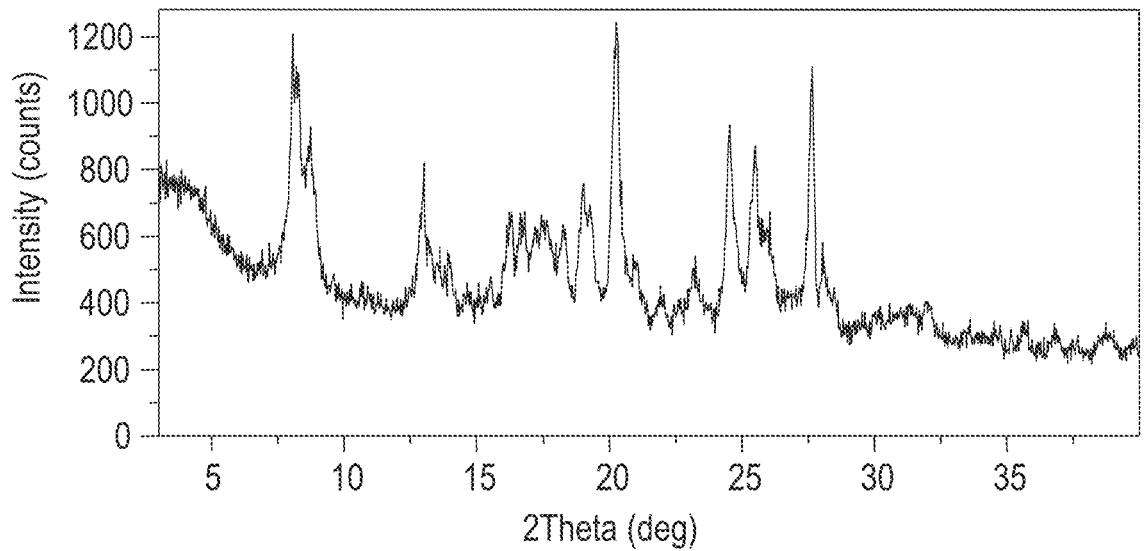
Figures 3, 4, 5, 6, 7, 8, 9, 10, 11, 12, 13, 14, 15, 16, 17, 18:
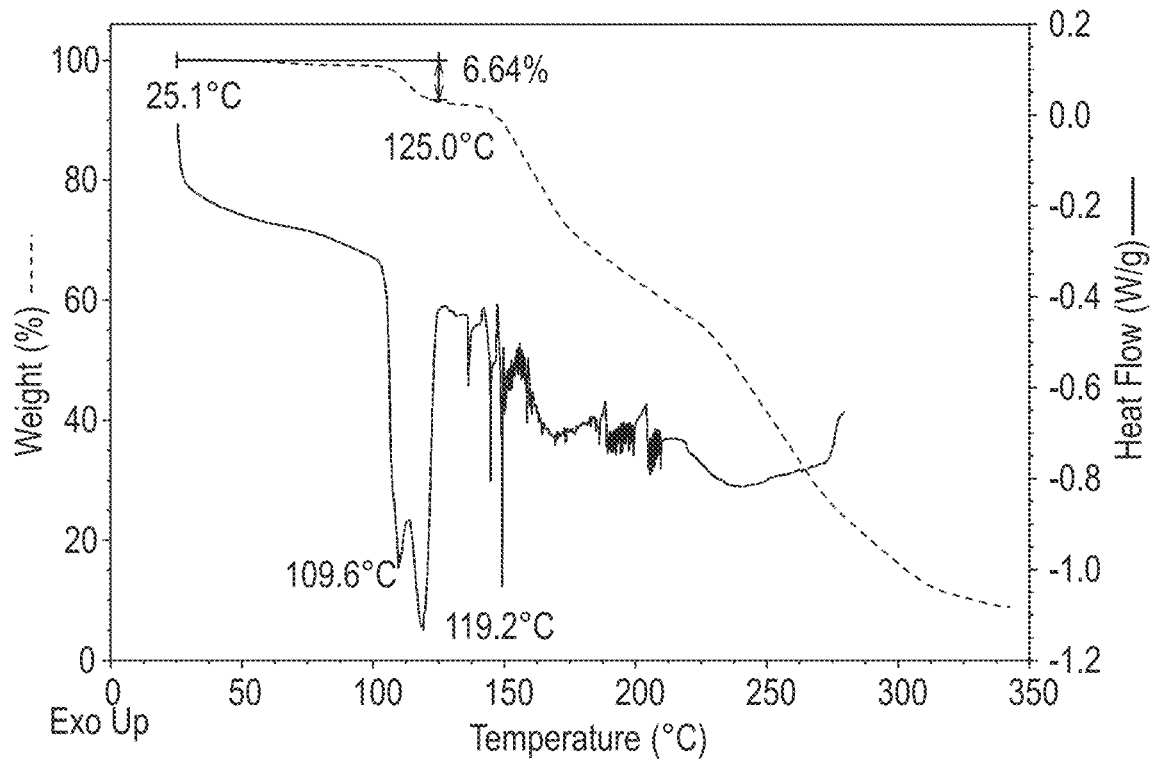
Figures 3, 4, 5, 6, 7, 8, 9, 10, 11, 12, 13, 14, 15, 16, 17, 18, 19:
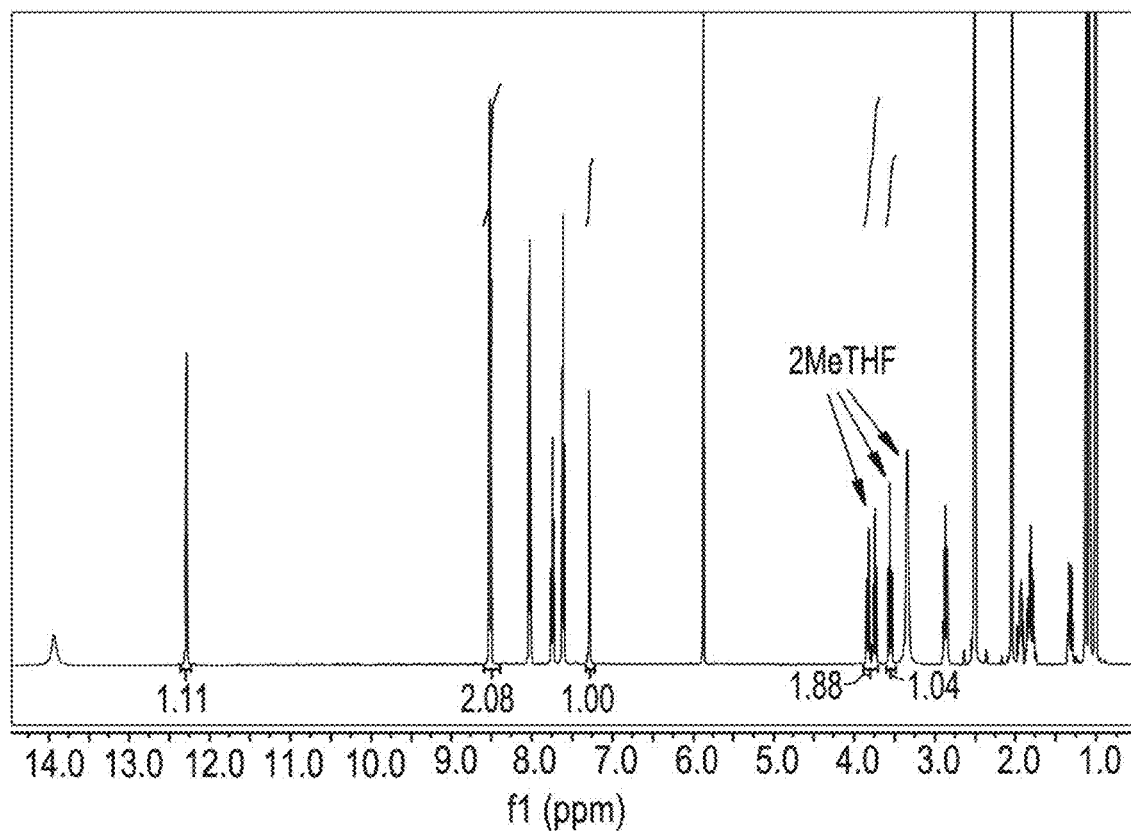
Figures 3, 4, 5, 6, 7, 8, 9, 10, 11, 12, 13, 14, 15, 16, 17, 18, 19, 20:
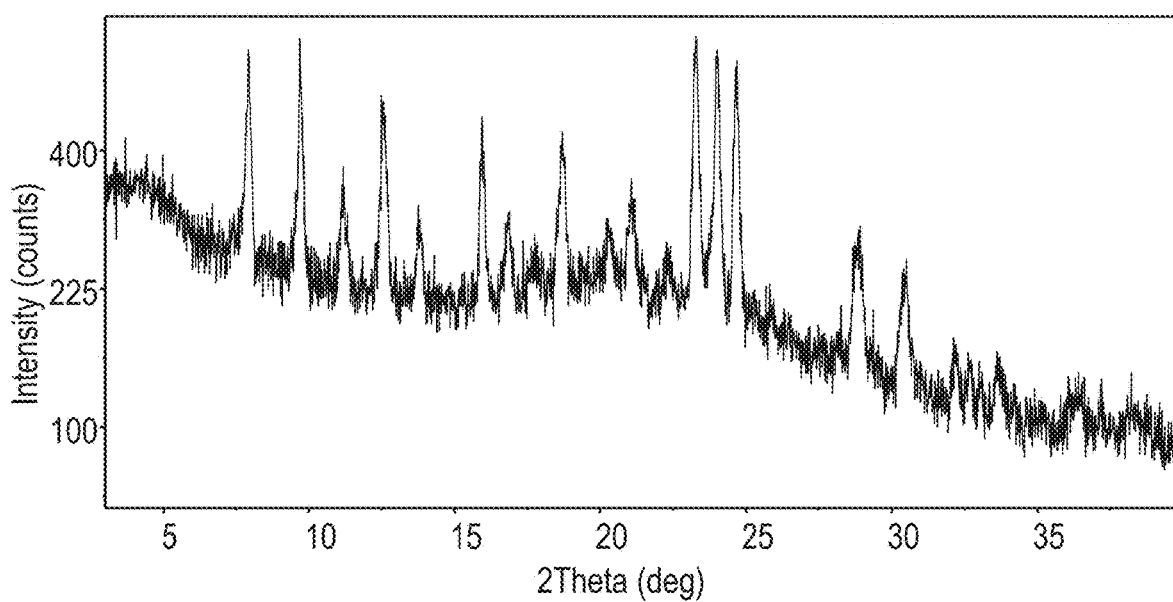
Figures 3, 4, 5, 6, 7, 8, 9, 10, 11, 12, 13, 14, 15, 16, 17, 18, 19, 20, 21:
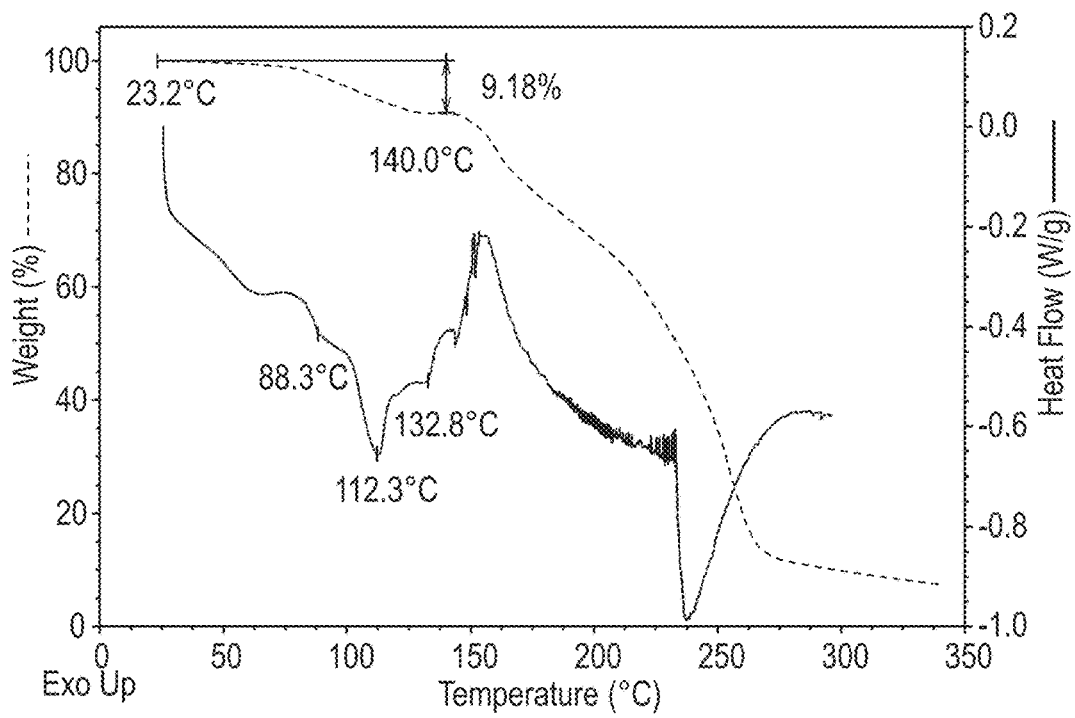
Figures 3, 4, 5, 6, 7, 8, 9, 10, 11, 12, 13, 14, 15, 16, 17, 18, 19, 20, 21, 22:
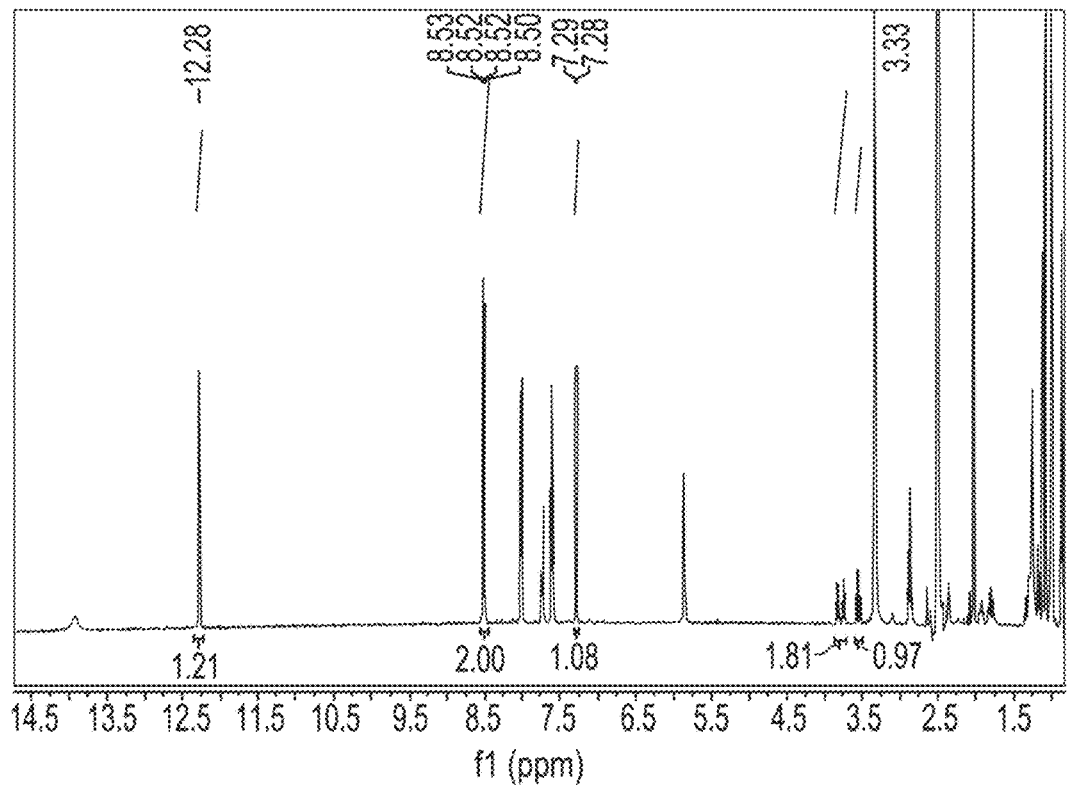
Figures 3, 4, 5, 6, 7, 8, 9, 10, 11, 12, 13, 14, 15, 16, 17, 18, 19, 20, 21, 22, 23:
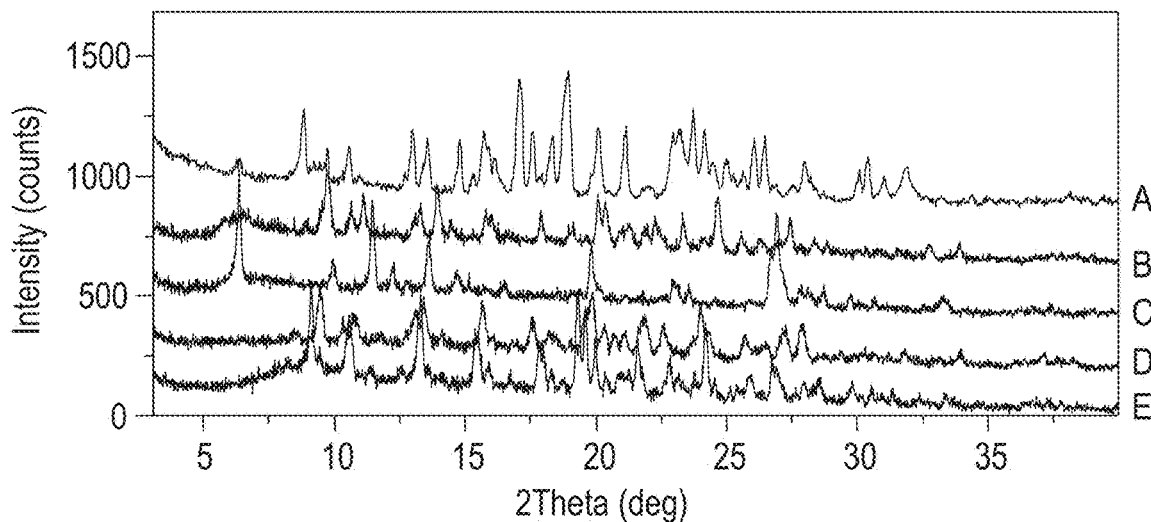
Figures 3, 4, 5, 6, 7, 8, 9, 10, 11, 12, 13, 14, 15, 16, 17, 18, 19, 20, 21, 22, 23, 24:
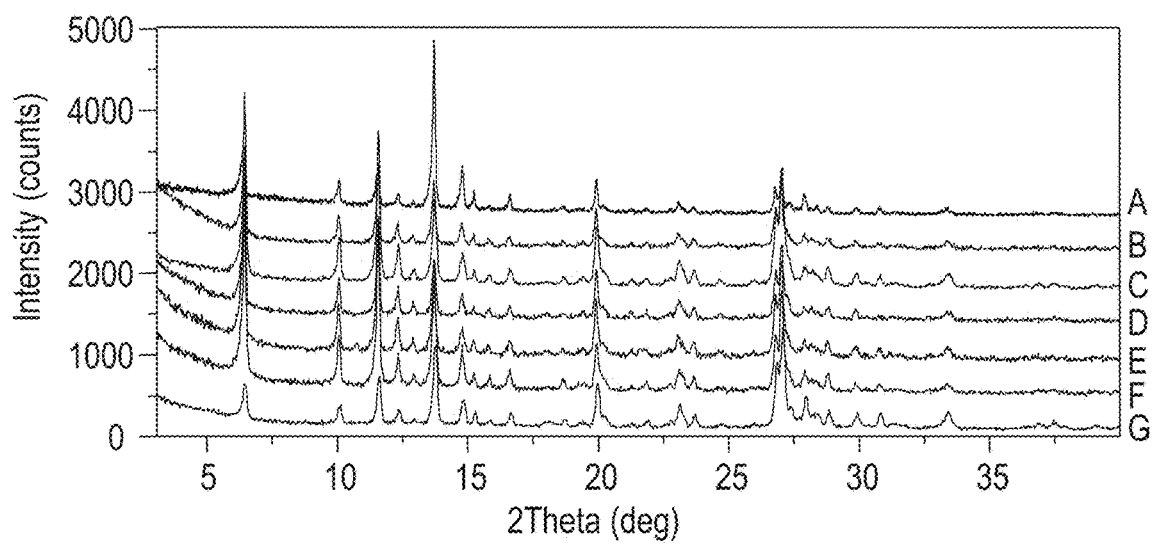
Figures 3, 4, 5, 6, 7, 8, 9, 10, 11, 12, 13, 14, 15, 16, 17, 18, 19, 20, 21, 22, 23, 24, 25:
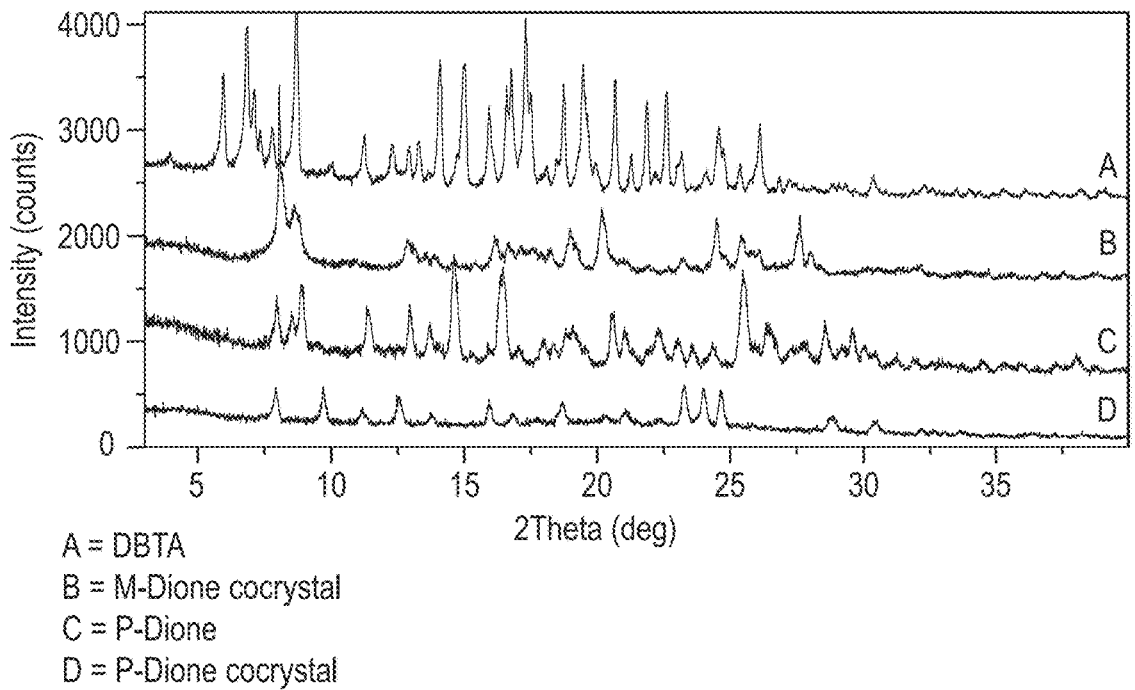
Figures 3, 4, 5, 6, 7, 8, 9, 10, 11, 12, 13, 14, 15, 16, 17, 18, 19, 20, 21, 22, 23, 24, 25, 26:
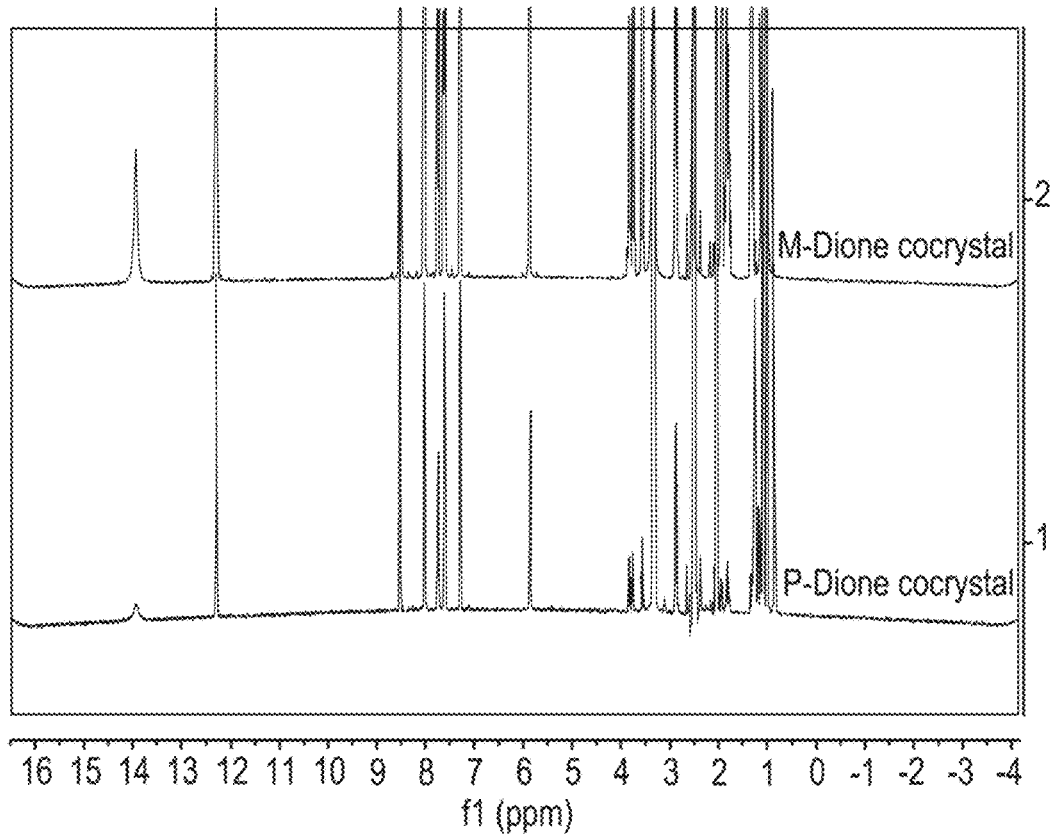
Figures 3, 4, 5, 6, 7, 8, 9, 10, 11, 12, 13, 14, 15, 16, 17, 18, 19, 20, 21, 22, 23, 24, 25, 26, 27:
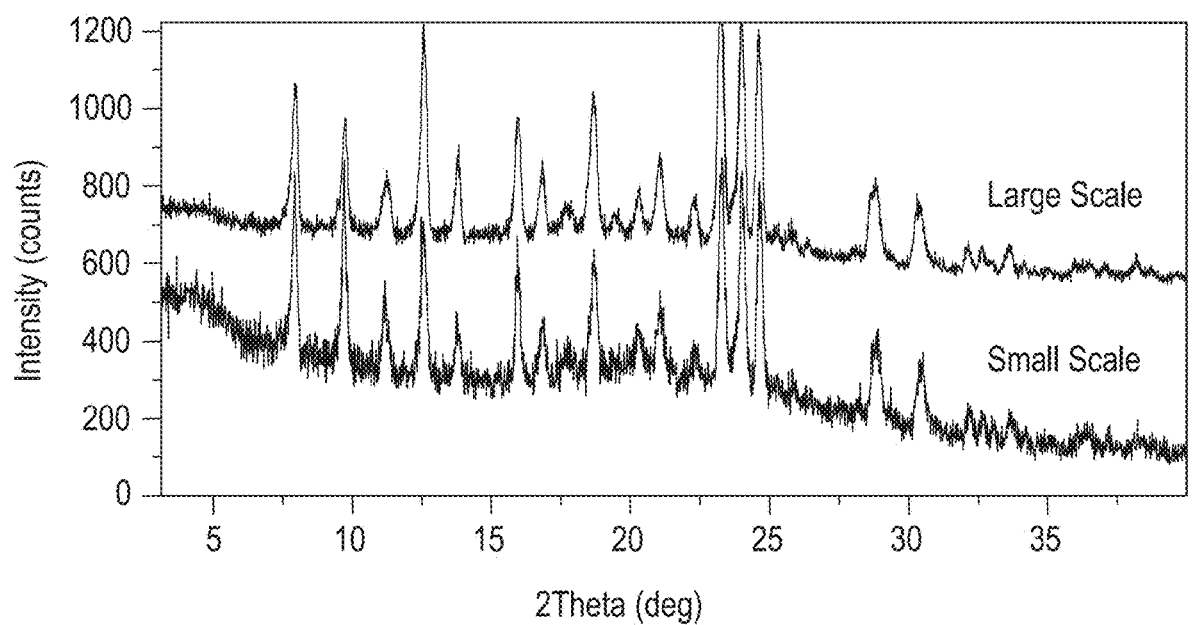
Figures 1, 4:
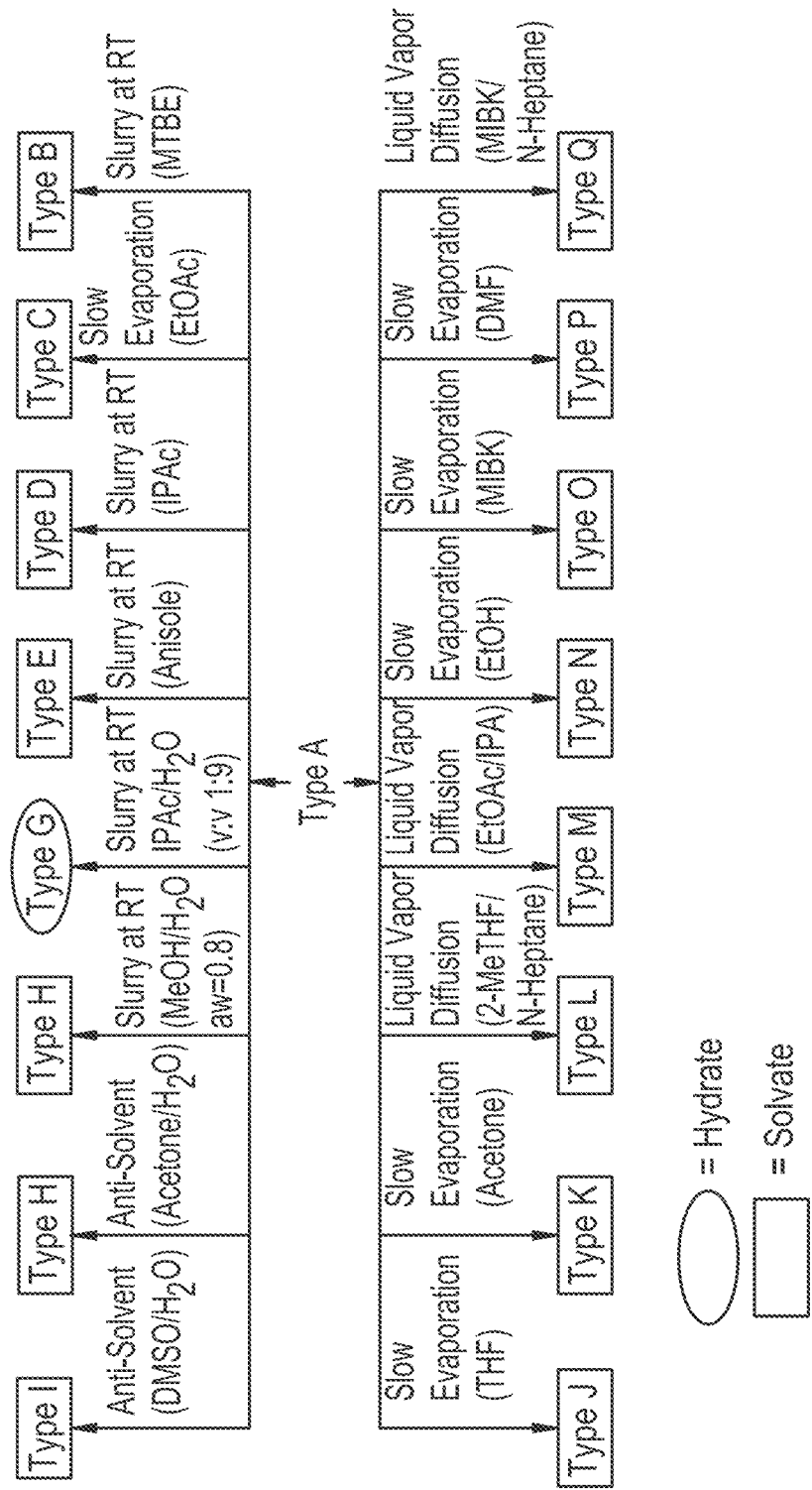
Figures 1, 5:
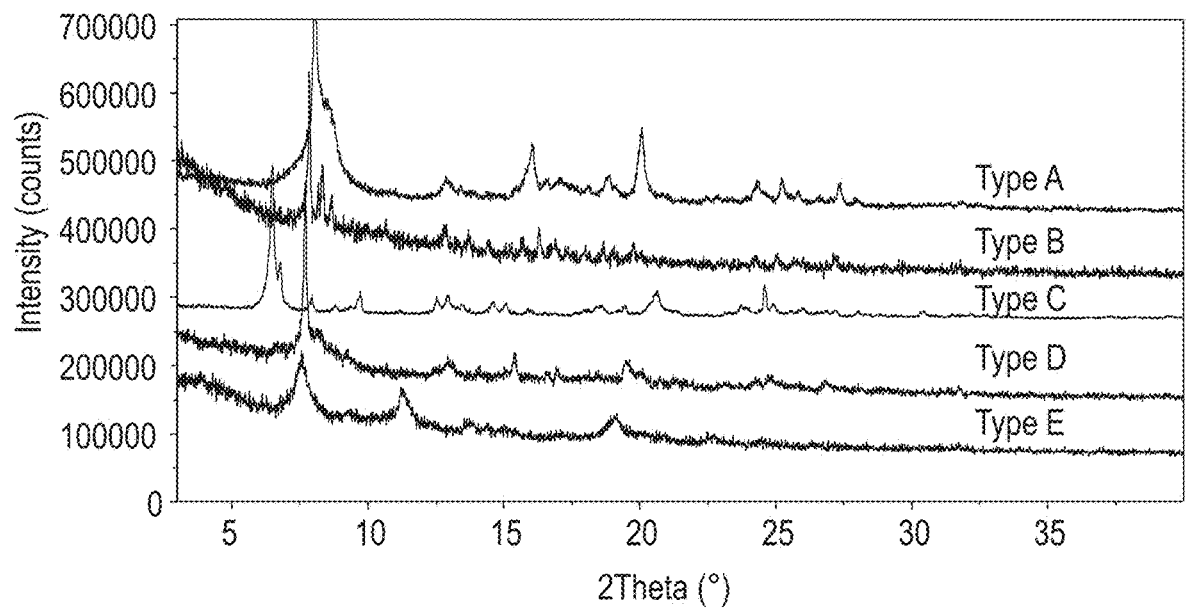
Figures 2, 5:
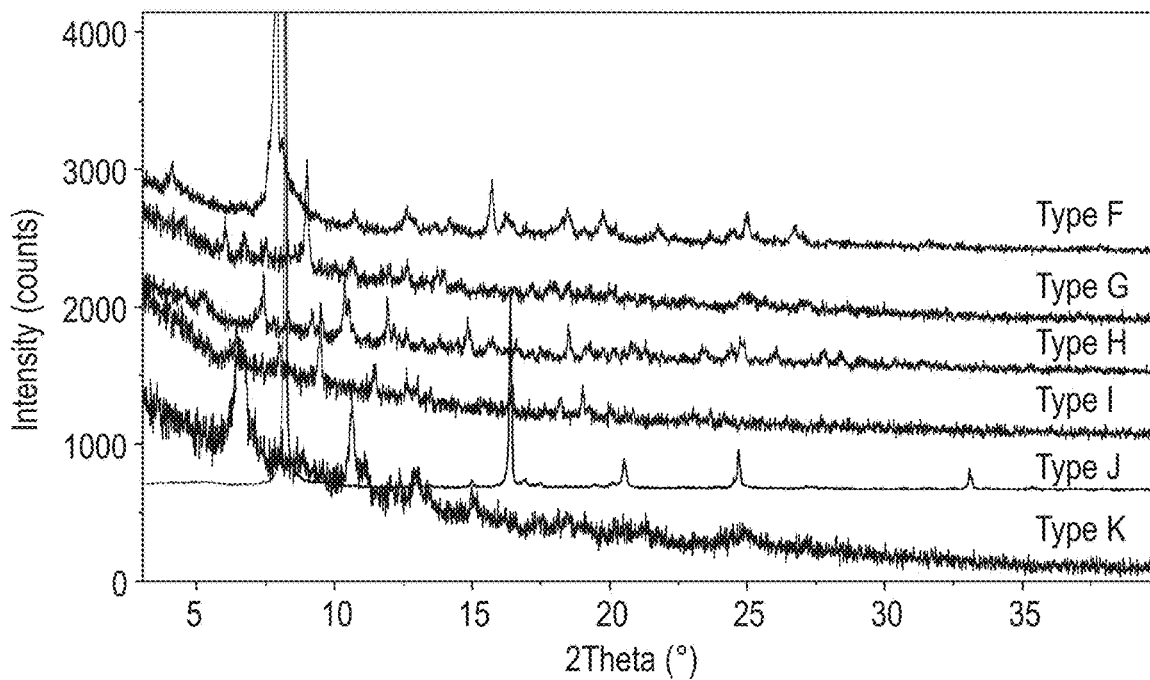
Figures 3, 5:
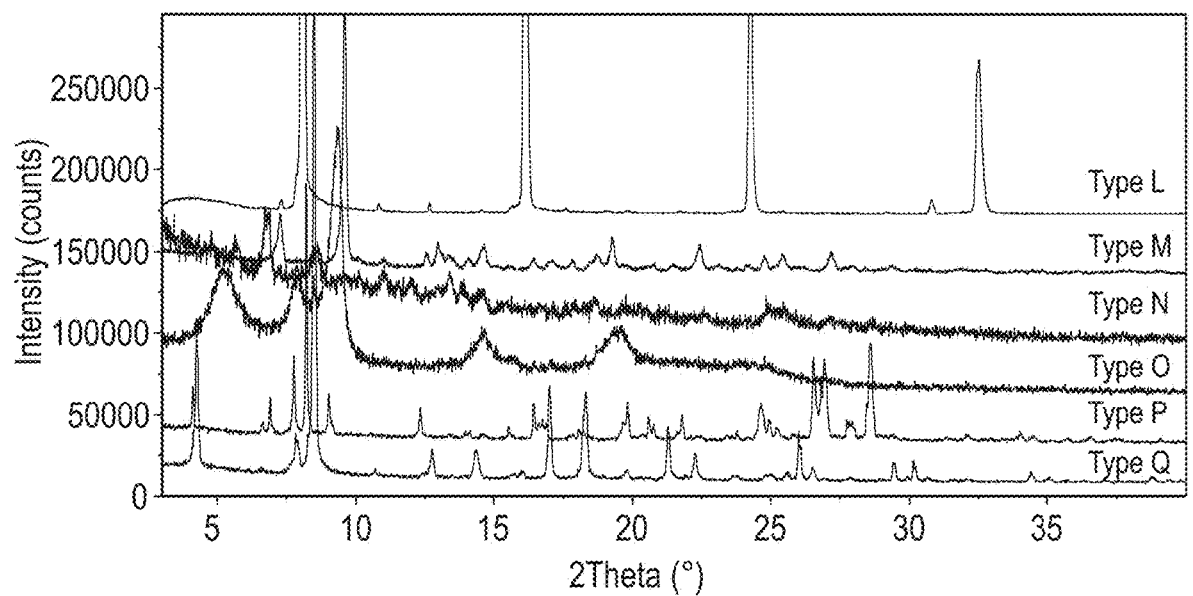
Figures 4, 5:
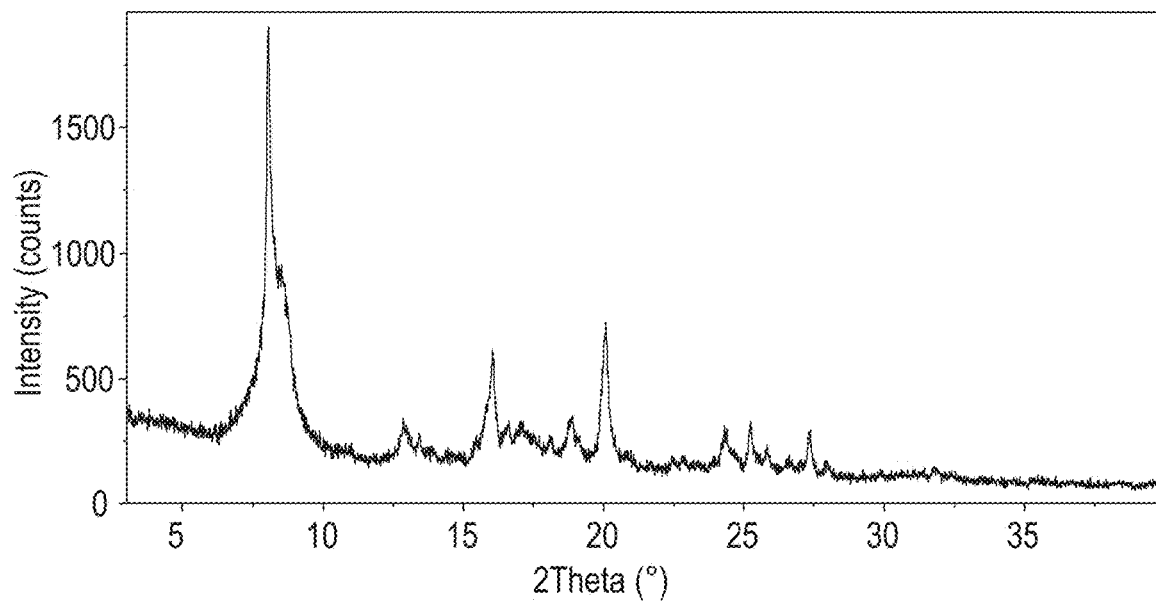
Figure 5:
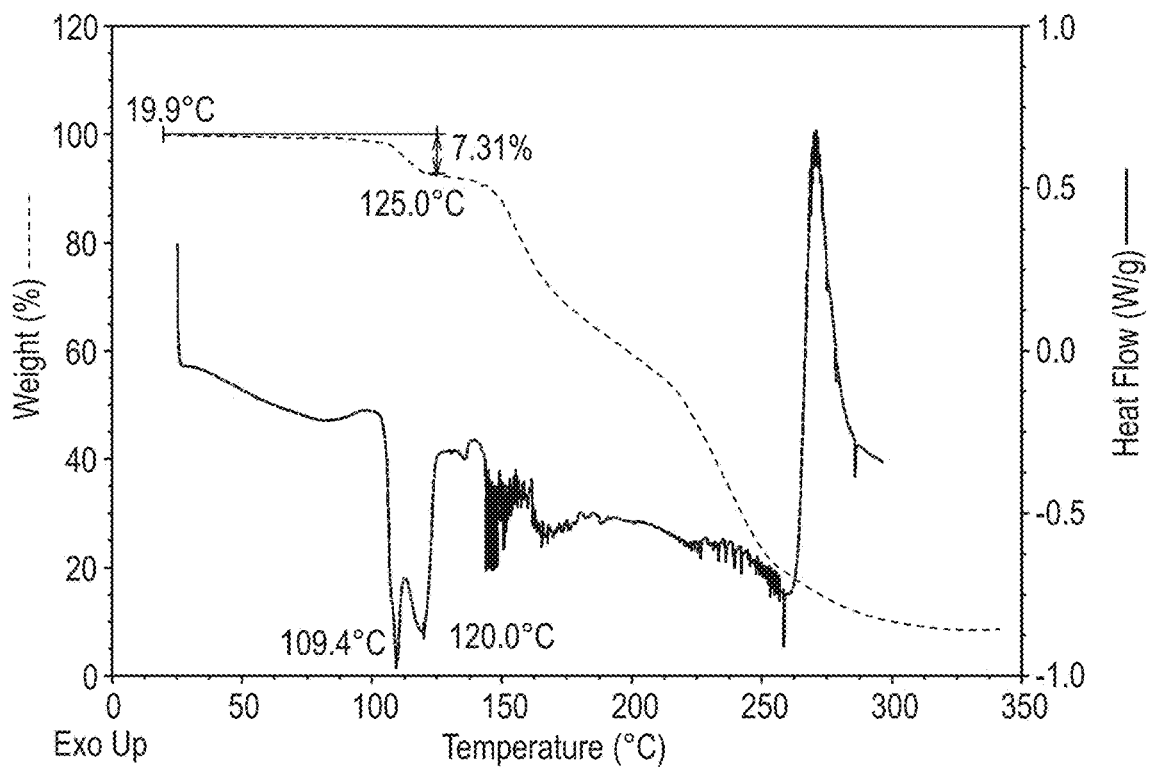
Figures 5, 6:
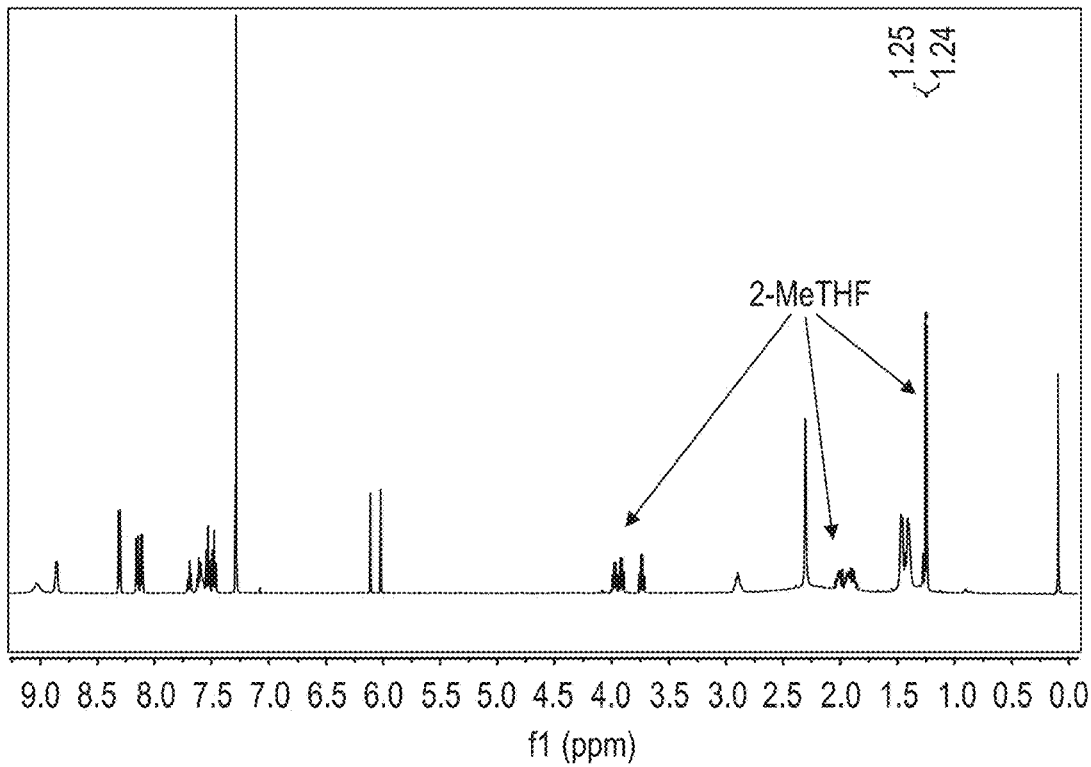
Figures 5, 6, 7:
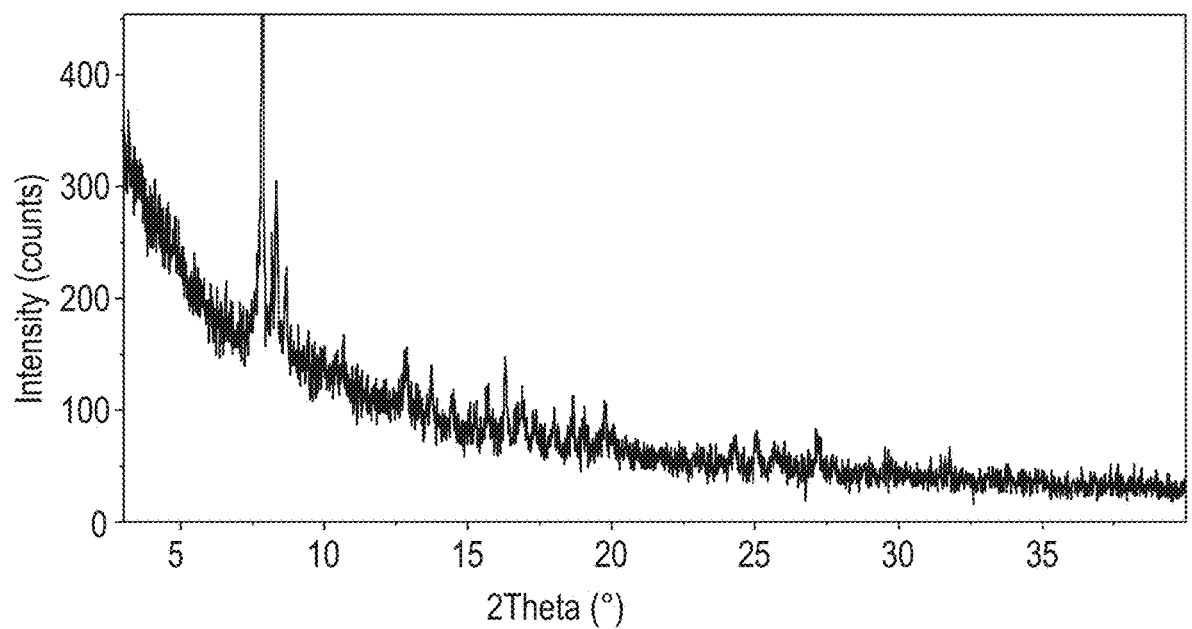
Figures 5, 6, 7, 8:
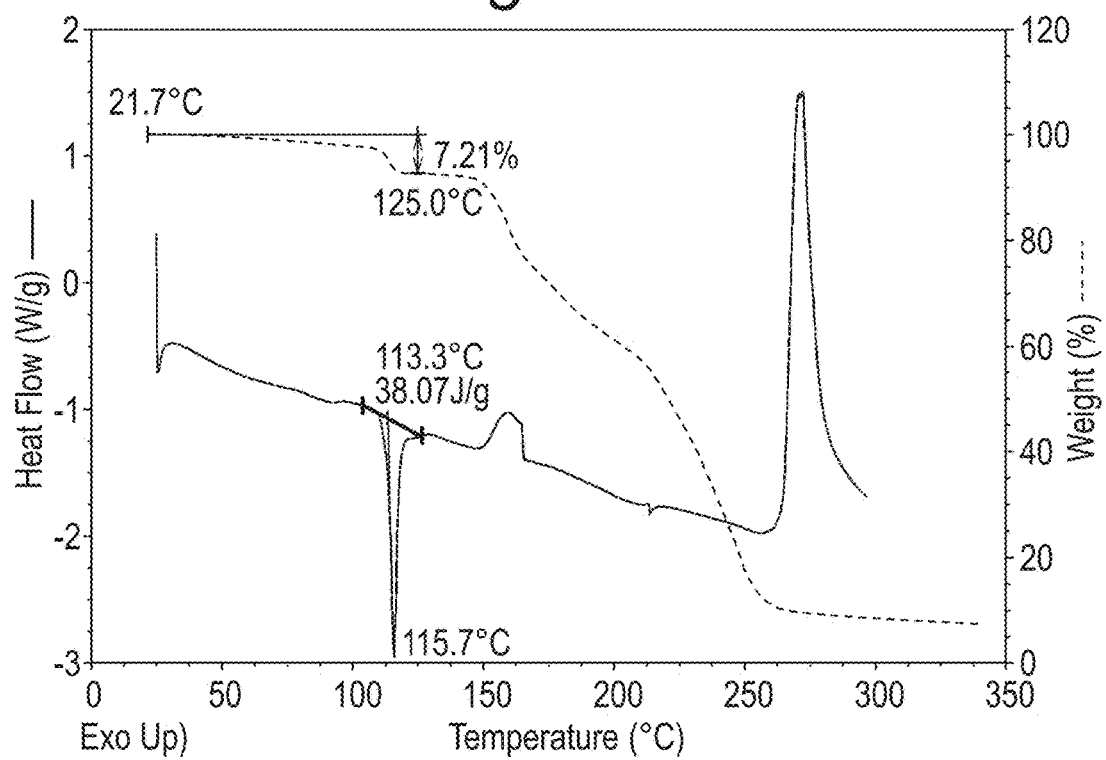
Figures 5, 6, 7, 8, 9:
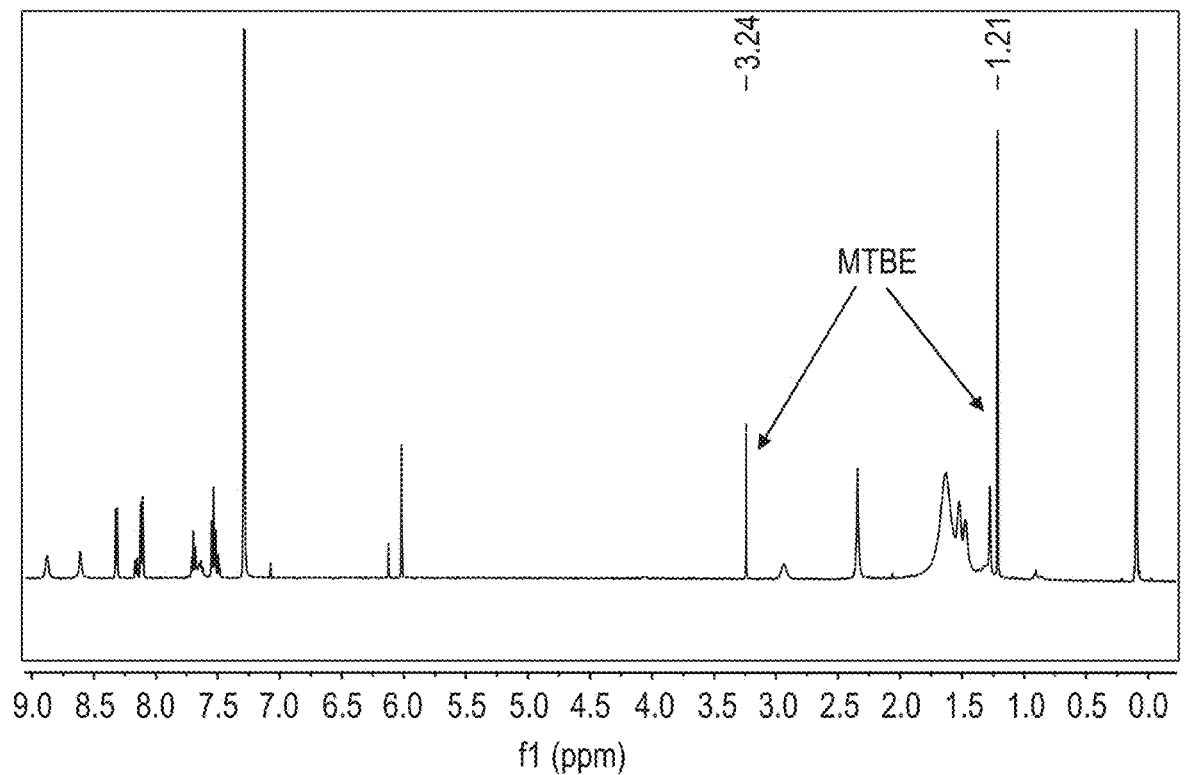
Figures 5, 6, 7, 8, 9, 10:
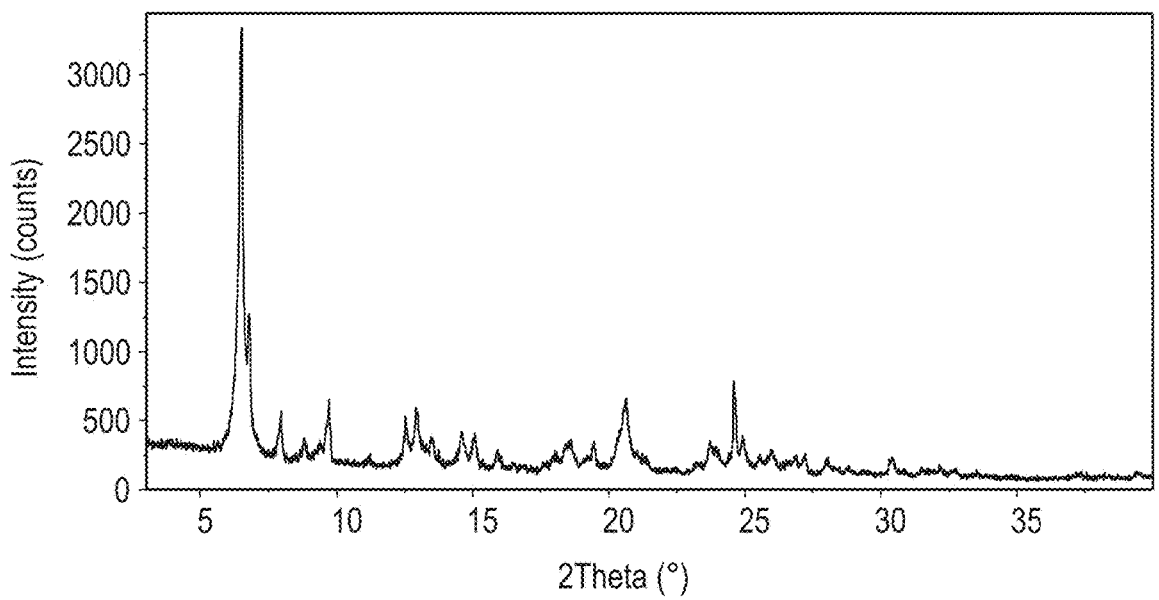
Figures 5, 6, 7, 8, 9, 10, 11:
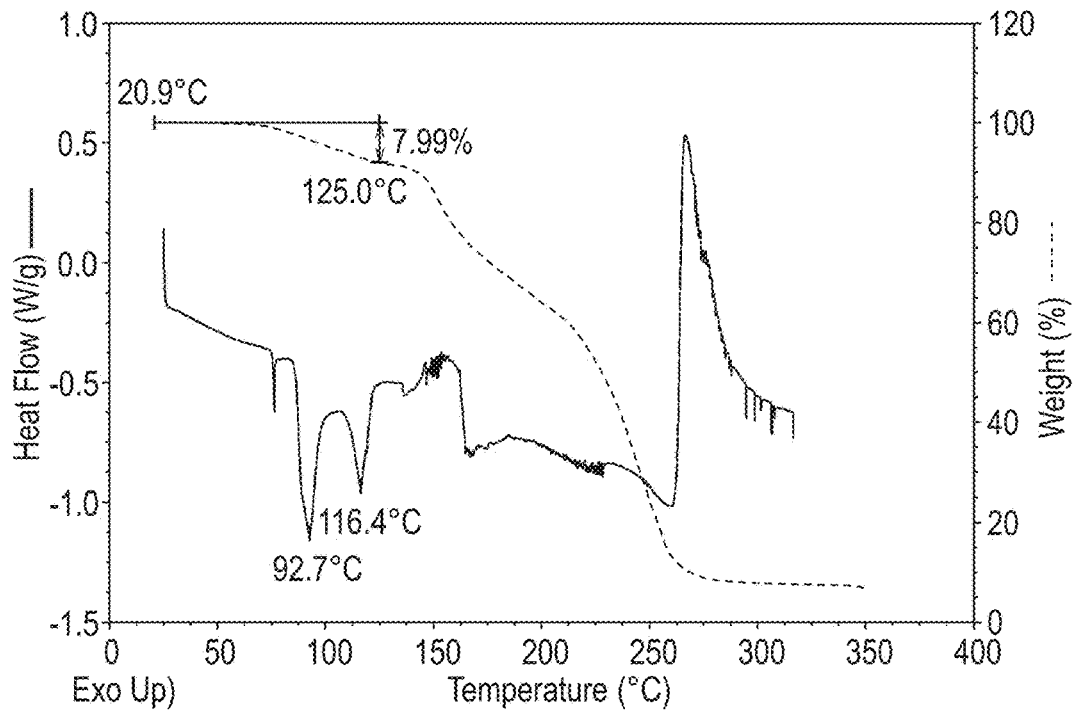
Figures 5, 6, 7, 8, 9, 10, 11, 12:
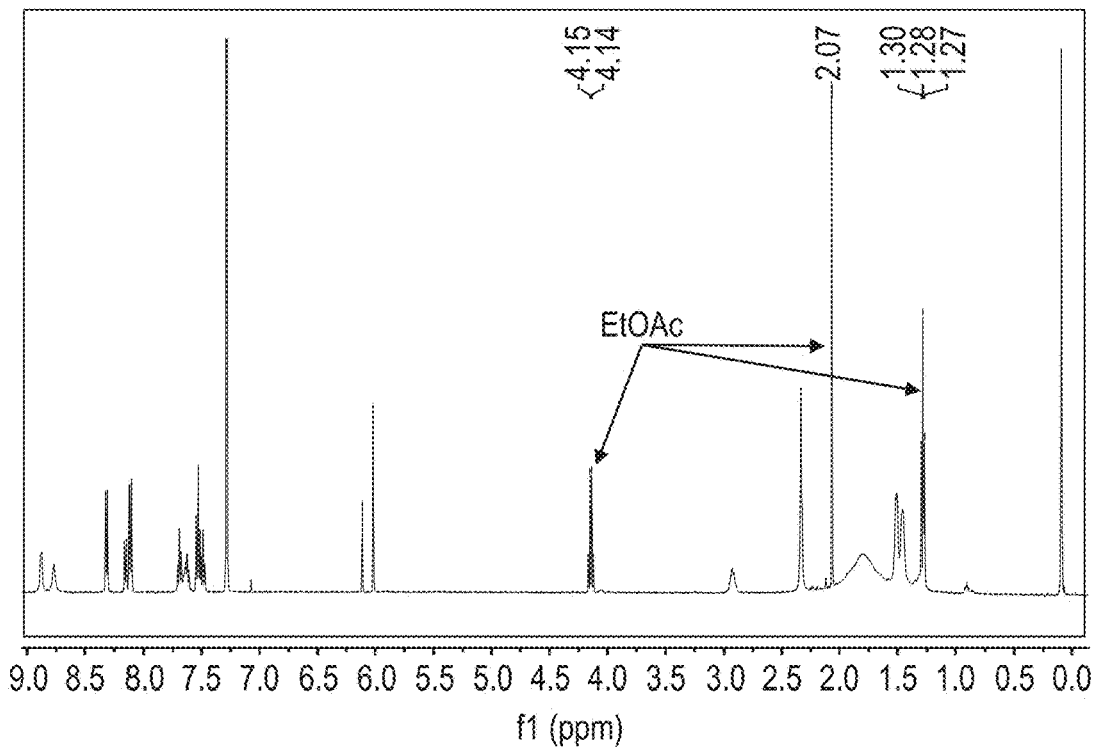
Figures 5, 6, 7, 8, 9, 10, 11, 12, 13:
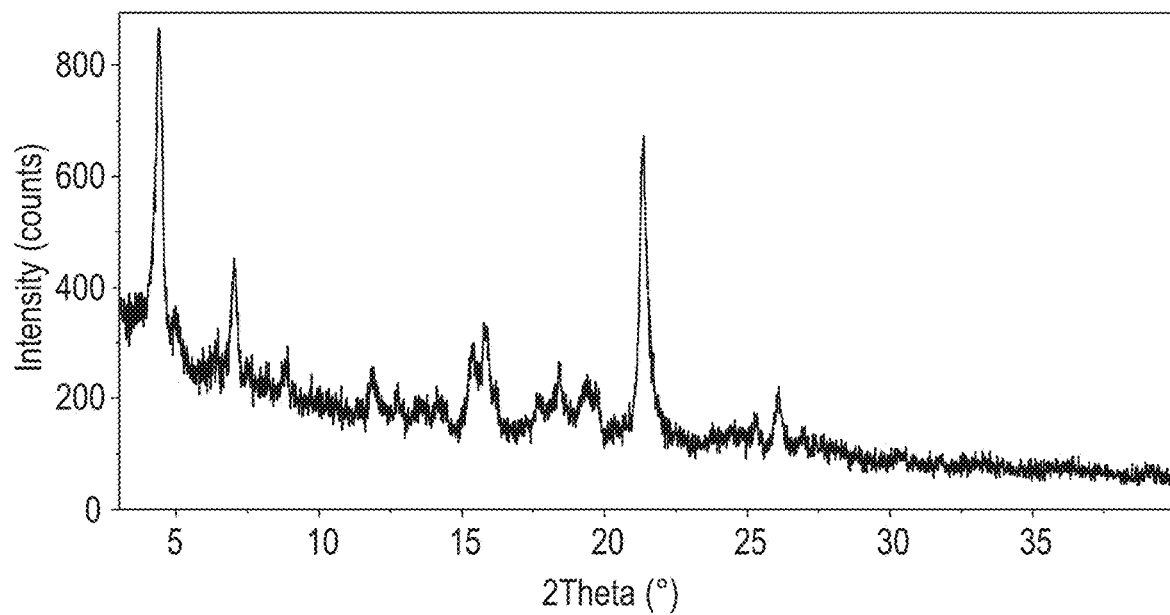
Figures 5, 6, 7, 8, 9, 10, 11, 12, 13, 14:
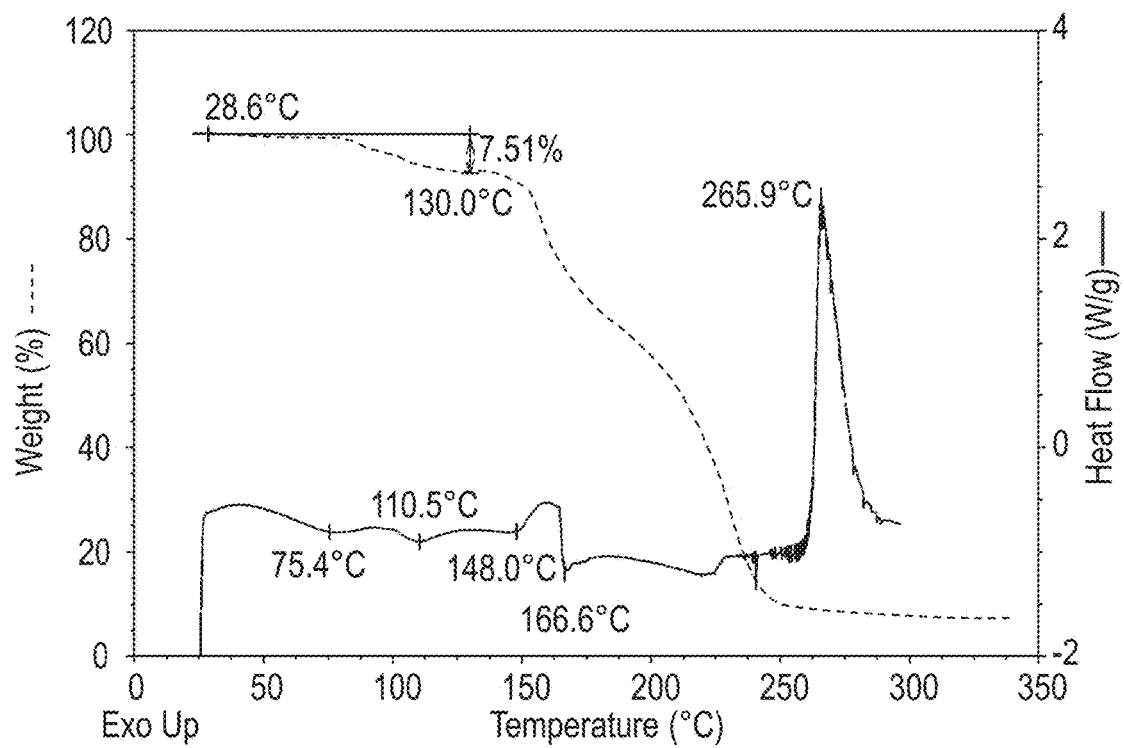
Figures 5, 6, 7, 8, 9, 10, 11, 12, 13, 14, 15:
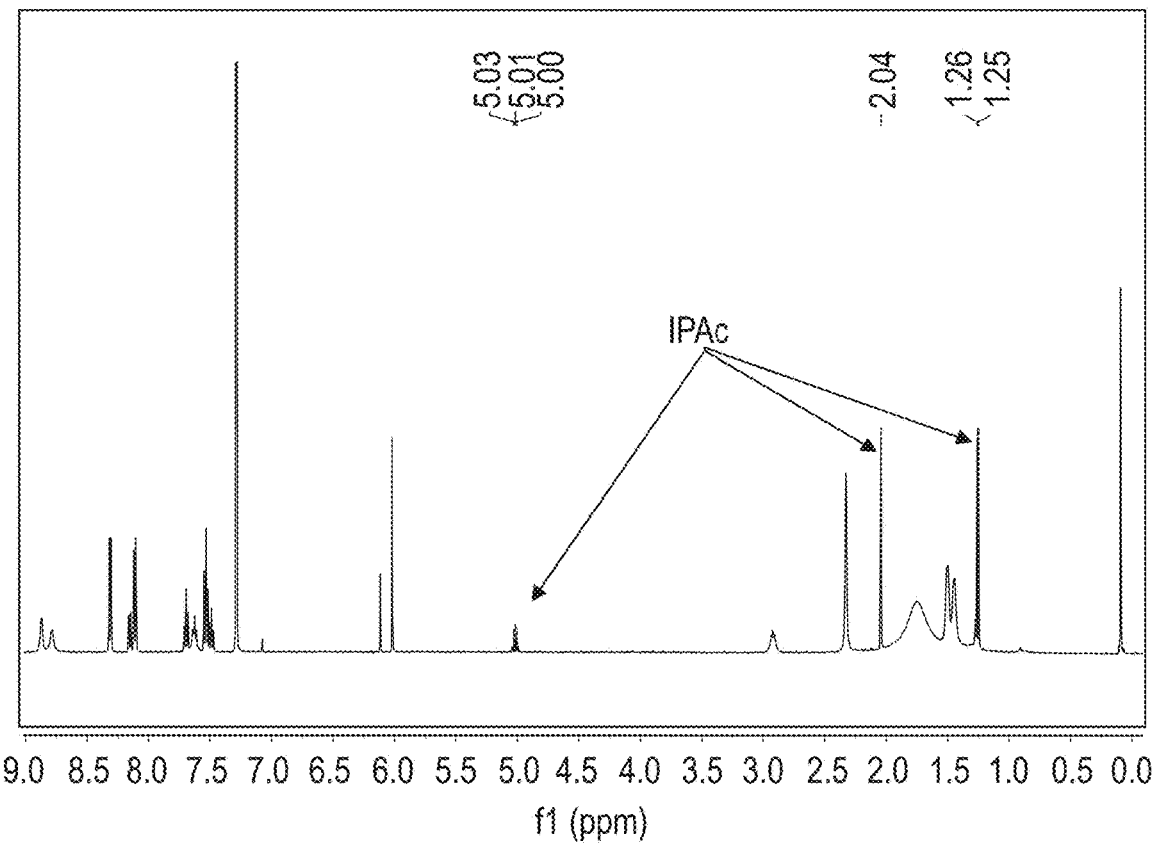
Figures 5, 6, 7, 8, 9, 10, 11, 12, 13, 14, 15, 16:
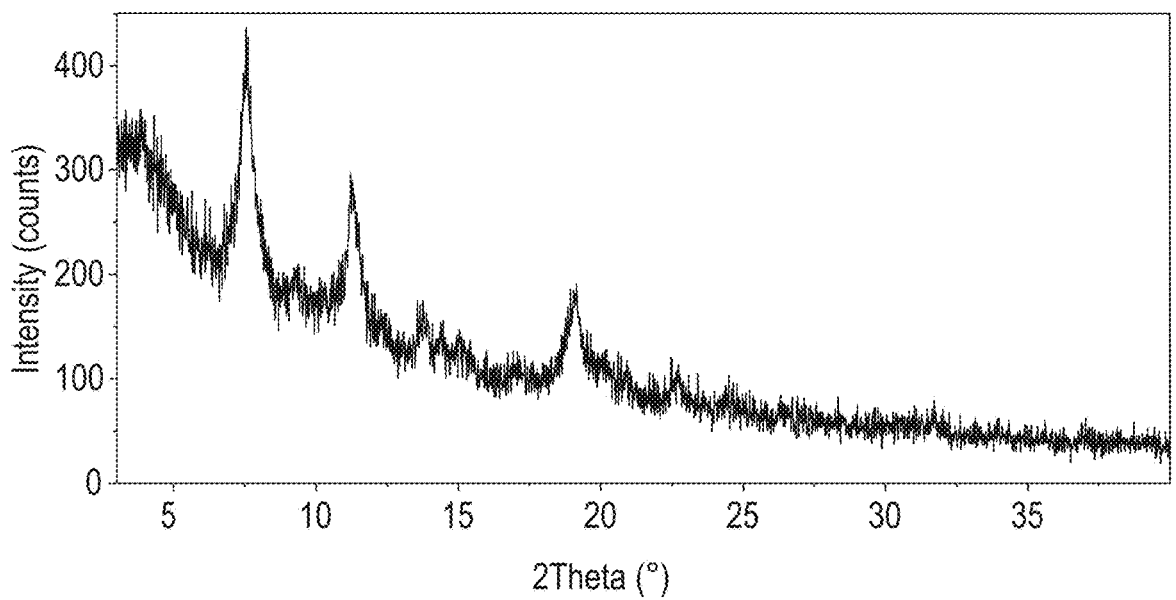
Figures 5, 6, 7, 8, 9, 10, 11, 12, 13, 14, 15, 16, 17:
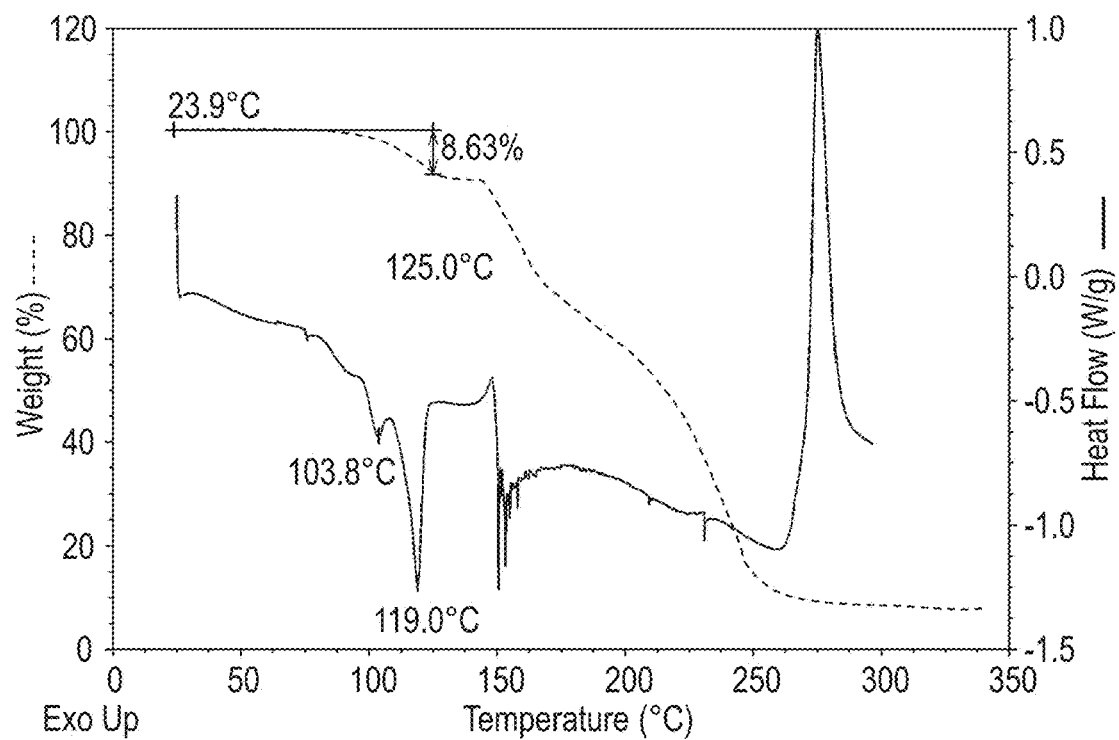
Figures 5, 6, 7, 8, 9, 10, 11, 12, 13, 14, 15, 16, 17, 18:
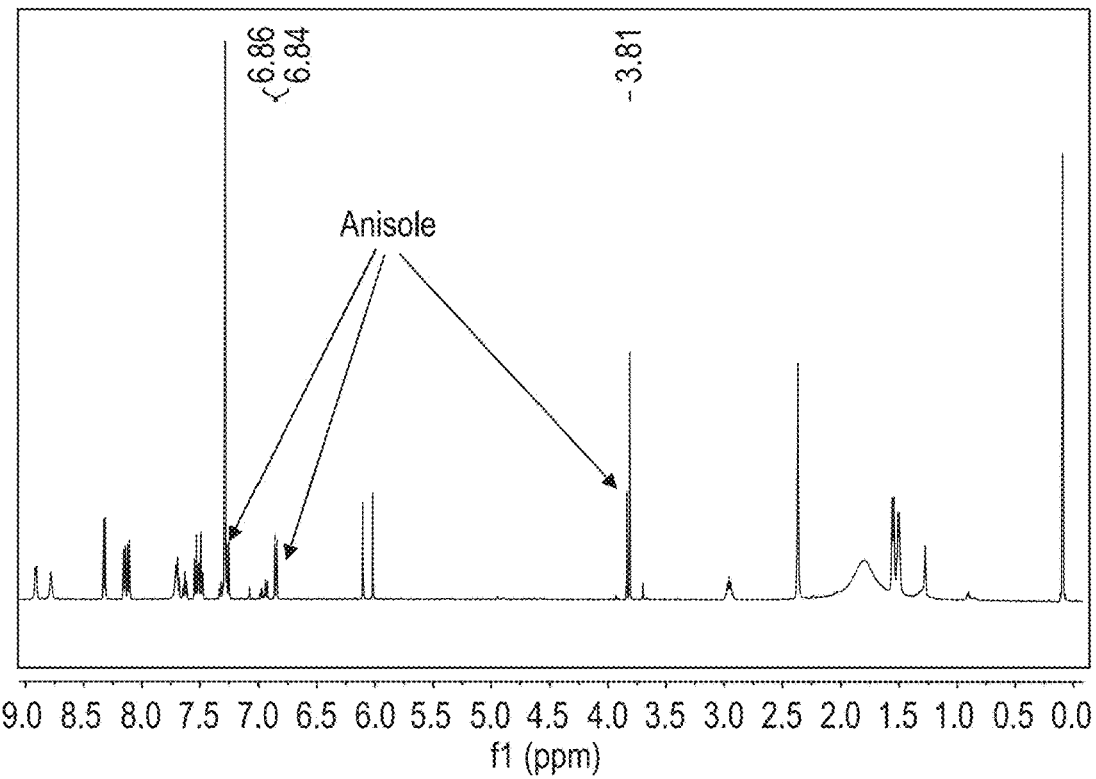
Figures 5, 6, 7, 8, 9, 10, 11, 12, 13, 14, 15, 16, 17, 18, 19:
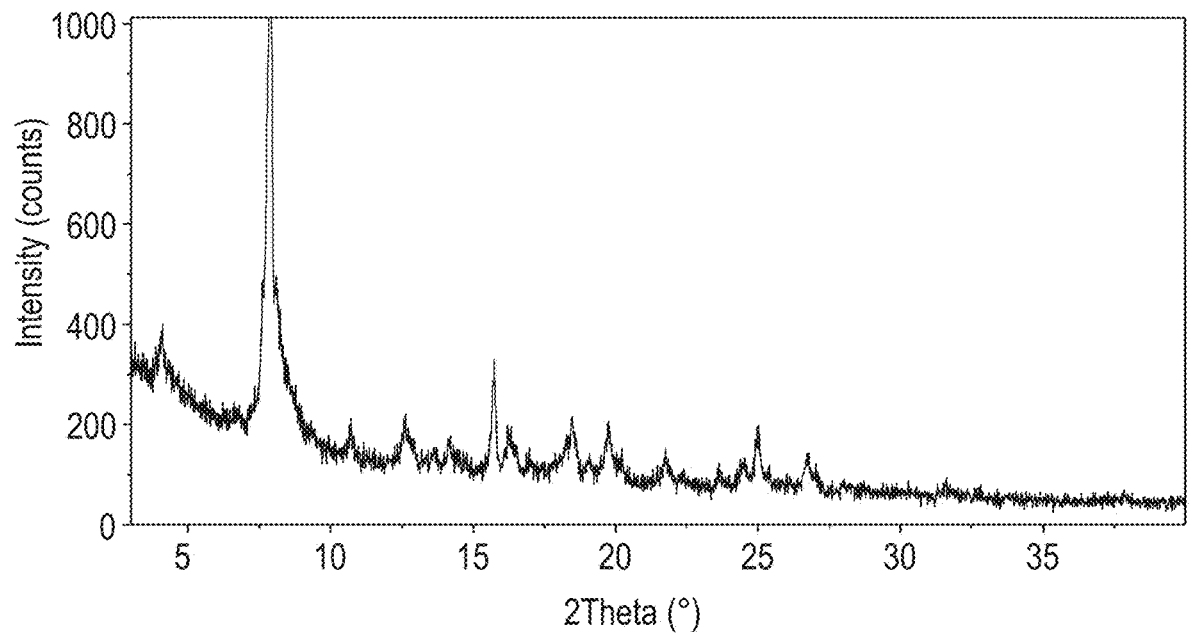
Figures 5, 6, 7, 8, 9, 10, 11, 12, 13, 14, 15, 16, 17, 18, 19, 20:
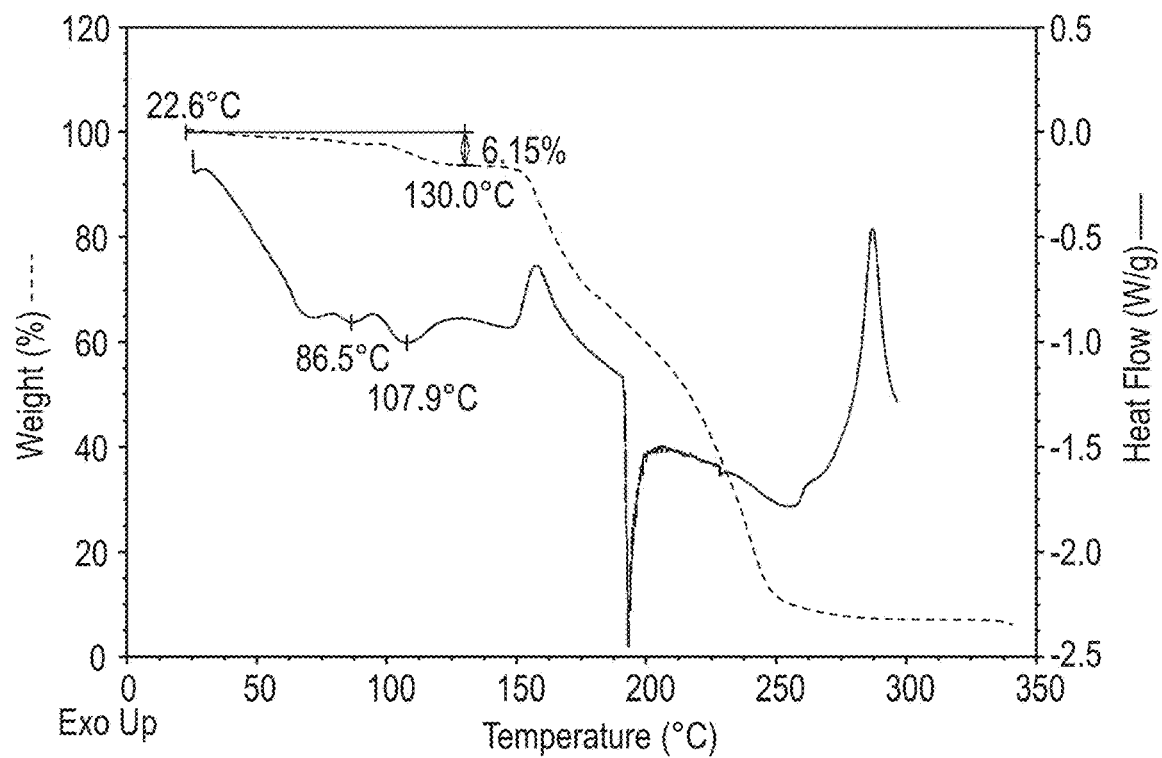
Figures 5, 6, 7, 8, 9, 10, 11, 12, 13, 14, 15, 16, 17, 18, 19, 20, 21:
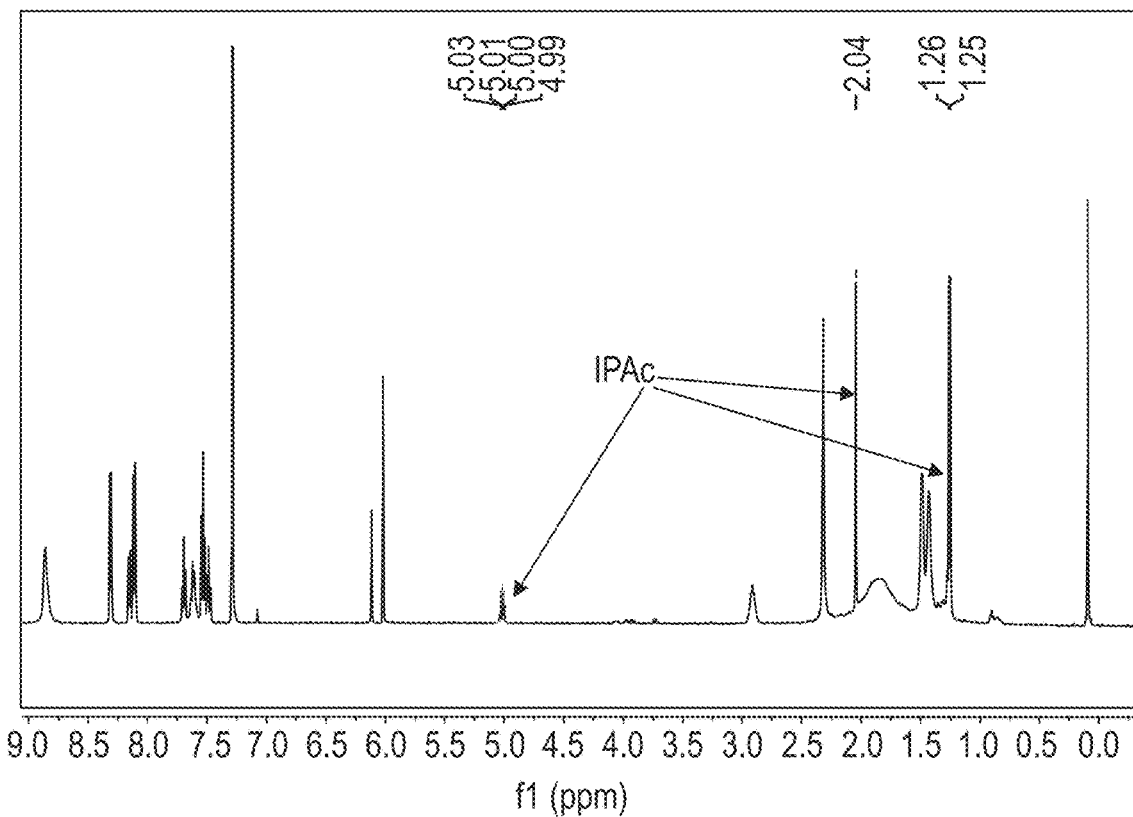
Figures 5, 6, 7, 8, 9, 10, 11, 12, 13, 14, 15, 16, 17, 18, 19, 20, 21, 22:
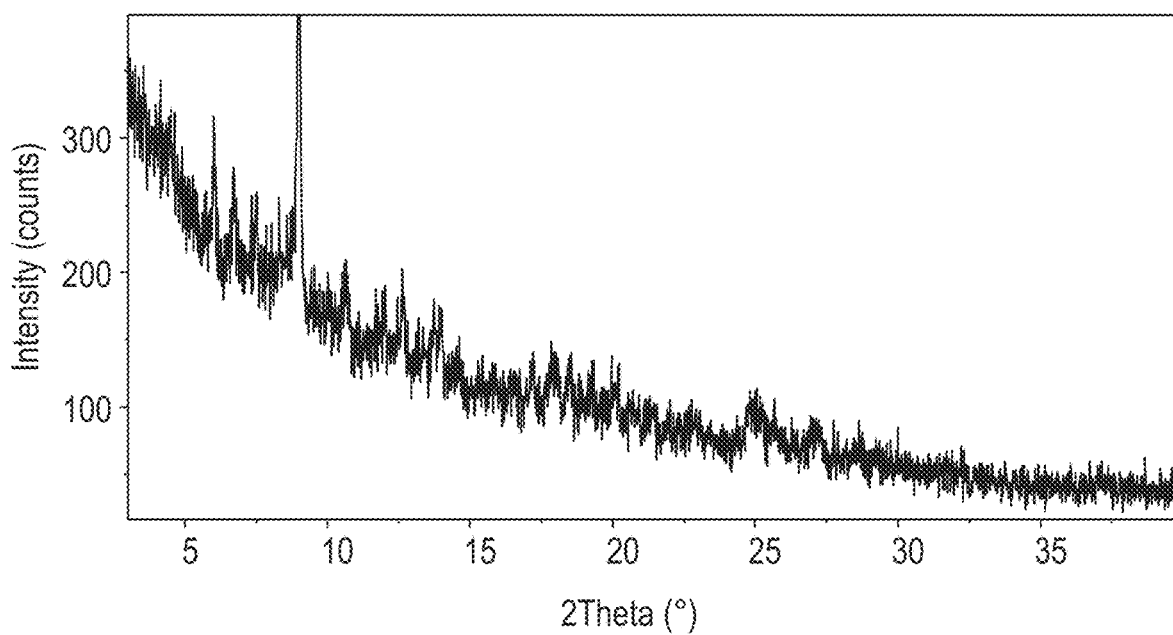
Figures 5, 6, 7, 8, 9, 10, 11, 12, 13, 14, 15, 16, 17, 18, 19, 20, 21, 22, 23:
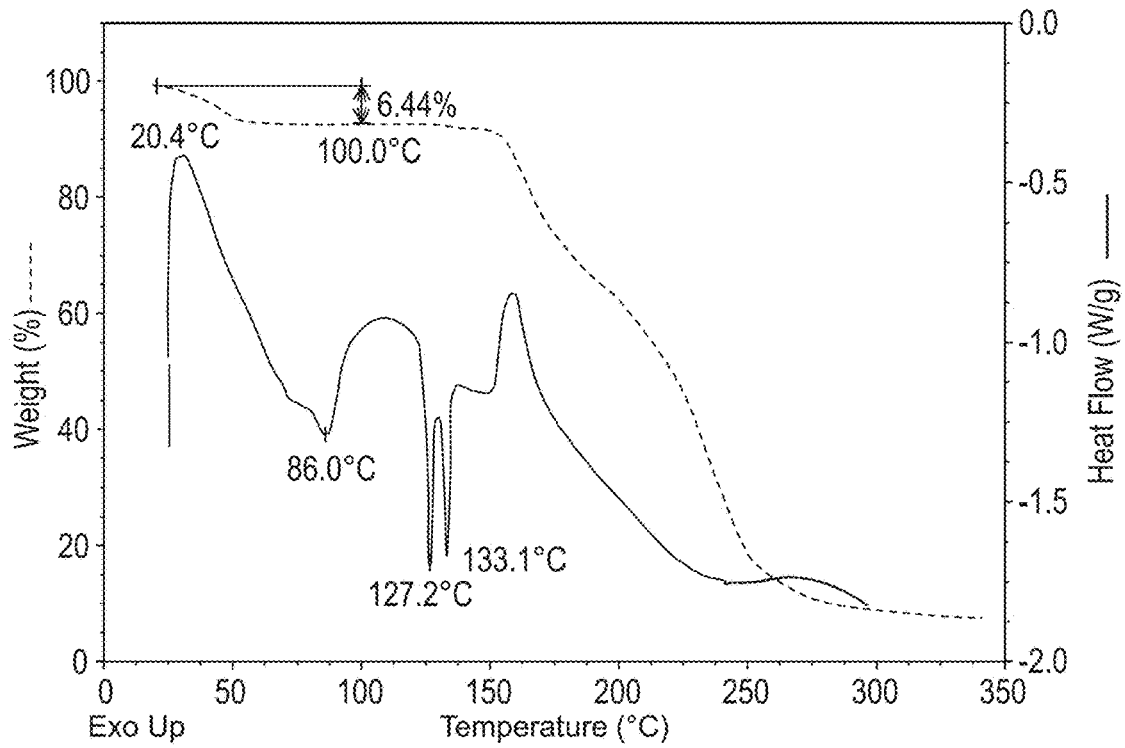
Figures 5, 6, 7, 8, 9, 10, 11, 12, 13, 14, 15, 16, 17, 18, 19, 20, 21, 22, 23, 24:
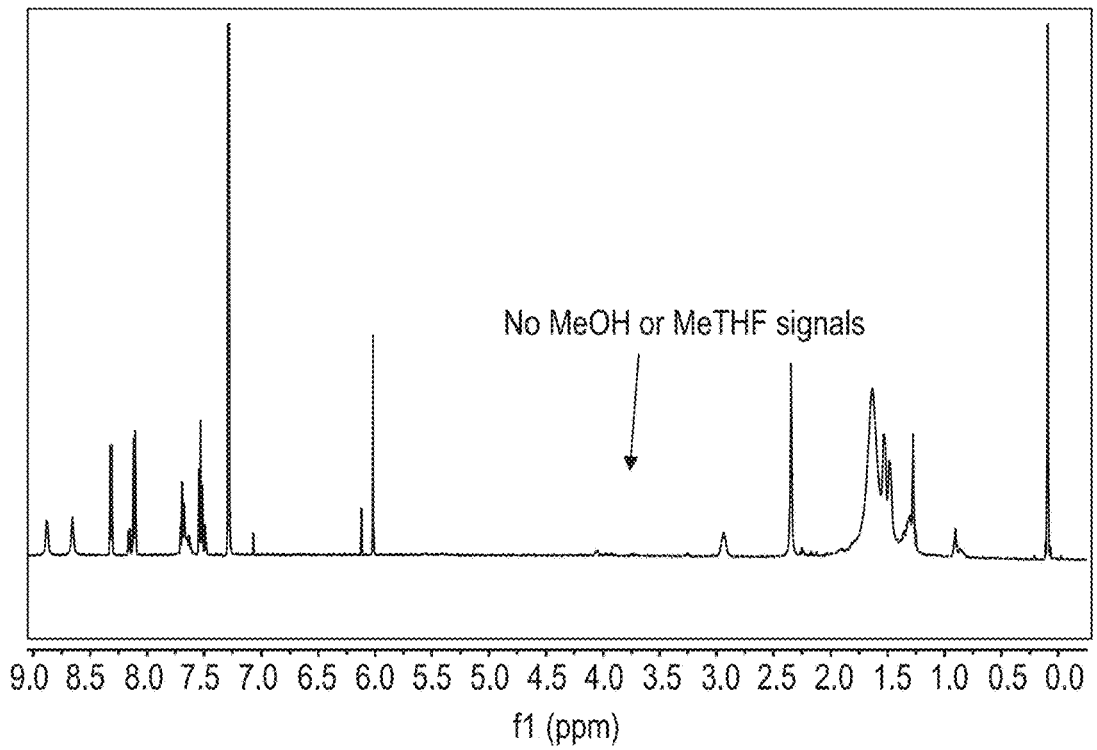
Figures 5, 6, 7, 8, 9, 10, 11, 12, 13, 14, 15, 16, 17, 18, 19, 20, 21, 22, 23, 24, 25:
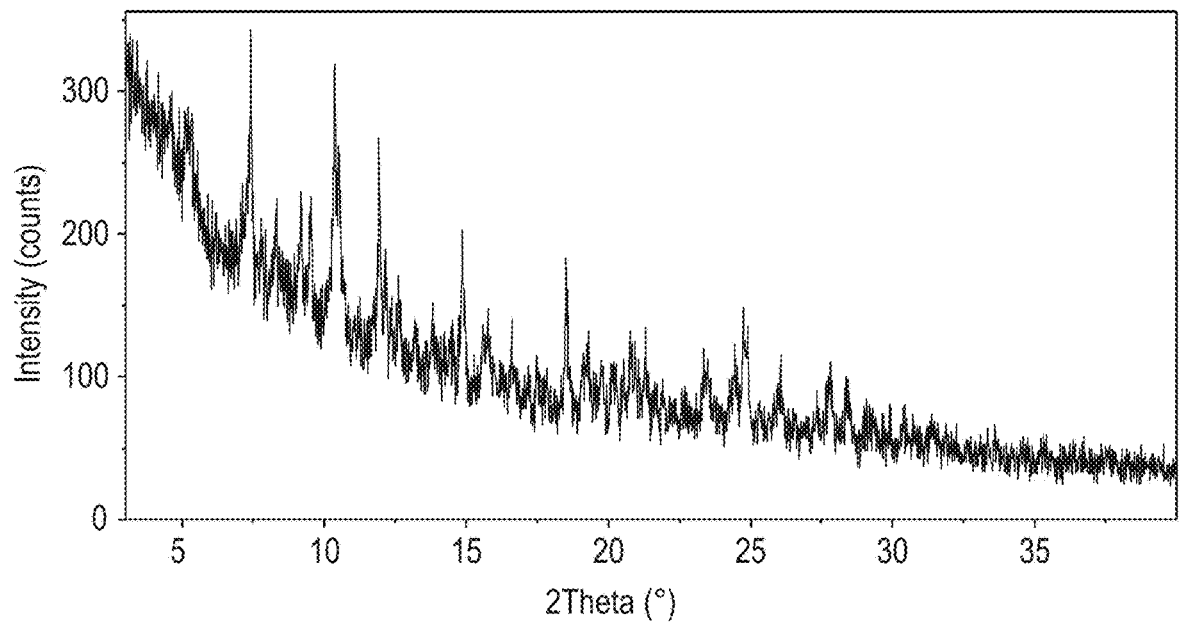
Figures 5, 6, 7, 8, 9, 10, 11, 12, 13, 14, 15, 16, 17, 18, 19, 20, 21, 22, 23, 24, 25, 26:
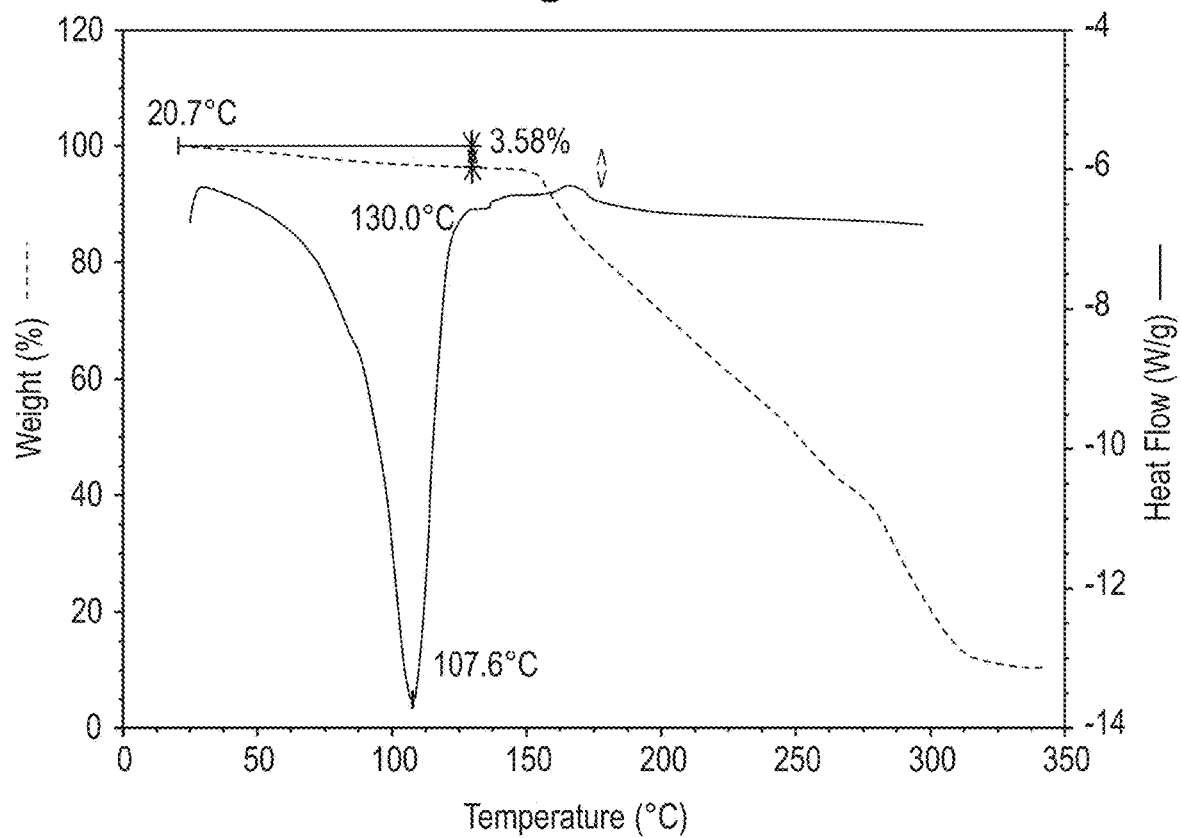
Figures 5, 6, 7, 8, 9, 10, 11, 12, 13, 14, 15, 16, 17, 18, 19, 20, 21, 22, 23, 24, 25, 26, 27:
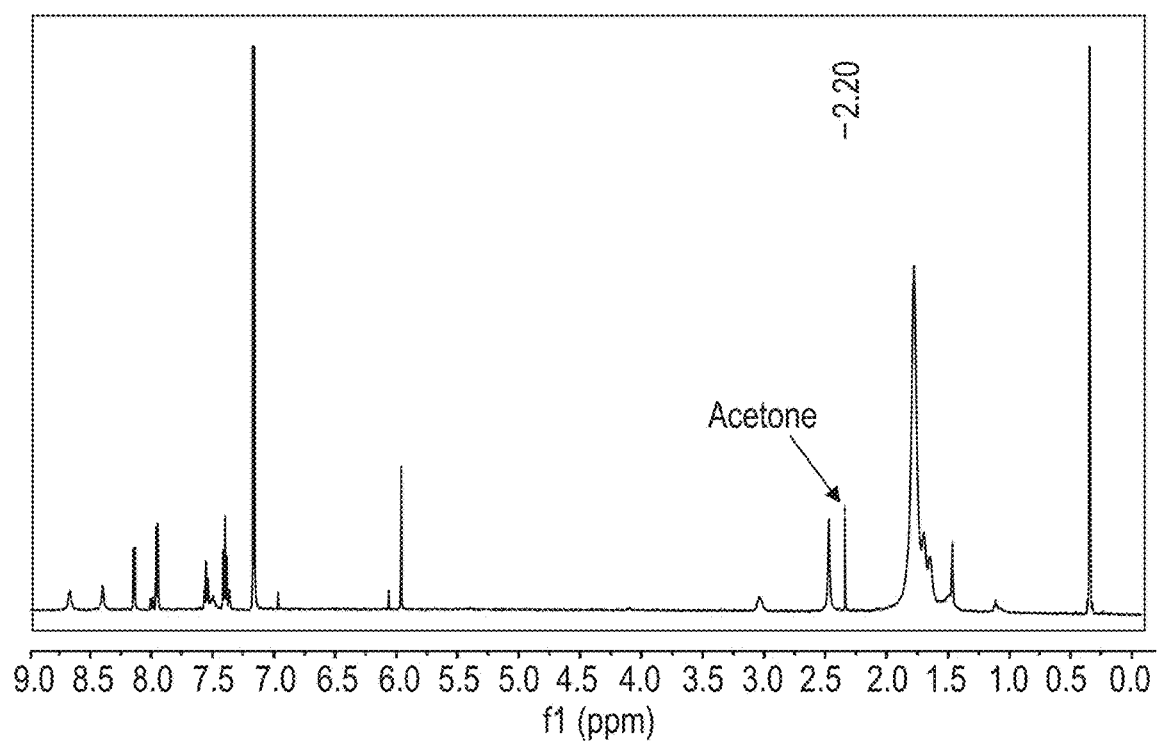
Figures 5, 6, 7, 8, 9, 10, 11, 12, 13, 14, 15, 16, 17, 18, 19, 20, 21, 22, 23, 24, 25, 26, 27, 28:
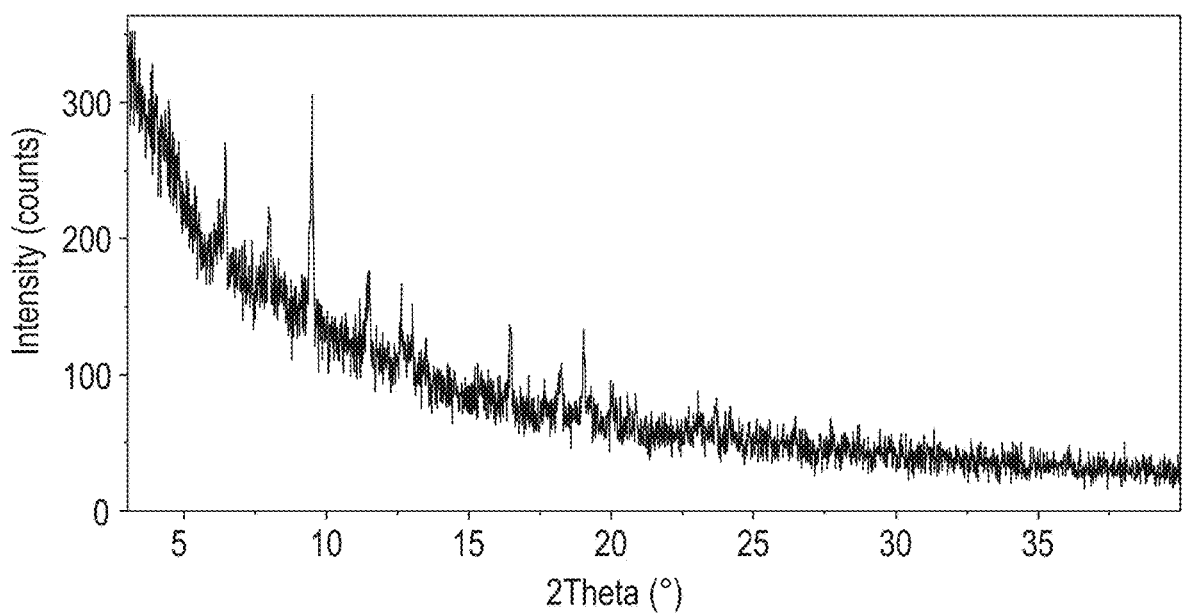
Figures 5, 6, 7, 8, 9, 10, 11, 12, 13, 14, 15, 16, 17, 18, 19, 20, 21, 22, 23, 24, 25, 26, 27, 28, 29:
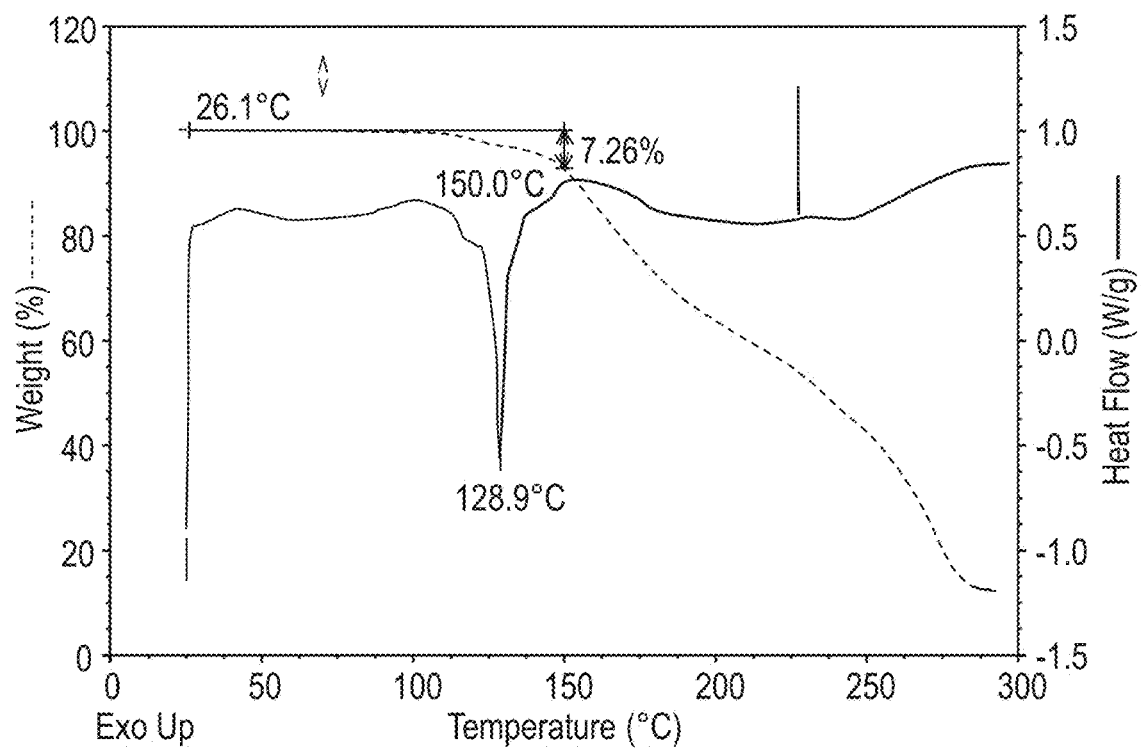
Figures 5, 6, 7, 8, 9, 10, 11, 12, 13, 14, 15, 16, 17, 18, 19, 20, 21, 22, 23, 24, 25, 26, 27, 28, 29, 30:
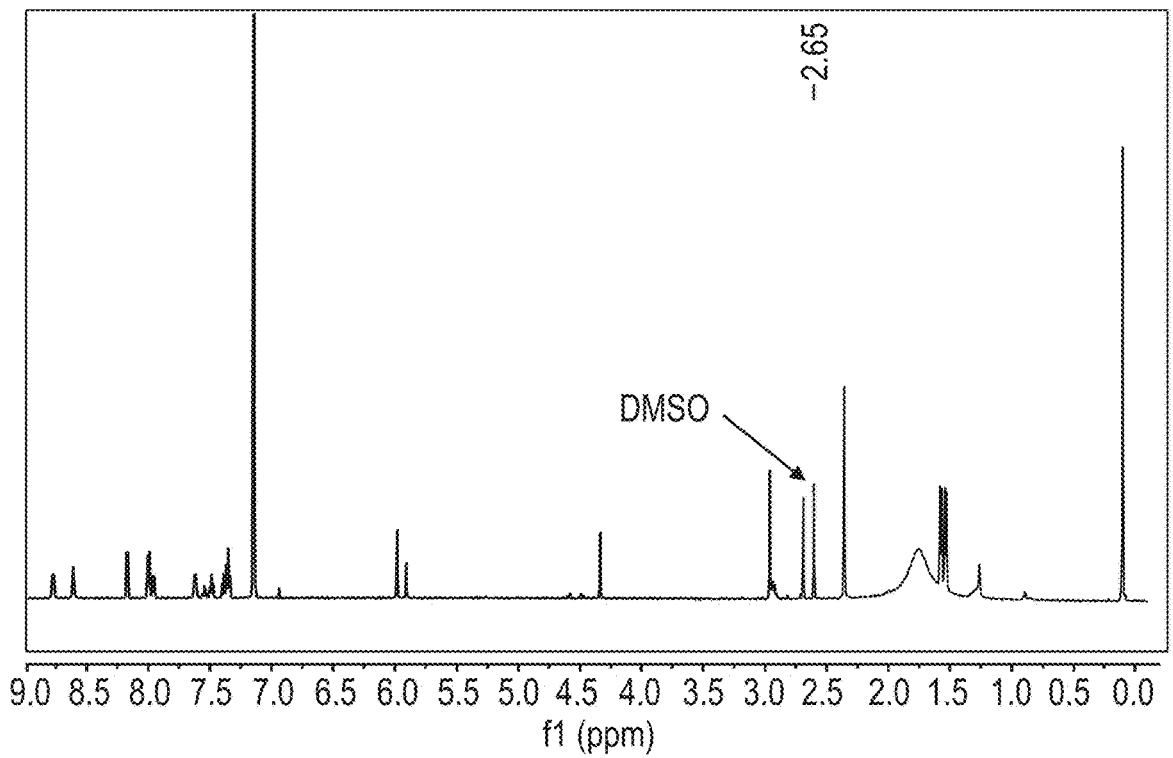
Figures 5, 6, 7, 8, 9, 10, 11, 12, 13, 14, 15, 16, 17, 18, 19, 20, 21, 22, 23, 24, 25, 26, 27, 28, 29, 30, 31:
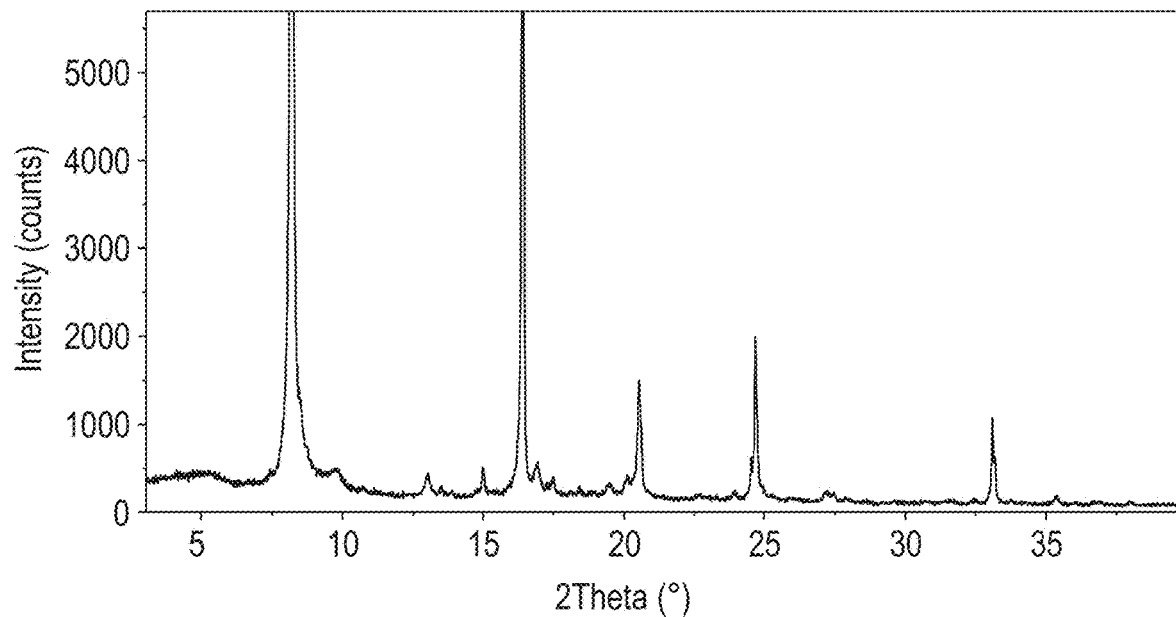
Figures 5, 6, 7, 8, 9, 10, 11, 12, 13, 14, 15, 16, 17, 18, 19, 20, 21, 22, 23, 24, 25, 26, 27, 28, 29, 30, 31, 32:
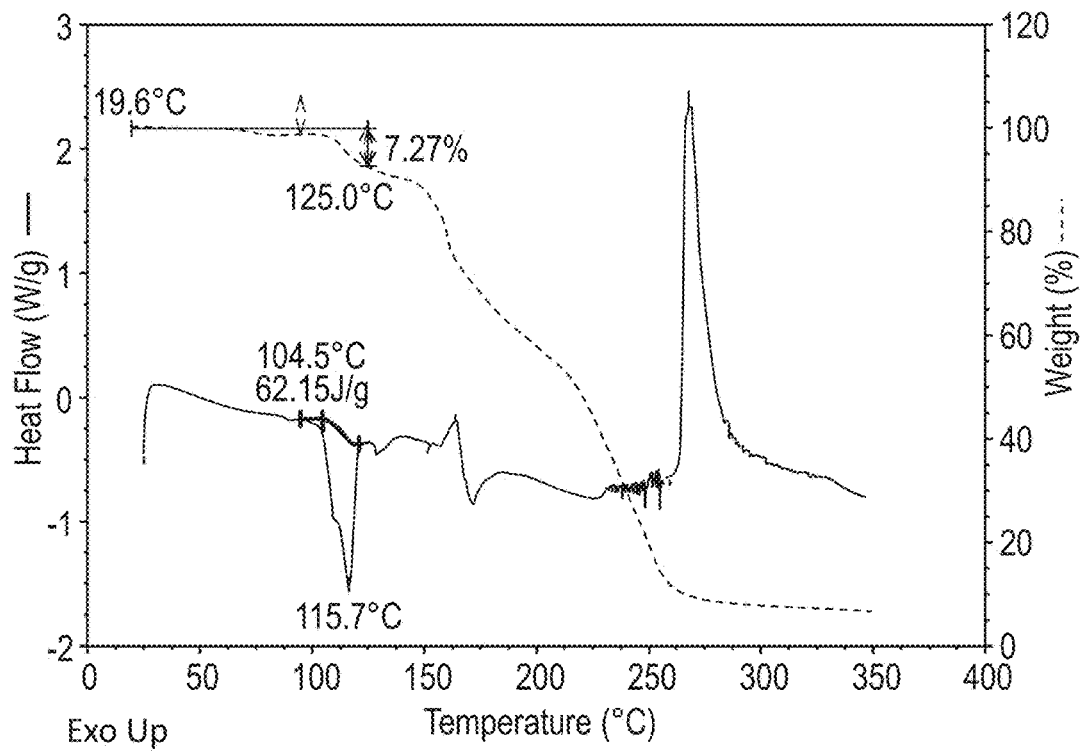
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33:
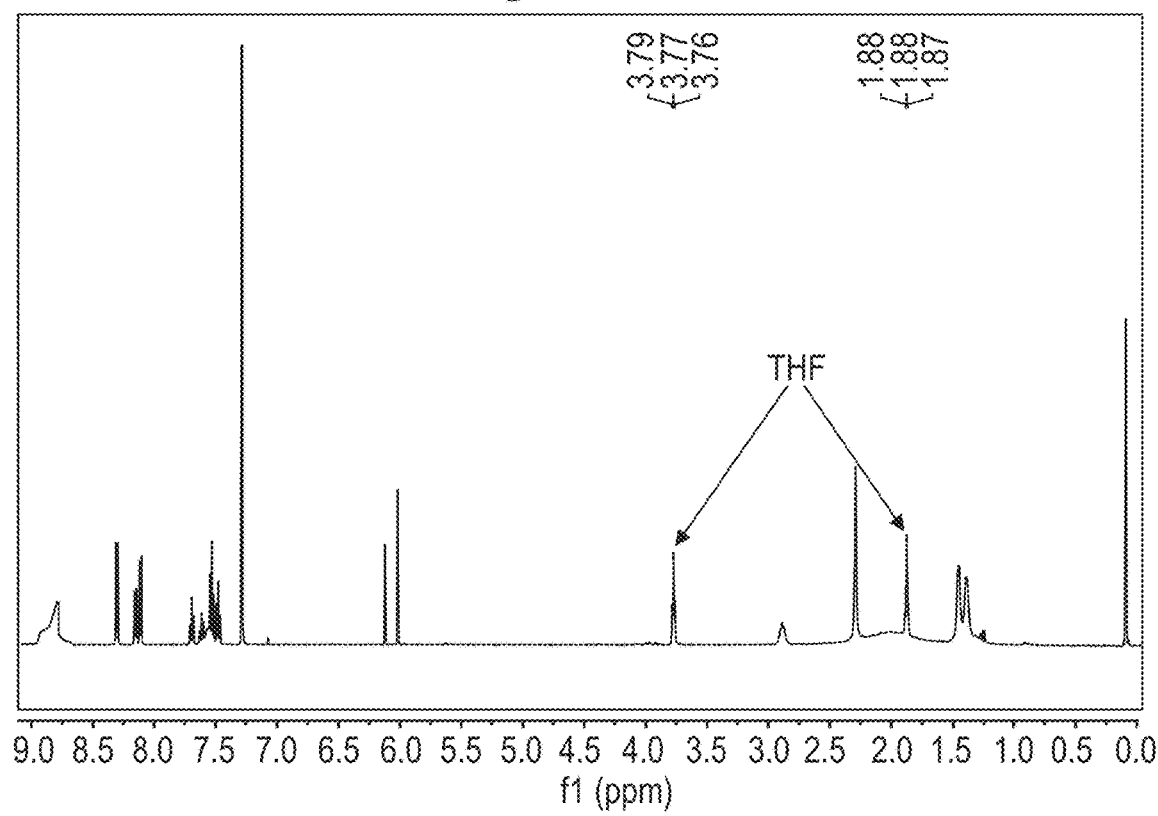
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
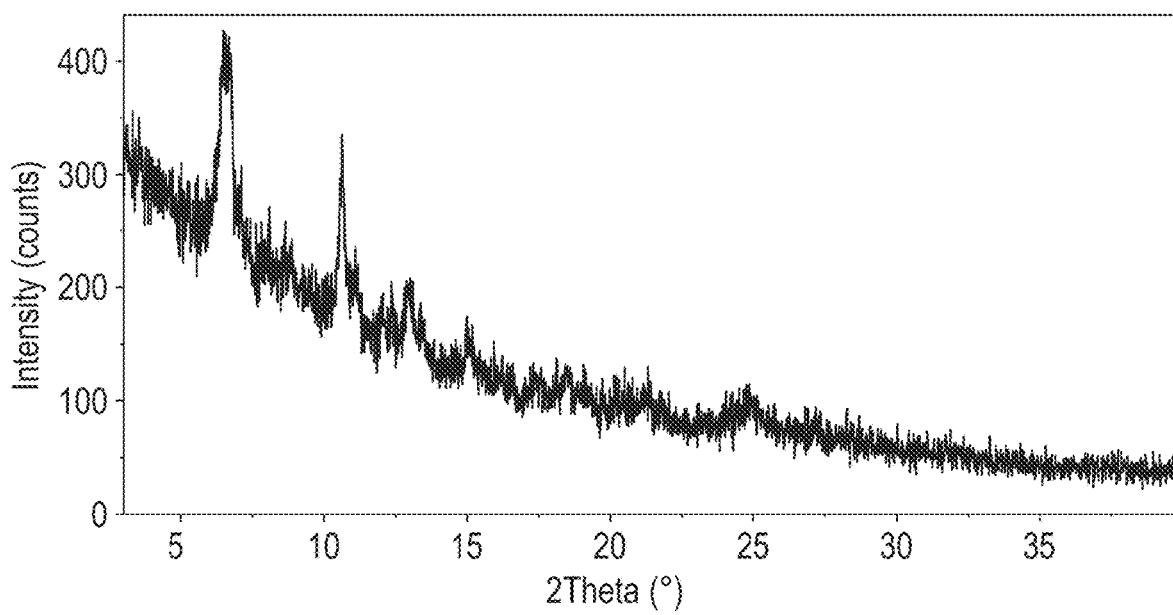
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
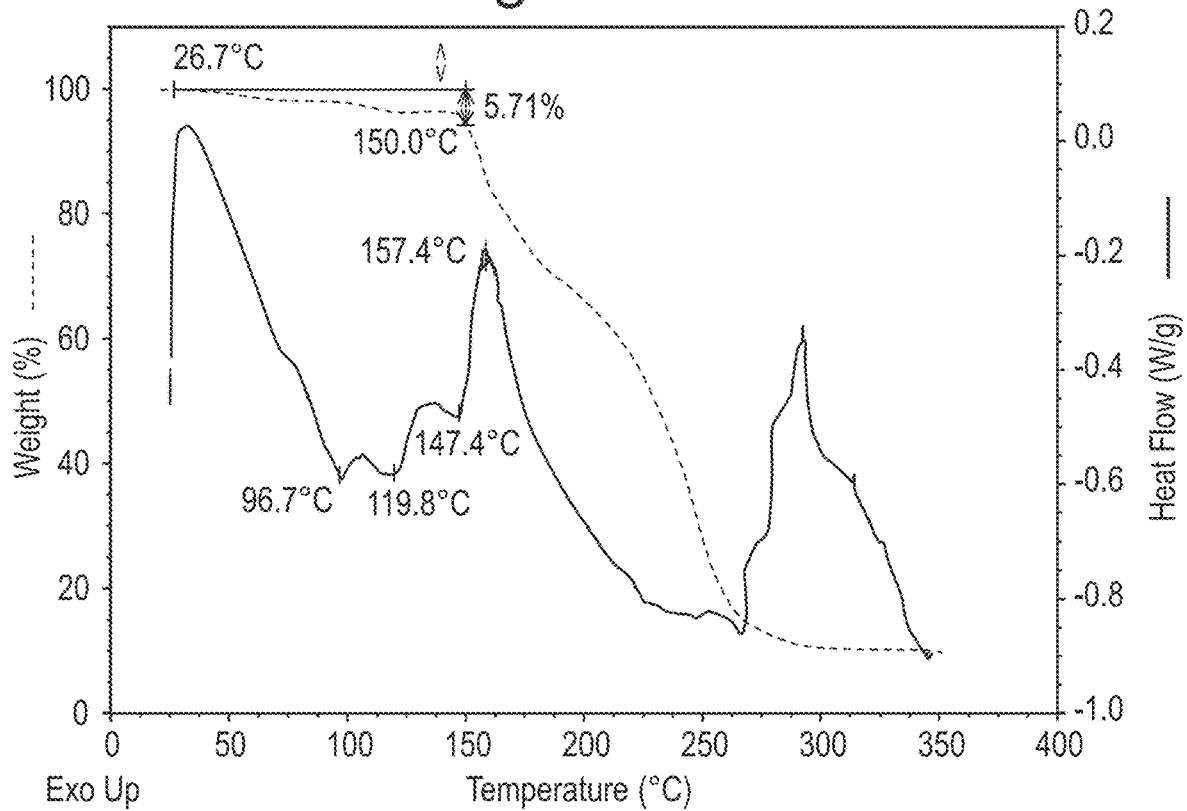
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
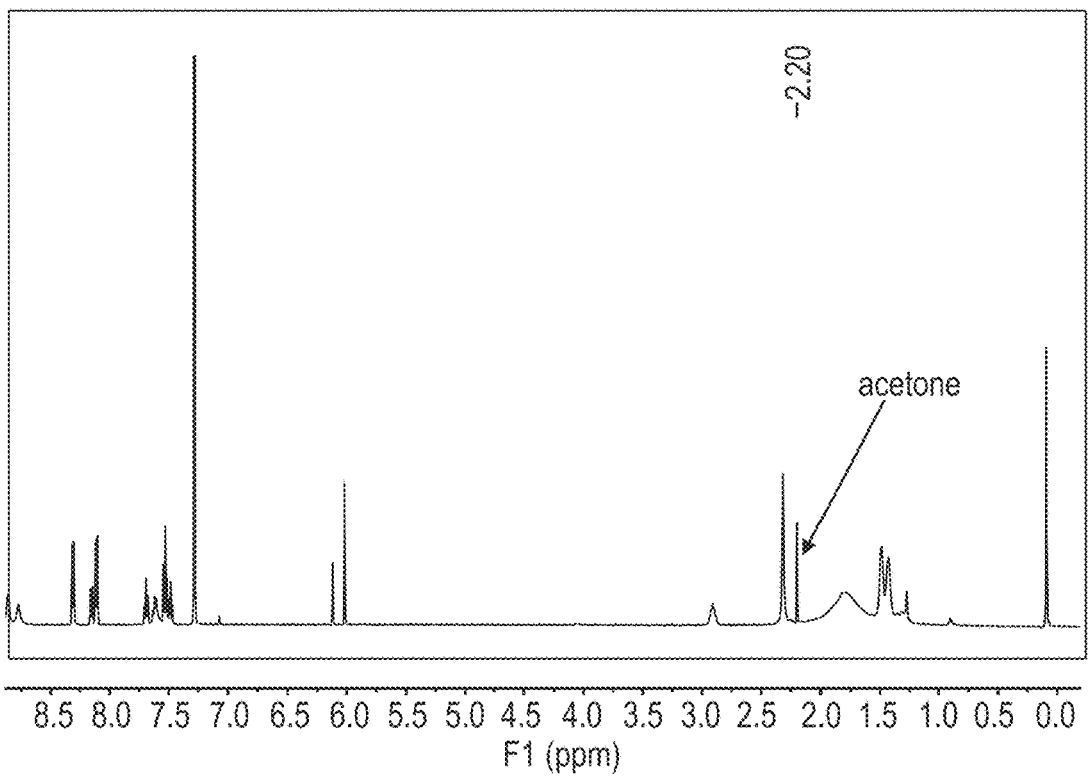
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
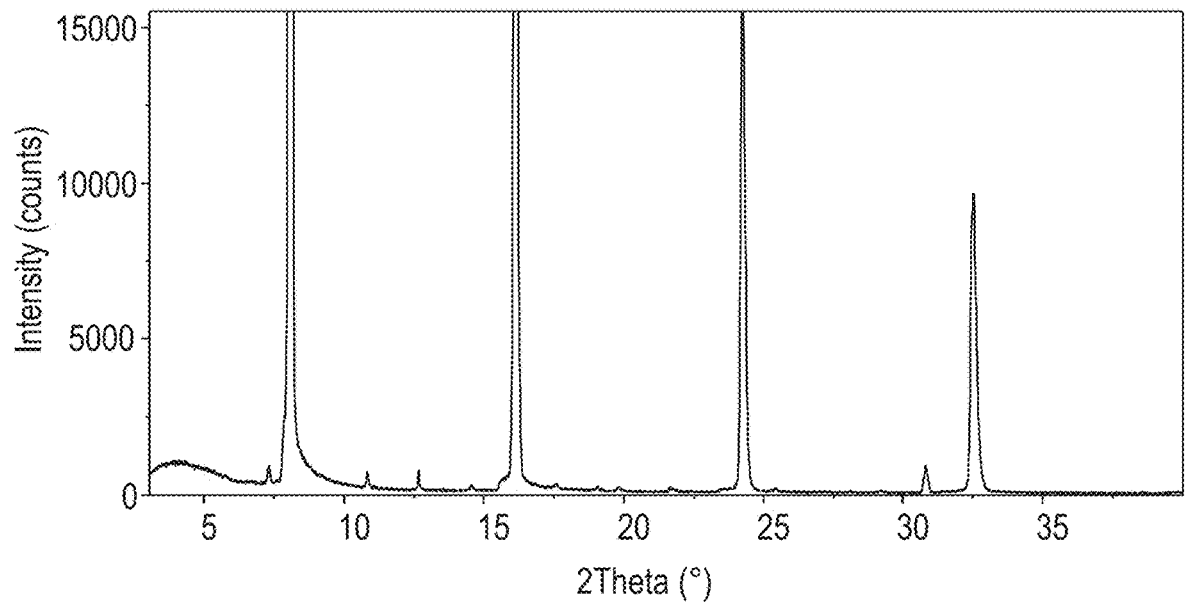
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
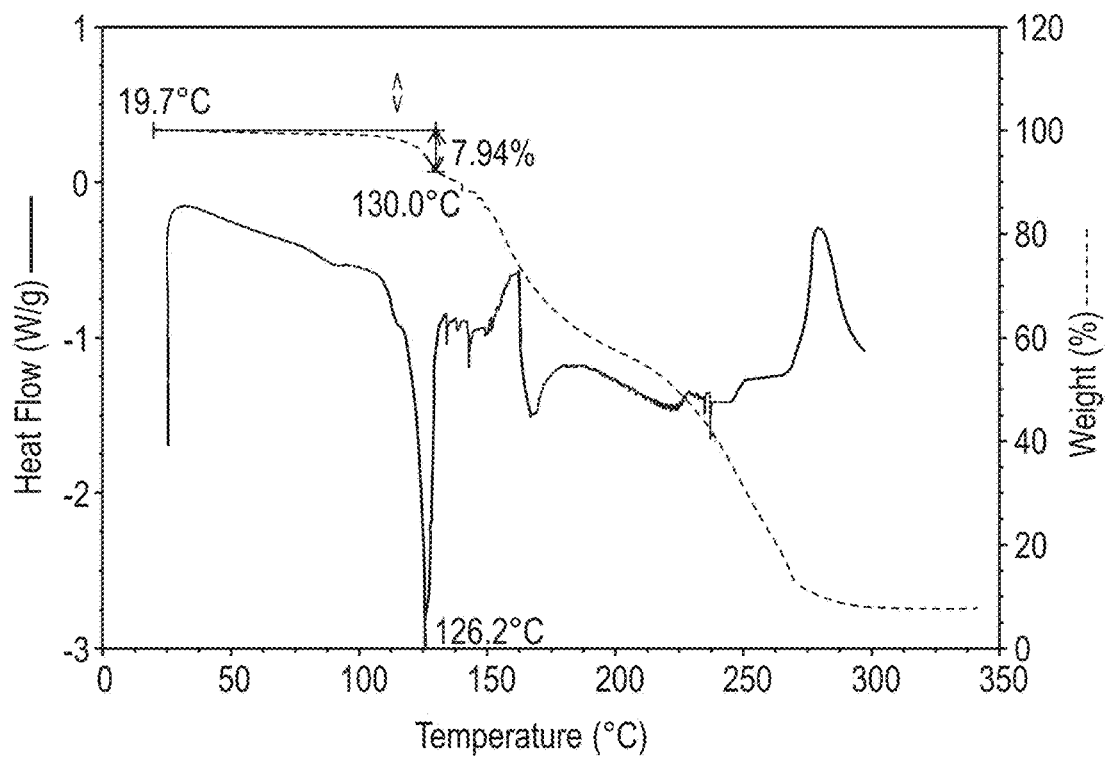
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
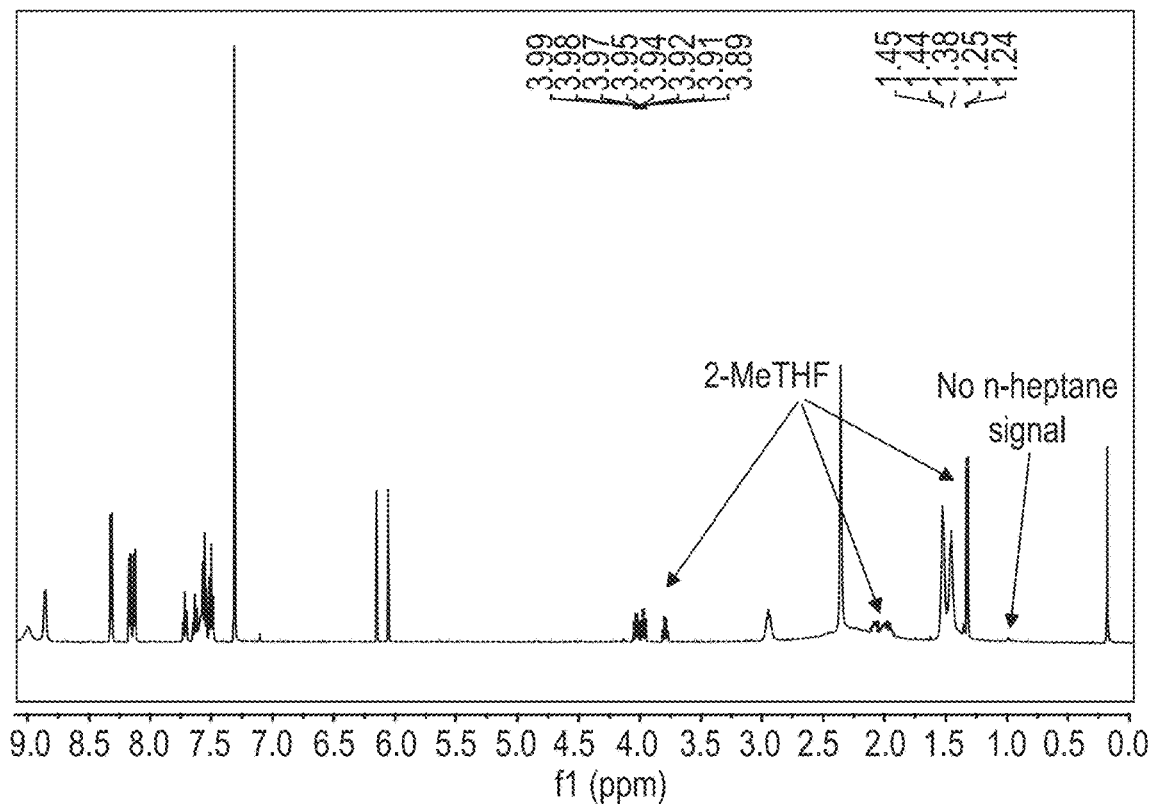
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
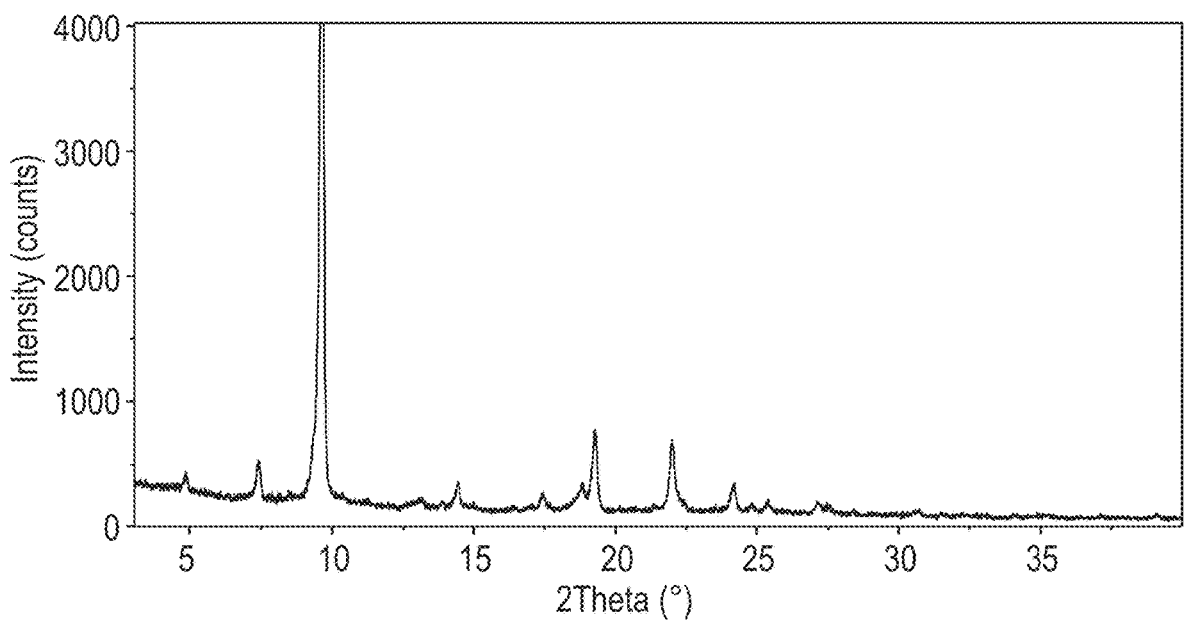
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
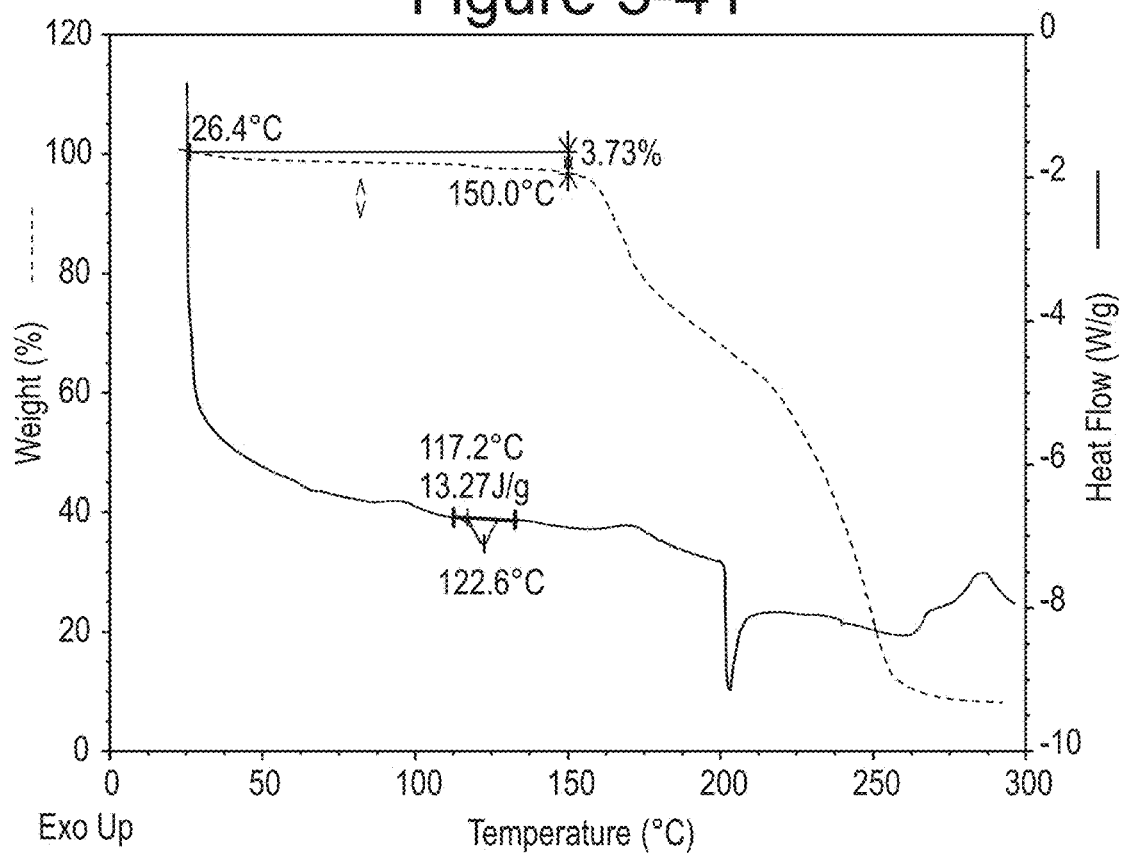
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
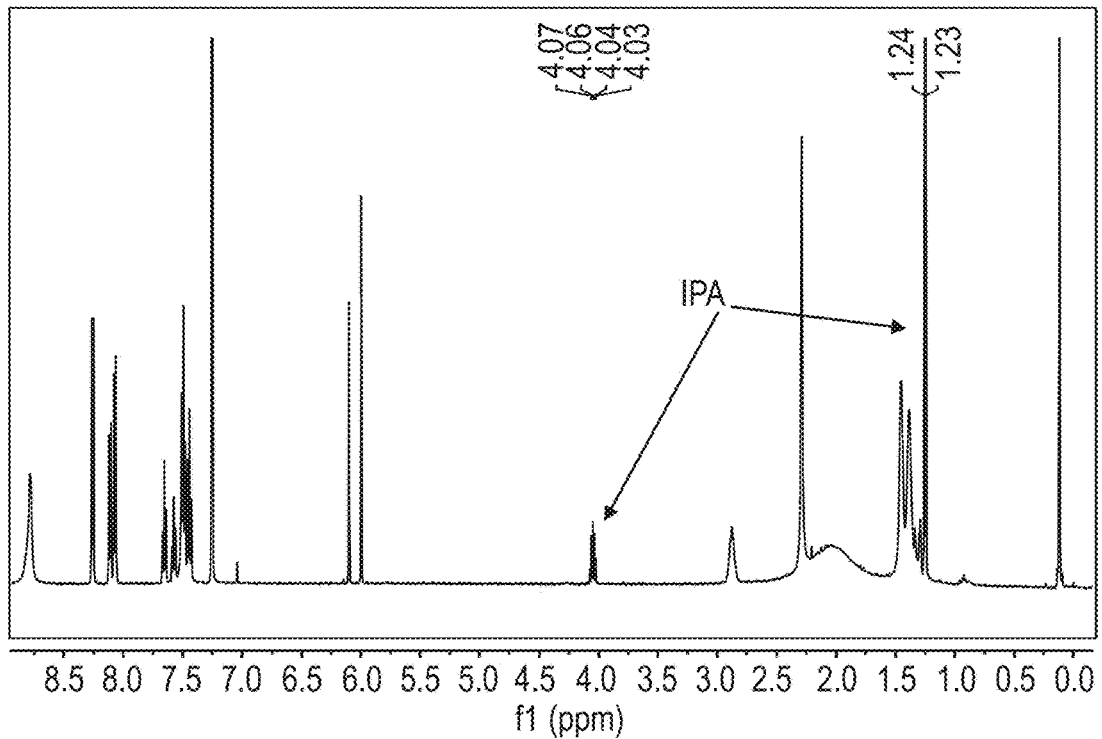
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
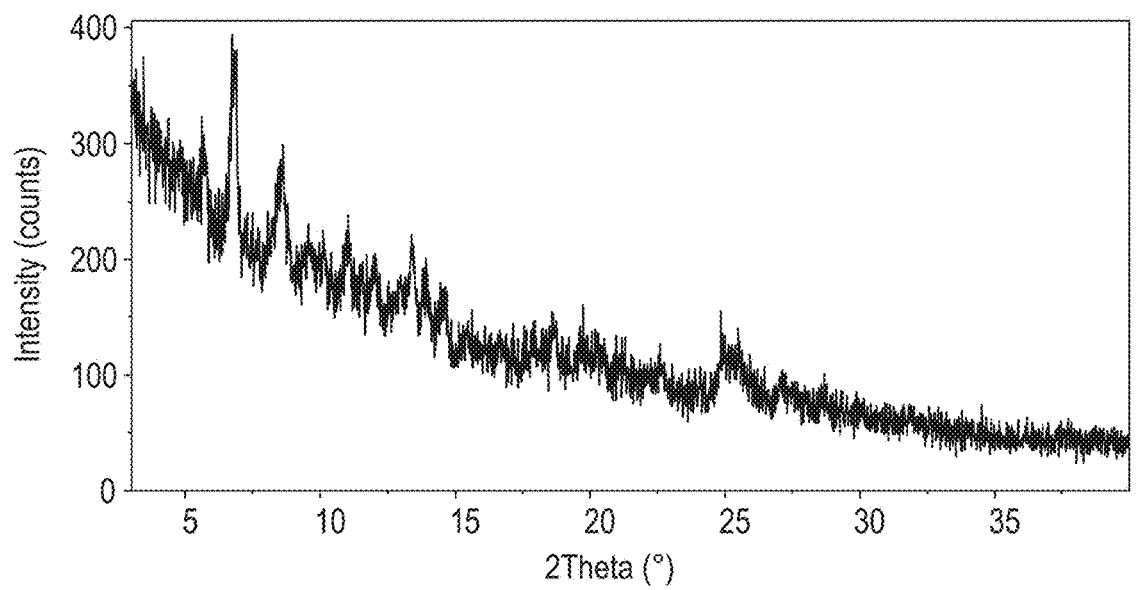
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
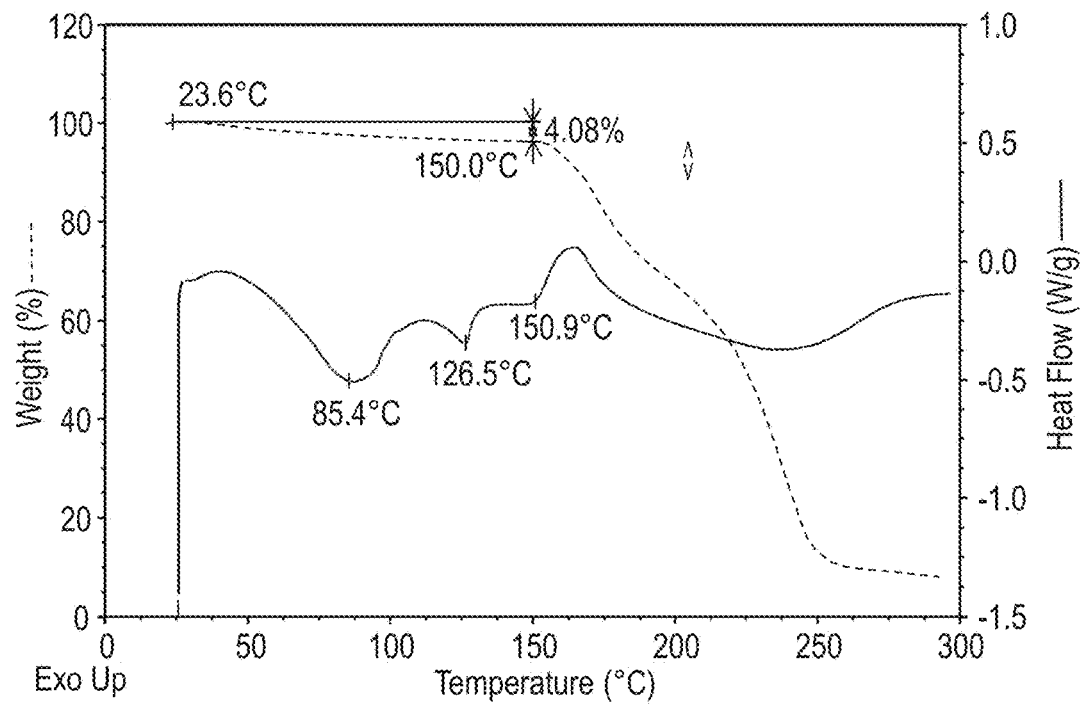
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
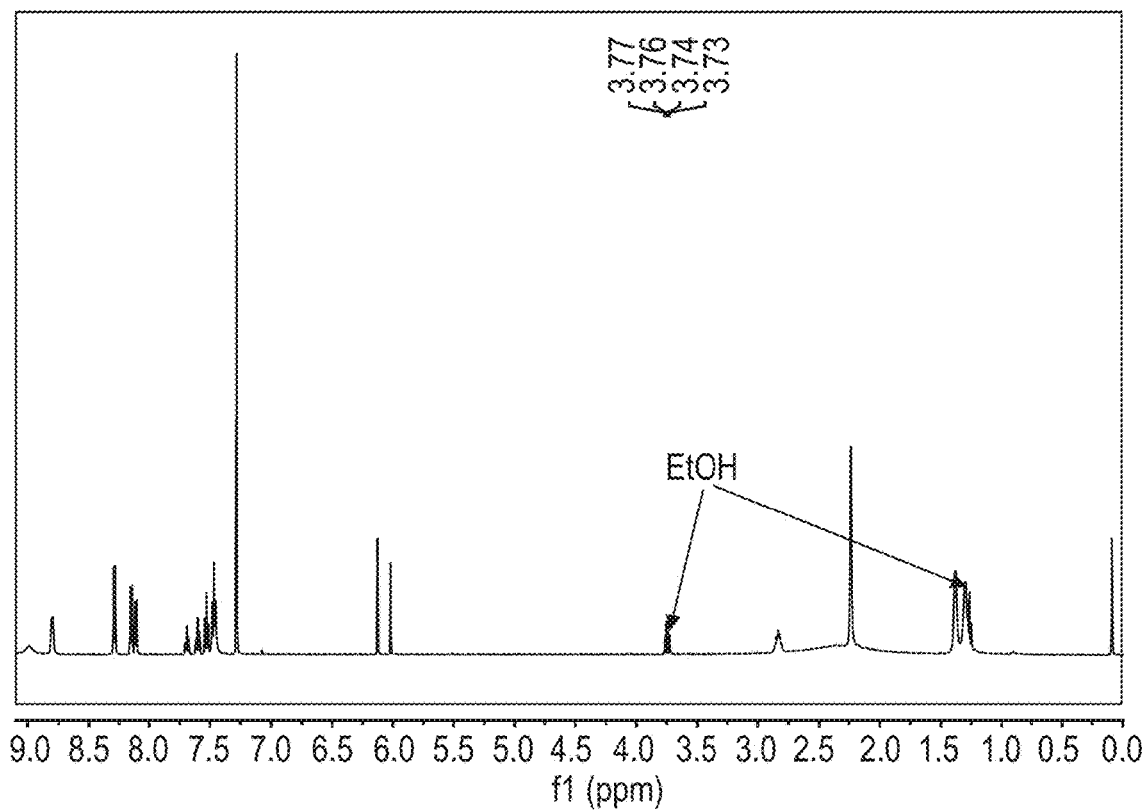
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
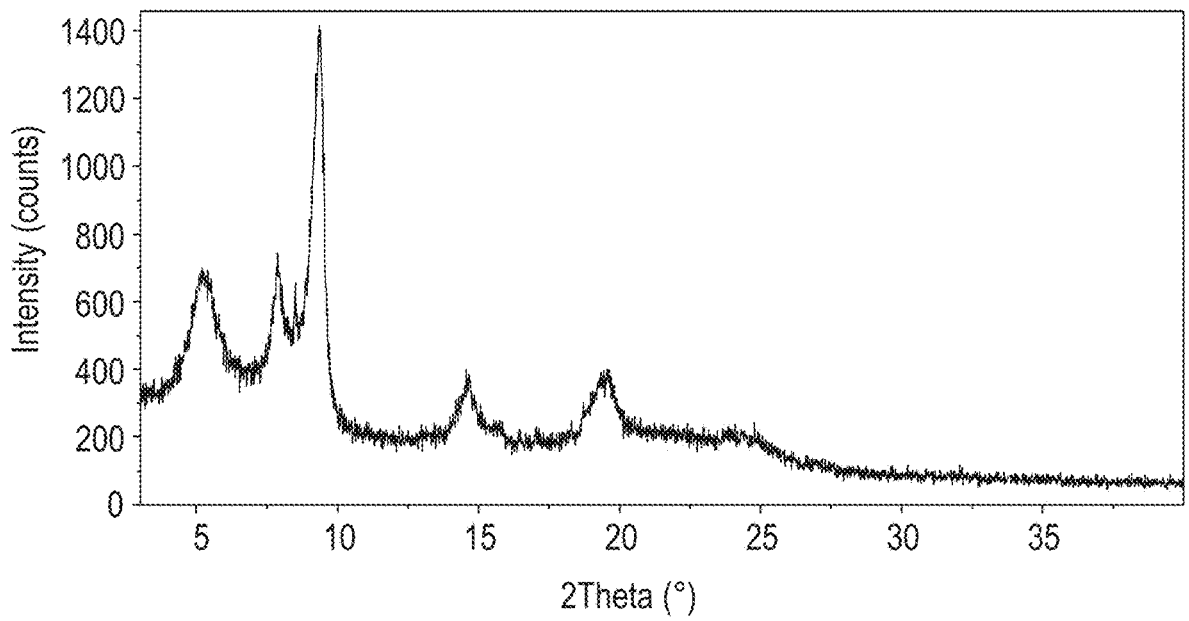
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
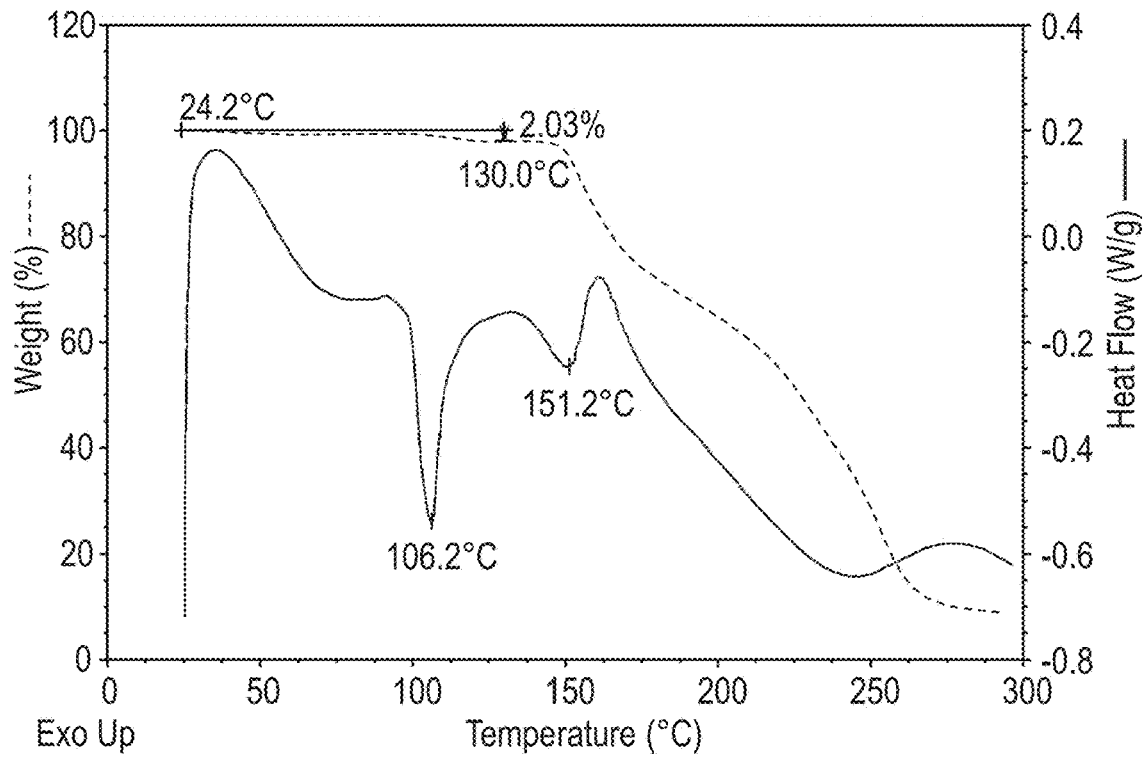
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
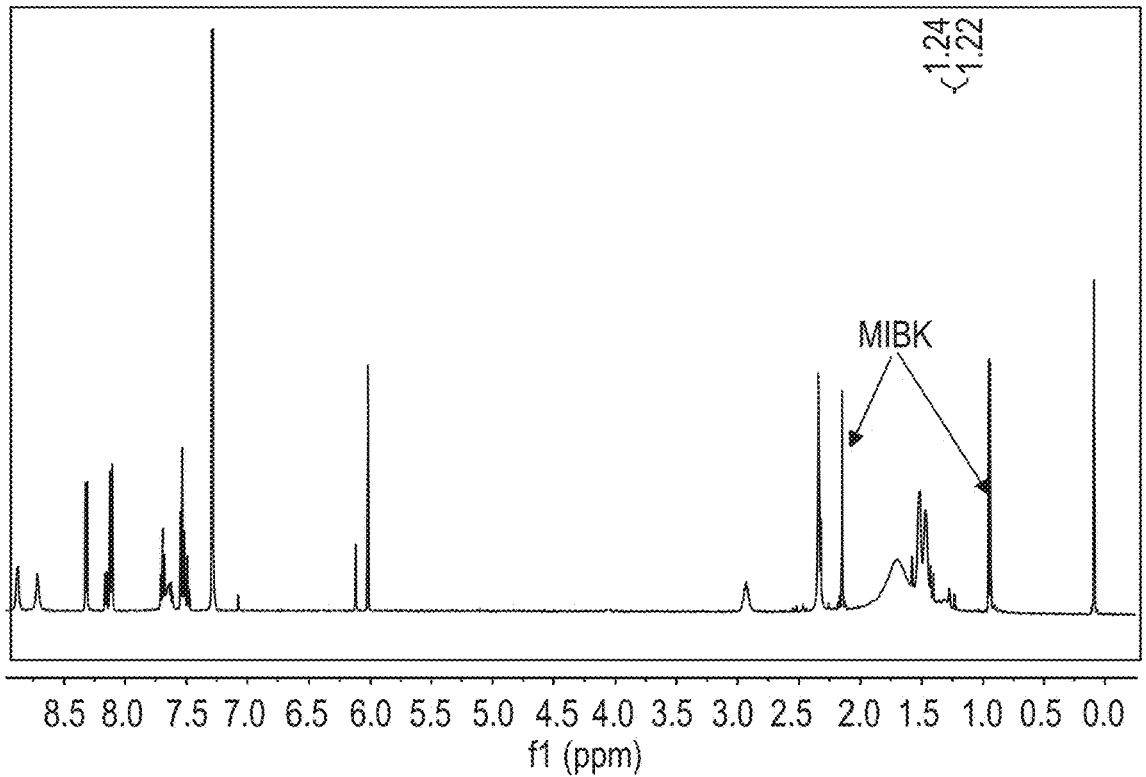
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
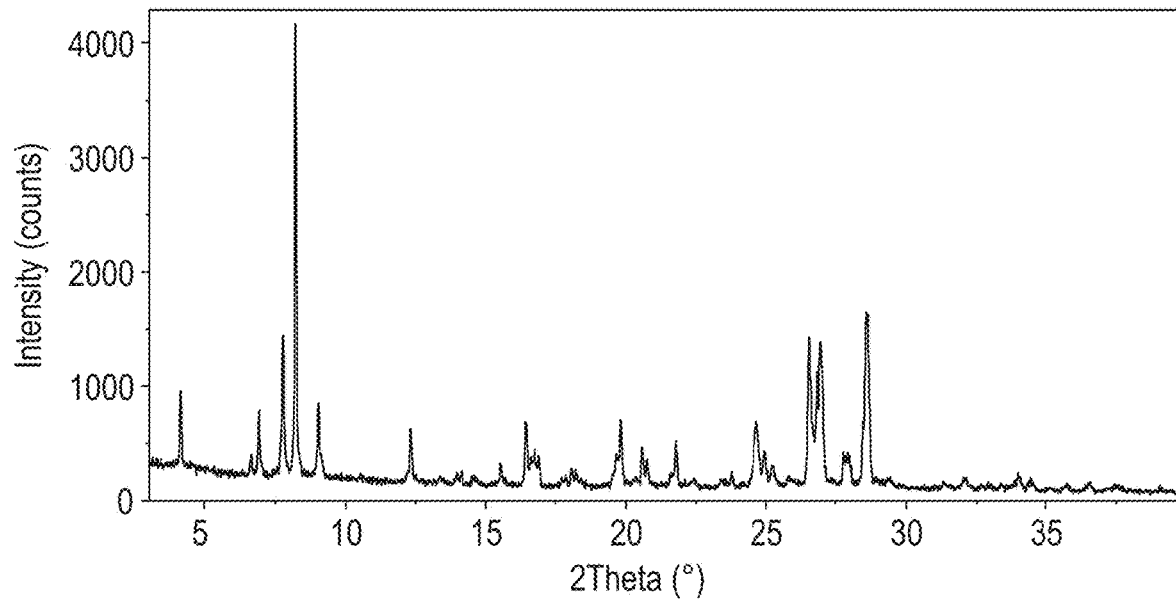
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
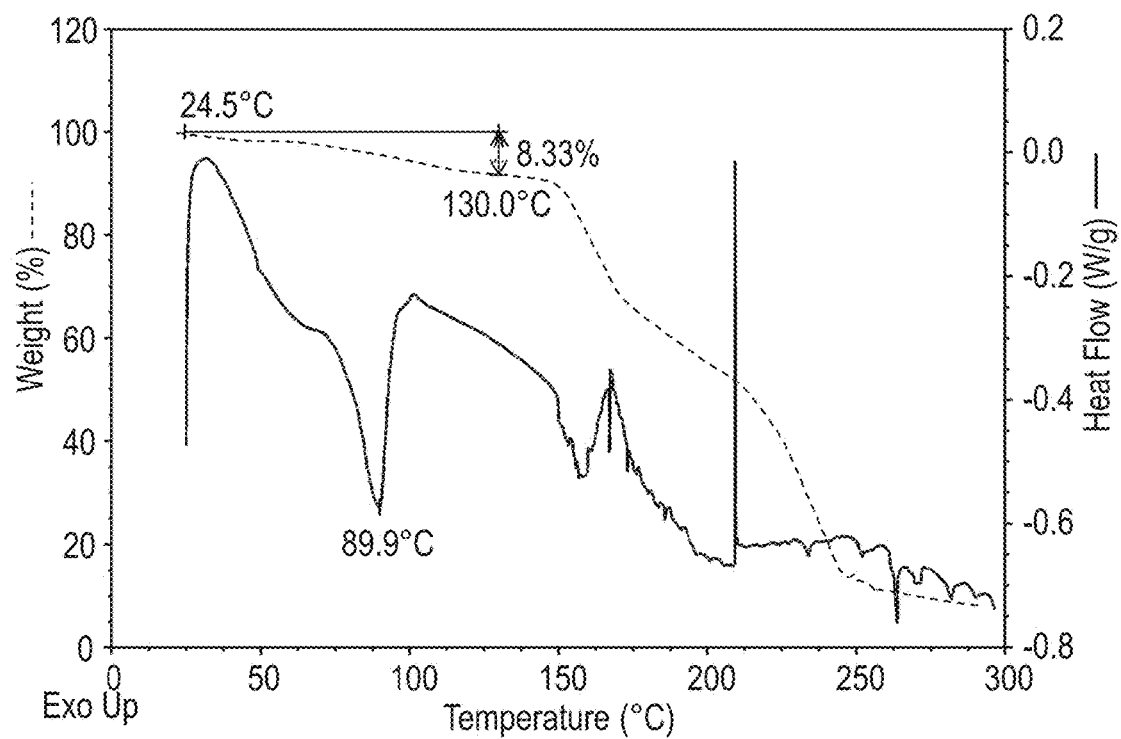
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
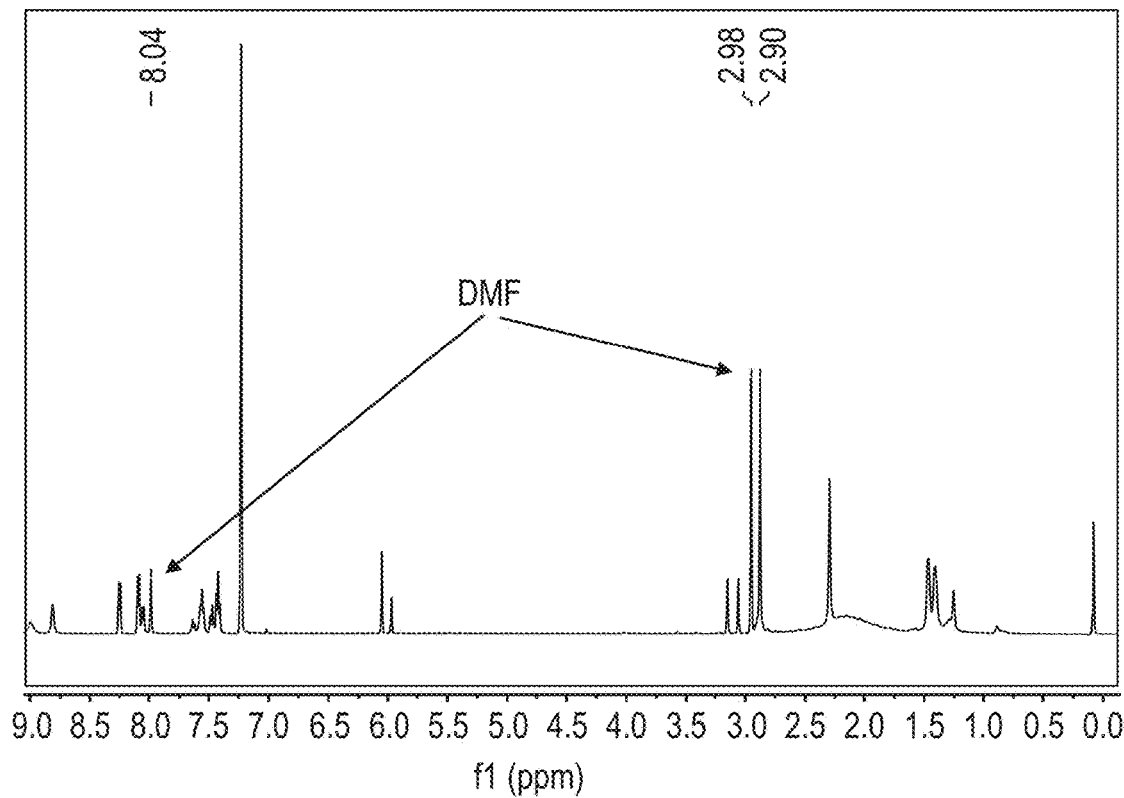
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
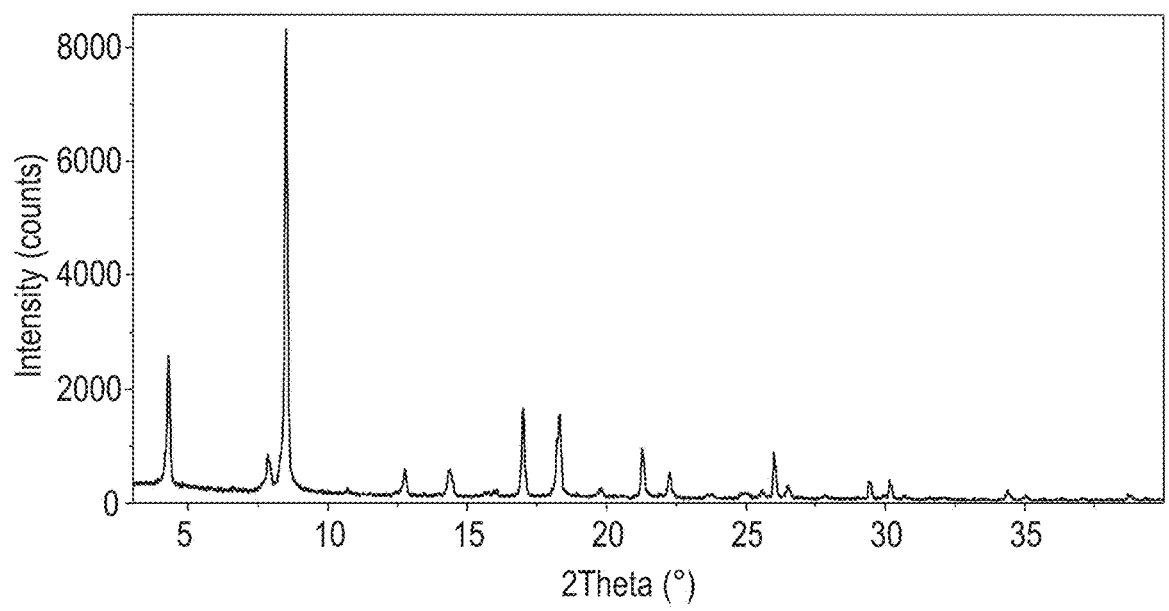
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
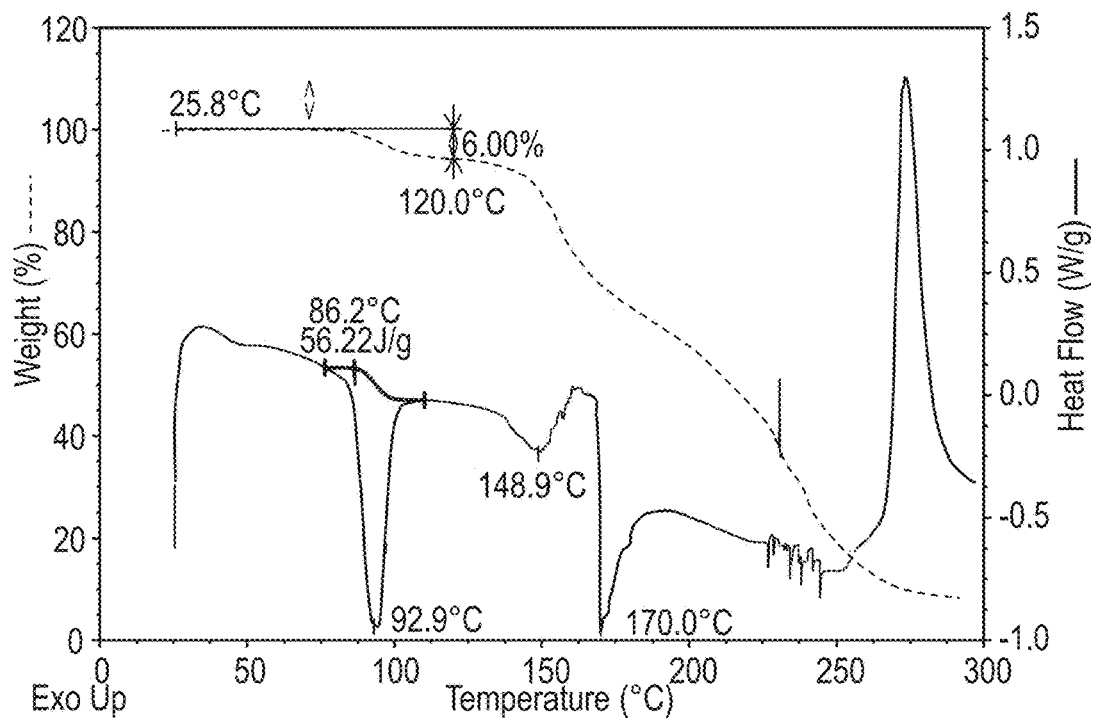
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
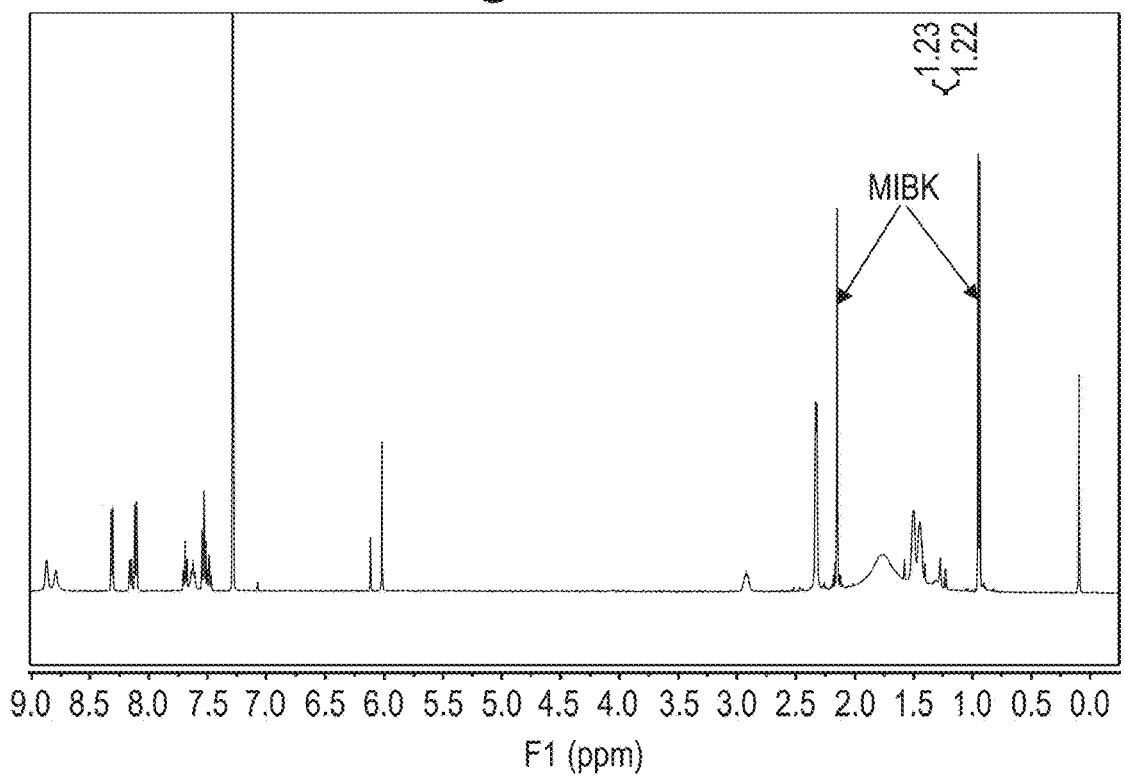

The clear mother liquor was evaporated to dryness. The yellow oily material was dissolved in $CH_2Cl_2$ and treated with a concentrated aqueous $NaHCO_3$ solution using a separatory funnel. The organic layer was isolated and the basic aqueous layer was extracted with $CH_2Cl_2$ (2×). The organic layers were combined and dried over $Na_2SO_3$. Evaporation of the solvent yielded 1579 mg of 5 (23% ee in (P)-atropisomer; FIG. 6-2).

Polymorph Screening on M-Dione DBTA Cocrystal

5 Characterization of Crystal Forms of M-Dione DBTA Cocrystal

Polymorph screening experiments for the M-Dione were set up under 100 conditions using methods of slurry conversion, slow evaporation, slow cooling, anti-solvent addition, vapor diffusion, temperature cycling, and wet grinding. A total of 17 crystal forms (Type A~Q) were obtained from the screening. The form relationship is shown in FIG. 4-1. The detailed characterization data are provided in Table 5-1 and the overlays of XRPD patterns are shown in FIG. 5-1. Solid state characterization results suggested Type G is a hydrate, while the other Types are solvates.

5.1 Instruments and Methods
5.1.1 XRPD

XRPD was performed with a Panalytical X'Pert[3] Powder XRPD on a Si zero-background holder. The 2θ position was calibrated against a Panalytical Si reference standard disc. The parameters used are listed in Table 5-a.

TABLE 5-a

Parameters for XRPD test

| Parameters | Reflection Mode |
|---|---|
| X-Ray wavelength | Cu, kα |
|  | Kα1 (Å): 1.540598, |
|  | Kα2 (Å): 1.544426, |
|  | Kα2/Kα1 intensity ratio: 0.50 |
| X-Ray tube setting | 45 kV, 40 mA |
| Divergence slit | Fixed ⅛° |
| Scan mode | Continuous |
| Scan range (°2TH) | 3-40 |
| Scan step time [s] | 18.87 |
| Step size (°2TH) | 0.0131 |
| Test Time | 4 min 15 s |

5.1.2 TGA/DSC

TGA data was collected using a TA Discovery 550 TGA from TA Instrument. DSC was performed using a TA Q2000 DSC from TA Instrument. DSC was calibrated with Indium reference standard and the TGA was calibrated using nickel reference standard. Detailed parameters used are listed in Table 5-b.

TABLE 5-b

Parameters for TGA and DSC test

| Parameters | TGA | DSC |
|---|---|---|
| Method | Ramp | Ramp |
| Sample pan | Platinum, open | Aluminum, crimped |
| Temperature | RT-desired temperature | |
| Heating rate | 10° C./min | |
| Purge gas | $N_2$ | |

5.2 Polymorph Screening

The solubility of Type A (3-05-A) was estimated at RT. Approximately 2 mg solids were added into a 3-mL glass vial. Solvents in Table 5-c were then added stepwise (50/50/200/700 μL) into the vials until the solids were dissolved or a total volume of 2 mL was reached. Results summarized in Table 5-c were used to guide the solvent selection in polymorph screening.

Polymorph screening experiments were performed using different crystallization or solid transition methods. The methods utilized and crystal types identified are summarized in Table 5-c.

TABLE 5-c

Approximate solubility of starting material (6010013-05-A) at RT

| Solvent | Solubility (mg/mL) | Solvent | Solubility (mg/mL) |
|---|---|---|---|
| MTBE | S < 3.1 | Acetone | S > 52.0 |
| H₂O | 2.4 < S < 8.0 | DMF | S > 40.0 |
| n-Heptane | 3.0 < S < 10.0 | Anisole | S > 40.0 |
| Toluene | 2.7 < S < 9.0 | Acetic acid | S > 40.0 |
| Hexanes | 2.9 < S < 9.7 | THF | S > 50.0 |
| IPA | 26.0 < S < 52.0 | ACN | S > 46.0 |
| 2-MeTHF | 24.0 < S < 48.0 | CHCl3 | S > 50.0 |

TABLE 5-c-continued

Approximate solubility of starting material (6010013-05-A) at RT

| Solvent | Solubility (mg/mL) | Solvent | Solubility (mg/mL) |
|---|---|---|---|
| 1,4-Dioxane | 25.0 < S < 50.0 | EtOAc | S > 72.0 |
| n-BuOH | 23.0 < S < 46.0 | DMSO | S > 72.0 |
| MIBK | 38.0 < S < 76.0 | MeOH | S > 78.0 |
| BuOAc | S > 28.0 | EtOH | S > 68.0 |
| IPAc | S > 32.0 | — | — |

TABLE 5-d

Summary of polymorph screening experiments

| Method | No. of Experiments | Crystal Type |
|---|---|---|
| Slurry at RT/5° C. | 37 | Type A~G, Type J, Type N, Type N |
| Slow Evaporation | 16 | Type A, Type C, Type D, Type J, Type K, Type L, Type N, Type O |
| Slow Cooling | 9 | Type C, Type J, Type L, Type O |
| Anti-solvent Addition | 9 | Type A, Type C, Type H and Type I |
| Liquid Vapor Diffusion | 5 | Type L, Type M, Type Q |
| Solid Vapor Diffusion | 6 | Type A and M |
| Temperature Cycling | 7 | Type A, Type G, Type O |
| Wet Grinding | 10 | Type A |
| Total | 99 | Type A~Q |

5.2.1 Slurry at RT

Slurry experiments were conducted at RT in different solvent systems. About 20 mg of Type A (3-05-A) was suspended in 0.2 mL of solvent in a 3-mL glass vial. After the suspension was stirred magnetically for 13 days at RT, the remaining solids were isolated for XRPD analysis. Results summarized in Table 5-e indicated that Type A~D and Type J were obtained.

TABLE 5-e

Summary of slurry experiments at RT

| Experiment ID | Solvent (v:v) | Solid Form |
|---|---|---|
| 3-07-A1 | MTBE | Type B |
| 3-07-A2 | H₂O | Type A |
| 3-07-A3 | n-Heptane | Low crystallinity |
| 3-07-A4 | Toluene | Low crystallinity |
| 3-07-A5 | Hexanes | Type A |
| 3-07-A6* | IPA | Type A |
| 3-07-A7* | 2-MeTHF | Type B |
| 3-07-A8* | 1,4-Dioxane | Type J |
| 3-07-A9 | n-BuOH | Low crystallinity |
| 3-07-A10* | MIBK | Type A |
| 3-07-A11 | BuOAc | Type C |
| 3-07-A12 | IPAc | Type D |
| 3-07-A13* | Acetone | Amorphous |
| 3-07-A14* | DMF | Type P |
| 3-07-A15 | Anisole | Type E |
| 3-07-A16 | THF/n-Heptane(1:9) | Low crystallinity |
| 3-07-A17 | 2-MeTHF/n-Heptane(1:9) | Type A |
| 3-07-A18 | IPA/H2O(1:9) | Type A |
| 3-07-A19 | IPAc/H2O(1:9) | Type F |
| 3-07-A20 | n-BuOH/H2O(1:9) | Type A |
| 3-07-A21 | n-BuOH/MTBE(1:9) | Type A |
| 3-07-A22 | CHCl3/MTBE(1:9) | Type A |
| 3-07-A23* | MeOH/H2O (937:63, aw = 0.2) | Amorphous |
| 3-07-A24* | MeOH/H2O (844:156, aw = 0.4) | Type N |
| 3-07-A25* | MeOH/H2O (693:304, aw = 0.6) | Type G |

TABLE 5-e-continued

Summary of slurry experiments at RT

| Experiment ID | Solvent (v:v) | Solid Form |
|---|---|---|
| 3-07-A26 | MeOH/H2O (569:431, aw = 0.8) | Type G |

*Solid obtained via slow evaporation at RT 5.2.2 Slow Evaporation

Slow evaporation experiments were performed under 16 conditions. Briefly, 20 mg of Type A (3-05-A) was dissolved in 0.2~0.8 mL of solvent in a 20-mL glass vial. If no dissolution was achieved, suspensions were filtered using a PTFE (pore size of 0.2 μM) and the filtrates were used for the following steps. The visually clear solutions were covered by Parafilm® with 5-10 pinholes and subjected to evaporation at RT. The solids were isolated for XRPD analysis. The results summarized in Table 5-f indicated that Type A, Type C, Type D, Type J, Type K, Type L, Type N, Type O were obtained.

TABLE 5-f

Summary of slow evaporation experiments

| Experiment ID | Solvent (v:v) | Solid Form |
|---|---|---|
| 3-08-A1 | Acetic acid | Amorphous |
| 3-08-A2 | THF | Type J |
| 3-08-A3 | ACN | Amorphous |
| 3-08-A4 | CHCl3 | Amorphous |
| 3-08-A5 | EtOAc | Type C |
| 3-08-A6 | DMSO | Amorphous |
| 3-08-A7 | MeOH | Amorphous |
| 3-08-A8 | EtOH | Type N |
| 3-08-A9 | 1,4-Dioxane | Type J |
| 3-08-A10 | n-BuOH | Type A |
| 3-08-A11 | MIBK | Type O |
| 3-08-A12 | BuOAc | Type C |
| 3-08-A13 | IPAc | Type D |
| 3-08-A14 | Acetone | Type K |
| 3-08-A15 | DMF | Gel |
| 3-08-A16 | 2-MeTHF | Type L |

5.2.3 Slow Cooling

Slow cooling experiments were conducted in 9 solvent systems. About 20 mg of Type A (3-05-A) was suspended in 1 mL of solvent in a 3-mL glass vial at RT. The suspension was then heated to 50° C., equilibrated for two hour and filtered using a PTFE membrane (pore size of 0.20 μm). Filtrates were slowly cooled down to 5° C. at a rate of 0.1° C./min. Results summarized in Table 5-g indicated Type C, Type G, Type J, Type L and Type O s were observed.

TABLE 5-g

Summary of slow cooling experiments

| Experiment ID | Solvent (v:v) | Solid Form |
|---|---|---|
| 3-09-A1* | IPA | Type O |
| 3-09-A2 | 2-MeTHF | Type L |
| 3-09-A3* | 1,4-Dioxane | Type J |
| 3-09-A4* | n-BuOH | Type L |
| 3-09-A5* | Acetic acid | Type G (Low crystallinity) |
| 3-09-A6 | THF | Type J |
| 3-09-A7* | ACN | Amorphous |
| 3-09-A8 | CHCl3 | Low crystallinity |
| 3-09-A9* | EtOAc | Type C |

*Solids obtained from evaporation at RT.

5.2.4 Anti-Solvent Addition

A total of 9 anti-solvent addition experiments were carried out. About 20 mg of starting material (3-05-A) was dissolved in 0.2-1.4 mL solvent to obtain a clear solution. The solution was magnetically stirred followed by addition of 0.2 mL anti-solvent stepwise till precipitate appeared or the total amount of anti-solvent reached 15.0 mL. The obtained precipitate was isolated for XRPD analysis. Results in Table 5-h showed that Type A, Type C, Type H and Type I were obtained.

TABLE 5-h

Summary of anti-solvent addition experiments

| Experiment ID | Solvent | Anti-solvent | Solid Form |
|---|---|---|---|
| 3-10-A1* | H2O | Acetone | Type H |
| 3-10-A2 |  | THF | Amorphous |
| 3-10-A3* |  | DMSO | Type I |
| 3-10-A4* | MTBE | EtOH | Type A |
| 3-10-A5* |  | CHCl3 | Type A |
| 3-10-A6 |  | EtOAc | Type A |
| 3-10-A7* |  | Acetone | Type C |
| 3-10-A8* | n-heptane | 2-MeTHF | Type A |
| 3-10-A9* |  | IPAc | Type C |

*Solids obtained from evaporation at RT.

5.2.5 Liquid Vapor Diffusion

Five liquid vapor diffusion experiments were conducted. Approximate 20 mg of starting material (3-05-A) was dissolved in appropriate solvent to obtain a clear solution in a 3-mL vial. This solution was then placed into a 20-mL vial with 3 mL of volatile solvents. The 20-mL vial was sealed with a cap and kept at RT allowing sufficient time for organic vapor to interact with the solution. The precipitates were isolated for XRPD analysis. The results summarized in Table 5-i showed that Type L, Type M and Type Q were generated.

TABLE 5-i

Summary of liquid vapor diffusion experiments

| Experiment ID | Solvent | Anti-solvent | Solid Form |
|---|---|---|---|
| 3-11-A1 | MIBK | n-Heptane | Type Q |
| 3-11-A2 | EtOAc | IPA | Type M |
| 3-11-A3 | THF | MTBE | Type L |
| 3-11-A4 | 2-MeTHF | n-Heptane | Type L |
| 3-11-A5* | DMF | Toluene | Gel |

*Solids were obtained via evaporation at RT.

5.2.6 Solid Vapor Diffusion

Solid vapor diffusion experiments were conducted using 6 different solvents. Approximate 10 mg of starting material (3-05-A) was weighed into a 3-mL vial, which was placed into a 20-mL vial with 2 mL of volatile solvent. The 20-mL vial was sealed with a cap and kept at RT for 7 days allowing solvent vapor to interact with sample. The solids were tested by XRPD and the results summarized in Table 5-j showed that Type A and Type M were generated.

TABLE 5-j

Summary of solid vapor diffusion experiments

| Experiment ID | Solvent | Solid Form |
|---|---|---|
| 3-12-A1 | EtOH | Type M |
| 3-12-A2 | MTBE | Type A |
| 3-12-A3 | H2O | Type A |

TABLE 5-j-continued

Summary of solid vapor diffusion experiments

| Experiment ID | Solvent | Solid Form |
|---|---|---|
| 3-12-A4 | acetone | Amorphous |
| 3-12-A5 | 2-MeTHF | Type A |
| 3-12-A6 | IPAc | Type A |

5.2.7 Temperature Cycling

Temperature cycling experiments were conducted in 7 solvent systems. About 20 mg of starting material (3-05-A) was suspended in 1 mL of solvent in a 3-mL glass vial at RT. The suspension was then heated to 50° C., equilibrated for one hour and filtered using a PTFE membrane (pore size of 0.20 µm). Filtrates were slowly cooled down to 5° C. at a rate of 0.2° C./min and then heat to 50° C. at a rate of 1° C./min. Repeat the cycle one more time and then cooling to 5° C. at a rate of 0.2° C./min. The samples were stored 5° C. before solids were isolated and analyzed using XRPD. Results summarized in Table 5-k indicated Type A, Type G and Type O were observed.

TABLE 5-k

Summary of temperature cycling experiments

| Experiment ID | Solvent (v:v) | Solid Form |
|---|---|---|
| 3-13-A1* | 2-MeTHF | Type A |
| 3-13-A2* | MeOH | Type G |
| 3-13-A3* | MIBK | Type A |
| 3-13-A4* | ACN | Amorphous |
| 3-13-A5 | CHCl3 | Low crystallinity |
| 3-13-A6* | Toluene | Amorphous |
| 3-13-A7* | IPA | Type O |

*Solids obtained from evaporation at RT.

5.2.8 Slurry at 5° C.

Slurry experiments were conducted at 5° C. in different solvent systems. About 20 mg of starting material (3-05-A) was suspended in 0.2 mL of solvent in a 3-mL glass vial. After the suspension was stirred magnetically for 7 days at 5° C., the remaining solids were isolated for XRPD analysis. Results summarized in Table 5-1 indicated that Type A, Type C Type E and Type J were obtained.

TABLE 5-1

Summary of slurry experiments at 5° C.

| Experiment ID | Solvent (v:v) | Solid Form |
|---|---|---|
| 3-14-A1* | BuOAc | Type C |
| 3-14-A2* | IPAc | Type D |
| 3-14-A3* | Acetone | Low crystallinity |
| 3-14-A4* | DMF | Gel |
| 3-14-A5 | Anisole | Type E |
| 3-14-A6* | 2MeTHF | Type A |
| 3-14-A7* | ACN | Low crystallinity |
| 3-14-A8* | CHCl3 | Low crystallinity |
| 3-14-A9* | EtOAc | Low crystallinity |
| 3-14-A10* | MeOH | Type C |
| 3-14-A11* | THF | Type J |

*Solids obtained from evaporation at RT.

5.2.9 Wet Grinding

Wet grinding experiments were performed under five conditions. Briefly, 10 mg of Type A (3-05-A) was put in mortar and grinding in ~20 µL of solvent for 5 min. The solids were isolated for XRPD analysis. The results summarized in Table 5-m indicated that Type A was obtained.

TABLE 5-m

Summary of wet grinding experiments

| Experiment ID | Solvent (v:v) | Solid Form |
|---|---|---|
| 3-15-A1 | MTBE | Amorphous |
| 3-15-A2 | H$_2$O | Amorphous |
| 3-15-A3 | n-Heptane | Amorphous |
| 3-15-A4 | Toluene | Amorphous |
| 3-15-A5 | Hexanes | Amorphous |
| 3-15-A6 | IPA | Amorphous |
| 3-15-A7 | 2-MeTHF | Type A (low crystallinity) |
| 3-15-A8 | 1,4-Dioxane | Type A |
| 3-15-A9 | n-BuOH | Amorphous |
| 3-15-A10 | MIBK | Amorphous |

TABLE 5-1

Characterization of M-dione DBTA cocrystal crystal forms

| Crystal Form (Batch No.) | Preparation Conditions | Weight Loss in TGA (%) | DSC Endo. (Peak, ° C.) | Form ID |
|---|---|---|---|---|
| Type A (3-05-A) | Classic resolution with DBTA (2-MeTHF) | 7.31 up to 125° C. | 109.4 120.0 | 2-MeTHF solvate |
| Type B (3-07-A1) | Slurry at RT (MTBE) | 7.21 up to 125° C. | 115.7 | MTBE solvate |
| Type C (3-08-A5) | Slow Evaporation (EtOAc) | 7.99 up to 125° C. | 92.7 116.4 | EtOAc solvate |
| Type D (3-07-A12) | Slurry at RT (IPAc) | 7.51 up to 130° C. | 75.4, 110.5, 148.0, 116.6, 265.9(exo). | IPAc solvate |
| Type E (3-07-A15) | Slurry at RT (Anisole) | 8.63 up to 125° C. | 103.8 119.0 | Anisole Solvate |
| Type F (3-07-A19) | Slurry at RT IPAc/H$_2$O (v:v 1:9) | 6.2 up to 130° C. | 86.5, 107.9 | IPAc solvate |
| Type G (3-07-A26) | Slurry at RT (MeOH/H$_2$O aw = 0.8) | 6.44 up to 100° C. | 86.0 127.2 133.1 | Hydrate |
| Type H (3-10-A1) | Anti-Solvent (Acetone/H$_2$O) | 3.58 up to 130° C. | 107.6 | Acetone solvate |
| Type I (3-10-A3) | Anti-Solvent (DMSO/H$_2$O) | 7.26 up to 150° C. | 128.9 | DMSO solvate |
| Type J (3-08-A2) | Slow Evaporation (THF) | 7.27% by 125° C. | 115.7 | THF Solvate |
| Type K (3-08-A14) | Slow Evaporation (Acetone) | 5.71 up to 150° C. | 96.7, 119.8 147.4 157.4° C.(exo). | Acetone solvate |
| Type L (3-11-A4) | Liquid Vapor Diffusion (2-MeTHF/n-Heptane) | 7.94 up to 130° C. | 126.2 | 2-MeTHF solvate |
| Type M (3-11-A2) | Liquid Vapor Diffusion (EtOAc/IPA) | 3.73 up to 150° C. | 122.6 | IPA solvate |
| Type N (3-08-A8) | Slow Evaporation (EtOH) | 4.08 up to 150° C. | 85.4, 126.5 150.9 | EtOH solvate |
| Type O (3-08-A11) | Slow Evaporation (MIBK) | 2.03 up to 130° C. | 106.2, 151.2 | MIBK solvate |
| Type P (3-07-A14) | Slow Evaporation (DMF) | 8.33 up to 130° C. | 89.9 | DMF solvate |
| Type Q (3-11-A1) | Liquid Vapor Diffusion (MIBK/n-Heptane) | 6.00 up to 120° C. | 92.9, 148.9 170.0 | MIBK solvate |

5.3 Type A

Type A (3-05-A) was provided by client. The XRPD result showed in FIG. 5-4 suggested crystalline. As shown by TGA and DSC data in FIG. 5-5, a weight loss of 7.3% up to 125° C. and two endotherms at 109.4 and 120.0° C. (peak) were observed. As displayed in FIG. 5-6, the presence of 2-MeTHF was evidenced in $^1$H NMR spectrum. Based on the results, Type A was considered as a 2-MeTHF solvate.

5.4 Type B

Type B sample (3-07-A1) was obtained via slurry of Type A in MTBE at RT. XRPD pattern shown in FIG. 5-7 suggested crystalline. As shown by TGA and DSC data in FIG. 5-10, a weight loss of 7.2% up to 125° C. and an endotherm at 115.7° C. (peak) were observed. As displayed in FIG. 5-9, the presence of MTBE was evidenced in $^1$H NMR spectrum. Based on the results, Type B was likely a MTBE solvate.

5.5 Type C

Type C sample (3-08-A5) was obtained via slow evaporation in EtOAc at RT. XRPD pattern shown in FIG. 5-10 suggested crystalline. TGA and DSC data displayed in FIG. 5-11 indicated a weight loss of 8.0% up to 125° C. and two endotherms at 92.7° C. and 116.4° C. (peak). As displayed in FIG. 5-12, the presence of EtOAc was evidenced in $^1$H NMR spectrum. Based on the results, Type C was likely an EtOAc solvate.

5.6 Type D

Type D (3-07-A12) was obtained by slurry of Type A in IPAc at RT. The XRPD result showed in FIG. 5-13 suggested crystalline. As shown by TGA and DSC data in FIG. 5-14, a weight loss of 7.5% up to 130° C. and endotherms at 75.4° C., 110.5° C., 148.0° C. and 116.6° C. (peak) and an exotherm at 265.9° C. were observed. As displayed in FIG. 5-15, the presence of IPAc was evidenced in $^1$H NMR spectrum. Based on the results, Type D was likely an IPAc solvate.

5.7 Type E

Type E (3-07-A15) was obtained via slurry of Type A in anisole at RT. The XRPD result showed in FIG. 5-16 suggested crystalline. As shown by TGA and DSC data in FIG. 5-17, a weight loss of 8.6% up to 125° C. and two endotherms at 103.8° C. and 119.0° C. (peak) were observed. As displayed in FIG. 5-18, the presence of IPAc was evidenced in $^1$H NMR spectrum. Based on the results, Type E was likely an anisole solvate.

5.8 Type F

Type F (3-07-A19) was obtained via slurry of Type A in IPAc/H$_2$O (v:v 1:9) at RT. The XRPD result showed in FIG. 5-19 suggested crystalline. As shown by TGA and DSC data in FIG. 5-20, a weight loss of 6.2% up to 130° C. and two endotherms at 86.5° C. and 107.9° C. (peak) were observed. As displayed in FIG. 5-18, the presence of IPAc was evidenced in $^1$H NMR spectrum. Based on the results, Type F was likely an IPAc solvate.

5.9 Type G

Type G (3-07-A26) was obtained via slurry of Type A in MeOH/H$_2$O (aw=0.8) at RT. The XRPD result showed in FIG. 5-22 suggested crystalline state. As shown by TGA and DSC data in FIG. 5-23, a weight loss of 6.4% up to 100° C. and endotherms at 86.0° C., 127.2° C. and 133.1° C. (peak) were observed. As displayed in FIG. 5-24, no signal for MeOH or MeTHF was observed in solution $^1$HNMR spectrum. Based on the results, Type G was likely a hydrate.

5.10 Type H

Type H (3-10-A1) was obtained via anti-solvent addition using Acetone/H$_2$O. The XRPD result showed in FIG. 5-25 suggested crystalline. As shown by TGA and DSC data in FIG. 5-26, a weight loss of 3.6% up to 130° C. and an endotherm at 107.6° C. (peak) were observed. As displayed in FIG. 5-27, the presence of acetone was evidenced in $^1$H NMR spectrum. Based on the results, Type H was likely an acetone solvate.

5.11 Type I

Type I (3-10-A3) was obtained via anti-solvent addition using DMSO/H$_2$O. The XRPD result showed in FIG. 5-28 suggested crystalline. As shown by TGA and DSC data in FIG. 5-29, a weight loss of 7.3% up to 150° C. and an endotherm at 128.9° C. (peak) were observed. As displayed in FIG. 5-30, the presence of DMSO was evidenced in $^1$H NMR spectrum. Based on the results, Type I was likely a DMSO solvate.

5.12 Type J

Type J (3-08-A2) was obtained via slow evaporation in THF. The XRPD result showed in FIG. 5-31 suggested crystalline. As shown by TGA and DSC data in FIG. 5-32, a weight loss of 7.3% up to 125° C. and an endotherm at 115.7° C. (peak) were observed. As displayed in FIG. 5-33, the presence of THF was evidenced in $^1$H NMR spectrum. Based on the results, Type J was likely a THF solvate.

5.13 Type K

Type K (3-08-A14) was obtained via slow evaporation in acetone. The XRPD result showed in FIG. 5-34 suggested crystalline. As shown by TGA and DSC data in FIG. 5-35, a weight loss of 5.7% up to 150° C. and endotherms at 96.7° C., 119.8° C. and 147.4° C. (peak) and an exotherm at 157.4° C. (peak) were observed. As displayed in FIG. 5-36, the presence of acetone was evidenced in $^1$H NMR spectrum. Based on the results, Type K was likely an acetone solvate.

5.14 Type L

Type L (3-11-A4) was obtained via liquid vapor diffusion in 2-MeTHF/n-Heptane. The XRPD result showed in FIG. 5-37 suggested crystalline with preferred orientation. As shown by TGA and DSC data in FIG. 5-38, a weight loss of 7.9% up to 130° C. and an endotherm at 126.2° C. (peak) were observed. As displayed in FIG. 5-39, the presence of acetone was evidenced while no signal for n-heptane was observed in $^1$H NMR spectrum. Based on the results, Type L was likely a 2-MeTHF solvate.

5.15 Type M

Type M (3-11-A2) was obtained from liquid vapor diffusion in EtOAc/IPA. The XRPD result showed in FIG. 5-40 suggested crystalline. As shown by TGA and DSC data in FIG. 5-41, a weight loss of 3.7% up to 150° C. and an endotherm at 122.6° C. (peak) were observed. As displayed in FIG. 5-42, the presence of IPA was evidenced while no signal for EtOAc was observed in $^1$H NMR. Based on the results, Type M was likely an IPA solvate.

5.16 Type N

Type N (3-08-A8) was obtained via slow evaporation in EtOH. The XRPD result showed in FIG. 5-43 suggested crystalline. As shown by TGA and DSC data in FIG. 5-44, a weight loss of 4.1% up to 150° C. and endotherms at 85.4° C., 126.5° C. and 150.9° C. (peak) were observed. As displayed in FIG. 5-45, the presence of EtOH was evidenced in $^1$H NMR spectrum. Based on the results, Type N was likely an EtOH solvate.

5.17 Type O

Type O (3-08-A11) was obtained via slow evaporation in MIBK. The XRPD result showed in FIG. 5-46 suggested crystalline. As shown by TGA and DSC data in FIG. 5-47, a weight loss of 2.0% up to 130° C. and two endotherms at 106.2° C. and 151.2° C. (peak) were observed. As displayed in FIG. 5-48, the presence of MIBK was evidenced in $^1$H NMR spectrum. Based on the results, Type O was likely a MIBK solvate.

5.18 Type P

Type P (3-07-A14) was obtained via slow evaporation in DMF. The XRPD result showed in FIG. 5-49 suggested crystalline. As shown by TGA and DSC data in FIG. 5-50, a weight loss of 8.3% up to 130° C. and an endotherm at 89.9° C. (peak) were observed. As displayed in FIG. 5-51, the presence of DMF was evidenced in $^1$H NMR spectrum. Based on the results, Type P was likely a DMF solvate.

5.19 Type Q

Type Q (3-11-A1) was obtained via liquid vapor diffusion in MIBK/n-Heptane. The XRPD result showed in FIG. 5-52 suggested crystalline. As shown by TGA and DSC data in FIG. 5-53, a weight loss of 6.0% up to 120° C. and endotherms at 92.9° C., 148.9° C. and 170.0° C. (peak) were observed. As displayed in FIG. 5-54, the presence of MIBK was evidenced while no signal of N-Heptane observed in $^1$H NMR spectrum. Based on the results, Type Q was likely a MIBK solvate.

6. Crystal Data and Experimental for Composition 4a

Experimental. Single colourless plate-shaped crystals of (Composition 4a) were used as received. A suitable crystal (0.28×0.18×0.09) mm$^3$ was selected and mounted on a nylon loop with paratone oil on a Bruker APEX-II CCD diffractometer. The crystal was kept at T=173(2) K during data collection. Using Olex2 (Dolomanov et al., 2009), the structure was solved with the XT (Sheldrick, 2015) structure solution program, using the Intrinsic Phasing solution method. The model was refined with version of XL (Sheldrick, 2008) using Least Squares minimisation.

Crystal Data. $C_{65}H_{72}Cl_2F_2N_8O_{15}$, MY=1314.20, triclinic, P1 (No. 1), a=11.5683(10) Å, b=11.6705(10) Å, c=13.9593(12) Å, α=68.1780(10)°, β=69.4150(10)°, γ=87.7760(10)°, V=1628.7(2) Å$^3$, T=173(2) K, Z=1, Z'=1, μ(MoK$_α$)=0.178, 26758 reflections measured, 11949 unique ($R_{int}$=0.0528) which were used in all calculations. The final wR$_2$ was 0.2465 (all data) and R$_1$ was 0.0835 (I>2(I)).p

TABLE 6-2

Fractional Atomic Coordinates (×10$^4$) and Equivalent Isotropic Displacement Parameters (Å$^2$ × 10$^3$) for COMPOSITION 4A. U$_{eq}$ is defined as ⅓ of the trace of the orthogonalised U$_{ij}$.

| Atom | x | y | z | U$_{eq}$ |
|---|---|---|---|---|
| O1C | 5607(5) | 3451(5) | 6493(5) | 44.9(14) |
| O2C | 6723(6) | 4580(6) | 6921(5) | 49.9(15) |
| O3C | 3704(5) | 3216(6) | 5826(5) | 45.6(14) |
| O4C | 2800(6) | 3841(6) | 4560(6) | 55.9(16) |
| O5C | 3369(5) | 5630(6) | 6567(5) | 50.2(15) |
| O6C | 3636(5) | 3990(6) | 7917(5) | 50.8(15) |
| O7C | 5703(6) | 2984(7) | 4257(5) | 55.4(16) |
| O8C | 6595(5) | 4867(6) | 3832(5) | 49.1(15) |
| C1C | 5032(7) | 4527(8) | 6031(7) | 41(2) |
| C2C | 4615(7) | 4267(8) | 5203(7) | 39.1(19) |
| C3C | 3928(8) | 4667(8) | 6968(7) | 42(2) |
| C4C | 5705(8) | 3954(9) | 4361(7) | 42(2) |
| C5C | 6393(8) | 3601(8) | 6961(7) | 42(2) |
| C6C | 6820(9) | 2403(9) | 7493(8) | 49(2) |
| C7C | 7721(15) | 2378(12) | 7941(13) | 98(3) |
| C8C | 8179(15) | 1311(13) | 8410(13) | 94(3) |
| C9C | 7697(17) | 223(14) | 8497(14) | 107(5) |
| C10C | 6708(16) | 185(12) | 8178(13) | 98(3) |
| C11C | 6265(15) | 1303(12) | 7665(13) | 94(3) |
| C12C | 2953(8) | 3028(9) | 5341(7) | 44(2) |
| C13C | 2359(9) | 1762(9) | 5860(8) | 54(2) |
| C14C | 1223(9) | 1501(10) | 5822(8) | 56(2) |
| C15C | 671(11) | 300(12) | 6312(10) | 75(3) |
| C16C | 1261(14) | −658(13) | 6805(13) | 98(5) |
| C17C | 2446(14) | −407(13) | 6720(13) | 97(4) |
| C18C | 2954(13) | 800(12) | 6325(12) | 87(4) |
| CUB | 6935(2) | 1601(2) | 11106(2) | 66.0(7) |

TABLE 6-2-continued

Fractional Atomic Coordinates (×10$^4$) and Equivalent Isotropic Displacement Parameters (Å$^2$ × 10$^3$) for COMPOSITION 4A. U$_{eq}$ is defined as ⅓ of the trace of the orthogonalised U$_{ij}$.

| Atom | x | y | z | U$_{eq}$ |
|---|---|---|---|---|
| F1B | 4643(5) | 1859(6) | 10647(5) | 66.7(16) |
| O1B | 8509(6) | 7968(6) | 7303(6) | 58.0(17) |
| O2B | 4575(6) | 6378(7) | 8234(6) | 66.1(19) |
| N1B | 7896(6) | 6005(6) | 8607(6) | 40.4(16) |
| N2B | 7345(6) | 3931(7) | 9798(6) | 42.2(17) |
| N3B | 6567(7) | 7139(7) | 7745(6) | 49.2(18) |
| N4B | 11242(6) | 5811(7) | 8040(6) | 47.4(18) |
| C1B | 7710(8) | 7096(9) | 7832(8) | 48(2) |
| C2B | 7030(8) | 4974(8) | 9152(6) | 40(2) |
| C3B | 6537(8) | 2952(8) | 10275(7) | 47(2) |
| C4B | 5411(8) | 2909(8) | 10151(7) | 47(2) |
| C5B | 5070(8) | 3977(10) | 9543(7) | 49(2) |
| C6B | 5884(8) | 5054(9) | 9031(7) | 44(2) |
| C7B | 5584(8) | 6210(9) | 8328(8) | 50(2) |
| C8B | 9103(7) | 5996(8) | 8717(7) | 41(2) |
| C9B | 9205(8) | 6331(8) | 9550(7) | 43(2) |
| C10B | 10370(9) | 6393(9) | 9588(7) | 49(2) |
| C11B | 11350(8) | 6131(8) | 8840(7) | 44(2) |
| C12B | 10113(7) | 5734(7) | 7981(7) | 38.9(19) |
| C13B | 8078(9) | 6634(9) | 10360(8) | 55(2) |
| C14B | 10040(9) | 5292(9) | 7127(8) | 54(2) |
| C15B | 10546(10) | 4041(10) | 7234(10) | 65(3) |
| C16B | 10688(11) | 6301(12) | 5939(9) | 73(3) |
| C11A | 11316(6) | −588(3) | 4003(3) | 82.7(9) |
| F1A | 13799(6) | −251(6) | 4033(5) | 77.9(18) |
| O1A | 12158(6) | 6025(6) | 1115(6) | 57.3(17) |
| O2A | 15430(6) | 4363(7) | 1981(6) | 63.4(18) |
| N1A | 11949(6) | 3944(6) | 2039(6) | 38.9(16) |
| N2A | 11735(7) | 1804(7) | 3004(6) | 48.6(19) |
| N3A | 13776(6) | 5170(7) | 1580(6) | 45.5(18) |
| N4A | 8608(6) | 4153(7) | 2689(6) | 46.4(18) |
| C1A | 12607(8) | 5110(9) | 1551(7) | 47(2) |
| C2A | 12449(7) | 2876(8) | 2555(7) | 40(2) |
| C3A | 12216(10) | 797(10) | 3464(8) | 56(2) |
| C4A | 13389(10) | 813(9) | 3546(8) | 56(3) |
| C5A | 14083(9) | 1886(10) | 3114(8) | 54(2) |
| C6A | 13638(8) | 2995(8) | 2564(7) | 44(2) |
| C7A | 14365(8) | 4199(9) | 2043(8) | 48(2) |
| C8A | 10709(7) | 3834(8) | 2039(6) | 37.4(19) |
| C9A | 10540(8) | 3371(9) | 1305(8) | 47(2) |
| C10A | 9326(8) | 3313(8) | 1314(7) | 47(2) |
| C11A | 8421(8) | 3689(8) | 2008(7) | 45(2) |
| C12A | 9733(7) | 4227(7) | 2738(7) | 39.4(19) |
| C13A | 11568(8) | 2995(10) | 522(8) | 55(2) |
| C14A | 9890(8) | 4703(9) | 3549(7) | 50(2) |
| C15A | 9619(11) | 6056(11) | 3255(11) | 71(3) |
| C16A | 9045(10) | 3875(11) | 4734(8) | 64(3) |
| O3S | 355(10) | 1070(10) | 9718(9) | 116(3) |
| C11S | −300(40) | −220(40) | 11630(40) | 142(14) |
| C11T | −1050(40) | −700(50) | 11410(40) | 190(20) |
| C12S | 160(30) | −310(30) | 10410(20) | 180(9) |
| C13S | 1360(40) | −510(50) | 10600(40) | 151(11) |
| C13T | 1220(40) | −820(40) | 9990(40) | 151(11) |
| C14S | 2240(20) | 280(20) | 9240(20) | 155(8) |
| C15S | 1510(20) | 1150(20) | 8834(18) | 139(7) |
| O2S | 6461(8) | −721(8) | 5995(7) | 83(2) |
| C6S | 5780(20) | −1920(20) | 5275(19) | 145(7) |
| C7S | 6000(20) | −720(20) | 5170(20) | 155(8) |
| C8S | 7200(30) | −180(30) | 4150(30) | 241(15) |
| C9S | 7990(20) | 670(20) | 4390(20) | 153(7) |
| C10S | 7490(30) | 340(30) | 5490(30) | 202(11) |
| O1S | 4966(9) | 7468(9) | 1097(8) | 99(3) |
| C1S | 5930(20) | 8160(20) | 2110(20) | 176(9) |
| C2S | 5018(15) | 7306(16) | 2147(14) | 105(5) |
| C3S | 3770(20) | 7280(20) | 2920(20) | 146(7) |
| C4S | 3200(30) | 8270(30) | 2170(30) | 207(12) |
| C5S | 4180(20) | 8430(20) | 990(20) | 162(8) |

TABLE 6-3

Anisotropic Displacement Parameters ($\times 10^4$) COMPOSITION 4A.
The anisotropic displacement factor exponent takes the form: $-2\pi^2[h^2 a^{*2} \times U_{11} + \ldots + 2hka^* \times b^* \times U_{12}]$\$

| Atom | $U_{11}$ | $U_{22}$ | $U_{33}$ | $U_{23}$ | $U_{13}$ | $U_{12}$ |
|---|---|---|---|---|---|---|
| O1C | 37(3) | 57(4) | 52(3) | −27(3) | −25(3) | 9(3) |
| O2C | 47(4) | 54(4) | 52(4) | −21(3) | −21(3) | 4(3) |
| O3C | 33(3) | 63(4) | 39(3) | −21(3) | −10(3) | −3(3) |
| O4C | 52(4) | 68(4) | 53(4) | −20(4) | −26(4) | 1(3) |
| O5C | 34(3) | 56(4) | 53(4) | −19(3) | −11(3) | 9(3) |
| O6C | 44(3) | 71(4) | 35(4) | −21(3) | −11(3) | 3(3) |
| O7C | 46(4) | 71(5) | 56(4) | −34(4) | −15(3) | 3(3) |
| O8C | 33(3) | 56(4) | 55(4) | −22(3) | −11(3) | 7(3) |
| C1C | 31(4) | 48(5) | 47(5) | −20(4) | −14(4) | 1(4) |
| C2C | 35(5) | 42(5) | 41(5) | −16(4) | −14(4) | 2(4) |
| C3C | 37(5) | 52(5) | 39(5) | −21(4) | −14(4) | 2(4) |
| C4C | 36(5) | 51(5) | 45(5) | −17(4) | −22(4) | 6(4) |
| C5C | 40(5) | 48(5) | 35(4) | −16(4) | −11(4) | 5(4) |
| C6C | 58(6) | 45(5) | 51(5) | −22(4) | −26(5) | 10(4) |
| C7C | 141(9) | 68(6) | 117(8) | −37(6) | −85(8) | 23(6) |
| C8C | 124(9) | 77(6) | 120(8) | −41(6) | −86(7) | 41(6) |
| C9C | 155(14) | 87(10) | 133(13) | −53(9) | −107(12) | 68(10) |
| C10C | 141(9) | 68(6) | 117(8) | −37(6) | −85(8) | 23(6) |
| C11C | 124(9) | 77(6) | 120(8) | −41(6) | −86(7) | 41(6) |
| C12C | 35(5) | 65(6) | 38(5) | −26(5) | −15(4) | 3(4) |
| C13C | 50(6) | 59(6) | 56(6) | −23(5) | −23(5) | 6(5) |
| C14C | 47(6) | 71(7) | 58(6) | −31(5) | −22(5) | 1(5) |
| C15C | 54(6) | 101(10) | 73(8) | −34(7) | −22(6) | −21(6) |
| C16C | 96(10) | 81(9) | 114(11) | −3(8) | −67(9) | −27(8) |
| C17C | 98(10) | 73(8) | 110(11) | −10(8) | −51(9) | −2(7) |
| C18C | 88(9) | 77(8) | 102(10) | −20(7) | −56(8) | −9(7) |
| Cl1B | 67.9(16) | 57.4(14) | 64.2(16) | −10.1(12) | −27.3(13) | −6.4(12) |
| F1B | 67(4) | 76(4) | 55(3) | −19(3) | −22(3) | −23(3) |
| O1B | 41(4) | 55(4) | 71(4) | −12(3) | −23(3) | −6(3) |
| O2B | 36(4) | 89(5) | 78(5) | −31(4) | −28(3) | 11(3) |
| N1B | 23(3) | 42(4) | 51(4) | −12(3) | −13(3) | −6(3) |
| N2B | 33(4) | 54(5) | 35(4) | −14(3) | −10(3) | −5(3) |
| N3B | 40(4) | 58(5) | 48(4) | −12(4) | −23(4) | 2(4) |
| N4B | 35(4) | 47(4) | 59(5) | −17(4) | −18(4) | 7(3) |
| C1B | 38(5) | 55(6) | 58(6) | −27(5) | −22(4) | 9(5) |
| C2B | 37(5) | 53(5) | 27(4) | −15(4) | −9(4) | 1(4) |
| C3B | 46(5) | 55(6) | 40(5) | −19(4) | −14(4) | 6(4) |
| C4B | 49(5) | 54(6) | 36(5) | −16(4) | −14(4) | −12(4) |
| C5B | 29(5) | 83(7) | 35(5) | −25(5) | −9(4) | −6(5) |
| C6B | 32(5) | 64(6) | 37(5) | −21(4) | −10(4) | −8(4) |
| C7B | 38(5) | 67(6) | 50(5) | −23(5) | −19(4) | 3(4) |
| C8B | 34(5) | 43(5) | 48(5) | −15(4) | −19(4) | 2(4) |
| C9B | 39(5) | 51(5) | 42(5) | −22(4) | −12(4) | 1(4) |
| C10B | 49(6) | 59(6) | 42(5) | −20(4) | −20(4) | 10(4) |
| C11B | 42(5) | 50(5) | 46(5) | −17(4) | −23(4) | 4(4) |
| C12B | 28(4) | 42(5) | 47(5) | −17(4) | −14(4) | 2(3) |
| C13B | 44(5) | 62(6) | 52(6) | −25(5) | −8(4) | 7(5) |
| C14B | 40(5) | 62(6) | 61(6) | −26(5) | −18(5) | 0(4) |
| C15B | 52(6) | 72(7) | 89(8) | −52(6) | −22(6) | 7(5) |
| C16B | 66(7) | 99(9) | 50(6) | −23(6) | −21(5) | −10(6) |
| Cl1A | 84(2) | 60.8(16) | 85(2) | −4.6(15) | −34.1(16) | −3.2(14) |
| F1A | 89(5) | 73(4) | 76(4) | −21(3) | −45(4) | 31(3) |
| O1A | 45(4) | 60(4) | 64(4) | −17(4) | −23(3) | 1(3) |
| O2A | 42(4) | 87(5) | 76(5) | −38(4) | −33(3) | 8(3) |
| N1A | 26(3) | 53(4) | 37(4) | −16(3) | −12(3) | 1(3) |
| N2A | 41(4) | 59(5) | 37(4) | −13(4) | −9(3) | 0(4) |
| N3A | 31(4) | 58(4) | 51(4) | −27(4) | −12(3) | −4(3) |
| N4A | 36(4) | 59(5) | 40(4) | −16(4) | −12(3) | 1(3) |
| C1A | 44(5) | 57(6) | 41(5) | −21(4) | −16(4) | 2(5) |
| C2A | 30(4) | 65(6) | 33(4) | −26(4) | −13(4) | 12(4) |
| C3A | 61(6) | 65(6) | 48(6) | −20(5) | −28(5) | 6(5) |
| C4A | 57(6) | 55(6) | 60(6) | −29(5) | −19(5) | 18(5) |
| C5A | 54(6) | 79(7) | 48(5) | −36(5) | −27(5) | 18(5) |
| C6A | 34(5) | 59(6) | 45(5) | −26(4) | −15(4) | 13(4) |
| C7A | 35(5) | 72(6) | 47(5) | −34(5) | −13(4) | 5(5) |
| C8A | 32(4) | 46(5) | 30(4) | −10(4) | −12(4) | 6(4) |
| C9A | 33(5) | 61(6) | 48(5) | −18(4) | −16(4) | 5(4) |
| C10A | 38(5) | 59(6) | 46(5) | −17(4) | −18(4) | −5(4) |
| C11A | 30(5) | 59(6) | 38(5) | −14(4) | −8(4) | −1(4) |
| C12A | 31(4) | 47(5) | 34(4) | −9(4) | −10(4) | 3(4) |
| C13A | 39(5) | 91(7) | 41(5) | −34(5) | −10(4) | 12(5) |
| C14A | 36(5) | 73(6) | 46(5) | −31(5) | −12(4) | 5(4) |

TABLE 6-3-continued

Anisotropic Displacement Parameters (×10⁴) COMPOSITION 4A.
The anisotropic displacement factor exponent takes the form: $-2\pi^2[h^2a^{*2} \times U_{11} + \ldots +2hka^* \times b^* \times U_{12}]$\$

| Atom | $U_{11}$ | $U_{22}$ | $U_{33}$ | $U_{23}$ | $U_{13}$ | $U_{12}$ |
|---|---|---|---|---|---|---|
| C15A | 64(7) | 81(8) | 78(8) | −44(6) | −22(6) | 6(6) |
| C16A | 58(6) | 96(8) | 39(5) | −21(5) | −25(5) | 16(6) |
| O3S | 113(8) | 120(8) | 98(7) | −25(6) | −37(6) | 19(7) |

TABLE 6-3

Bond Lengths in Å for COMPOSITION 4A.

| Atom | Atom | Length/Å |
|---|---|---|
| O1C | C1C | 1.439(10) |
| O1C | C5C | 1.341(10) |
| O2C | C5C | 1.194(10) |
| O3C | C2C | 1.427(10) |
| O3C | C12C | 1.341(10) |
| O4C | C12C | 1.215(11) |
| O5C | C3C | 1.313(10) |
| O6C | C3C | 1.193(10) |
| O7C | C4C | 1.194(10) |
| O8C | C4C | 1.306(10) |
| C1C | C2C | 1.525(11) |
| C1C | C3C | 1.528(12) |
| C2C | C4C | 1.532(12) |
| C5C | C6C | 1.478(13) |
| C6C | C7C | 1.386(16) |
| C6C | C11C | 1.358(16) |
| C7C | C8C | 1.358(17) |
| C8C | C9C | 1.35(2) |
| N3B | C1B | 1.367(11) |
| N3B | C7B | 1.385(12) |
| N4B | C11B | 1.346(11) |
| N4B | C12B | 1.346(10) |
| C2B | C6B | 1.391(12) |
| C3B | C4B | 1.378(13) |
| C4B | C5B | 1.357(13) |
| C5B | C6B | 1.389(12) |
| C6B | C7B | 1.456(14) |
| C8B | C9B | 1.400(12) |
| C8B | C12B | 1.369(12) |
| C9B | C10B | 1.372(12) |
| C9B | C13B | 1.526(13) |
| C10B | C11B | 1.359(13) |
| C12B | C14B | 1.492(13) |
| C14B | C15B | 1.526(14) |
| C14B | C16B | 1.562(15) |
| C11A | C3A | 1.714(11) |
| F1A | C4A | 1.336(11) |
| O1A | C1A | 1.216(11) |
| O2A | C7A | 1.223(11) |
| N1A | C1A | 1.386(11) |
| N1A | C2A | 1.405(11) |
| N1A | C8A | 1.446(10) |
| N2A | C2A | 1.331(11) |
| N2A | C3A | 1.321(12) |
| N3A | C1A | 1.373(12) |
| N3A | C7A | 1.368(11) |
| N4A | C11A | 1.335(11) |
| N4A | C12A | 1.335(11) |
| C2A | C6A | 1.394(12) |
| C3S | C4S | 1.53(3) |
| C4S | C5S | 1.59(4) |
| C9C | C10C | 1.373(19) |
| C10C | C11C | 1.411(17) |
| C12C | C13C | 1.454(14) |
| C13C | C14C | 1.384(13) |
| C13C | C18C | 1.366(16) |
| C14C | C15C | 1.375(15) |
| C15C | C16C | 1.375(18) |
| C16C | C17C | 1.368(19) |
| C17C | C18C | 1.375(18) |
| CUB | C3B | 1.732(10) |
| F1B | C4B | 1.339(10) |

TABLE 6-3-continued

Bond Lengths in Å for COMPOSITION 4A.

| Atom | Atom | Length/Å |
|---|---|---|
| O1B | C1B | 1.212(11) |
| O2B | C7B | 1.221(11) |
| N1B | C1B | 1.398(12) |
| N1B | C2B | 1.381(10) |
| N1B | C8B | 1.458(10) |
| N2B | C2B | 1.344(11) |
| N2B | C3B | 1.305(11) |
| C3A | C4A | 1.402(14) |
| C4A | C5A | 1.324(14) |
| C5A | C6A | 1.419(13) |
| C6A | C7A | 1.453(13) |
| C8A | C9A | 1.393(12) |
| C8A | C12A | 1.398(12) |
| C9A | C10A | 1.405(12) |
| C9A | C13A | 1.485(13) |
| C10A | C11A | 1.339(13) |
| C12A | C14A | 1.497(12) |
| C14A | C15A | 1.527(16) |
| C14A | C16A | 1.541(14) |
| O3S | C12S | 1.51(3) |
| O3S | C15S | 1.44(2) |
| C11S | C12S | 1.64(5) |
| C11T | C12S | 1.51(3) |
| C12S | C13S | 1.49(5) |
| C12S | C13T | 1.39(5) |
| C13S | C14S | 1.70(5) |
| C13T | C14S | 1.55(5) |
| C14S | C15S | 1.39(3) |
| O2S | C7S | 1.43(2) |
| O2S | C10S | 1.52(3) |
| C6S | C7S | 1.38(3) |
| C7S | C8S | 1.54(4) |
| C8S | C9S | 1.57(4) |
| C9S | C10S | 1.34(3) |
| O1S | C2S | 1.429(18) |
| O1S | C5S | 1.41(2) |
| C1S | C2S | 1.45(3) |
| C2S | C3S | 1.46(3) |

TABLE 6-4

Bond Angles in for COMPOSITION 4A.

| Atom | Atom | Atom | Angle/° |
|---|---|---|---|
| C5C | O1C | C1C | 116.5(6) |
| C12C | O3C | C2C | 117.1(7) |
| O1C | C1C | C2C | 105.3(6) |
| O1C | C1C | C3C | 108.6(7) |
| C3C | C1C | C2C | 111.5(7) |
| O3C | C2C | C1C | 106.6(6) |
| O3C | C2C | C4C | 108.9(6) |
| C1C | C2C | C4C | 110.9(7) |
| O5C | C3C | C1C | 109.9(7) |
| O6C | C3C | O5C | 126.1(8) |
| O6C | C3C | C1C | 124.0(8) |
| O7C | C4C | O8C | 127.3(8) |
| O7C | C4C | C2C | 122.3(8) |
| O8C | C4C | C2C | 110.4(7) |
| O1C | C5C | C6C | 110.8(8) |

TABLE 6-4-continued

Bond Angles in for COMPOSITION 4A.

| Atom | Atom | Atom | Angle/° |
|---|---|---|---|
| O2C | C5C | O1C | 124.1(8) |
| O2C | C5C | C6C | 125.1(8) |
| C7C | C6C | C5C | 119.6(9) |
| C11C | C6C | C5C | 121.9(8) |
| C11C | C6C | C7C | 118.1(10) |
| C8C | C7C | C6C | 122.4(12) |
| C9C | C8C | C7C | 119.1(13) |
| C10C | C9C | C8C | 120.6(12) |
| C9C | C10C | C11C | 119.5(13) |
| C6C | C11C | C10C | 119.7(12) |
| O3C | C12C | C13C | 112.4(8) |
| O4C | C12C | O3C | 122.7(8) |
| O4C | C12C | C13C | 124.9(8) |
| C14C | C13C | C12C | 120.6(9) |
| C18C | C13C | C12C | 120.4(9) |
| C18C | C13C | C14C | 118.8(10) |
| C15C | C14C | C13C | 120.1(10) |
| C16C | C15C | C14C | 120.5(10) |
| C15C | C16C | C17C | 118.7(12) |
| C16C | C17C | C18C | 120.4(14) |
| C13C | C18C | C17C | 120.5(12) |
| C1B | N1B | C8B | 115.5(7) |
| C2B | N1B | C1B | 121.7(7) |
| C2B | N1B | C8B | 122.6(7) |
| C3B | N2B | C2B | 116.6(7) |
| C1B | N3B | C7B | 126.9(8) |
| C12B | N4B | CHB | 118.8(8) |
| O1B | C1B | N1B | 121.2(8) |
| O1B | C1B | N3B | 122.4(9) |
| N3B | C1B | N1B | 116.3(8) |
| N1B | C2B | C6B | 119.7(8) |
| N2B | C2B | N1B | 117.3(7) |
| N2B | C2B | C6B | 123.1(8) |
| N2B | C3B | C11B | 116.9(7) |
| N2B | C3B | C4B | 125.0(8) |
| C4B | C3B | C11B | 118.0(7) |
| F1B | C4B | C3B | 121.5(8) |
| F1B | C4B | C5B | 120.2(8) |
| C5B | C4B | C3B | 118.3(8) |
| C4B | C5B | C6B | 119.2(8) |
| C2B | C6B | C7B | 120.9(8) |
| C5B | C6B | C2B | 117.7(8) |
| C5B | C6B | C7B | 121.2(8) |
| O2B | C7B | N3B | 121.3(9) |
| O2B | C7B | C6B | 124.9(9) |
| N3B | C7B | C6B | 113.8(8) |
| C9B | C8B | N1B | 118.0(7) |
| C12B | C8B | N1B | 120.2(7) |
| C12B | C8B | C9B | 121.7(7) |
| C8B | C9B | C13B | 121.4(8) |
| C10B | C9B | C8B | 116.6(8) |
| C10B | C9B | C13B | 122.0(8) |
| C11B | C10B | C9B | 119.9(8) |
| N4B | C11B | C10B | 123.0(8) |
| N4B | C12B | C8B | 119.9(8) |
| N4B | C12B | C14B | 116.2(7) |
| C8B | C12B | C14B | 123.8(7) |
| C12B | C14B | C 15B | 113.0(8) |
| C12B | C14B | C16B | 110.5(8) |
| C15B | C14B | C16B | 111.7(9) |
| C1A | N1A | C2A | 121.5(7) |
| C1A | N1A | C8A | 118.9(7) |
| C2A | N1A | C8A | 119.5(7) |
| C3A | N2A | C2A | 116.6(8) |
| C7A | N3A | C1A | 126.9(8) |
| C12A | N4A | C11A | 120.6(7) |
| O1A | C1A | N1A | 120.7(8) |
| O1A | C1A | N3A | 122.4(8) |
| N3A | C1A | N1A | 116.9(8) |
| N2A | C2A | N1A | 116.6(7) |
| N2A | C2A | C6A | 124.3(8) |
| C6A | C2A | N1A | 119.1(7) |
| N2A | C3A | C11A | 116.6(7) |
| N2A | C3A | C4A | 123.7(9) |
| C4A | C3A | C11A | 119.7(8) |
| F1A | C4A | C3A | 119.7(9) |

TABLE 6-4-continued

Bond Angles in for COMPOSITION 4A.

| Atom | Atom | Atom | Angle/° |
|---|---|---|---|
| C5A | C4A | F1A | 121.1(9) |
| C5A | C4A | C3A | 119.2(9) |
| C4A | C5A | C6A | 119.7(9) |
| C2A | C6A | C5A | 116.4(9) |
| C2A | C6A | C7A | 121.0(8) |
| C5A | C6A | C7A | 122.6(8) |
| O2A | C7A | N3A | 120.9(9) |
| O2A | C7A | C6A | 124.4(9) |
| N3A | C7A | C6A | 114.7(8) |
| C9A | C8A | N1A | 118.0(7) |
| C9A | C8A | C12A | 122.2(7) |
| C12A | C8A | N1A | 119.7(7) |
| C8A | C9A | C10A | 115.9(8) |
| C8A | C9A | C13A | 123.3(8) |
| C10A | C9A | C13A | 120.7(8) |
| C11A | C10A | C9A | 119.5(8) |
| C10A | C11A | N4A | 123.5(8) |
| N4A | C12A | C8A | 118.2(8) |
| N4A | C12A | C14A | 118.8(7) |
| C8A | C12A | C14A | 123.0(7) |
| C12A | C14A | C15A | 110.2(8) |
| C12A | C14A | C16A | 109.8(8) |
| C15A | C14A | C16A | 111.6(9) |
| C15S | O3S | C12S | 101.0(16) |
| O3S | C12S | C11S | 98(2) |
| C11T | C12S | O3S | 114(3) |
| C13S | C12S | O3S | 101(3) |
| C13S | C12S | C11T | 119(4) |
| C13T | C12S | O3S | 108(3) |
| C13T | C12S | C11S | 124(4) |
| C12S | C13S | C14S | 94(3) |
| C12S | C13T | C14S | 106(3) |
| C15S | C14S | C13S | 105(2) |
| C15S | C14S | C13T | 98(2) |
| C14S | C15S | O3S | 109.6(18) |
| C7S | O2S | C10S | 109.8(17) |
| O2S | C7S | C8S | 98(2) |
| C6S | C7S | O2S | 110(2) |
| C6S | C7S | C8S | 105(2) |
| C7S | C8S | C9S | 108(3) |
| C10S | C9S | C8S | 104(3) |
| C9S | C10S | O2S | 110(2) |
| C5S | O1S | C2S | 99.3(14) |
| O1S | C2S | C1S | 115.3(16) |
| O1S | C2S | C3S | 109.3(14) |
| C1S | C2S | C3S | 113.3(18) |
| C2S | C3S | C4S | 102.4(19) |
| C3S | C4S | C5S | 100(2) |
| O1S | C5S | C4S | 110(2) |

TABLE 6-5

Hydrogen Fractional Atomic Coordinates ($\times 10^4$) and Equivalent Isotropic Displacement Parameters ($\text{Å}^2 \times 10^3$) for COMPOSITION 4A. $U_{eq}$ is defined as 1/3 of the trace of the orthogonalised $U_{ij}$.

| Atom | x | y | z | $U_{eq}$ |
|---|---|---|---|---|
| H5C | 2738 | 5676 | 7079 | 75 |
| H8C | 7257 | 4612 | 3523 | 74 |
| H1C | 5642 | 5286 | 5648 | 49 |
| H2C | 4246 | 5000 | 4813 | 47 |
| H7C | 8030 | 3133 | 7918 | 117 |
| H8CA | 8829 | 1329 | 8674 | 113 |
| H9C | 8046 | −520 | 8781 | 129 |
| H10C | 6325 | −589 | 8302 | 117 |
| H11C | 5582 | 1286 | 7440 | 113 |
| H14C | 824 | 2153 | 5456 | 67 |

TABLE 6-5-continued

Hydrogen Fractional Atomic Coordinates (×10⁴) and Equivalent Isotropic Displacement Parameters (Å² × 10³) for COMPOSITION 4A. $U_{eq}$ is defined as 1/3 of the trace of the orthogonalised $U_{ij}$.

| Atom | x | y | z | $U_{eq}$ |
|---|---|---|---|---|
| H15C | −125 | 131 | 6310 | 90 |
| H16C | 854 | −1479 | 7197 | 118 |
| H17C | 2922 | −1070 | 6936 | 117 |
| H18C | 3724 | 966 | 6375 | 104 |
| H3B | 6442 | 7830 | 7268 | 59 |
| H5B | 4284 | 3988 | 9467 | 59 |
| H10B | 10491 | 6619 | 10136 | 58 |
| H11B | 12147 | 6175 | 8883 | 53 |
| H13A | 7637 | 7233 | 9947 | 82 |
| H13B | 8351 | 6990 | 10789 | 82 |
| H13C | 7521 | 5873 | 10864 | 82 |
| H14B | 9141 | 5177 | 7246 | 64 |
| H15A | 11415 | 4105 | 7168 | 98 |
| H15B | 10492 | 3806 | 6645 | 98 |
| H15D | 10055 | 3410 | 7957 | 98 |
| H16A | 10303 | 7074 | 5885 | 109 |
| H16B | 10596 | 6013 | 5392 | 109 |
| H16D | 11573 | 6448 | 5797 | 109 |
| H3A | 14191 | 5912 | 1268 | 55 |
| H5A | 14875 | 1914 | 3171 | 65 |
| H10A | 9147 | 3010 | 831 | 57 |
| H11A | 7601 | 3622 | 2016 | 54 |
| H13D | 12178 | 3715 | 8 | 83 |
| H13E | 11236 | 2674 | 104 | 83 |
| H13F | 11970 | 2347 | 938 | 83 |
| H14A | 10773 | 4660 | 3501 | 60 |
| H15E | 9817 | 6386 | 3737 | 106 |
| H15F | 8738 | 6107 | 3360 | 106 |
| H15G | 10127 | 6543 | 2480 | 106 |
| H16E | 8174 | 3966 | 4816 | 96 |
| H16F | 9227 | 4126 | 5267 | 96 |
| H16G | 9198 | 3006 | 4874 | 96 |
| H11D | 403 | 121 | 11721 | 212 |
| H11E | −600 | −1054 | 12212 | 212 |
| H11F | −968 | 318 | 11703 | 212 |
| H11G | −1060 | −259 | 11882 | 290 |
| H11H | −1114 | −1599 | 11825 | 290 |
| H11I | −1750 | −509 | 11154 | 290 |
| H12S | 128 | −753 | 9931 | 215 |
| H12A | −557 | −686 | 10345 | 215 |
| H13G | 1497 | −1393 | 10872 | 182 |
| H13H | 1451 | −115 | 11089 | 182 |
| H13I | 1087 | −1267 | 9548 | 182 |
| H13J | 1458 | −1412 | 10592 | 182 |
| H14D | 3019 | 696 | 9168 | 186 |
| H14E | 2460 | −284 | 8839 | 186 |
| H14F | 2628 | 537 | 9673 | 186 |
| H14G | 2896 | 104 | 8645 | 186 |
| H15H | 1338 | 997 | 8243 | 167 |
| H15I | 1947 | 1996 | 8512 | 167 |
| H6SA | 6575 | −2283 | 5108 | 218 |
| H6SB | 5393 | −1922 | 4756 | 218 |
| H6SC | 5233 | −2417 | 6034 | 218 |
| H7S | 5282 | −222 | 5136 | 186 |
| H8SA | 7003 | 307 | 3490 | 290 |
| H8SB | 7680 | −861 | 4007 | 290 |
| H9SA | 8880 | 527 | 4152 | 184 |
| H9SB | 7923 | 1561 | 4003 | 184 |
| H10D | 7155 | 1055 | 5667 | 243 |
| H10E | 8144 | 66 | 5812 | 243 |
| H1SA | 6626 | 7716 | 2249 | 264 |
| H1SB | 5541 | 8496 | 2685 | 264 |
| H1SC | 6226 | 8839 | 1383 | 264 |
| H2S | 5277 | 6457 | 2441 | 126 |
| H3SA | 3789 | 7506 | 3528 | 175 |
| H3SB | 3293 | 6455 | 3231 | 175 |
| H4SA | 3168 | 9048 | 2302 | 249 |
| H4SB | 2364 | 7965 | 2275 | 249 |
| H5SA | 3745 | 8410 | 500 | 195 |
| H5SB | 4689 | 9246 | 647 | 195 |

TABLE 6-4

Hydrogen Bond information for COMPOSITION 4A.

| D | H | A | d (D—H)/Å | d (H—A)/Å | d (D—A)/Å | D—H—A/deg |
|---|---|---|---|---|---|---|
| O5C | H5C | N4B[1] | 0.84 | 1.82 | 2.656(9) | 170.9 |
| O8C | H8C | N4A | 0.84 | 1.79 | 2.624(9) | 171.6 |
| N3B | H3B | O2S[2] | 0.88 | 1.94 | 2.805(12) | 168.1 |
| C14B | H14B | N1B | 1.00 | 2.44 | 2.937(12) | 110.1 |
| N3A | H3A | O1S[3] | 0.88 | 1.95 | 2.798(12) | 160.7 |

[1]−1 + x, +y, +z;
[2]+x, 1 + y, +z;
[3]1 + x, +y, +z

TABLE 6-5

Atomic Occupancies for all atoms that are not fully occupied in COMPOSITION 4A.

| Atom | Occupancy |
|---|---|
| C11S | 0.5 |
| H11D | 0.5 |
| H11E | 0.5 |
| H11F | 0.5 |
| C11T | 0.5 |
| H11G | 0.5 |
| H11H | 0.5 |
| H11I | 0.5 |
| H12S | 0.5 |
| H12A | 0.5 |
| C13S | 0.5 |
| H13G | 0.5 |
| H13H | 0.5 |
| C13T | 0.5 |
| H13I | 0.5 |
| H13J | 0.5 |
| H14D | 0.5 |
| H14E | 0.5 |
| H14F | 0.5 |
| H14G | 0.5 |

The foregoing is merely illustrative of the invention and is not intended to limit the invention to the disclosed uses. Variations and changes, which are routine to one skilled in the art, are intended to be within the scope and nature of the invention, which are defined in the appended claims. All mentioned references, patents, applications and publications, are hereby incorporated by reference in their entirety, as if here written.

What is claimed is:

1. A composition, the composition comprising a compound of Formula 4:

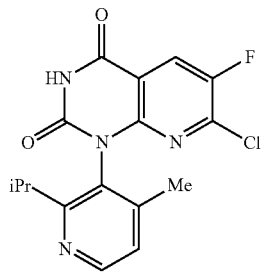

4 and a compound of Formula B:

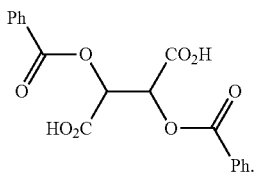

B

2. The composition of claim 1, wherein the compound of Formula 4 is:

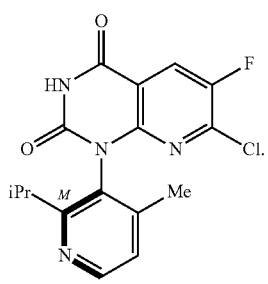

5M

3. The composition of claim 1, wherein the compound of Formula 4 is:

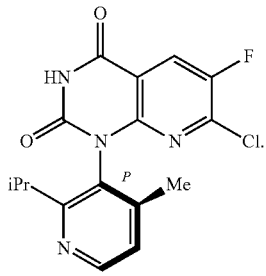

5P

4. The composition of claim 1, wherein the compound of Formula B is:

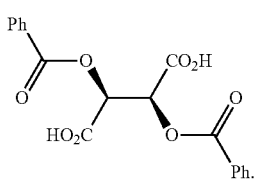

B1

5. The composition of claim 1, wherein the compound of Formula B is:

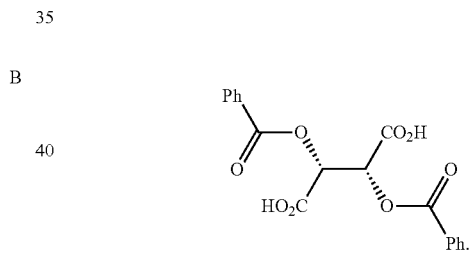

B2

6. The composition of claim 1, wherein the composition comprises a 2 to 1 ratio of the compound of Formula 4 to the compound of Formula B.

7. The composition of claim 1, wherein the composition further comprises 2-methyltetrahydrofuran having the formula:

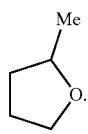

8. The composition of claim 7, wherein the ratio of the 2-methyltetrahydrofuran to the compound of formula B is 2 to 1.

9. The composition of claim 7, wherein the composition comprises:
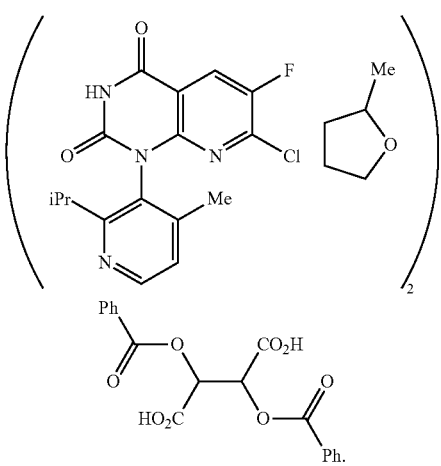
10. The composition of claim 9, wherein the composition comprises:
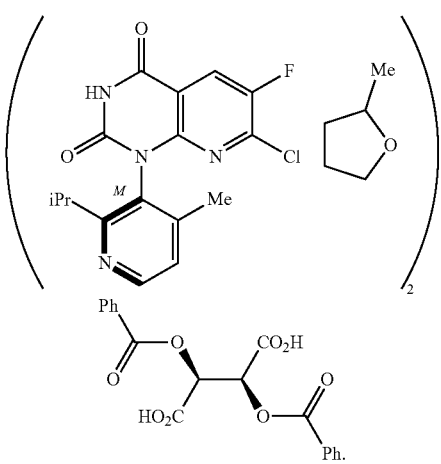
11. The composition of claim 9, wherein the composition comprises:
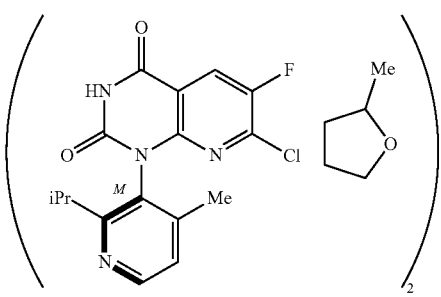
4a
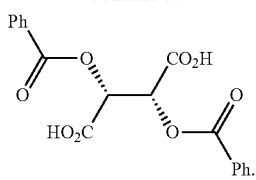
12. The composition of claim 9, wherein the composition comprises:
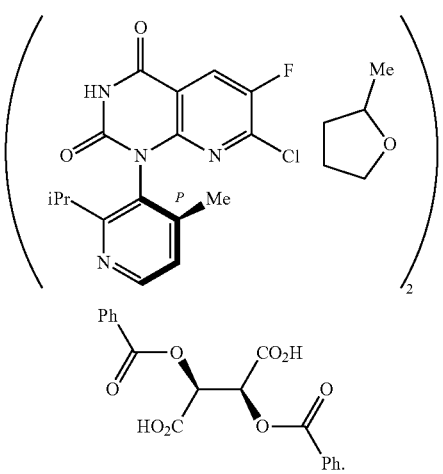
13. The composition of claim 9, wherein the composition comprises:
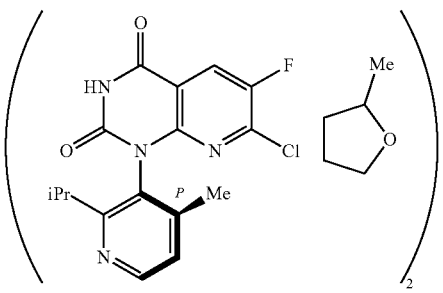
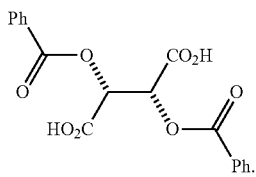
\* \* \* \* \*